US012721904B2

(12) United States Patent
Myers et al.

(10) Patent No.: US 12,721,904 B2
(45) Date of Patent: Sep. 1, 2026

(54) STABILIZED TRIOXACARCIN ANTIBODY DRUG CONJUGATES AND USES THEREOF

(71) Applicant: President and Fellows of Harvard College, Cambridge, MA (US)

(72) Inventors: Andrew G. Myers, Cambridge, MA (US); Ethan L. Magno, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 777 days.

(21) Appl. No.: 18/009,265

(22) PCT Filed: Jun. 10, 2021

(86) PCT No.: PCT/US2021/036718
§ 371 (c)(1),
(2) Date: Dec. 8, 2022

(87) PCT Pub. No.: WO2021/252708
PCT Pub. Date: Dec. 16, 2021

(65) Prior Publication Data

US 2024/0148889 A1 May 9, 2024

Related U.S. Application Data

(60) Provisional application No. 63/201,333, filed on Apr. 23, 2021, provisional application No. 63/141,808, filed on Jan. 26, 2021, provisional application No. 63/038,022, filed on Jun. 11, 2020.

(51) Int. Cl.
*A61K 47/68* (2017.01)
*A61P 35/00* (2006.01)

(52) U.S. Cl.
CPC ...... *A61K 47/6889* (2017.08); *A61K 47/6803* (2017.08); *A61K 47/6809* (2017.08); *A61P 35/00* (2018.01)

(58) Field of Classification Search
CPC ............ A61K 47/6889; A61K 47/6803; A61K 47/6809; A61K 47/6849; A61K 47/6851; A61P 35/00; C07D 493/22; C07H 15/203; C07K 16/32
See application file for complete search history.

(56) References Cited

U.S. PATENT DOCUMENTS 4,270,537 A 6/1981 Romaine
4,355,023 A 10/1982 Ehrlich et al.
4,459,291 A 7/1984 Shirahata et al.
4,470,925 A 9/1984 Auditore-Hargreaves
4,511,560 A 4/1985 Tomita et al.
4,596,556 A 6/1986 Morrow et al.
4,626,503 A 12/1986 Lee et al.
4,790,824 A 12/1988 Morrow et al.
4,816,567 A 3/1989 Cabilly et al.
4,886,499 A 12/1989 Cirelli et al.
4,940,460 A 7/1990 Casey et al.
4,941,880 A 7/1990 Burns
4,946,778 A 8/1990 Ladner et al.
5,015,235 A 5/1991 Crossman
5,064,413 A 11/1991 McKinnon et al.
5,141,496 A 8/1992 Dalto et al.
5,190,521 A 3/1993 Hubbard et al.
5,202,238 A 4/1993 Fell et al.
5,204,244 A 4/1993 Fell et al.
5,312,335 A 5/1994 McKinnon et al.
5,328,483 A 7/1994 Jacoby
5,334,144 A 8/1994 Alchas et al.
5,339,163 A 8/1994 Homma et al.
5,383,851 A 1/1995 McKinnon, Jr. et al.
5,399,163 A 3/1995 Peterson et al.
5,417,662 A 5/1995 Hjertman et al.
5,466,220 A 11/1995 Brenneman
5,480,381 A 1/1996 Weston
5,503,627 A 4/1996 McKinnon et al.
5,520,639 A 5/1996 Peterson et al.
(Continued)

FOREIGN PATENT DOCUMENTS

JP 58-065293 A 4/1983
JP 63-135389 A 6/1988
(Continued)

OTHER PUBLICATIONS

Rivas, et al., Organic and Biomol. Chem. 2019 17:4705 (Year: 2019).*
International Search Report and Written Opinion for PCT/US2011/029343, mailed Jul. 22, 2011.
International Preliminary Report on Patentability for PCT/US2011/029343, mailed Oct. 4, 2012.
International Search Report and Written Opinion for PCT/US2013/071924, mailed Feb. 6, 2014.
International Preliminary Report on Patentability for PCT/US2013/071924, mailed Jun. 4, 2015.
(Continued)

*Primary Examiner* — Julie Wu
*Assistant Examiner* — Sydney Van Druff
(74) *Attorney, Agent, or Firm* — Wolf, Greenfield & Sacks, P.C.

(57) ABSTRACT

Provided herein are antibody drug conjugates of Formula (I): G-$R^7$(I) and pharmaceutically acceptable salts thereof, wherein G is a molecular payload; and $R^7$ is -L-A-B, wherein L is a linking group, A is a conjugating group, and B is an antibody or antibody fragment. Also provided are methods of preparing the antibody-drug conjugates, pharmaceutically acceptable compositions thereof, and methods of their use and treatment. Further provided are precursors to the antibody drug conjugates (e.g., compounds of Formula (III), novel trioxacarcins without an antibody conjugated thereto), pharmaceutical compositions thereof, and methods of their use and treatment.

20 Claims, 2 Drawing Sheets

(56) References Cited

U.S. PATENT DOCUMENTS

| | | | |
|---|---|---|---|
| 5,527,288 | A | 6/1996 | Gross et al. |
| 5,565,354 | A | 10/1996 | Ostberg |
| 5,567,610 | A | 10/1996 | Borrebaeck et al. |
| 5,569,189 | A | 10/1996 | Parsons |
| 5,569,825 | A | 10/1996 | Lonberg et al. |
| 5,599,302 | A | 2/1997 | Lilley et al. |
| 5,649,912 | A | 7/1997 | Peterson |
| 5,704,911 | A | 1/1998 | Parsons |
| 5,893,397 | A | 4/1999 | Peterson et al. |
| 5,993,412 | A | 11/1999 | Deily et al. |
| 7,846,915 | B2 | 12/2010 | Wong et al. |
| 9,102,697 | B2 | 8/2015 | Myers et al. |
| 9,611,287 | B2 | 4/2017 | Myers et al. |
| 9,775,915 | B2 | 10/2017 | Myers et al. |
| 10,639,381 | B2 | 5/2020 | Myers et al. |
| 2011/0165155 | A1 | 7/2011 | Agresta et al. |
| 2012/0177568 | A1 | 7/2012 | Williams et al. |
| 2013/0150314 | A1 | 6/2013 | Myers et al. |
| 2014/0227180 | A1 | 8/2014 | Govindan et al. |
| 2015/0297747 | A1 | 10/2015 | Myers et al. |
| 2016/0355537 | A1 | 12/2016 | Myers et al. |
| 2018/0221504 | A1 | 8/2018 | Myers et al. |
| 2022/0233708 | A1* | 7/2022 | Bao .................. A61K 47/68037 |
| 2025/0144227 | A1* | 5/2025 | Myers ................ A61K 47/6849 |

FOREIGN PATENT DOCUMENTS

| | | | | |
|---|---|---|---|---|
| JP | 63-135390 | A | 6/1988 | |
| JP | 63-135391 | A | 6/1988 | |
| WO | WO 97/13537 | A1 | 4/1997 | |
| WO | WO 97/37705 | A1 | 10/1997 | |
| WO | WO 99/34850 | A1 | 7/1999 | |
| WO | WO 2005/080549 | A2 | 9/2005 | |
| WO | WO 2011/119549 | A1 | 9/2011 | |
| WO | WO 2014/02065 | A1 | 5/2014 | |
| WO | WO-2019032961 | A1 * | 2/2019 | ............ C07K 16/32 |
| WO | WO 2020/177568 | A1 | 9/2020 | |
| WO | WO 2021/252708 | A1 | 12/2021 | |

OTHER PUBLICATIONS

Invitation to Pay Additional Fees for Application No. PCT/US2018/046210, mailed Sep. 24, 2018.
International Search Report and Written Opinion for PCT/US2018/046210, mailed on Dec. 11, 2018.
International Preliminary Report on Patentability for PCT/US2018/046210, mailed on Feb. 20, 2020.
International Search Report and Written Opinion for Application No. PCT/US2021 /036718, mailed Aug. 21, 2021.
International Preliminary Report on Patentability for Application No. PCT/US2021 /036718, mailed Dec. 22, 2022.
Invitation to Pay Additional Fees for Application No. PCT/US2022/050726, mailed Apr. 4, 2023.
International Search Report and Written Opinion for Application No. PCT/US2022/050726, mailed May 25, 2023.
Anelli et al., Fast and selective oxidation of primary alcohols to aldehydes or to carboxylic acids and of secondary alcohols to ketones mediated by oxoammonium salts under two-phase conditions. J Org Chem. 1987;52(12):2559-2562.
Bargh et al., Cleavable Linkers in Antibody-Drug Conjugates. Chem Soc Rev. Aug. 12, 2019;48(16):4361-4374. doi: 10.1039/c8cs00676h.
Beck et al., Strategies and Challenges for the next Generation of Antibody-Drug Conjugates. Nat Rev Drug Discov. May 2017;16(5):315-337. doi: 10.1038/nrd.2016.268. Epub Mar. 17, 2017.
Boeckman et al., Catechol Boron Halides: Mild and Selective Reagents for Cleavage of Common Protecting Groups. Tetrahedron Lett. 1985;26:1411-14.
Bondar et al., Pectenotoxin-2 synthetic studies. 2. Construction and conjoining of ABC and DE Eastern hemisphere subtargets. Org Lett. Apr. 28, 2005;7(9):1813-6.
Brubaker et al., A practical, enantioselective synthetic route to a key precursor to the tetracycline antibiotics. Org Lett. Aug. 30, 2007;9(18):3523-5. Epub Aug. 11, 2007.
Brzezinski et al., The Asymmetric Baylis-Hillman Reaction. J Am Chem Soc. 1997;119(18):4317-4318.
Burke et al., Optimization of a PEGylated Glucuronide-Monomethylauristatin E Linker for Antibody-Drug Conjugates. Mol Cancer Ther. Jan. 2017;16(1):116-123. doi: 10.1158/1535-7163.MCT-16-0343. Epub Nov. 9, 2016.
Cardillo et al., Humanized Anti-Trop-2 IgG-SN-38 Conjugate for Effective Treatment of Diverse Epithelial Cancers: Preclinical Studies in Human Cancer Xenograft Models and Monkeys. Clin Cancer Res. May 15, 2011;17(10):3157-69. doi: 10.1158/1078-0432.CCR-10-2939. Epub Mar. 3, 2011.
Carter et al., Next Generation Antibody Drugs: Pursuit of the 'High-Hanging Fruit'. Nat Rev Drug Discov. Mar. 2018;17(3):197-223. doi: 10.1038/nrd.2017.227. Epub Dec. 1, 2017.
Cassidy et al., Phase I clinical study of LL-D49194 alpha 1 with retrospective pharmacokinetic investigations in mice and humans. The EORTC ECTG. Cancer Chemother Pharmacol. 1993;31(5):395-400.
Chari et al., Antibody-Drug Conjugates: An Emerging Concept in Cancer Therapy. Angew Chem Int Ed Engl. Apr. 7, 2014;53(15):3796-827. doi: 10.1002/anie.201307628. Epub Feb. 20, 2014.
Chau et al., Antibody-Drug Conjugates for Cancer. Lancet. Aug. 31, 2019;394(10200): 793-804. doi: 10.1016/S0140-6736(19)31774-X.
Chudasama et al., Recent Advances in the Construction of Antibody-Drug Conjugates. Nat Chem. Feb. 2016;8(2):114-9. doi: 10.1038/nchem.2415. Epub Jan. 4, 2016.
Collum et al., Synthesis of the polyether antibiotic monensin. 2. Preparation of intermediates. J Am Chem Soc. 1980;102(6):2118-2120.
Damen et al., Synthesis of Novel Paclitaxel Prodrugs Designed for Bioreductive Activation in Hypoxic Tumour Tissue. Bioorg Med Chem. Jan. 2002;10(1):71-7. doi: 10.1016/s0968-0896(01)00235-8.
De Groot et al., Synthesis and Biological Evaluation of 2'-Carbamate-Linked and 2'-Carbonate-Linked Prodrugs of Paclitaxel: Selective Activation by the Tumor-Associated Protease Plasmin. J Med Chem. Aug. 10, 2000;43(16):3093-102. doi: 10.1021/jm0009078.
Dewit et al., Design, Synthesis, and Cyclization of 4-Aminobutyric Acid Derivatives: Potential Candidates as Self-Immolative Spacers. Org Biomol Chem. Mar. 21, 2011;9(6):1846-54. doi: 10.1039/c0ob00890g. Epub Jan. 26, 2011.
Dimond, Antibody-Drug Conjugates Stage a Comeback. GEN Genetic Engineering & Biotechnology News. Mar. 10, 2010. 3 pages. Accessed at http://www.genengnews.com/insight-and-intelligenceand153/antibody-drug-conjugates-stage-a-comeback/77899350.
Dokter et al., Preclinical Profile of the HER2-Targeting ADC SYD983/SYD985: Introduction of a New Duocarmycin-Based Linker-Drug Platform. Mol Cancer Ther. Nov. 2014;13(11):2618-29. doi: 10.1158/1535-7163.MCT-14-0040-T. Epub Sep. 4, 2014.
Dong et al., Discovery of Druggability-Improved Analogues by Investigation of the LL-D49194α1 Biosynthetic Pathway. Org Lett. Apr. 5, 2019;21(7):2322-2325. doi: 10.1021/acs.orglett.9b00610. Epub Mar. 11, 2019.
Doronina et al., Development of Potent Monoclonal Antibody Auristatin Conjugates for Cancer Therapy. Nat Biotechnol. Jul. 2003;21(7):778-84. doi: 10.1038/nbt832. Epub Jun. 1, 2003.
Drewes et al., Facile Diastereoselective Synthesis of 2,6-Dialkyl-5-methylene-1,3-dioxan-4-ones via α-Activated Vinyl Esters. Chem Ber. 1990;123:1447-48.
Dubowchik et al., Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity. Bioconjug Chem. Jul.-Aug. 2002;13(4):855-69. doi: 10.1021/bc025536j.
Dubowchik et al., Cathepsin B-Sensitive Dipeptide Prodrugs. 2. Models of Anticancer Drugs Paclitaxel (Taxol®), Mitomycin C and Doxorubicin. Bioorg Med Chem Lett. Dec. 1, 1998;8(23):3347-52. doi: 10.1016/s0960-894x(98)00610-6.

(56) References Cited

OTHER PUBLICATIONS

Ducry et al., Antibody-drug conjugates: linking cytotoxic payloads to monoclonal antibodies. Bioconjug Chem. Jan. 2010;21(1):5-13. doi: 10.1021/bc9002019.
Elgersma et al., Design, Synthesis, and Evaluation of Linker-Duocarmycin Payloads: Toward Selection of HER2-Targeting Antibody-Drug Conjugate SYD985. Mol Pharm. Jun. 1, 2015;12(6):1813-35. doi: 10.1021/mp500781a. Epub Feb. 18, 2015.
Finniss et al., A Versatile Acid-Labile Linker for Antibody-Drug Conjugates. Med Chem Commun. 2014; 5(9): 1355-58. https://doi.org/10.1039/C4MD00150H.
Fitzner et al., Formation of gutingimycin: analytical investigation of trioxacarcin A-mediated alkylation of dsDNA. Anal Bioanal Chem. Feb. 2008;390(4):1139-47. Epub Jan. 22, 2008.
Fujimoto et al., Antitumor activity of trioxacarcin C. J Antibiot (Tokyo). Sep. 1983;36(9):1216-21.
Garegg et al., Synthesis of Methyl 2,6-Dideoxy-3-C-methyl-α-L-xylo-hexopyranoside ("Methyl-α-Axenoside"). Acta Chemica Scandinavica B. 1975;29:507-12.
Gauzy-Lazo et al., Advances in Antibody-Drug Conjugate Design: Current Clinical Landscape and Future Innovations. SLAS Discov. Sep. 2020;25(8):843-868. doi: 10.1177/2472555220912955. Epub Mar. 20, 2020.
Hill et al., Anhydrous tert-butyl hydroperoxide in toluene: the preferred reagent for applications requiring dry TBHP. J Org Chem. 1983;48(20):3607-3608.
Hutchins et al., Selective formation of covalent protein heterodimers with an unnatural amino acid. Chem Biol. Mar. 25, 2011;18(3):299-303. doi: 10.1016/j.chembiol.2011.01.006.
Jeffrey et al., Expanded Utility of the β-Glucuronide Linker: ADCs That Deliver Phenolic Cytotoxic Agents. ACS Med Chem Lett. Jun. 14, 2010;1(6):277-80. doi: 10.1021/ml100039h. eCollection Sep. 9, 2010.
Jeffrey et al., Design, Synthesis, and in Vitro Evaluation of Dipeptide-Based Antibody Minor Groove Binder Conjugates. J Med Chem. Mar. 10, 2005;48(5):1344-58. doi: 10.1021/jm040137q.
Kato et al., Fluorescence study on the nyctinasty of *Phyllanthus urinaria* L. using novel-fluorescence-labeled probe compounds. Tetrahedron. 2006;62:7307-18.
Kern et al., Discovery of Pyrophosphate Diesters as Tunable, Soluble, and Bioorthogonal Linkers for Site-Specific Antibody-Drug Conjugates. J Am Chem Soc. Feb. 3, 2016;138(4):1430-45. doi: 10.1021/jacs.5b12547. Epub Jan. 25, 2016.
Kolakowski et al., The Methylene Alkoxy Carbamate Self-Immolative Unit: Utilization for the Targeted Delivery of Alcohol-Containing Payloads with Antibody-Drug Conjugates. Angew Chem Int Ed Engl. Jul. 4, 2016;55(28):7948-51. doi: 10.1002/anie.201601506. Epub May 20, 2016.
Kovtun et al., Antibody-drug conjugates designed to eradicate tumors with homogeneous and heterogeneous expression of the target antigen. Cancer Res. Mar. 15, 2006;66(6):3214-21.
Kovtun et al., Cell killing by antibody-drug conjugates. Cancer Lett. Oct. 8, 2007;255(2):232-40. Epub Jun. 5, 2007.
Kraus et al., An Annelation Route to Quinones. Tetrahedron Lett. 1978;19(26):2263-66.
Lambert et al., Antibody-Drug Conjugates for Cancer Treatment. Annu Rev Med. Jan. 29, 2018;69:191-207. doi: 10.1146/annurev-med-061516-121357.
Lau et al., Lactone Stabilization Is Not a Necessary Feature for Antibody Conjugates of Camptothecins. Mol Pharm. Sep. 4, 2018;15(9):4063-4072. doi: 10.1021/acs.molpharmaceut.8b00477. Epub Aug. 14, 2018.
Le Pecq et al., A new fluorometric method for RNA and DNA determination. Anal Biochem. Oct. 1966;17(1):100-7.
Li et al. Intracellular Released Payload Influences Potency and Bystander-Killing Effects of Antibody-Drug Conjugates in Preclinical Models. Cancer Res. May 1, 2016;76(9):2710-9. doi: 10.1158/0008-5472.CAN-15-1795. Epub Feb. 26, 2016.
Li et al., An Enzymatic Deconjugation Method for the Analysis of Small Molecule Active Drugs on Antibody-Drug Conjugates. Mabs. May-Jun. 2016;8(4):698-705. doi: 10.1080/19420862.2016.1151590. Epub Feb. 18, 2016.
Lim et al., A method for the preparation of differentiated trans-1,2-diol derivatives with enantio- and diastereocontrol. J Am Chem Soc. Apr. 29, 2009;131(16):5763-5.
Lin et al., Mechanistic Investigation of the Staudinger Ligation. J Am Chem Soc. Mar. 2, 2005;127(8):2686-95. doi: 10.1021/ja044461m.
Loganzo et al. Tumor Cells Chronically Treated with a Trastuzumab-Maytansinoid Antibody-Drug Conjugate Develop Varied Resistance Mechanisms but Respond to Alternate Treatments. Mol Cancer Ther. Apr. 2015;14(4):952-63. doi: 10.1158/1535-7163.MCT-14-0862. Epub Feb. 2, 2015.
Magauer et al., Component-based syntheses of trioxacarcin A, DC-45-A1 and structural analogues. Nat Chem. Oct. 2013;5(10):886-93. https://doi.org/10.1038/nchem.1746.
Magno, Poster Spotlight I: Fully Synthetic Trioxacarcin Analogs for Use in Antibody-Drug Conjugates. Antibody Drug Conjugates 2017 Pegs Summit. May 2017. pp. 1-11. https://www.pegsummit.com/Antibody-Drug-Conjugates/17.
Maiese et al., LL-D49194 antibiotics, a novel family of antitumor agents: taxonomy, fermentation and biological properties. J Antibiot (Tokyo). Mar. 1990;43(3):253-8.
Marshall et al., Synthesis of Protected Carbohydrate Derivatives Through Homologation of Threose and Erythrose Derivatives with Chiral .gamma.-Alkoxy Allylic Stannanes. J Org Chem. 1994;59(12):3413-3420.
Maskey et al., Anti-cancer and antibacterial trioxacarcins with high anti-malaria activity from a marine Streptomycete and their absolute stereochemistry. J Antibiot (Tokyo). Dec. 2004;57(12):771-9.
Maskey et al.. Gutingimycin: a highly complex metabolite from a marine streptomycete. Angew Chem Int Ed Engl. Feb. 27, 2004;43(10):1281-3. https://doi.org/10.1002/anie.200352312.
Masters et al., Clinical Toxicity of Antibody Drug Conjugates: A Meta-Analysis of Payloads. Invest New Drugs. Feb. 2018;36(1):121-135. doi: 10.1007/s10637-017-0520-6. Epub Oct. 13, 2017.
Mattes et al., Mechanism of DNA strand breakage by piperidine at sites of N7-alkylguanines. Biochim Biophys Acta. Oct. 16, 1986;868(1):71-6.
Maxam et al., A new method for sequencing DNA. Proc Natl Acad Sci U S A. Feb. 1977;74(2):560-4.
Mccombs et al., Antibody Drug Conjugates: Design and Selection of Linker, Payload and Conjugation Chemistry. AAPS J. Mar. 2015;17(2):339-51. doi: 10.1208/s12248-014-9710-8. Epub Jan. 22, 2015.
Moon et al., Antibody Conjugates of 7-Ethyl-10-Hydroxycamptothecin (SN-38) for Targeted Cancer Chemotherapy. J Med Chem. Nov. 13, 2008;51(21):6916-26. doi: 10.1021/jm800719t. Epub Oct. 22, 2008.
Müller et al., Schiff Bases Derived from P-Aminobenzyl Alcohol as Trigger Groups for PH-Dependent Prodrug Activation. Tetrahedron Lett. 2010, 51 (33), 4371-74. https://doi.org/10.1016/j.tetlet.2010.06.055.
Nicolaou et al., Total Synthesis of Trioxacarcin DC-45-A2. Angew Chem. 2015; 127:3117-3121.
Nicolaou et al., Total Synthesis of Trioxacarcins DC-45-A1, A, D, C, and C7"-epi-C and Full Structural Assignment of Trioxacarcin C. J Am Chem Soc. Mar. 9, 2016;138(9):3118-24. doi: 10.1021/jacs.5b12687. Epub Feb. 24, 2016.
Nicolaou et al., Streamlined Total Synthesis of Trioxacarcins and Its Application to the Design, Synthesis, and Biological Evaluation of Analogues Thereof. Discovery of Simpler Designed and Potent Trioxacarcin Analogues. J Am Chem Soc. Nov. 1, 2017;139(43):15467-15478. doi: 10.1021/jacs.7b08820. Epub Oct. 20, 2017.
No Author Listed, Caplus accession No. 2019:286932. Last accessed: Aug. 18, 2021. 55 pages.
No Author Listed, Reaxys Query for WO2019032961A1—Trioxacarcin-Antibody Conjugates and Uses Thereof. Elsevier Life Sciences IP Limited. Last accessed: Aug. 18, 2021. 5 pages.
Oppolzer et al., Enantioselective Addition of (Z)- and (E)-Alkenylzinc Bromides to Aldehydes: Asymmetric Synthesis of Sec-Allylalcohols. Tetrahedron Lett. 1991;32:5777-80.

(56) References Cited

OTHER PUBLICATIONS

Pangborn et al., Safe and Convenient Procedure for Solvent Purification. Organometallics. 1996;15(5):1518-1520.
Pfoh et al., Crystal structure of trioxacarcin A covalently bound to DNA. Nucleic Acids Res. Jun. 2008;36(10):3508-14. Epub May 3, 2008.
Pröpper et al., Crystalline guanine adducts of natural and synthetic trioxacarcins suggest a common biological mechanism and reveal a basis for the instability of trioxacarcin A. Bioorg Med Chem Lett. Sep. 15, 2014;24(18):4410-3. doi: 10.1016/j.bmcl.2014.08.016.
Sato et al., A Novel Synthetic Method for Tetronic Acids from 1,3-Dioxin-4-Ones via Intra- or Intermolecular Ketene Trapping. Chem Pharm Bull (Tokyo). 1990; 38 (1): 94-98. https://doi.org/10.1248/cpb.38.94.
Saxon et al., A "Traceless" Staudinger Ligation for the Chemoselective Synthesis of Amide Bonds. Org Lett. Jul. 13, 2000;2(14):2141-3. doi: 10.1021/01006054v.
Schinzer et al., Syntheses of (-)-Epothilone B. J Chem—Euro J. 1999;5:2492-500.
Senter et al., The Discovery and Development of Brentuximab Vedotin for Use in Relapsed Hodgkin Lymphoma and Systemic Anaplastic Large Cell Lymphoma. Nat Biotechnol. Jul. 10, 2012;30(7):631-7. doi: 10.1038/nbt.2289.
Sharpless et al., Metal-Catalyzed, Highly Selective Oxygenations of Olefins and Acetylenes with tert-Butyl Hydroperoxide. Practical Considerations and Mechanisms. Aldrichimica Acta. 1979;12:63-74.
Shen et al., Conjugation Site Modulates the in Vivo Stability and Therapeutic Activity of Antibody-Drug Conjugates. Nat Biotechnol. Jan. 22, 2012;30(2):184-9. doi: 10.1038/nbt.2108.
Shen et al., Production of a Trioxacarcin Analog by Introducing a C-3 Dehydratase into Deoxysugar Biosynthesis. Acta Biochim Biophys Sin (Shanghai). May 23, 2019;51(5):539-541. doi: 10.1093/abbs/gmz024.
Smaltz et al., Diastereoselective additions of allylmetal reagents to free and protected syn-α,β-dihydroxyketones enable efficient synthetic routes to methyl trioxacarcinoside A. Org Lett. Apr. 6, 2012;14(7):1812-5. Epub Mar. 9, 2012.
Still et al., Rapid chromatographic technique for preparative separations with moderate resolution. J Org Chem. 1978;43(14):2923-2925.
Strebhardt et al., Paul Ehrlich's Magic Bullet Concept: 100 Years of Progress. Nat Rev Cancer. Jun. 2008;8(6):473-80. doi: 10.1038/nrc2394. Epub May 12, 2008.
Su et al., Antibody-Drug Conjugates Derived from Cytotoxic Seco-CBI-Dimer Payloads Are Highly Efficacious in Xenograft Models and Form Protein Adducts In Vivo. Bioconjug Chem. May 15, 2019;30(5):1356-1370. doi: 10.1021/acs.bioconjchem.9b00133. Epub Apr. 22, 2019.
Suami et al., Synthesis of Methyl α-Trioxacarcinoside B. Chem Lett. 1982:1245-48.
Suami et al., Synthetic Studies on Methyl α-Trioxacarcinoside B. Bull Chem Soc Jpn. 1983;56:1431-34.
Švenda et al., A multiply convergent platform for the synthesis of trioxacarcins. Proc Natl Acad Sci U S A. Apr. 26, 2011;108(17):6709-14. Epub Jan. 18, 2011.
Švenda et al., Anti-selective epoxidation of methyl alpha-methylene-beta-tert-butyldimethylsilyloxycarboxylate esters. Evidence for stereospecific oxygen atom transfer in a nucleophilic epoxidation process. Org Lett. Jun. 4, 2009;11(11):2437-40.
Švenda et al., A Multiply Convergent Platform for the Synthesis of Trioxacarcins. Proc Natl Acad Sci U. S. A. Apr. 26, 2011;108(17):6709-14. doi: 10.1073/pnas.1015257108. Epub Jan. 18, 2011.
Tamaoki et al., Trioxacarcins, novel antitumor antibiotics. II. Isolation, physico-chemical properties and mode of action. J Antibiot (Tokyo). Dec. 1981;34(12):1525-30. https://doi.org/10.7164/antibiotics.34.1525.
Teicher et al., Antibody conjugate therapeutics: challenges and potential. Clin Cancer Res. Oct. 15, 2011;17(20):6389-97. doi: 10.1158/1078-0432.CCR-11-1417.
Tolcher, Antibody Drug Conjugates: Lessons from 20 Years of Clinical Experience. Ann Oncol. Dec. 2016;27(12):2168-2172. doi: 10.1093/annonc/mdw424. Epub Oct. 11, 2016.
Tomita et al., Trioxacarcins, Novel Antitumor Antibiotics. I. Producing Organism, Fermentation and Biological Activities. J Antibiotics. 1981;34(12):1520-24. https://doi.org/10.7164/antibiotics.34.1519.
Tsuchikama et al., Antibody-Drug Conjugates: Recent Advances in Conjugation and Linker Chemistries. Protein Cell. Jan. 2018;9(1):33-46. doi: 10.1007/s13238-016-0323-0. Epub Oct. 14, 2016.
Underberg et al., Bio-analysis and preliminary pharmacokinetics of the experimental antitumour drug LL-D49194 alpha 1. J Pharm Biomed Anal. 1989;7(12):1791-7. doi: 10.1016/0731-7085(89)80195-5.
Vezina et al., Antibody-Drug Conjugates as Cancer Therapeutics: Past, Present, and Future. J Clin Pharmacol. Oct. 2017;57 Suppl 10:S11-S25. doi: 10.1002/jcph.981.
Wahl et al., Improved radioimaging and tumor localization with monoclonal F(ab')2. J Nucl Med. Apr. 1983;24(4):316-25.
Wilen et al., Strategies in Optical Resolution. Tetrahedron. 1977;33:2725-36.
Wilen, Tables of Resolving Agents and Optical Resolutions. University of Notre Dame Press. Notre Dame, Indiana. 1972:268-98.
Williams et al., A New General Method of Preparation of N-Methoxy-N-Methylamides. Applications in Direct Conversion of an Ester to a Ketone. Tetrahedron. 1995;36:5461-64.
Yamashita et al., Total Syntheses of Nobilamides B and D: Application of Traceless Staudinger Ligation. Tetrahedron. 2014; 70 (42): 7746-52. https://doi.org/10.1016/j.tet.2014.05.091.
Yang et al., The SARP Family Regulator Txn9 and Two-Component Response Regulator Txn11 Are Key Activators for Trioxacarcin Biosynthesis in Streptomyces Bottropensis. Curr Microbiol. Oct. 2015;71(4):458-64. doi: 10.1007/s00284-015-0868-9. Epub Jul. 16, 2015.
Yu et al., Improved procedure for the oxidative cleavage of olefins by OsO4—NaIO4. Org Lett. Sep. 16, 2004;6(19):3217-9.
Zhang et al., Immolation of p-Aminobenzyl Ether Linker and Payload Potency and Stability Determine the Cell-Killing Activity of Antibody-Drug Conjugates with Phenol-Containing Payloads. Bioconjug Chem. Feb. 21, 2018;29(2):267-274. doi: 10.1021/acs.bioconjchem.7b00576. Epub Feb. 7, 2018.
Zhang et al., Biosynthesis of Trioxacarcin Revealing a Different Starter Unit and Complex Tailoring Steps for Type II Polyketide Synthase. Chem Sci. Jun. 1, 2015;6(6):3440-3447. doi: 10.1039/c5sc00116a. Epub Apr. 7, 2015.
International Preliminary Report on Patentability for Application No. PCT/US2022/050726, mailed Jun. 6, 2024.

* cited by examiner

Half-life: 0.23 h (95% CI 0.17, 0.31)
$R^2 = 0.9685$

STABILIZED TRIOXACARCIN ANTIBODY DRUG CONJUGATES AND USES THEREOF

RELATED APPLICATIONS

This application is a national stage filing under 35 U.S.C. § 371 of International PCT Application PCT/US2021/036718, filed Jun. 10, 2021, which claims priority under 35 U.S.C. § 119(e) to U.S. Provisional Applications, U.S. Ser. No. 63/038,022, filed Jun. 11, 2020; U.S. Ser. No. 63/141,808, filed Jan. 26, 2021; and U.S. Ser. No. 63/201,333, filed Apr. 23, 2021, each of which is incorporated herein by reference.

GOVERNMENT SUPPORT

This invention was made with government support under CA047148 awarded by the National Institutes of Health. The government has certain rights in the invention.

BACKGROUND

Antibody-drug conjugates (ADCs) are a targeted therapy consisting of three components: a target-specific antibody (e.g., a monoclonal antibody, mAb) or antibody fragment (e.g., a single-chain variable fragment (scFv)); a payload, often a cytotoxic drug; and a linker connecting the drug to the antibody. Upon administration, the antibody binds to a target cell and the drug exerts its therapeutic effect, for example, by optional cleavage from the ADC and/or by internalization in the cell or proximity to the outside of the cell. See, e.g., Ducry et al., *Bioconjugate Chemistry* (2010) 21: 5-13; Kovtun et al., *Cancer Research* (2006) 66: 3214-21; and Kovtun et al., *Cancer Letters* (2007) 255 (2): 232-40. Targeted therapies are envisioned to provide many advantages including, but not limited to, decreased side effects and a wider therapeutic window as compared to untargeted therapies.

The type of linker used is an important consideration in the design of the ADC. For example, ADCs with cleavable linkers are thought to have a less favorable therapeutic window, and are best designed for targets, such as tumor cell surface antigens that are internalized efficiently. The linker should also be designed in a manner that ensures stability during circulation in blood but allows for the rapid release of the drug, preferably inside the target cell. Several types of enzymatically degradable and non-degradable linkers for ADCs have also been explored, such as cleavable acid- and peptidase-labile linkers and non-cleavable linkers such as thioethers. See, e.g., Ducry et al., *Bioconjugate Chemistry* (2010) 21: 5-13.

Natural products that bind and often covalently modify duplex DNA figure prominently in chemotherapy for human cancers. The trioxacarcins are a class of DNA-modifying natural products with antiproliferative effects. The trioxacarcins were first described in 1981 by Tomita and coworkers. See, e.g., Tomita et al., *J. Antibiotics,* 34(12):1520-1524, 1981; Tamaoki et al., *J. Antibiotics* 34(12):1525-1530, 1981; Fujimoto et al., *J. Antibiotics* 36(9):1216-1221, 1983. Trioxacarcin A, B, and C were isolated by Tomita and coworkers from the culture broth of *Streptomyces bottropensis* DO-45 and shown to possess anti-tumor activity in murine models as well as gram-positive antibiotic activity. Subsequent work led to the discovery of other members of this family. Trioxacarcin A is a powerful anticancer agent with subnanmolar $IC_{70}$ values against lung (LXFL 529L, H-460), mammary (MCF-7), and CNS (SF-268) cancer cell lines. The trioxacarcins have also been shown to have antimicrobial activity, e.g., anti-bacterial and anti-malarial activity. See, e.g., Maskey et al., *J. Antibiotics* (2004) 57:771-779. An X-ray crystal structure of trioxacarcin A bound to N-7 of a guanidylate residue in a duplex DNA oligonucleotide substrate has provided compelling evidence for a proposed pathyway of DNA modification that proceeds by duplex intercalation and alkylation. See, e.g., Pfoh et al., *Nucleic Acids Research* (2008) 36:3508-3514. All trioxacarcins appear to be derivatives of the aglycone, which is itself a bacterial isolate referred to in the patent literature as DC-45-$A_2$. U.S. Pat. No. 4,459,291, issued Jul. 10, 1984, describes the preparation of DC-45-$A_2$ by fermentation. DC-45-$A_2$ is the algycone of trioxacarcins A, B, and C and is prepared by the acid hydrolysis of the fermentation products trioxacarcins A and C or the direct isolation from the fermentation broth of *Streptomyces bottropensis.*

Prior to this work, the inventors developed a fully synthetic method to access known trioxacarcins and novel trioxacarcin analogs. See, e.g., PCT Application Publication No. WO 2011/119549 and PCT Application Publication No. WO 2014/082065, both of which are incorporated herein by reference. A wide variety of fully synthetic natural and nonnatural trioxacarcin compounds have been prepared by a process that is amenable to scaling. The inventors also created ADCs of novel trioxacarcin-antibody drug conjugates. See, e.g., PCT Application Publication No. WO 2019/032961, which is incorporated herein by reference. However, it has since been discovered that these ADCs are unstable and decompose under physiological conditions. Therefore, new strategies for creating stable trioxacarin ADCs are needed.

SUMMARY

The present disclosure provides antibody drug conjugates and antibody drug conjugate precursor compounds. In particular, the present disclosure provides access to novel trioxacarcin-antibody drug conjugates and trioxacarcin-antibody drug conjugate precursor compounds with advantageous properties (e.g., stability, release kinetics). The trioxacarcins are highly toxic to a variety of cell types. Linking a trioxacarcin to an antibody preserves the trioxacarcin's potency against a particular cell type while increasing specificity for the target cell, and optionally increasing endocytosis of the trioxacarcin. These effects enable lowering the overall amount of trioxacarcin to be delivered, thereby reducing the associated toxicity and any undesired side effects.

In one aspect, provided is a compound of Formula (I):

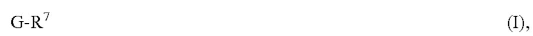

$$G\text{-}R^7 \quad (I),$$

or a pharmaceutically acceptable salt, solvate, hydrate, polymorph, co-crystal, tautomer, stereoisomer, isotopically labeled derivative, or prodrug thereof; wherein:

G is a molecular payload;

$R^7$ is -L-A-B;

L is of the formula:

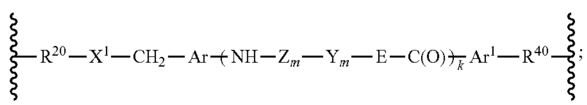

;

$R^{20}$ is substituted or unsubstituted alkylene; or substituted or unsubstituted heteroalkylene;

$X^1$ is

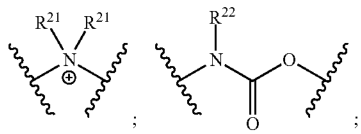

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

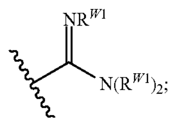

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene;

A is a group of the formula:

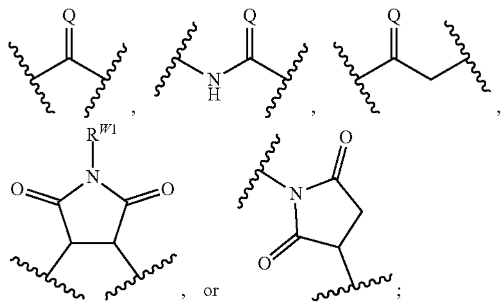

Q is —S— or —O—;

$R^{W1}$ is independently hydrogen, substituted or unsubstituted alkyl; or a nitrogen protecting group; and B is an antibody or an antibody fragment.

In certain embodiments, G is

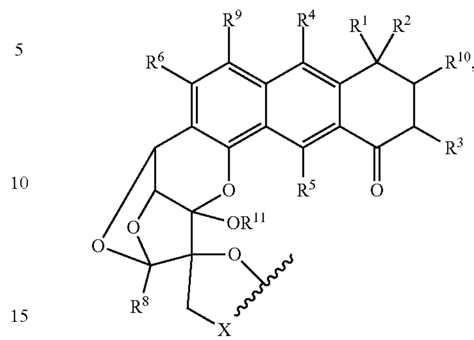

and the compound of Formula (I) is of Formula (II):

(II)

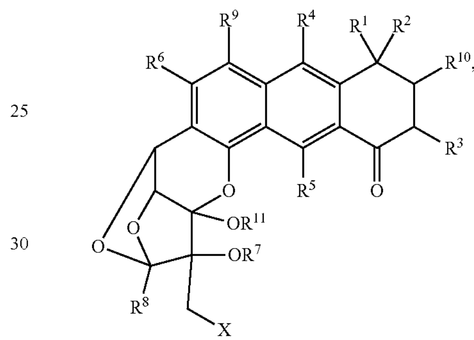

or a pharmaceutically acceptable salt, solvate, hydrate, polymorph, co-crystal, tautomer, stereoisomer, isotopically labeled derivative, or prodrug thereof;

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{A1}$; $—C(═O)R^{A2}$; $CO_2R^{A2}$; —CN; —SCN; $—SR^{A1}$; $—SOR^{A1}$; $SO_2R^{A1}$; $—NO_2$; $—N_3$; $—N(R^{A2})_2$; $—NR^{A2}C(═O)R^{A2}$; $—NR^{A2}C(═O)N(R^{A2})_2$; $—OC(═O)OR^{A1}$; $—OC(═O)R^{A2}$; $—OC(═O)N(R^{A2})_2$; $—NR^{A}C(═O)OR^{A1}$; or $—C(R^{A2})_3$; wherein each occurrence of $R^{A1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{A2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino, or two $R^{A2}$ groups are optionally joined to form a heterocyclyl or heteroaryl ring;

$R^2$ is hydrogen; or $R^1$ and $R^2$ are joined to form ═O; $═N(R^{A2})$; or ═S;

$R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{C1}$; $—C(═O)R^{C2}$; $—CO_2R^{C1}$; —CN; —SCN; $—SR^{C1}$; $—SOR^{C1}$; $—SO_2R^{C2}$; $—NO_2$; $—N_3$; ═O; $═N(R^{C2})$; ═S; $—N(R^{C2})_2$; $—NHC(═O)R^{C2}$; $—NR^{C2}C(═O)N(R^{C2})_2$; $—OC(═O)OR^{C1}$; $—OC(═O)R^{C2}$; $—OC(═O)N(R^{C2})_2$; $—NR^{C2}C(═O)OR^{C1}$; or $—C(R^{C2})_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{C2}$ groups are optionally joined to form a heterocyclyl or heteroaryl ring;

$R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{D1}$; $—C(═O)R^{D2}$; $—CO_2R^{D2}$; —CN; —SCN; $—SR^{D1}$; $—SOR^{D1}$; $SO_2R^{D2}$; $—NO_2$; $—N_3$; $—N(R^{D2})_2$; $—NR^{D2}C(═O)R^{D2}$; $—NR^{D2}C(═O)N(R^{D2})_2$; $—OC(═O)OR^{D1}$; $—OC(═O)R^{D2}$; $—OC(═O)N(R^{D2})_2$; $—NR^{D2}C(═O)OR^{D1}$; or $—C(R^{D2})_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{D2}$ groups are optionally joined to form a heterocyclyl or heteroaryl ring;

$R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{E1}$; $—C(═O)R^{E2}$; $—CO_2R^{E1}$; —CN; —SCN; $—SR^{E1}$; $—SOR^{E1}$; $—SO_2R^{E2}$; $—NO_2$; $—N_3$; $—N(R^{E2})_2$; $—NR^{E2}C(═O)R^{E2}$; $—NR^{E2}C(═O)N(R^{E2})_2$; $—OC(═O)OR^{E1}$; $—OC(═O)R^{E2}$; $—OC(═O)N(R^{E2})_2$; $—NR^{E2}C(═O)OR^{E1}$; or $—C(R^{E2})_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{F1}$; $—C(═O)R^{F2}$; $—CO_2R^{F1}$; —CN; —SCN; $—SR^{F1}$; $—SOR^{F1}$; $SO_2R^{F2}$; $—NO_2$; $—N_3$; $—N(R^{F2})_2$; $—NR^{F2}C(═O)R^{F2}$; $—NR^{F2}C(═O)N(R^{F2})_2$; $—OC(═O)OR^{F1}$; $—OC(═O)R^{F2}$; $—OC(═O)N(R^{F2})_2$; $—NR^{F2}C(═O)OR^{F1}$; or $—C(R^{F2})_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{F2}$ groups are optionally joined to form a heterocyclyl or heteroaryl ring;

$R^7$ is -L-A-B;

X is a halogen;

$R^8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{I1}$; $—C(═O)R^{I2}$; $—CO_2R^{I1}$; —CN; —SCN; $—SR^{I1}$; $—SOR^{I1}$; $—SO_2R^{I2}$; $—NO_2$; $—N_3$; $—N(R^{I2})_2$; $—NR^{I2}C(═O)R^{I2}$; $—NR^{I2}C(═O)N(R^{I2})_2$; $—OC(═O)OR^{I1}$; $—OC(═O)R^{I2}$; $—OC(═O)N(R^{I2})_2$; $—NR^{I2}C(═O)OR^{I1}$; or $—C(R^{I2})_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{I2}$ groups are optionally joined to form a heterocyclyl or heteroaryl ring;

$R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{G1}$; $—C(=O)R^{G2}$; $—CO_2R^{G1}$; —CN; —SCN; $—SR^{G1}$; $—SOR^{G1}$; $—SO_2R^{G2}$; $—NO_2$; $—N_3$; $—N(R^{G})_2$; $—NR^{G2}C(=O)R^{G2}$; $—NR^{G2}C(=O)N(R^{G2})_2$; $—OC(=O)OR^{G1}$; $—OC(=O)R^{G2}$; $—OC(=O)N(R^{G2})_2$; $—NR^{G2}C(=O)OR^{G1}$; or $—C(R^{G2})_3$; wherein each occurrence of $R^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{G2}$ groups are optionally joined to form a heterocyclyl or heteroaryl ring;

$R^{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{B1}$; $—C(=O)R^{B2}$; $—CO_2R^{B2}$; —CN; —SCN; $—SR^{B1}$; $—SOR^{B1}$; $SO_2R^{B2}$; $—NO_2$; $—N_3$; =O; $=N(R^{B2})$; =S; $—N(R^{B2})_2$; $—NR^{B2}C(=O)R^{B2}$; $—NR^{B2}C(=O)N(R^{B2})_2$; $—OC(=O)OR^{B1}$; $—OC(=O)R^{B2}$; $—OC(=O)N(R^{B2})_2$; $—NR^{B2}C(=O)OR^{B1}$; or $—C(R^{B2})_3$; wherein each occurrence of $R^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{B2}$ groups are optionally joined to form a heterocyclyl or heteroaryl ring;

$R^{11}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or $—C(=O)R^{H1}$; wherein $R^{H1}$ is hydrogen, substituted or unsubstituted alkyl; $—OR^{H9}$; $—OC(=O)R^{H9}$; $—N(R^{H9})_2$; or $—NHC(=O)R^{H9}$; wherein each occurrence of $R^{H9}$ is independently hydrogen; substituted or unsubstituted alkyl; an oxygen protecting group when attached to an oxygen atom; a nitrogen protecting group when attached to a nitrogen atom; or two $R^{H9}$ groups are joined to form a substituted or unsubstituted heterocyclic or substituted or unsubstituted heteroaryl ring;

or $R^1$ and $R^{10}$ are optionally taken together with the intervening carbon atoms to form an optionally substituted cyclic moiety;

or $R^{10}$ and $R^3$ are optionally taken together with the intervening carbon atoms to form an optionally substituted cyclic moiety;

or $R^1$ and $R^4$ are optionally taken together with the intervening carbon atoms to form an optionally substituted cyclic moiety;

or $R^4$ and $R^9$ are optionally taken together with the intervening carbon atoms to form an optionally substituted cyclic moiety;

or $R^6$ and $R^9$ are optionally taken together with the intervening carbon atoms to form an optionally substituted cyclic moiety;

L is of the formula:

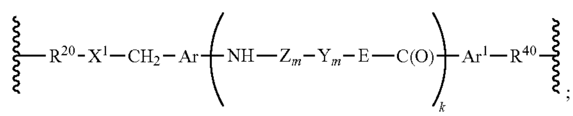

$R^{20}$ is substituted or unsubstituted alkylene; or substituted or unsubstituted heteroalkylene;

$X^1$ is

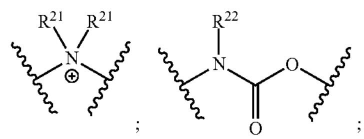

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

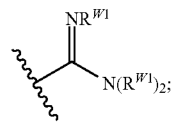

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene;

A is a group of the formula:

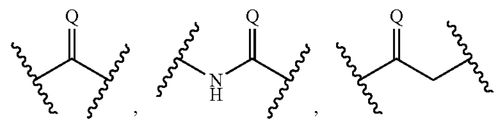

-continued

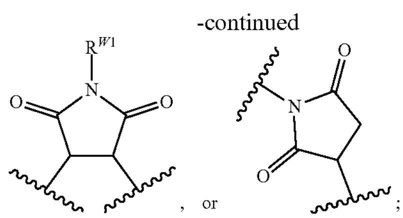

, or ;

Q is —S— or —O—;

$R^{W1}$ is independently hydrogen; substituted or unsubstituted alkyl; or a nitrogen protecting group; and B is an antibody or an antibody fragment.

In another aspect, provided is a compound of Formula (III):

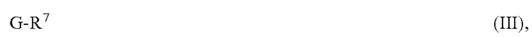

$G\text{-}R^7$ (III), or a pharmaceutically acceptable salt, solvate, hydrate, polymorph, co-crystal, tautomer, stereoisomer, isotopically labeled derivative, or prodrug thereof;

wherein:

G is a molecular payload;

$R^7$ is -L-T;

L is a bond, or of the formula:

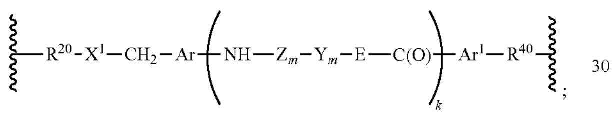

$R^{20}$ is substituted or unsubstituted alkylene; or substituted or unsubstituted heteroalkylene;

$X^1$ is

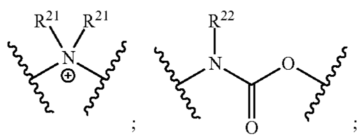

; ;

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

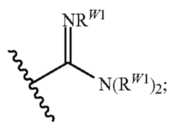

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene; and combinations thereof;

T is hydrogen, —N═C═S,

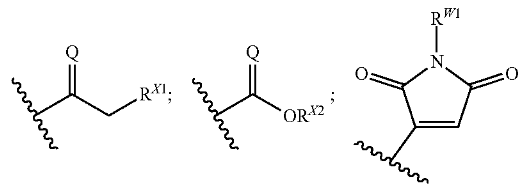

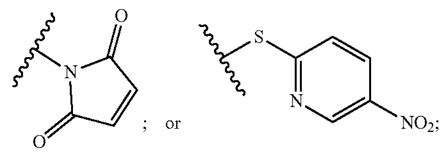

; or

Q is —S— or —O—;

$R^{X1}$ is a leaving group;

$R^{X2}$ is hydrogen; substituted or unsubstituted alkyl; substituted or unsubstituted heterocyclyl; substituted or unsubstituted aryl; substituted or unsubstituted heteroaryl; or an oxygen protecting group; and $R^{W1}$ is independently hydrogen; substituted or unsubstituted alkyl; or a nitrogen protecting group.

In certain embodiments, G is

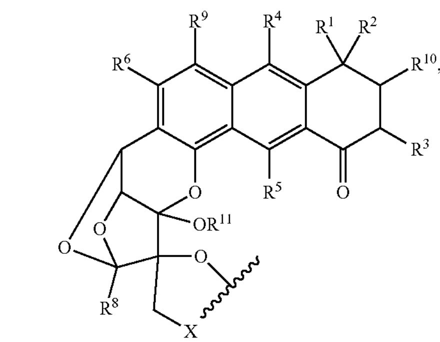

and the compound of Formula (III) is of Formula (IV):

(IV)

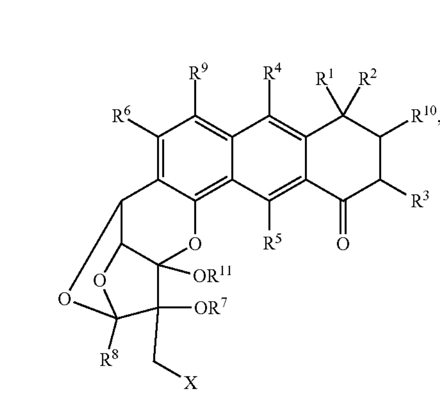

or a pharmaceutically acceptable salt thereof;

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{A1}$; $-C(=O)R^{A2}$; $-CO_2R^{A2}$; —CN; —SCN; $-SR^{A1}$; $-SOR^{A1}$; $SO_2R^{A}$; $-NO_2$; $-N_3$; =O; $=N(R^{A2})$; =S; $-N(R^{A2})_2$; $-NR^{A2}C(=O)R^{A2}$; $-NR^{A2}C(=O)N(R^{A2})_2$; $-OC(=O)OR^{A1}$; $-OC(=O)R^{A2}$; $-OC(=O)N(R^{A2})_2$; $-NR^{A}C(=O)OR^{A1}$; or $-C(R^{A2})_3$; wherein each occurrence of $R^{A1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{A2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino, or two $R^{A2}$ groups are optionally joined to form a heterocyclyl or heteroaryl ring;

$R^2$ is hydrogen; or $R^1$ and $R^2$ are joined to form =O; $=N(R^{A2})$; or =S;

$R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{C1}$; $-C(=O)R^{C2}$; $-CO_2R^{C1}$; —CN; —SCN; $-SR^{C1}$; $-SOR^{C1}$; $-SO_2R^{C2}$; $-NO_2$; $-N_3$; =O; $=N(R^{C2})$; =S; $-N(R^{C2})_2$; $-NHC(=O)R^{C2}$; $-NR^{C2}C(=O)N(R^{C2})_2$; $-OC(=O)OR^{C1}$; $-OC(=O)R^{C2}$; $-OC(=O)N(R^{C2})_2$; $-NR^{C2}C(=O)OR^{C1}$; or $-C(R^{C2})_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{C2}$ groups are optionally joined to form a heterocyclyl or heteroaryl ring;

$R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{D1}$; $-C(=O)R^{D2}$; $-CO_2R^{D2}$; —CN; —SCN; $-SR^{D1}$; $-SOR^{D1}$; $SO_2R^{D2}$; $-NO_2$; $-N_3$; $-N(R^{D2})_2$; $-NR^{D2}C(=O)R^{D2}$; $-NR^{D2}C(=O)N(R^{D2})_2$; $-OC(=O)OR^{D1}$; $-OC(=O)R^{D2}$; $-OC(=O)N(R^{D2})_2$; $-NR^{D2}C(=O)OR^{D1}$; or $-C(R^{D2})_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{D2}$ groups are optionally joined to form a heterocyclyl or heteroaryl ring;

$R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{E1}$; $-C(=O)R^{E2}$; $-CO_2R^{E1}$; —CN; —SCN; $-SR^{E1}$; $-SOR^{E1}$; $-SO_2R^{E2}$; $-NO_2$; $-N_3$; $-N(R^{E2})_2$; $-NR^{E2}C(=O)R^{E2}$; $-NR^{E2}C(=O)N(R^{E2})_2$; $-OC(=O)OR^{E1}$; $-OC(=O)R^{E2}$; $-OC(=O)N(R^{E2})_2$; $-NR^{E2}C(=O)OR^{E1}$; or $-C(R^{E2})_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{F1}$; $-C(=O)R^{F2}$; $-CO_2R^{F1}$; —CN; —SCN; $-SR^{F1}$; $-SOR^{F1}$; $SO_2R^{F2}$; $-NO_2$; $-N_3$; $-N(R^{F2})_2$; $-NR^{F2}C(=O)R^{F2}$; $-NR^{F2}C(=O)N(R^{F2})_2$; $-OC(=O)OR^{F1}$; $-OC(=O)R^{F2}$; $-OC(=O)N(R^{F2})_2$; $-NR^{F2}C(=O)OR^{F1}$; or $-C(R^{F2})_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{F2}$ groups are optionally joined to form a heterocyclyl or heteroaryl ring;

$R^7$ is -L-T;

X is a halogen;

$R^8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{I1}$; $—C(=O)R^{I2}$; $—CO_2R^{I1}$; —CN; —SCN; $—SR^{I1}$; $—SOR^{I1}$; $—SO_2R^{I2}$; $—NO_2$; $—N_3$; $—N(R^{I2})_2$; $—NR^{I2}C(=O)R^{I2}$; $—NR^{I2}C(=O)N(R^{I2})_2$; $—OC(=O)OR^{I1}$; $—OC(=O)R^{I2}$; $—OC(=O)N(R^{I2})_2$; $—NR^{I2}C(=O)OR^{I1}$; or $—C(R^{I2})_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{I2}$ groups are optionally joined to form a heterocyclyl or heteroaryl ring;

$R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{G1}$; $—C(=O)R^{G2}$; $—CO_2R^{G1}$; —CN; —SCN; $—SR^{G1}$; $—SOR^{G1}$; $—SO_2R^{G2}$; $—NO_2$; $—N_3$; $—N(R^{G})_2$; $—NR^{G2}C(=O)R^{G2}$; $—NR^{G2}C(=O)N(R^{G2})_2$; $—OC(=O)OR^{G1}$; $—OC(=O)R^{G2}$; $—OC(=O)N(R^{G2})_2$; $—NR^{G2}C(=O)OR^{G1}$; or $—C(R^{G2})_3$; wherein each occurrence of $R^G1$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{G2}$ groups are optionally joined to form a heterocyclyl or heteroaryl ring;

$R^{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{B1}$; $—C(=O)R^{B2}$; $—CO_2R^{B2}$; —CN; —SCN; $—SR^{B1}$; $—SOR^{B1}$; $SO_2R^{B2}$; $—NO_2$; $—N_3$; =O; $=N(R^{B2})$; =S; $—N(R^{B2})_2$; $—NR^{B2}C(=O)R^{B2}$; $—NR^{B2}C(=O)N(R^{B2})_2$; $—OC(=O)OR^{B1}$; $—OC(=O)R^{B2}$; $—OC(=O)N(R^{B2})_2$; $—NR^{B2}C(=O)OR^{B1}$; or $—C(R^{B2})_3$; wherein each occurrence of $R^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{B2}$ groups are optionally joined to form a heterocyclyl or heteroaryl ring;

$R^{11}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; $—C(=O)R^{H1}$; wherein $R^{H1}$ is hydrogen, substituted or unsubstituted alkyl; $—OR^{H9}$; $—OC(=O)R^{H9}$; $—N(R^{H9})_2$; $—NHC(=O)R^{H9}$; wherein each occurrence of $R^{H9}$ is independently hydrogen; substituted or unsubstituted alkyl; an oxygen protecting group when attached to an oxygen atom; a nitrogen protecting group when attached to a nitrogen atom; or two $R^{H9}$ groups are joined to form a substituted or unsubstituted heterocyclic or substituted or unsubstituted heteroaryl ring;

or $R^1$ and $R^{10}$ are optionally taken together with the intervening carbon atoms to form an optionally substituted cyclic moiety;

or $R^{10}$ and $R^3$ are optionally taken together with the intervening carbon atoms to form an optionally substituted cyclic moiety;

or $R^1$ and $R^4$ are optionally taken together with the intervening carbon atoms to form an optionally substituted cyclic moiety;

or $R^4$ and $R^9$ are optionally taken together with the intervening carbon atoms to form an optionally substituted cyclic moiety;

or $R^6$ and $R^9$ are optionally taken together with the intervening carbon atoms to form an optionally substituted cyclic moiety;

L is a bond, or of the formula:

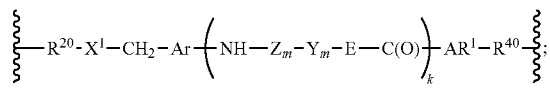

$R^{20}$ is substituted or unsubstituted alkylene; or substituted or unsubstituted heteroalkylene;

$X^1$ is

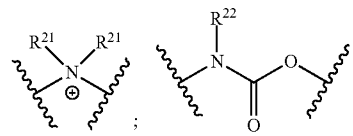

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

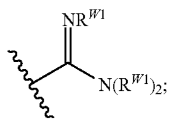

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene; and combinations thereof;

T is hydrogen, —N═C═S,

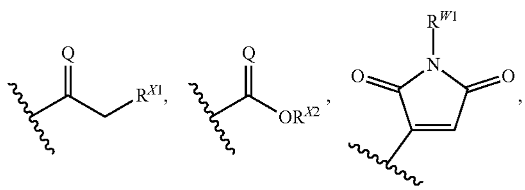

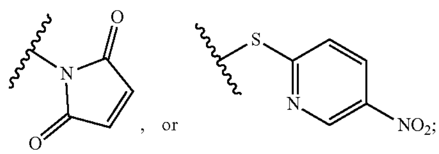

or

Q is —S— or —O—;

$R^{X1}$ is a leaving group;

$R^{X2}$ is hydrogen; substituted or unsubstituted alkyl; substituted or unsubstituted heterocyclyl; substituted or unsubstituted aryl; substituted or unsubstituted heteroaryl; or an oxygen protecting group; and $R^{W1}$ is independently hydrogen; substituted or unsubstituted alkyl; or a nitrogen protecting group.

In certain embodiments, G is

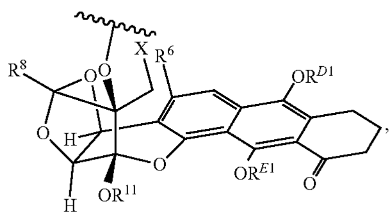

and the compound of Formula (I), (II), (III), or (IV) is of the formula:

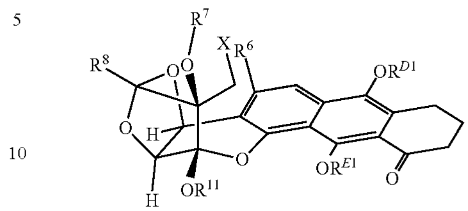

or a pharmaceutically acceptable salt thereof.

In certain embodiments, G is

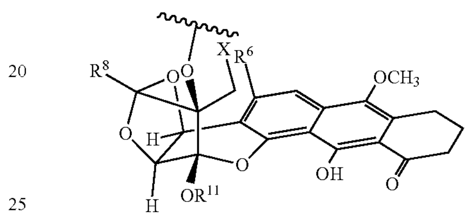

and the compound of Formula (I), (II), (III), or (IV) is of the formula:

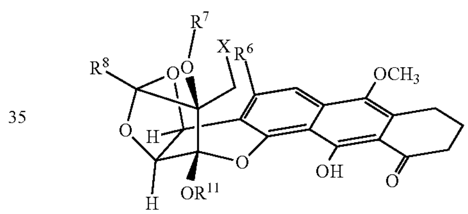

or a pharmaceutically acceptable salt thereof.

In certain embodiments, G is

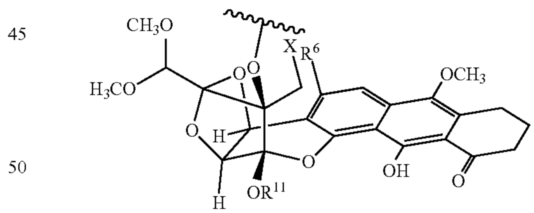

and the compound of Formula (I), (II), (III), or (IV) is of the formula:

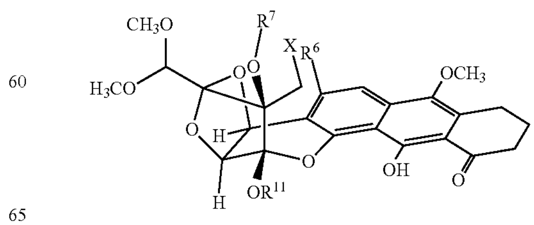

or a pharmaceutically acceptable salt thereof.

In certain embodiments, G is

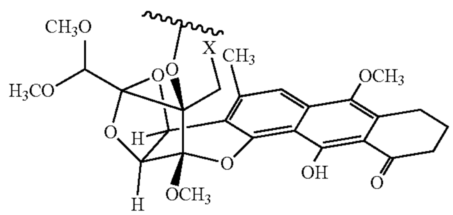

and the compound of Formula (I), (II), (III), or (IV) is of the formula:

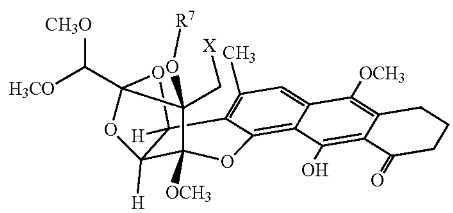

or a pharmaceutically acceptable salt thereof.

In certain embodiments, G is

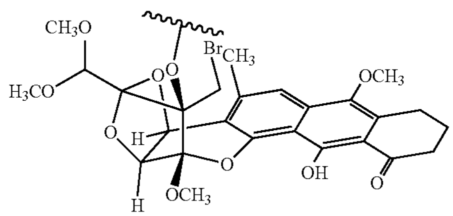

and the compound of Formula (I), (II), (III), or (IV)) is of the formula:

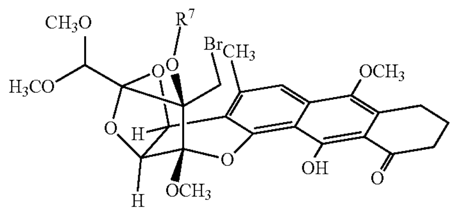

or a pharmaceutically acceptable salt thereof.

In another aspect, provided are pharmaceutical compositions comprising any of the compounds of Formula (I), (II), (III), or (IV), or pharmaceutically acceptable salts thereof, and optionally a pharmaceutically acceptable carrier.

In another aspect, provided are methods of treating cardiovascular disease, proliferative disease (e.g., cancer), diabetic retinopathy, inflammatory disease, autoimmune disease, or infectious disease in a subject in need thereof, the method comprising administering to the subject an effective amount of any of the compounds of Formula (I), (II), (III), or (IV), or novel trioxacarcin analogs as described herein, or pharmaceutically acceptable salts thereof, or a pharmaceutical composition comprising such to the subject.

In another aspect, provided are kits comprising compounds of Formula (I), (II), (III), or (IV), or novel trioxacarcin analogs as described herein, or pharmaceutically acceptable salts thereof, or pharmaceutical compositions comprising such. In certain embodiments, the kits further comprise instructions for administration (e.g., human administration).

Also within the scope of the present disclosure are pharmaceutical compositions comprising any of the compounds of Formula (I), (II), (III), or (IV), or novel trioxacarcin analogs as described herein, or pharmaceutically acceptable salts thereof, and a pharmaceutically acceptable carrier for use in treating cardiovascular disease, proliferative disease (e.g., cancer), diabetic retinopathy, inflammatory disease, autoimmune disease, or infectious disease, as well as uses of any of the compounds of Formula (I), (II), (III), or (IV), or novel trioxacarcin analogs as described herein, or pharmaceutically acceptable salts thereof, for manufacturing a medicament for use in treating any of the target diseases.

Also provided are methods of preparing compounds of Formula (I), (II), (III), and (IV), and the novel trioxacarcin analogs as described herein.

The details of one or more embodiments of the invention are set forth in the accompanying Figures and the Detailed Description below. Other features, objects, and advantages of the invention will be apparent from the Examples and the Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

Compounds described herein may comprise one or more asymmetric centers, and thus may exist as stereoisomers, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *E. L. Stereochemistry of Carbon Compounds* (McGraw-Hill, NY, 1962); and Wilen, S. H. Tables of Resolving Agents and Optical Resolutions p. 268 (E. L. Eliel, Ed., Univ. of Notre Dame Press, Notre Dame, IN 1972). Compounds may exist as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., $—CH_3$). In certain embodiments, the alkyl group is a substituted $C_{1-10}$ alkyl.

As used herein, "heteroalkyl" refers to an alkyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_5$), octatrienyl ($C_5$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_5$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl (C), cyclohexenyl (C), cyclohexadienyl (C), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14, electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as described herein, substituted by an aryl group, as described herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as described herein, substituted by a heteroaryl group, as described herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as described herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —OR—, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C({=}O)R^{aa}$, —$CO_2H$, —CHO, —$C(OR^{cc})_3$, —$CO_2R^{aa}$, —$OC({=}O)R^{aa}$, —$OCO_2R^{aa}$, —$C({=}O)N(R^{bb})_2$, —$OC({=}O)N(R^{bb})_2$, —$NR^{bb}C({=}O)R^{aa}$, —$NR^{bb}CO_2R^{aa}$, —$NR^{bb}C({=}O)N(R^{bb})_2$, —$C({=}NR^{bb})R^{aa}$, —$C({=}NR^{bb})OR^{aa}$, —$OC({=}NR^{bb})R^{aa}$, —$OC({=}NR^{bb})OR^{aa}$, —$C({=}NR^{bb})N(R^{bb})_2$, —$OC({=}NR^{bb})N(R^{bb})_2$, —$NR^{bb}C({=}NR^{bb})N(R^{bb})_2$, —$C({=}O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S({=}O)R^{aa}$, —$OS({=}O)R^{aa}$, —$Si(R^{aa})_3$, —$OSi(R^{aa})_3$—$C({=}S)N(R^{bb})_2$, —$C({=}O)SR^{aa}$, —$C({=}S)SR^{aa}$, —$SC({=}S)SR^{aa}$, —$SC({=}O)SR^{aa}$, —$OC({=}O)SR^{aa}$, —$SC({=}O)OR^{aa}$, —$SC({=}O)R^{aa}$, —$P({=}O)(R^{aa})_2$, —$P({=}O)(OR^{cc})_2$, —$OP({=}O)(R^{aa})_2$, —$OP({=}O)(OR^{cc})_2$, —$P({=}O)(N(R^{bb})_2)_2$, —$OP({=}O)(N(R^{bb})_2)_2$, —$NR^{bb}P({=}O)(R^{aa})_2$, —$NR^{bb}P({=}O)(OR^{cc})_2$, —$NR^{bb}P({=}O)(N(R^{bb})_2)_2$, —$P(R^{cc})_2$, —$P(OR^{cc})_2$, —$P(R^{cc})_3{}^+X^-$, —$P(OR^{cc})_3{}^+X^-$, —$P(R^{cc})_4$, —$P(OR^{cc})_4$, —$OP(R^{cc})_2$, —$OP(R^{cc})_3{}^+X^-$, —$OP(OR^{cc})_2$, —$OP(OR^{cc})_3{}^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, $C_{3-14}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =$NN(R^{bb})_2$, =$NNR^{bb}C({=}O)R$—, =$NNR^{bb}C({=}O)OR^{aa}$, =$NNR^{bb}S({=}O)_2R^{aa}$, =$NR^{bb}$, or =$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C({=}O)R^{aa}$, —$C({=}O)N(R^{cc})_2$, —$CO_2R^{aa}$, —$SO_2R^{aa}$, —$C({=}NR^{cc})OR^{aa}$, —$C({=}NR^{cc})N(R^{cc})_2$, —$SO_2N(R^{cc})_2$, —$SO_2R^{cc}$, —$SO_2OR^{cc}$, —$SOR^{aa}$, —$C({=}S)N(R^{cc})_2$, —$C({=}O)SR^{cc}$, —$C({=}S)SR^{cc}$, —$P({=}O)(R^{aa})_2$, —$P({=}O)(OR^{cc})_2$, —$P({=}O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —$C({=}O)R^{ee}$, —$CO_2H$, —$CO_2R^{ee}$, —$OC({=}O)R^{ee}$, —$OCO_2R^{ee}$, —$C({=}O)N(R^{ff})_2$, —$OC({=}O)N(R^{ff})_2$, —$NR^{ff}C({=}O)R^{ee}$, —$NR^{ff}CO_2R^{ee}$, —$NR^{ff}C({=}O)N(R^{ff})_2$, —$C({=}NR^{ff})OR^{ee}$, —$OC({=}NR^{ff})R^{ee}$, —$OC({=}NR^{ff})OR^{ee}$, —$C({=}NR^{ff})N(R^{ff})_2$, —$OC({=}NR^{ff})N(R^{ff})_2$, —$NR^{ff}C({=}NR^{ff})N(R^{ee})_2$, —$NR^{ee}SO_2R^{ee}$, —$SO_2N(R^{ff})_2$, —$SO_2R^{ee}$, —$SO_2OR^{ee}$, —$OSO_2R^{ee}$, —$S({=}O)R^{ee}$, —$Si(R^{ee})_3$, —$OSi(R^{ee})_3$, —$C({=}S)N(R^{ff})_2$, —$C({=}O)SR^{ee}$, —$C({=}S)SR^{ee}$, —$SC({=}S)SR^{ee}$, —$P({=}O)_2R^{ee}$, —$P({=}O)(R^{ee})_2$, —$OP({=}O)(R^{ee})_2$, —$OP({=}O)(OR^{ee})_2$, $C_{1-6}$ alkyl, $C_{1-6}$ perhaloalkyl, $C_{2-6}$ alkenyl, $C_{2-6}$ alkynyl, hetero$C_{1-5}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-5}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-5}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl)($C_{1-6}$ alkyl), —$N(OH)(C_{1-6}$ alkyl), —NH(OH), —SH, —$SC_{1-6}$ alkyl, —$SS(C_{1-6}$ alkyl), —$C({=}O)(C_{1-6}$ alkyl), —$CO_2H$, —$CO_2(C_{1-6}$ alkyl), —$OC({=}O)(C_{1-6}$ alkyl), —$OCO_2(C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(=NH)NH($C_{1-6}$ alkyl), —OC(=NH)$NH_2$, —NHC(=NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2$($C_{1-6}$ alkyl), —$SO_2$O($C_{1-6}$ alkyl), —$OSO_2$($C_{1-6}$ alkyl), —SO($C_{1-6}$ alkyl), —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)($OC_{1-6}$ alkyl)$_2$, —P(=O)($C_{1-6}$ alkyl)$_2$, —OP(=O)($C_{1-6}$ alkyl)$_2$, —OP(=O)($OC_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$ alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

As used herein, the term "halo" or "halogen" refers to fluorine (fluoro, —F), chlorine (chloro, —Cl), bromine (bromo, —Br), or iodine (iodo, —I).

The term "acyl" refers to a group having the general formula —C(=O)$R^{X1}$, —C(=O)$OR^{X1}$, —C(=O)—O—C(=O)$R^{X1}$, —C(=O)$SR^{X1}$, —C(=O)N($R^{X1}$)$_2$, —C(=S)$R^{X1}$, —C(=S)N($R^{X1}$)$_2$, —C(=S)O($R^{X1}$), —C(=S)S($R^{X1}$), —C(=$NR^{X1}$)$R^{X1}$, —C(=$NR^{X1}$)$OR^{X1}$, —C(=$NR^{X1}$)$SR^{X1}$, and —C(=$NR^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, March Advanced Organic Chemistry 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$($CF_2$)$_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OP($R^{cc}$)$_2$, —OP($R^{cc}$)$_3$, —OP(=O)$_2R^{aa}$, —OP(=O)($R^{aa}$)$_2$, —OP(=O)($OR^{cc}$)$_2$, —OP(=O)$_2$N($R^{bb}$)$_2$, and —OP(=O)($NR^{bb}$)$_2$, wherein $R^{aa}$, $R^{bb}$, and $R^{cc}$ are as defined herein).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OSi($R^{aa}$)$_3$, —OP($R^{cc}$)$_2$, —OP($R^{cc}$)$_3^+X^-$, —OP($OR^{cc}$)$_2$, —OP($OR^{cc}$)$_3^+X^-$, —OP(═O)($R^{aa}$)$_2$, —OP(═O)($OR^{cc}$)$_2$, and —OP(═O)(N($R^{bb}$)$_2$)$_2$, wherein $X^-$, $R^{aa}$, $R^{bb}$, and $R^{cc}$ are as described herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S═$SR^{cc}$, —SC(═S)$SR^{aa}$, —SC(═O)$SR^{aa}$, —SC(═O)$OR^{aa}$, and —SC(═O)$R^{aa}$, wherein $R^{aa}$ and $R^{cc}$ are as described herein.

As used herein, the term, "amino" refers to the group —$NH_2$. The term "substituted amino," by extension, refers to a monosubstituted amino, a disubstituted amino, or a trisubstituted amino, as described herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH($R^{bb}$), —NHC(═O)$R^{aa}$, —NHC$O_2R^{aa}$, —NHC(═O)N($R^{bb}$)$_2$, —NHC(═$NR^{bb}$)N($R^{bb}$)$_2$, —NHS$O_2R^{aa}$, —NHP(═O)($OR^{cc}$)$_2$, and —NHP(═O)(N($R^{bb}$)$_2$)$_2$, wherein $R^{aa}$, $R^{bb}$ and $R^{cc}$ are as described herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(═O)$R^{aa}$, —$NR^{bb}$C$O_2R^{aa}$, —$NR^{bb}$C(═O)N($R^{bb}$)$_2$, —$NR^{bb}$C(═$NR^{bb}$)N($R^{bb}$)$_2$, —$NR^{bb}$S$O_2R^{aa}$, —$NR^{bb}$P(═O)($OR^{cc}$)$_2$, and —$NR^{bb}$P(═O)(N($R^{bb}$)$_2$)$_2$, wherein $R^{aa}$, $R^{bb}$, and $R^{cc}$ are as described herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$ $X^-$, wherein $R^{bb}$ and $X^-$ are as described herein.

As used herein, the term "oxo" refers to the group ═O, and the term "thiooxo" refers to the group ═S.

As used herein, a "counterion" is a negatively charged group associated with a positively charged quarternary amine in order to maintain electronic neutrality. Exemplary counterions include halide ions (e.g., $F^-$, $Cl^-$, $Br^-$, $I^-$), $NO_3$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —N($R^{cc}$)$_2$, —CN, —C(═O)$R^{aa}$, —C(═O)N($R^{cc}$)$_2$, —C$O_2R^{aa}$, —S$O_2R^{aa}$, —C(═$NR^{bb}$)$R^{aa}$, —C(═$NR^{cc}$)$OR^{aa}$, —C(═$NR^{cc}$)N($R^{cc}$)$_2$, —S$O_2$N($R^{cc}$)$_2$, —S$O_2R^{cc}$, —S$O_2OR^{cc}$, —$SOR^{aa}$, —C(═S)N($R^{cc}$)$_2$, —C(═O)$SR^{cc}$, —C(═S)$SR^{cc}$, —P(═O)($OR^{cc}$)$_2$, —P(═O)($R^{aa}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —N($R^{cc}$)$_2$, —C(═O)$R^{aa}$, —C(═O)N($R^{cc}$)$_2$, —C$O_2R^{aa}$, —S$O_2R^{aa}$, —C(═$NR^{cc}$)$R^{aa}$, —C(═$NR^{cc}$)$OR^{aa}$, —C(═$NR^{cc}$)N($R^{cc}$)$_2$, —S$O_2$N($R^{cc}$)$_2$, —S$O_2R^{cc}$, —S$O_2OR^{cc}$, —$SOR^{aa}$, —C(═S)N($R^{cc}$)$_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as described herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $—S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as described herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2- picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as described herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

These and other exemplary substituents are described in more detail in the Detailed Description, Examples, and Claims. The invention is not intended to be limited in any manner by the above exemplary listing of substituents.

Other Definitions

The term "salt" and "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as rodents (e.g., mice, rats), guinea pigs, cattle, pigs, horses, sheep, goats, cats, and/or dogs. The non-human animal may be male or female and at any stage of development. A non-human animal may be a transgenic animal.

"Disease," "disorder," and "condition" are used interchangeably herein.

As used herein, and unless otherwise specified, the terms "treat," "treating" and "treatment" contemplate an action that occurs while a subject is suffering from the specified disease, disorder, or condition, which reduces the severity of the disease, disorder, or condition, or retards or slows the progression of the disease, disorder, or condition ("therapeutic treatment" or "therapeutically treating"), and also contemplates an action that occurs before a subject begins to suffer from the specified disease, disorder, or condition, and which inhibits or reduces the severity of the disease, disorder, or condition ("prophylactic treatment" or "prophylactically treating").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. For example, the effective amount of a compound with anti-proliferative activity is the amount that results in a sufficient concentration to inhibit the proliferation of cells. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder, or condition, or to delay or minimize one or more symptoms associated with the disease, disorder, or condition. A therapeutically effective amount of a compound means an amount of therapeutic agent, alone or in combination with other therapies, which provides a therapeutic benefit in the treatment of the disease, disorder, or condition. The term "therapeutically effective amount" can encompass an amount that improves overall therapy, reduces or avoids symptoms or causes of the disease, disorder, or condition, or enhances the therapeutic efficacy of another therapeutic agent.

As used herein, and unless otherwise specified, a "prophylactically effective amount" of a compound is an amount sufficient to prevent a disease, disorder, or condition, or one or more symptoms associated with the disease, disorder, or condition, or prevent its recurrence. A prophylactically effective amount of a compound means an amount of a therapeutic agent, alone or in combination with other agents, which provides a prophylactic benefit in the prevention of the disease, disorder, or condition. The term "prophylactically effective amount" can encompass an amount that improves overall prophylaxis or enhances the prophylactic efficacy of another prophylactic agent.

As used herein, use of the phrase "at least one instance" refers to 1, 2, 3, 4, or more instances, but also encompasses a range, for example, from 1 to 4, from 1 to 3, from 1 to 2, from 2 to 4, from 2 to 3, or from 3 to 4 instances, inclusive.

As used herein, "small molecule" refers to molecules, whether naturally occurring or artificially created (e.g., via chemical synthesis) that have a relatively low molecular weight. Typically, a small molecule is an organic compound (e.g., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Proteins of the disclosure preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

Exemplary amino acids contemplated useful in providing the proteins of interest include, without limitation, natural alpha-amino acids such as D- and L-isomers of the 20 common naturally occurring alpha-amino acids found in peptides (e.g., A, R, N, C, D, Q, E, G, H, I, L, K, M, F, P, S, T, W, Y, V), natural beta-amino acids (e.g., beta-alanine), and unnnatural amino acids. There are many known unnatural amino acids any of which may be included in the proteins of the present disclosure. See for example, S. Hunt, *The Non-Protein Amino Acids: In Chemistry and Biochemistry of*

*the Amino Acids*, edited by G. C. Barrett, Chapman and Hall, 1985. Additional examples of amino acids contemplated useful in providing the proteins of interest include without limitation, ornithine, citrulline (Cit), α-methyl-Alanine (Aib), 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with $—C(═O)C_6H_5$; $—CF_3$; —CN; -halo; $—NO_2$; $CH_3$), disubstituted phenylalanines, substituted tyrosines (e.g., further substituted with $—C(═O)C_6H_5$; $—CF_3$; —CN; -halo; $—NO_2$; $CH_3$), and statine.

DETAILED DESCRIPTION OF CERTAIN EMBODIMENTS OF THE INVENTION

Figure 1:
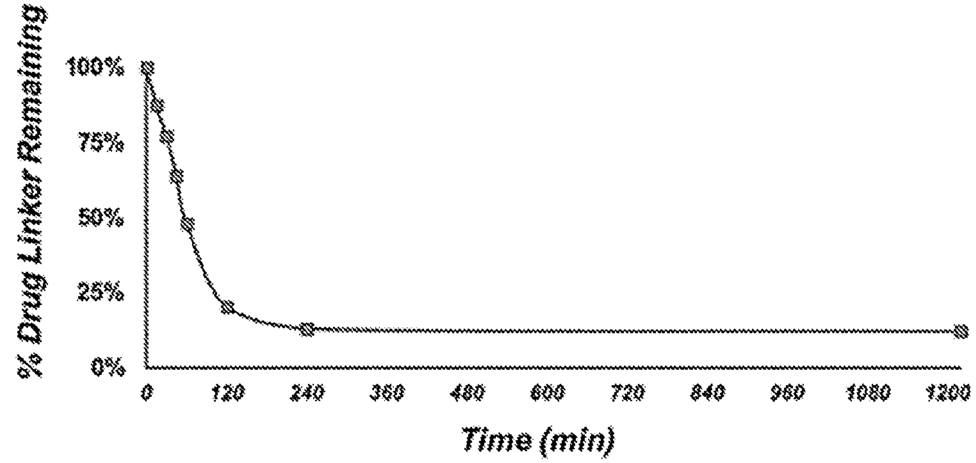
FIG. 1 is a series of graphs showing the stability of exemplary trioxacarcin-linker species 19 and its release kinetics upon exposure to cathepsin B at 37° C.
Figure 1:
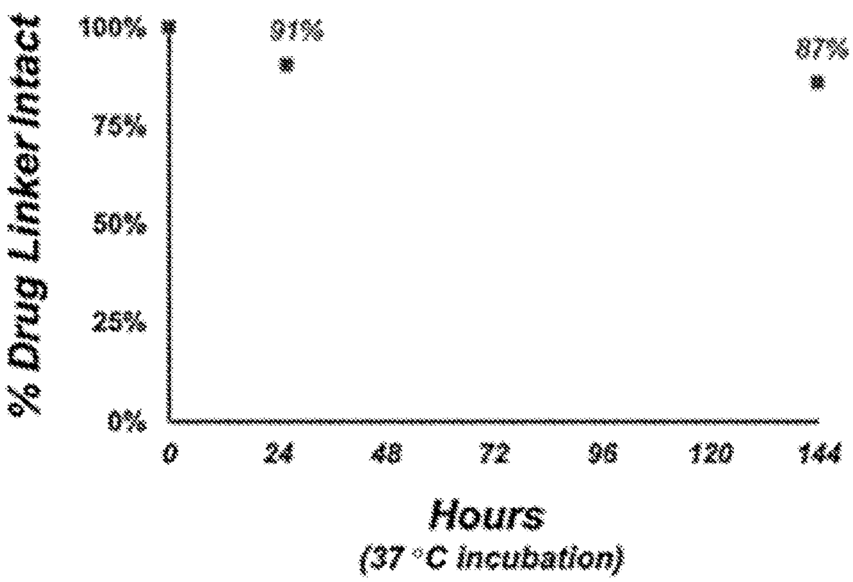

Trioxacarcins are highly toxic to a variety of cell types. Linking a trioxacarcin to an antibody preserves the trioxacarcin's potency against the cell type while increasing specificity for the target cell, and optionally increasing endocytosis of the trioxacarcin. These effects enable lowering the overall amount of trioxacarcin to be delivered, thereby reducing the associated toxicity. By taking advantage of established synthetic methods, complex and therapeutically relevant trioxacarcins are accessible. In turn, conjugating these trioxacarcins to antibodies through linking groups provide trioxacarcin-antibody drug conjugates.

Recent studies have demonstrated that decomposition of previously prepared trioxacarcin ADCs (e.g., those disclosed in WO 2019/032961) under physiological conditions is a result of opening of the epoxide of trioxacarin by an endogenous antibody nucleophile. In response, described herein are compounds that mask the epoxide until the trioxacarcin payload is delivered inside the cell and released from the antibody of the ADC.

Accordingly, provided herein are antibody drug conjugates (e.g., compounds of Formula (I)), including novel trioxacarcin-antibody drug conjugates (e.g., compounds of Formula (II)). Compounds of Formula (I) may comprise a molecular payload other than a trioxacarcin, such as a diagnostic agent or a therapeutic agent, i.e., the compounds of the disclosure are not limited to the delivery of trioxacarcins. Also provided are antibody drug conjugate precursor compounds (e.g., compounds of Formula (III)), including trioxacarcin-antibody drug conjugate precursors comprising a trioxacarcin and a linking group (e.g., compounds of Formula (IV)), novel trioxacarcin analogs (e.g., free drug species). The compounds may be provided for use in any composition, kit, or method described herein as a pharmaceutically acceptable salt.

Provided is a compound of Formula (I):

$$G\text{-}R^7 \quad (I),$$

or a pharmaceutically acceptable salt, solvate, hydrate, polymorph, co-crystal, tautomer, stereoisomer, isotopically labeled derivative, or prodrug thereof;

wherein:

G is a molecular payload;

$R^7$ is -L-A-B;

L is of the formula:

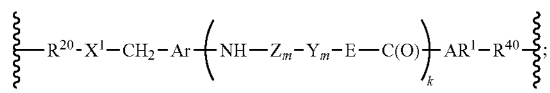

$R^{20}$ is substituted or unsubstituted alkylene; or substituted or unsubstituted heteroalkylene;

$X^1$ is

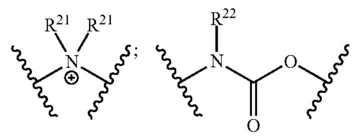

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

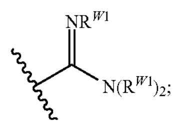

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene;

A is a group of the formula:

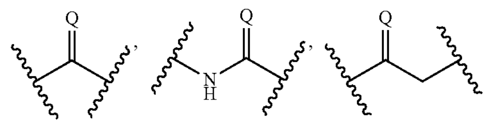

-continued

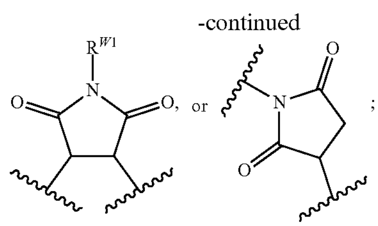

Q is —S— or —O—;

$R^{W1}$ is independently hydrogen; substituted or unsubstituted alkyl; or a nitrogen protecting group; and B is an antibody or an antibody fragment.

In certain embodiments, G is

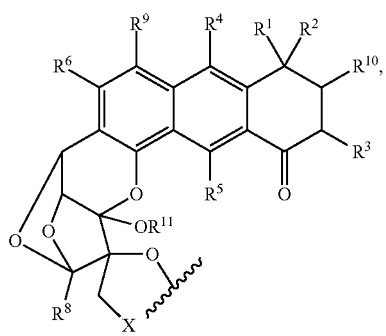

and the compound of Formula (I) is of Formula (II):

(II)

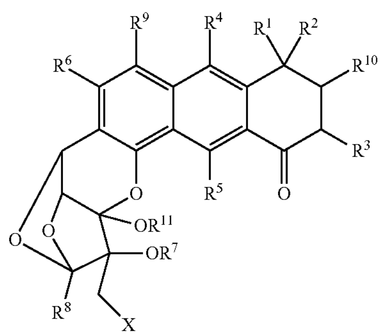

or a pharmaceutically acceptable form thereof;

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{A1}$; $—C(═O)R^{A2}$; $—CO_2R^{A2}$; —CN; —SCN; $—SR^{A1}$; $—SOR^{A1}$; $SO_2R^{A1}$; $—NO_2$; $—N_3$; $—N(R^{A2})_2$; $—NR^{A2}C(═O)R^{A2}$; $—NR^{A2}C(═O)N(R^{A2})_2$; $—OC(═O)OR^{A1}$; $—OC(═O)R^{A2}$; $—OC(═O)N(R^{A2})_2$; $—NR^{A}C(═O)OR^{A1}$; or $—C(R^{A2})_3$; wherein each occurrence of $R^{A1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{A2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino, or two $R^{A2}$ groups are optionally joined to form a heterocyclyl or heteroaryl ring;

$R^2$ is hydrogen; or $R^1$ and $R^2$ are joined to form ═O; $═N(R^{A2})$; or ═S;

$R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{C1}$; $—C(═O)R^{C2}$; $—CO_2R^{C1}$; —CN; —SCN; $—SR^{C1}$; $—SOR^{C1}$; $—SO_2R^{C2}$; $—NO_2$; $—N_3$; ═O; $═N(R^{C2})$; ═S; $—N(R^{C2})_2$; $—NHC(═O)R^{C2}$; $—NR^{C2}C(═O)N(R^{C2})_2$; $—OC(═O)OR^{C1}$; $—OC(═O)R^{C2}$; $—OC(═O)N(R^{C2})_2$; $—NR^{C2}C(═O)OR^{C1}$; or $—C(R^{C2})_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{C2}$ groups are optionally joined to form a heterocyclyl or heteroaryl ring;

$R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{D1}$; $—C(═O)R^{D2}$; $—CO_2R^{D2}$; —CN; —SCN; $—SR^{D1}$; $—SOR^{D1}$; $SO_2R^{D2}$; $—NO_2$; $—N_3$; $—N(R^{D2})_2$; $—NR^{D2}C(═O)R^{D2}$; $—NR^{D2}C(═O)N(R^{D2})_2$; $—OC(═O)OR^{D1}$; $—OC(═O)R^{D2}$; $—OC(═O)N(R^{D2})_2$; $—NR^{D2}C(═O)OR^{D1}$; or $—C(R^{D2})_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{D2}$ groups are optionally joined to form a heterocyclyl or heteroaryl ring;

$R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{E1}$; —C(═O)$R^{E2}$; —$CO_2R^{E1}$; —CN; —SCN; —$SR^{E1}$; —$SOR^{E1}$; —$SO_2R^{E2}$; —$NO_2$; —$N_3$; —N($R^{E2}$)$_2$; —$NR^{E2}$C(═O)$R^{E2}$; —$NR^{E2}$C(═O)N($R^{E2}$)$_2$; —OC(═O)$OR^{E1}$; —OC(═O)$R^{E2}$; —OC(═O)N($R^{E2}$)$_2$; —$NR^{E2}$C(═O)$OR^{E1}$; or —C($R^{E2}$)$_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{F1}$; —C(═O)$R^{F2}$; —$CO_2R^{F1}$; —CN; —SCN; —$SR^{F1}$; —$SOR^{F1}$; $SO_2R^{F2}$; —$NO_2$; —$N_3$; —N($R^{F2}$)$_2$; —$NR^{F2}$C(═O)$R^{F2}$; —$NR^{F2}$C(═O)N($R^{F2}$)$_2$; —OC(═O)$OR^{F1}$; —OC(═O)$R^{F2}$; —OC(═O)N($R^{F2}$)$_2$; —$NR^{F2}$C(═O)$OR^{F1}$; or —C($R^{F2}$)$_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{F2}$ groups are optionally joined to form a heterocyclyl or heteroaryl ring;

$R^7$ is -L-A-B;

X is a halogen;

$R^8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{I1}$; —C(═O)$R^{I2}$; —$CO_2R^{I1}$; —CN; —SCN; —$SR^{I1}$; —$SOR^{I1}$; —$SO_2R^{I2}$; —$NO_2$; —$N_3$; —N($R^{I2}$)$_2$; —$NR^{I2}$C(═O)$R^{I2}$; —$NR^{I2}$C(═O)N($R^{I2}$)$_2$; —OC(═O)$OR^{I1}$; —OC(═O)$R^{I2}$; —OC(═O)N($R^{I2}$)$_2$; —$NR^{I2}$C(═O)$OR^{I1}$; or —C($R^{I2}$)$_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{I2}$ groups are optionally joined to form a heterocyclyl or heteroaryl ring;

$R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{G1}$; —C(═O)$R^{G2}$; —$CO_2R^{G1}$; —CN; —SCN; —$SR^{G1}$; —$SOR^{G1}$; —$SO_2R^{G2}$; —$NO_2$; —$N_3$; —N($R^{G}$)$_2$; —$NR^{G2}$C(═O)$R^{G2}$; —$NR^{G2}$C(═O)N($R^{G2}$)$_2$; —OC(═O)$OR^{G1}$; —OC(═O)$R^{G2}$; —OC(═O)N($R^{G2}$)$_2$; —$NR^{G2}$C(═O)$OR^{G1}$; or —C($R^{G2}$)$_3$; wherein each occurrence of $R^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{G2}$ groups are optionally joined to form a heterocyclyl or heteroaryl ring;

$R^{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{B1}$; —C(═O)$R^{B2}$; —$CO_2R^{B2}$; —CN; —SCN; —$SR^{B1}$; —$SOR^{B1}$; $SO_2R^{B2}$; —$NO_2$; —$N_3$; ═O; ═N($R^{B2}$); ═S; —N($R^{B2}$)$_2$; —$NR^{B2}$C(═O)$R^{B2}$; —$NR^{B2}$C(═O)N($R^{B2}$)$_2$; —OC(═O)$OR^{B1}$; —OC(═O)$R^{B2}$; —OC(═O)N($R^{B2}$)$_2$; —$NR^{B2}$C(═O)$OR^{B1}$; or —C($R^{B2}$)$_3$; wherein each occurrence of $R^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{B2}$ groups are optionally joined to form a heterocyclyl or heteroaryl ring;

$R^{11}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or —C(═O)$R^{H1}$; wherein $R^{H1}$ is hydrogen, substituted or unsubstituted alkyl; —$OR^{H9}$; —OC(═O)$R^{H9}$; —N($R^{H9}$)$_2$; or —NHC(═O)$R^{H9}$; wherein each occurrence of $R^{H9}$ is independently hydrogen; substituted or unsubstituted alkyl; an oxygen protecting group when attached to an oxygen atom; a nitrogen protecting group when attached to a nitrogen atom; or two $R^{H9}$ groups are joined to form a substituted or unsubstituted heterocyclic or substituted or unsubstituted heteroaryl ring;

or $R^1$ and $R^{10}$ are optionally taken together with the intervening carbon atoms to form an optionally substituted cyclic moiety;

or $R^{10}$ and $R^3$ are optionally taken together with the intervening carbon atoms to form an optionally substituted cyclic moiety;

or $R^1$ and $R^4$ are optionally taken together with the intervening carbon atoms to form an optionally substituted cyclic moiety;

or $R^4$ and $R^9$ are optionally taken together with the intervening carbon atoms to form an optionally substituted cyclic moiety;

or $R^6$ and $R^9$ are optionally taken together with the intervening carbon atoms to form an optionally substituted cyclic moiety;

L is of the formula:

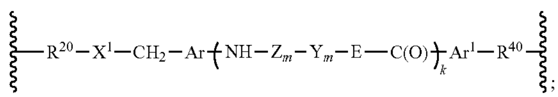

$R^{20}$ is substituted or unsubstituted alkylene; or substituted or unsubstituted heteroalkylene;

$X^1$ is

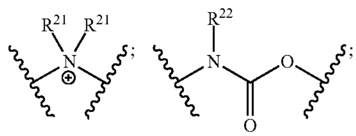

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

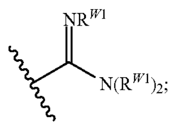

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene;

A is a group of the formula:

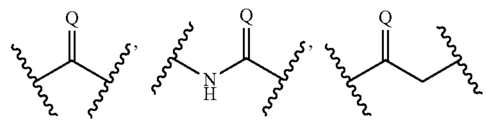

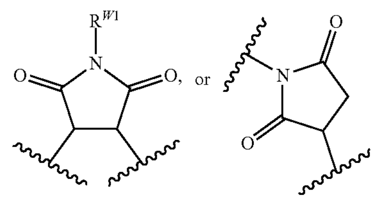

Q is —S— or —O—;

$R^{W1}$ is independently hydrogen; substituted or unsubstituted alkyl; or a nitrogen protecting group; and B is an antibody or an antibody fragment.

In certain embodiments, the compound of Formula (II) is of Formula (II-a):

(II-a)

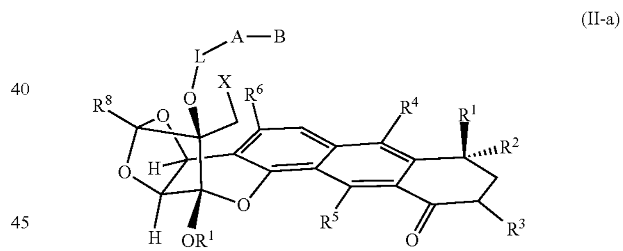

or a pharmaceutically acceptable salt thereof.

In certain embodiments, the compound of Formula (II) is of Formula (II-b):

(II-b)

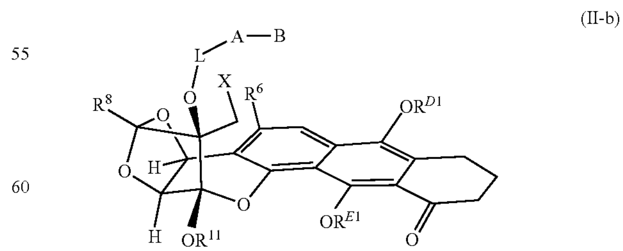

or a pharmaceutically acceptable salt thereof.

In certain embodiments, the compound of Formula (II) is of Formula (II-c):

(II-c)

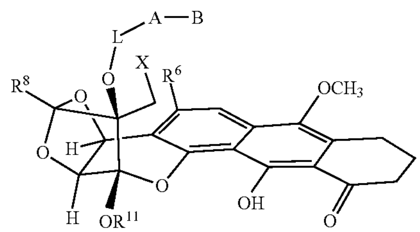

or a pharmaceutically acceptable salt thereof.

In certain embodiments, the compound of Formula (II) is of Formula (II-d):

(II-d)

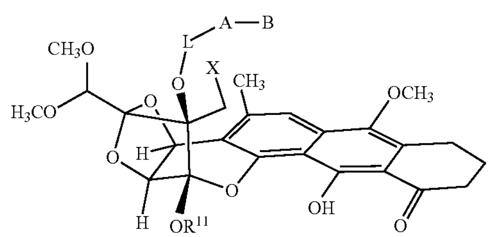

or a pharmaceutically acceptable salt thereof.

In certain embodiments, the compound of Formula (II) is of Formula (II-e):

(II-e)

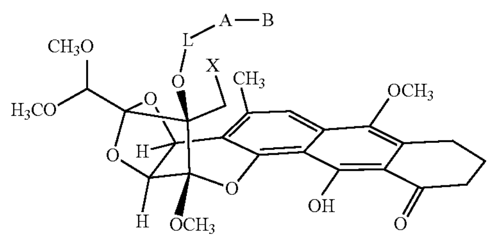

or a pharmaceutically acceptable salt thereof.

In certain embodiments, the compound of Formula (II) is of Formula (II-f):

(II-f)

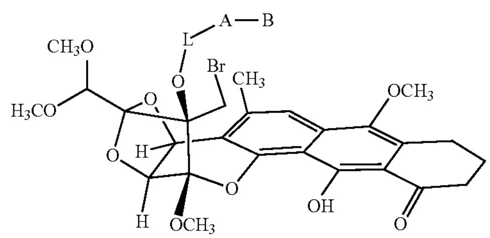

or a pharmaceutically acceptable salt thereof.

The antibody or antibody fragment B is a large molecule with many sites of attachment, and thus may have many instances of a compound of Formula (I) or (II) attached thereto. In certain embodiments, the antibody or antibody fragment comprises 1 to 200 independent instances of a compound of Formula (I) or (II) attached thereto, inclusive, e.g., 1 to 150, 1 to 100, 1 to 75, 1 to 50, 1 to 25, 1 to 15, 1 to 10, inclusive, e.g., 1, 2, 3, 4, 5, 6, 7, 8, 9, or 10 independent instances.

Also provided are precursor compounds to Formula (I), which are compounds that include a moiety useful for conjugating to an antibody. Such compounds are referred to herein as compounds of Formula (III):

$$G\text{-}R^7 \quad \text{(III)},$$

or pharmaceutically acceptable salts thereof;

wherein:

G is a molecular payload;

$R^7$ is -L-T;

L is a bond, or of the formula:

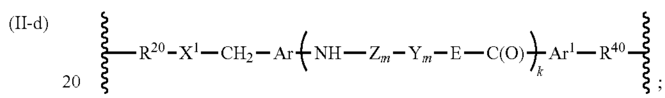

$R^{20}$ is substituted or unsubstituted alkylene; or substituted or unsubstituted heteroalkylene;

$X^1$ is

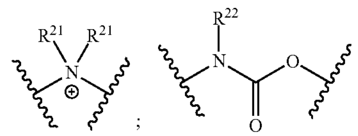

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

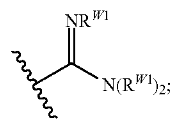

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene; and combinations thereof;

T is hydrogen, —N═C═S,

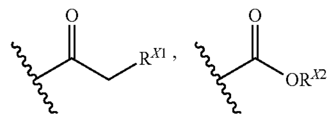

-continued

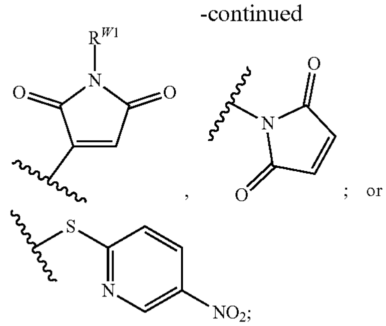

Q is —S— or —O—;

$R^{X1}$ is a leaving group;

$R^{X2}$ is hydrogen; substituted or unsubstituted alkyl; substituted or unsubstituted heterocyclyl; substituted or unsubstituted aryl; substituted or unsubstituted heteroaryl; or an oxygen protecting group; and $R^{W1}$ is independently hydrogen; substituted or unsubstituted alkyl; or a nitrogen protecting group.

In certain embodiments, G is

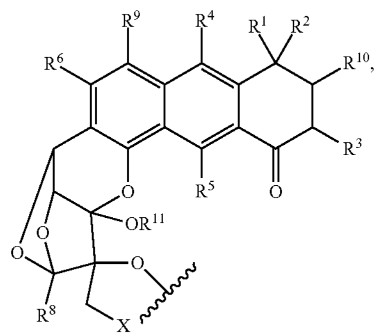

and the compound of Formula (III) is a compound of Formula (IV):

(IV)

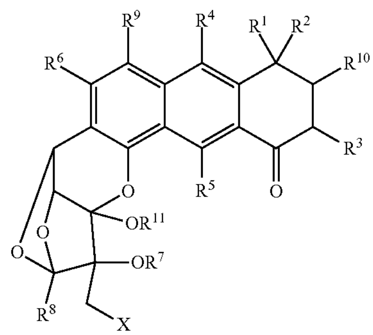

or a pharmaceutically acceptable salt thereof;

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{A1}$; $—C(═O)R^{A2}$; $—CO_2R^{A2}$; —CN; —SCN; $—SR^{A1}$; $—SOR^{A1}$; $SO_2R^{A}$; $—NO_2$; $—N_3$; ═O; $═N(R^{A2})$; ═S; $—N(R^{A2})_2$; $—NR^{A2}C(═O)R^{A2}$; $—NR^{A2}C(═O)N(R^{A2})_2$; $—OC(═O)OR^{A1}$; $—OC(═O)R^{A2}$; $—OC(═O)N(R^{A2})_2$; $—NR^{A}C(═O)OR^{A1}$; or $—C(R^{A2})_3$; wherein each occurrence of $R^{A1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{A2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino, or two $R^{A2}$ groups are optionally joined to form a heterocyclyl or heteroaryl ring;

$R^2$ is hydrogen; or $R^1$ and $R^2$ are joined to form ═O; $═N(R^{A2})$; or ═S;

$R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{C1}$; $—C(═O)R^{C2}$; $—CO_2R^{C1}$; —CN; —SCN; $—SR^{C1}$; $—SOR^{C1}$; $—SO_2R^{C2}$; $—NO_2$; $—N_3$; ═O; $═N(R^{C2})$; ═S; $—N(R^{C2})_2$; $—NHC(═O)R^{C2}$; $—NR^{C2}C(═O)N(R^{C2})_2$; $—OC(═O)OR^{C1}$; $—OC(═O)R^{C2}$; $—OC(═O)N(R^{C2})_2$; $—NR^{C2}C(═O)OR^{C1}$; or $—C(R^{C2})_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{C2}$ groups are optionally joined to form a heterocyclyl or heteroaryl ring;

$R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{D1}$; $—C(═O)R^{D2}$; $—CO_2R^{D2}$; —CN; —SCN; $—SR^{D1}$; $—SOR^{D1}$; $SO_2R^{D2}$; $—NO_2$; $—N_3$; $—N(R^{D2})_2$; $—NR^{D2}C(═O)R^{D2}$; $—NR^{D2}C(═O)N(R^{D2})_2$; $—OC(═O)OR^{D1}$; $—OC(═O)R^{D2}$; $—OC(═O)N(R^{D2})_2$; $—NR^{D2}C(═O)OR^{D1}$; or $—C(R^{D2})_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{D2}$ groups are optionally joined to form a heterocyclyl or heteroaryl ring;

$R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{E1}$; $—C(═O)R^{E2}$; $—CO_2R^{E1}$; —CN; —SCN; $—SR^{E1}$; $—SOR^{E1}$; $—SO_2R^{E2}$; $—NO_2$; $—N_3$; $—N(R^{E2})_2$; $—NR^{E2}C(═O)R^{E2}$; $—NR^{E2}C(═O)N(R^{E2})_2$; $—OC(═O)OR^{E1}$; $—OC(═O)R^{E2}$; $—OC(═O)N(R^{E2})_2$; $—NR^{E2}C(═O)OR^{E1}$; or $—C(R^{E2})_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{F1}$; $—C(═O)R^{F2}$; $—CO_2R^{F1}$; —CN; —SCN; $—SR^{F1}$; $—SOR^{F1}$; $SO_2R^{F2}$; $—NO_2$; $—N_3$; $—N(R^{F2})_2$; $—NR^{F2}C(═O)R^{F2}$; $—NR^{F2}C(═O)N(R^{F2})_2$; $—OC(═O)OR^{F1}$; $—OC(═O)R^{F2}$; $—OC(═O)N(R^{F2})_2$; $—NR^{F2}C(═O)OR^{F1}$; or $—C(R^{F2})_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{F2}$ groups are optionally joined to form a heterocyclyl or heteroaryl ring;

$R^7$ is -L-T;

X is a halogen;

$R^8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{I1}$; $—C(═O)R^{I2}$; $—CO_2R^{I1}$; —CN; —SCN; $—SR^{I1}$; $—SOR^{I1}$; $—SO_2R^{I2}$; $—NO_2$; $—N_3$; $—N(R^{I2})_2$; $—NR^{I2}C(═O)R^{I2}$; $—NR^{I2}C(═O)N(R^{I2})_2$; $—OC(═O)OR^{I1}$; $—OC(═O)R^{I2}$; $—OC(═O)N(R^{I2})_2$; $—NR^{I2}C(═O)OR^{I1}$; or $—C(R^{I2})_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{I2}$ groups are optionally joined to form a heterocyclyl or heteroaryl ring;

$R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{G1}$; $—C(═O)R^{G2}$; $—CO_2R^{G1}$; —CN; —SCN; $—SR^{G1}$; $—SOR^{G1}$; $—SO_2R^{G2}$; $—NO_2$; $—N_3$; $—N(R^{G})_2$; $—NR^{G2}C(═O)R^{G2}$; $—NR^{G2}C(═O)N(R^{G2})_2$; $—OC(═O)OR^{G1}$; $—OC(═O)R^{G2}$; $—OC(═O)N(R^{G2})_2$; $—NR^{G2}C(═O)OR^{G1}$; or $—C(R^{G2})_3$; wherein each occurrence of $R^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{G2}$ groups are optionally joined to form a heterocyclyl or heteroaryl ring;

$R^{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{B1}$; $—C(═O)R^{B2}$; $—CO_2R^{B2}$; —CN; —SCN; $—SR^{B1}$; $—SOR^{B1}$; $SO_2R^{B2}$; $—NO_2$; $—N_3$; ═O; $═N(R^{B2})$; ═S; $—N(R^{B2})_2$; $—NR^{B2}C(═O)R^{B2}$; $—NR^{B2}C(═O)N(R^{B2})_2$; $—OC(═O)OR^{B1}$; $—OC(═O)R^{B2}$; $—OC(═O)N(R^{B2})_2$; $—NR^{B2}C(═O)OR^{B1}$; or $—C(R^{B2})_3$; wherein each occurrence of $R^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{B2}$ groups are optionally joined to form a heterocyclyl or heteroaryl ring;

$R^{11}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —C(═O)$R^{H1}$; wherein $R^{H1}$ is hydrogen, substituted or unsubstituted alkyl; —O$R^{H9}$; —OC(═O)$R^{H9}$; —N$(R^{H9})_2$; —NHC(═O)$R^{H9}$; wherein each occurrence of $R^{H9}$ is independently hydrogen; substituted or unsubstituted alkyl; an oxygen protecting group when attached to an oxygen atom; a nitrogen protecting group when attached to a nitrogen atom; or two $R^{H9}$ groups are joined to form a substituted or unsubstituted heterocyclic or substituted or unsubstituted heteroaryl ring;

or $R^1$ and $R^{10}$ are optionally taken together with the intervening carbon atoms to form an optionally substituted cyclic moiety;

or $R^{10}$ and $R^3$ are optionally taken together with the intervening carbon atoms to form an optionally substituted cyclic moiety;

or $R^1$ and $R^4$ are optionally taken together with the intervening carbon atoms to form an optionally substituted cyclic moiety;

or $R^4$ and $R^9$ are optionally taken together with the intervening carbon atoms to form an optionally substituted cyclic moiety;

or $R^6$ and $R^9$ are optionally taken together with the intervening carbon atoms to form an optionally substituted cyclic moiety;

L is a bond, or of the formula:

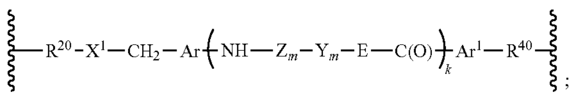

$R^{20}$ is substituted or unsubstituted alkylene; or substituted or unsubstituted heteroalkylene;

$X^1$ is

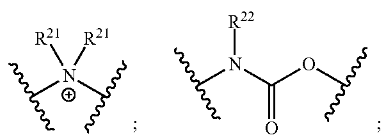

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

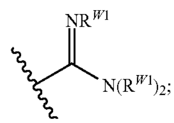

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene; and combinations thereof;

T is hydrogen, —N═C═S,

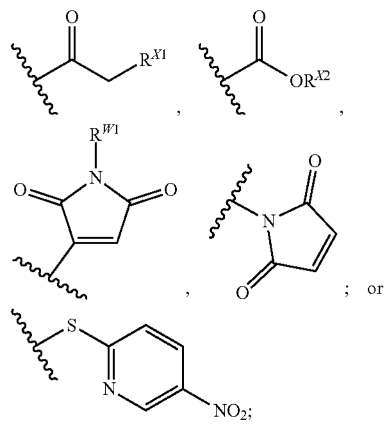

Q is —S— or —O—;

$R^{X1}$ is a leaving group;

$R^{X2}$ is hydrogen; substituted or unsubstituted alkyl; substituted or unsubstituted heterocyclyl; substituted or unsubstituted aryl; substituted or unsubstituted heteroaryl; or an oxygen protecting group; and $R^{W1}$ is independently hydrogen; substituted or unsubstituted alkyl; or a nitrogen protecting group.

In certain embodiments, the compound of Formula (IV) is of Formula (IV-a):

(IV-a)

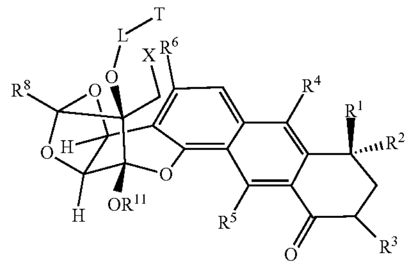

or a pharmaceutically acceptable salt thereof.

In certain embodiments, the compound of Formula (IV) is of Formula (IV-b):

(IV-b)

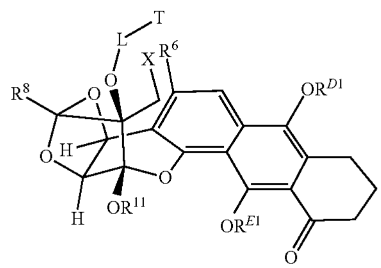

or a pharmaceutically acceptable salt thereof.

In certain embodiments, the compound of Formula (IV) is of Formula (IV-c):

(IV-c)

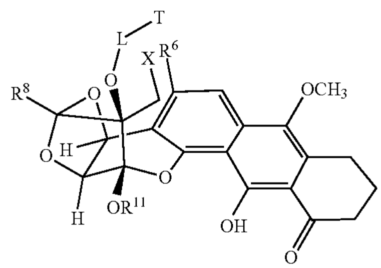

or a pharmaceutically acceptable salt thereof.

In certain embodiments, the compound of Formula (IV) is of Formula (IV-d):

(IV-d)

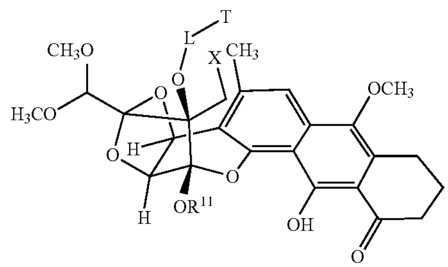

or a pharmaceutically acceptable salt thereof.

In certain embodiments, the compound of Formula (IV) is of Formula (IV-e):

(IV-e)

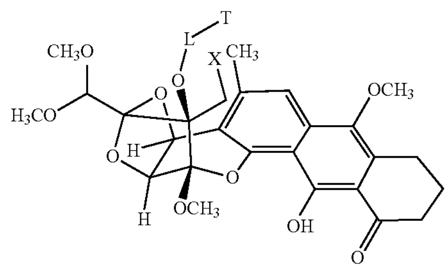

or a pharmaceutically acceptable salt thereof.

In certain embodiments, the compound of Formula (IV) is of Formula (IV-f):

(IV-F)

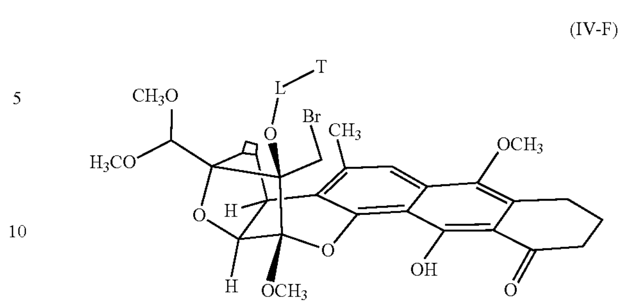

or a pharmaceutically acceptable salt thereof.

Compounds of Formula (I) (e.g., compounds of Formula (II)) are prepared by coupling a compound of Formula (III) (e.g., a compound of Formula (IV)) with an antibody or antibody fragment. In certain embodiments, an antibody or fragment thereof is coupled with 1 to 200 compounds of Formula (III) (e.g., compounds of Formula (IV)) to form a corresponding compound of Formula (I) (e.g., compounds of Formula (II)).

G

As generally defined above, G is a molecular payload. In certain embodiments, G is a therapeutic agent or a diagnostic agent. In certain embodiments, G is a therapeutic agent. In certain embodiments, G is a diagnostic agent.

In certain embodiments, the diagnostic agent is an inorganic compound or an organic compound. In certain embodiments, G is an inorganic compound or an organic compound. In certain embodiments, the diagnostic agent is a dye, stain, radioactive tracer, or culture-media chemical-based constituent. In certain embodiments, G is a dye, stain, radioactive tracer, or culture-media chemical-based constituent.

In certain embodiments, the therapeutic agent is a small molecule drug, a protein, a peptide, a polysaccharide, a nucleic acid, or an oligonucleotide. In certain embodiments, G is a small molecule drug, a protein, a peptide, a polysaccharide, a nucleic acid, or an oligonucleotide. In certain embodiments, the therapeutic agent is a small molecule drug. In certain embodiments, G is a small molecule drug. In certain embodiments, G is a trioxacarcin. In certain embodiments, G is a trioxacarcin analog. In certain embodiments G is a trioxacarcin derivative.

In certain embodiments, G is of the formula:

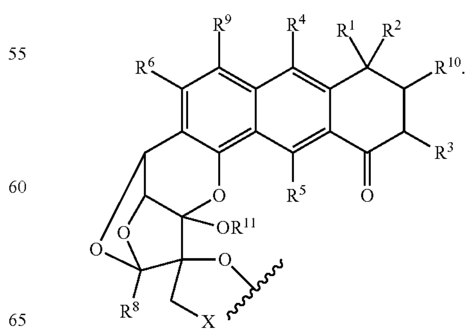

In certain embodiments, G is of the formula:

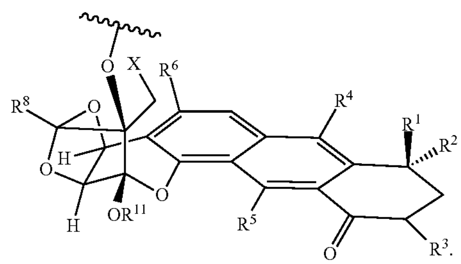

In certain embodiments, G is of the formula:

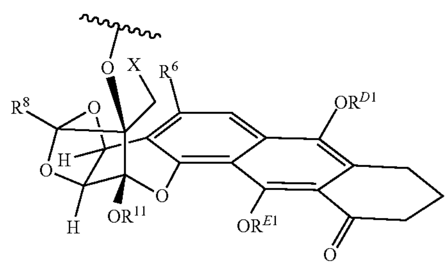

In certain embodiments, G is of the formula:

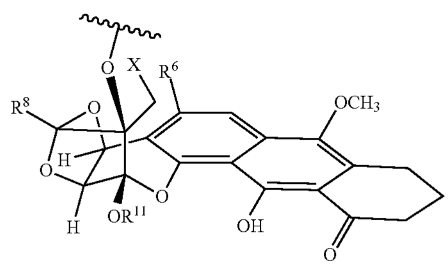

In certain embodiments, G is of the formula:

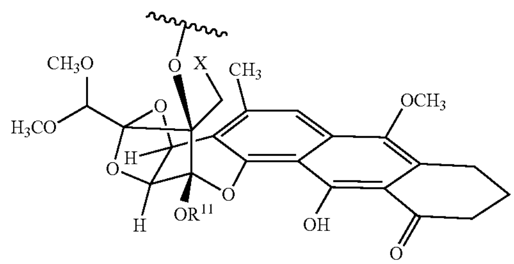

In certain embodiments, G is of the formula:

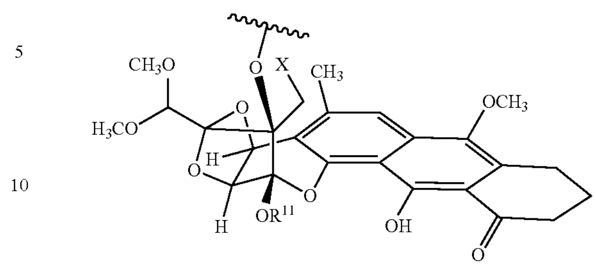

In certain embodiments, G is of the formula:

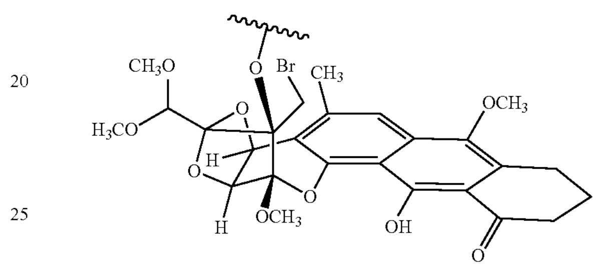

Groups $R^1$ and $R^2$

As generally defined above, $R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{A1}$; $—C(=O)R^{A2}$; $CO_2R^{A2}$; —CN; —SCN; $—SR^{A1}$; $—SOR^{A1}$; $SO_2R^{A1}$; $—NO_2$; $—N_3$; $—N(R^{A2})_2$; $—NR^{A2}C(=O)R^{A2}$; $—NR^{A2}C(=O)N(R^{A2})_2$; $—OC(=O)OR^{A1}$; $—OC(=O)R^{A2}$; $—OC(=O)N(R^{A2})_2$; —NRAC(=O)$OR^{A1}$; or $—C(R^{A2})_3$; and $R^2$ is hydrogen; or $R^1$ and $R^2$ are joined to form =O; $=N(R^{A2})$; or =S.

In certain embodiments, $R^1$ is hydrogen; and $R^2$ is hydrogen.

In certain embodiments, $R^1$ is halogen (e.g., —F, —Cl, Br, or —I); and $R^2$ is hydrogen.

In certain embodiments, $R^1$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, and $R^2$ is hydrogen. Exemplary $R^1C_{1-6}$ alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

In certain embodiments, $R^1$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl, and $R^2$ is hydrogen.

In certain embodiments, $R^1$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl, and $R^2$ is hydrogen.

In certain embodiments, $R^1$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl, and $R^2$ is hydrogen.

In certain embodiments, $R^1$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl, and $R^2$ is hydrogen.

In certain embodiments, $R^1$ is substituted or unsubstituted aryl, e.g., substituted or unsubstituted phenyl, and $R^2$ is hydrogen.

In certain embodiments, $R^1$ is substituted or unsubstituted heteroaryl, e.g., substituted or unsubstituted 5-6 membered heteroaryl, and $R^2$ is hydrogen.

In certain embodiments, $R^1$ is $—OR^{A1}$, and $R^2$ is hydrogen. In certain embodiments, $R^1$ is $—C(═O)R^{A2}$ and $R^2$ is hydrogen. In certain embodiments, $R^1$ is $—CO_2R^{A2}$ and $R^2$ is hydrogen. In certain embodiments, $R^1$ is —CN and $R^2$ is hydrogen. In certain embodiments, $R^1$ is —SCN and $R^2$ is hydrogen. In certain embodiments, $R^1$ is $—SR^{A1}$ and $R^2$ is hydrogen. In certain embodiments, $R^1$ is $—SOR^{A1}$ and $R^2$ is hydrogen. In certain embodiments, $R^1$ is $—SO_2R^{A2}$ and $R^2$ is hydrogen. In certain embodiments, $R^1$ is $—NO_2$ and $R^2$ is hydrogen. In certain embodiments, $R^1$ is $—N_3$ and $R^2$ is hydrogen. In certain embodiments, $R^1$ is $—N(R^{A2})_2$ and $R^2$ is hydrogen. In certain embodiments, $R^1$ is $—NR^{A2}C(═O)R^{A2}$ and $R^2$ is hydrogen. In certain embodiments, $R^1$ is $—NR^{A2}C(═O)N(R^{A2})_2$ and $R^2$ is hydrogen. In certain embodiments, $R^1$ is $—OC(═O)OR^{A1}$ and $R^2$ is hydrogen. In certain embodiments, $R^1$ is $—OC(═O)R^{A2}$ and $R^2$ is hydrogen. In certain embodiments, $R^1$ is $—OC(═O)N(R^{A2})_2$ and $R^2$ is hydrogen. In certain embodiments, $R^1$ is $—NR^{A2}C(═O)OR^{A1}$ and $R^2$ is hydrogen. In certain embodiments, $R^1$ is $—C(R^{A2})_3$ and $R^2$ is hydrogen.

In certain embodiments, $R^1$ and $R^2$ are joined to form ═O.

As generally defined above, each occurrence of $R^{A1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; each occurrence of $R^{A2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; or substituted amino; or two $R^{A2}$ groups are optionally joined to form a heterocyclyl or heteroaryl ring.

In certain embodiments, $R^{A1}$ or $R^{A2}$ represent a group of Formula (i):

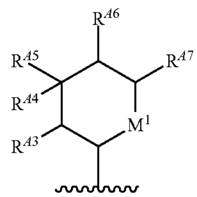

(i)

each occurrence of $R^{A3}$, $R^{A4}$, $R^{A5}$, $R^{A6}$, and $R^{A7}$ is independently hydrogen, substituted or unsubstituted alkyl; $—OR^{A9}$; $—OC(═O)R^{A9}$; $—N(R^{A9})_2$; or $—NHC(═O)R^{A9}$; wherein each occurrence of $R^{A9}$ is independently hydrogen; substituted or unsubstituted alkyl; an oxygen protecting group when attached to an oxygen atom; or a nitrogen protecting group when attached to a nitrogen atom; or two $R^{A9}$ groups are joined to form a substituted or unsubstituted heterocyclic or substituted or unsubstituted heteroaryl ring; and $M^1$ is —O—, $—NR^{A8}—$, or $—CHR^{A8}—$, wherein $R^{A8}$ is hydrogen; substituted or unsubstituted alkyl; or a nitrogen protecting group if attached to nitrogen; or $—OR^{A9}$; wherein $R^{A9}$ is independently hydrogen; substituted or unsubstituted alkyl; acyl; or an oxygen protecting group.

In certain embodiments, $R^{A1}$ or $R^{A2}$ is hydrogen.

In certain embodiments, $R^{A3}$ is hydrogen, substituted or unsubstituted alkyl; $—OR^{A9}$; $—OC(═O)R^{A9}$; or $—NHC(═O)R^{A9}$; wherein each occurrence of $R^{A9}$ is independently hydrogen; substituted or unsubstituted alkyl; or an oxygen protecting group. In certain embodiments, $R^{A3}$ is hydrogen. In certain embodiments, $R^{A3}$ is substituted or unsubstituted alkyl, e.g., methyl. In certain embodiments, $R^{A3}$ is $—OR^{A9}$, e.g., —OH or —O-alkyl.

In certain embodiments, $R^{A4}$ is hydrogen; substituted or unsubstituted alkyl; $—OR^{A9}$; $—OC(═O)R^{A9}$; or $—NHC(═O)R^{A9}$; wherein each occurrence of $R^{A9}$ is independently hydrogen; substituted or unsubstituted alkyl; or an oxygen protecting group. In certain embodiments, $R^{A4}$ is hydrogen. In certain embodiments, $R^{A4}$ is substituted or unsubstituted alkyl, e.g., methyl. In certain embodiments, $R^{A4}$ is $—OR^{A9}$, e.g., —OH or —O-alkyl.

In certain embodiments, $R^{A5}$ is hydrogen, substituted or unsubstituted alkyl; $—OR^{A9}$; $—OC(═O)R^{A9}$; or $—NHC(═O)R^{A9}$; wherein each occurrence of $R^{A9}$ is independently hydrogen; substituted or unsubstituted alkyl; or an oxygen protecting group. In certain embodiments, $R^{A5}$ is hydrogen. In certain embodiments, $R^{A5}$ is substituted or unsubstituted alkyl, e.g., methyl. In certain embodiments, $R^{A5}$ is $—OR^{A9}$, e.g., —OH or —O-alkyl.

In certain embodiments, $R^{A6}$ is hydrogen, substituted or unsubstituted alkyl; $—OR^{A9}$; $—OC(═O)R^{A9}$; or $—NHC(═O)R^{A9}$; wherein each occurrence of $R^{A9}$ is independently hydrogen; substituted or unsubstituted alkyl; or an oxygen protecting group. In certain embodiments, $R^{A6}$ is hydrogen. In certain embodiments, $R^{A6}$ is substituted or unsubstituted alkyl, e.g., methyl. In certain embodiments, $R^{A6}$ is $—OR^{A9}$, e.g., —OH or —O-alkyl.

In certain embodiments, $R^{A7}$ is hydrogen; substituted or unsubstituted alkyl; $—OR^{A9}$; $—OC(═O)R^{A9}$; or $—NHC(═O)R^{A9}$; wherein each occurrence of $R^{A9}$ is independently hydrogen; substituted or unsubstituted alkyl; or an oxygen protecting group. In certain embodiments, $R^{A7}$ is hydrogen.

In certain embodiments, $R^{A7}$ is substituted or unsubstituted alkyl, e.g., methyl. In certain embodiments, $R^{A7}$ is —$OR^{A9}$, e.g., —OH or —O-alkyl.

In certain embodiments, $M^1$ is —O—, —$NR^{A8}$—, or —$CHR^{A8}$—, wherein $R^{A8}$ is hydrogen; substituted or unsubstituted alkyl; a nitrogen protecting group if attached to nitrogen; or —$OR^{A9}$; wherein $R^{A9}$ is independently hydrogen; substituted or unsubstituted alkyl; acyl; or an oxygen protecting group.

In certain embodiments, $M^1$ is —O—. In certain embodiments, $M^1$ is —$NR^{A8}$—, e.g., —NH—. In certain embodiments, $M^1$ is —$CHR^{A8}$—, e.g., —$CH_2$—.

In certain embodiments, $R^{A3}$ is hydrogen; $R^{A4}$ is hydrogen or —$OR^{A9}$; $R^{A5}$ is methyl, —NHC(═O)$R^{A9}$; $R^{A6}$ is hydrogen, —$OR^{A9}$, —OC(═O)$R^{A9}$, or —NHC(═O)$R^{A9}$; $R^{A7}$ is methyl; and $M^1$ is —O—.

In certain embodiments, $R^{A3}$ is hydrogen; $R^{A4}$ is hydrogen or —$OR^{A9}$; $R^{A5}$ is methyl, —NHC(═O)$R^{A9}$; $R^{A6}$ is hydrogen, —$OR^{A9}$, —OC(═O)$R^{A9}$, or —NHC(═O)$R^{A9}$; and $R^{A7}$ is methyl. In certain embodiments, $R^{A3}$ is a non-hydrogen equatorial group.

Groups $R^3$, $R^4$, $R^5$, and $R^6$

As generally defined above, $R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{C1}$; —C(═O)$R^{C2}$; —$CO_2R^{C1}$; —CN; —SCN; —$SR^{C1}$; —$SOR^{C1}$; —$SO_2R^{C2}$; —$NO_2$; —$N_3$; ═O; ═N($R^{C2}$); ═S; —N($R^{C2}$)$_2$; —NHC(═O)$R^{C2}$; —$NR^{C2}$C(═O)N($R^{C2}$)$_2$; —OC(═O)$OR^{C1}$; —OC(═O)$R^{C2}$; —OC(═O)N($R^{C2}$)$_2$; —$NR^{C2}$C(═O)$OR^{C1}$; or —C($R^{C2}$)$_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{C2}$ groups are optionally joined to form a heterocyclyl or heteroaryl ring.

In certain embodiments, $R^3$ is hydrogen or —$OR^{C1}$, wherein $R^{C1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or acyl. In certain embodiments, $R^3$ is hydrogen. In certain embodiments, $R^3$ is —$OR^{C1}$, e.g., —OH or —$OCH_3$.

As generally defined above, $R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{D1}$; —C(═O)$R^{D2}$; —$CO_2R^{D2}$; —CN; —SCN; —$SR^{D1}$; —$SOR^{D1}$; —$SO_2R^{D2}$; —$NO_2$; —$N_3$; —N($R^{D2}$)$_2$; —$NR^{D2}$C(═O)$R^{D2}$; —$NR^{D2}$C(═O)N($R^{D2}$)$_2$; —OC(═O)$OR^{D1}$; —OC(═O)$R^{D2}$; —OC(═O)N($R^{D2}$)$_2$; —$NR^{D2}$C(═O)$OR^{D1}$; or —C($R^{D2}$)$_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{D2}$ groups are optionally joined to form a heterocyclyl or heteroaryl ring.

In certain embodiments, $R^4$ is hydrogen or —$OR^{D1}$, wherein $R^{D1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or acyl. In certain embodiments, $R^4$ is hydrogen. In certain embodiments, $R^4$ is —$OR^{D1}$, e.g., —OH or —$OCH_3$.

As generally defined above, $R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{E1}$; —C(═O)$R^{E2}$; —$CO_2R^{E1}$; —CN; —SCN; —$SR^{E1}$; —$SOR^{E1}$; —$SO_2R^{E2}$; —$NO_2$; —$N_3$; —N($R^{E2}$)$_2$; —$NR^{E2}$C(═O)$R^{E2}$; —$NR^{E2}$C(═O)N($R^{E2}$)$_2$; —OC(═O)$OR^{E1}$; —OC(═O)$R^{E2}$; —OC(═O)N($R^{E2}$)$_2$; —$NR^{E2}$C(═O)$OR^{E1}$; or —C($R^{E2}$)$_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{E2}$ groups are optionally joined to form a heterocyclyl or heteroaryl ring.

In certain embodiments, $R^5$ is hydrogen or —$OR^{E1}$, wherein $R^{E1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or acyl. In certain embodiments, $R^5$ is hydrogen. In certain embodiments, $R^5$ is —$OR^{E1}$, e.g., —OH or —$OCH_3$. In certain embodiments, $R^5$ is —$OR^{E1}$, wherein $R^{E1}$ is a protecting group. In certain embodiments, $R^5$ is —$OR^{E1}$, wherein $R^{E1}$ is a Boc protecting group.

As generally defined above, $R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{F1}$; —C(═O)$R^{F2}$; —$CO_2R^{F1}$; —CN; —SCN; —$SR^{F1}$; —$SOR^{F1}$; $SO_2R^{F2}$; —$NO_2$; —$N_3$; —N($R^{F2}$)$_2$;

—$NR^{F2}C(=O)R^{F2}$; —$NR^{F2}C(=O)N(R^{F2})_2$; —$OC(=O)OR^{F1}$; —$OC(=O)R^{F2}$; —$OC(=O)N(R^{F2})_2$; —$NR^{F2}C(=O)OR^{F1}$; or —$C(R^{F2})_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{F2}$ groups are optionally joined to form a heterocyclyl or heteroaryl ring.

In certain embodiments, $R^6$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —$OR^{F1}$; —$C(=O)R^{F2}$; —$CO_2R^{F1}$; —CN; —SCN; —$SR^{F1}$; —$SOR^{F1}$; —$SO_2R^{F2}$; —$NO_2$; —$N_3$; —$N(R^{F2})_2$; —$NR^{F2}C(=O)R^{F2}$; —$NR^{F2}C(=O)N(R^{F2})_2$; —$OC(=O)OR^{F1}$; —$OC(=O)R^{F2}$; —$OC(=O)N(R^{F2})_2$; —$NR^{F2}C(=O)OR^{F1}$; or —$C(R^{F2})_3$.

In certain embodiments, $R^6$ is hydrogen.

In certain embodiments, $R^6$ is halogen; e.g., —F, —Cl, Br, or —I.

In certain embodiments, $R^6$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^6C_{1-6}$ alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$).

In certain embodiments, $R^6$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, $R^6$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl.

In certain embodiments, $R^6$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl. In certain embodiments, $R^6$ is substituted or unsubstituted cyclopropyl.

In certain embodiments, $R^6$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, $R^6$ is substituted or unsubstituted aryl, e.g., substituted or unsubstituted phenyl.

In certain embodiments, $R^6$ is substituted or unsubstituted heteroaryl, e.g., substituted or unsubstituted 5-6 membered heteroaryl.

In certain embodiments, $R^6$ is —$OR^{F1}$. In certain embodiments, $R^6$ is —$C(=O)R^{F2}$. In certain embodiments, $R^6$ is —$CO_2R^{F1}$. In certain embodiments, $R^6$ is —CN. In certain embodiments, $R^6$ is —SCN. In certain embodiments, $R^6$ is —$SR^{F1}$. In certain embodiments, $R^6$ is —$SOR^{F1}$. In certain embodiments, $R^6$ is —$SO_2R^{F2}$. In certain embodiments, $R^6$ is —$NO_2$. In certain embodiments, $R^6$ is —$N_3$. In certain embodiments, $R^6$ is —$N(R^{F2})_2$. In certain embodiments, $R^6$ is —$NR^{F2}C(=O)R^{F2}$. In certain embodiments, $R^6$ is —$NR^{F2}C(=O)N(R^{F2})_2$. In certain embodiments, $R^6$ is —$OC(=O)OR^{F1}$. In certain embodiments, $R^6$ is —$OC(=O)R^{F2}$. In certain embodiments, $R^6$ is —$OC(=O)N(R^{F2})_2$. In certain embodiments, $R^6$ is —$NR^{F2}C(=O)OR^{F1}$. In certain embodiments, $R^6$ is —$C(R^{F2})_3$.

In certain embodiments, each occurrence of $R^{F1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or acyl; and each occurrence of $R^{F2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; or substituted amino; or two $R^{F2}$ groups are optionally joined to form a heterocyclyl or heteroaryl ring.

In certain embodiments, $R^{F1}$ or $R^{F2}$ is hydrogen.

In certain embodiments, $R^3$ is hydrogen or —OH, $R^4$ is —$OCH_3$, and $R^5$ is —OH.

In certain embodiments, $R^3$ is hydrogen or —OH, $R^4$ is —$OCH_3$, $R^5$ is —OH, and $R^6$ substituted or unsubstituted alkyl or —$OR^{F1}$ Group X As generally defined above, X is a halogen. In certain embodiments, X is —Cl, —Br, or —I. In certain embodiments, X is —Br or —I. In certain embodiments, X is —Cl. In certain embodiments, X is —Br. In certain embodiments, X is —I.

Group $R^7$—Compounds of Formula (I) and (II)

As generally defined above for compounds of Formula (I) and (II), $R^7$ is -L-A-B; wherein L is a group of the formula:

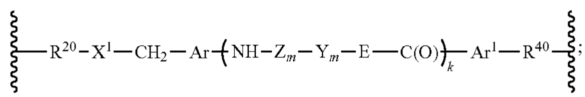

$R^{20}$ is substituted or unsubstituted alkylene; or substituted or unsubstituted heteroalkylene;

$X^1$ is

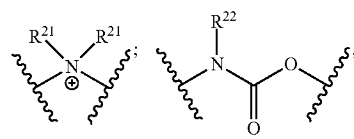

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

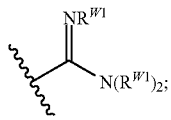

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene;

A is a group of the formula:

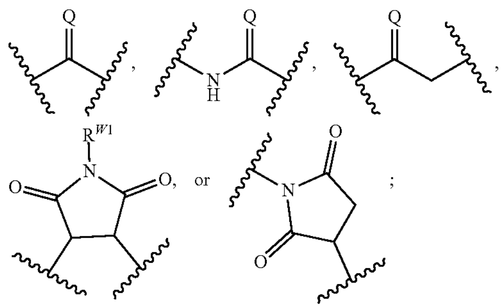

Q is —S— or —O—;

$R^{W1}$ is independently hydrogen, substituted or unsubstituted alkyl; or a nitrogen protecting group; and B is an antibody or an antibody fragment.

In certain embodiments, $R^7$ is -L-A-B; wherein L is a group of the formula:

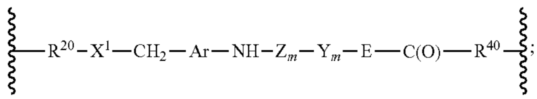

$R^{20}$ is substituted or unsubstituted alkylene; or substituted or unsubstituted heteroalkylene;

$X^1$ is

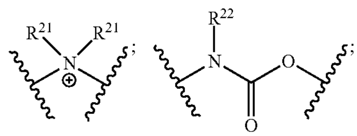

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

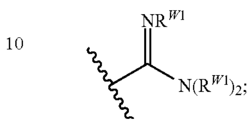

Ar is substituted or unsubstituted arylene;

each occurrence of Z is independently an amino acid;

each occurrence of Y is independently an amino acid;

E is a bond or an amino acid;

m is independently 1, 2, or 3;

$R^{40}$ is substituted or unsubstituted alkylene; or substituted or unsubstituted heteroalkylene;

A is a group of the formula:

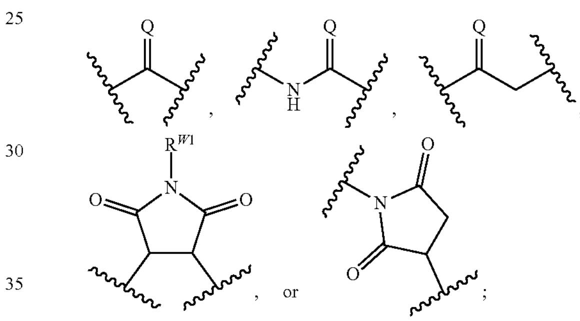

Q is —S— or —O—;

$R^{W1}$ is independently hydrogen, substituted or unsubstituted alkyl; or a nitrogen protecting group; and B is an antibody or an antibody fragment.

In certain embodiments, $R^{20}$ is substituted or unsubstituted alkylene. In certain embodiments, $R^{20}$ is unsubstituted alkylene. In certain embodiments, $R^{20}$ is unsubstituted $C_{1-6}$ alkylene. In certain embodiments, $R^{20}$ is unsubstituted $C_{1-5}$ alkylene. In certain embodiments, $R^{20}$ is unsubstituted $C_{1-4}$ alkylene. In certain embodiments, $R^{20}$ is unsubstituted $C_{2-6}$ alkylene. In certain embodiments, $R^{20}$ is unsubstituted $C_{2-5}$ alkylene. In certain embodiments, $R^{20}$ is unsubstituted $C_{2-4}$ alkylene. In certain embodiments, $R^{20}$ is unsubstituted $C_{2-3}$ alkylene. In certain embodiments, $R^{20}$ is unsubstituted methylene. In certain embodiments, $R^{20}$ is unsubstituted ethylene. In certain embodiments, $R^{20}$ is unsubstituted propylene. In certain embodiments, $R^{20}$ is unsubstituted butylene. In certain embodiments, $R^{20}$ is unsubstituted pentylene. In certain embodiments, $R^{20}$ is unsubstituted hexylene.

In certain embodiments, $X^1$ is

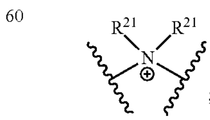

and $R^{21}$ is independently substituted or unsubstituted alkyl; or substituted or unsubstituted carbocyclyl; or two $R^{21}$ groups are joined to form an optionally substituted heterocyclyl ring. In certain embodiments, $X^1$ is

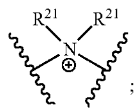

and $R^{21}$ is independently substituted or unsubstituted alkyl; or substituted or unsubstituted carbocyclyl. In certain embodiments, $X^1$ is

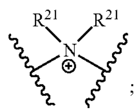

and $R^{21}$ is independently substituted or unsubstituted alkyl. In certain embodiments, $X^1$ is

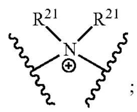

and $R^{21}$ is independently unsubstituted alkyl. In certain embodiments, $X^1$ is

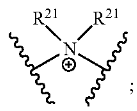

and $R^{21}$ is independently unsubstituted $C_{1-6}$ alkyl. In certain embodiments, $X^1$ is

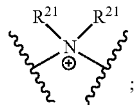

and $R^{21}$ is independently unsubstituted $C_{1-4}$ alkyl. In certain embodiments, $X^1$ is

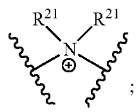

and $R^{21}$ is independently unsubstituted $C_{1-3}$ alkyl. In certain embodiments, $X^1$ is

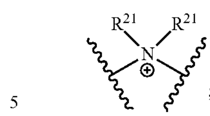

and $R^{21}$ is independently unsubstituted $C_{1-2}$ alkyl. In certain embodiments, $X^1$ is

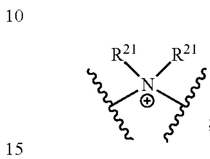

and two $R^{21}$ groups are joined to form an optionally substituted heterocyclyl ring. In certain embodiments, $X^1$ is

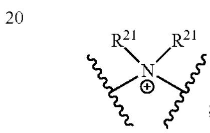

and two $R^{21}$ groups are optionally joined to form an optionally substituted 5-6 membered heterocyclyl ring. In certain embodiments, $X^1$ is

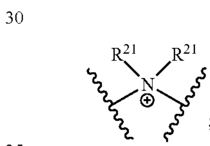

and two $R^{21}$ groups are joined to form an optionally substituted 6 membered heterocyclyl ring. In certain embodiments, $X^1$ is

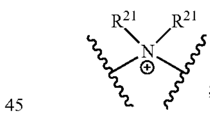

and two $R^{21}$ groups are joined to form an unsubstituted 6 membered heterocyclyl ring. In certain embodiments, $X^1$ is

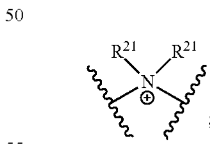

and two $R^{21}$ groups are joined to form an optionally substituted pyrrolidine, piperidine, piperazine, thiomorpholine 1,1-dioxide, or morpholine. In certain embodiments, $X^1$ is

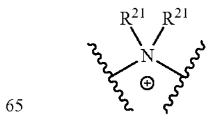

and two $R^{21}$ groups are joined to form an optionally substituted morpholine. In certain embodiments, $X^1$ is

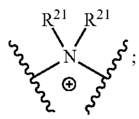

and two $R^{21}$ groups are joined to form an unsubstituted morpholine.

In certain embodiments, $X^1$ is

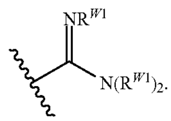

and $R^{22}$ is hydrogen; substituted or unsubstituted carbocyclyl; substituted or unsubstituted alkyl; or

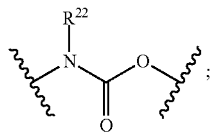

In certain embodiments, $X^1$ is

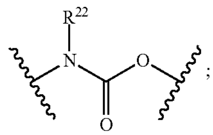

and $R^{22}$ is hydrogen; substituted or unsubstituted carbocyclyl, or substituted or unsubstituted alkyl. In certain embodiments, $X^1$ is

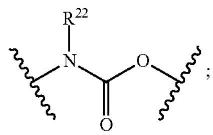

and $R^{22}$ is hydrogen; or substituted or unsubstituted alkyl. In certain embodiments, $X^1$ is

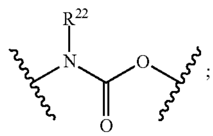

and $R^{22}$ is hydrogen; or substituted or unsubstituted $C_{1-6}$ alkyl. In certain embodiments, $X^1$ is

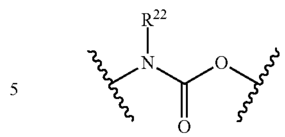

and $R^{22}$ is hydrogen; or substituted or unsubstituted $C_{1-2}$ alkyl. In certain embodiments, $X^1$ is

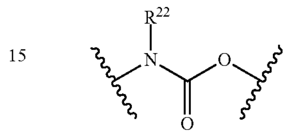

and $R^{22}$ is hydrogen; or substituted or unsubstituted $C_{1-2}$ alkyl.

In certain embodiments, $X^1$ is

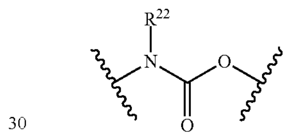

and $R^{22}$ is hydrogen; or substituted $C_{1-2}$ alkyl. In certain embodiments, $X^1$ is

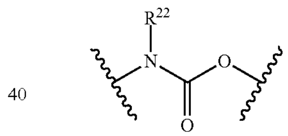

and $R^{22}$ is hydrogen; or unsubstituted $C_{1-2}$ alkyl. In certain embodiments, $X^1$ is

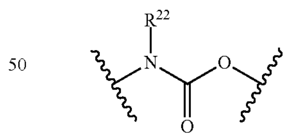

and $R^{22}$ is hydrogen. In certain embodiments, $X^1$ is

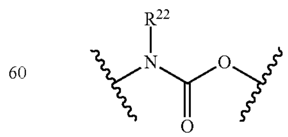

and $R^{22}$ is substituted or unsubstituted $C_{1-2}$ alkyl. In certain embodiments, $X^1$ is

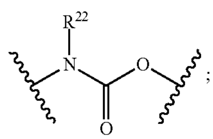

and $R^{22}$ is substituted $C_{1-2}$ alkyl (e.g., haloalkyl). In certain embodiments, $X^1$ is

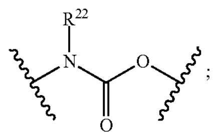

and $R^{22}$ is unsubstituted $C_{1-2}$ alkyl. In certain embodiments, $X^1$ is

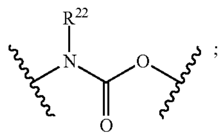

and $R^{22}$ is unsubstituted carbocyclyl (e.g., $C_{3-6}$ cycloalkyl). In certain embodiments, $X^1$ is

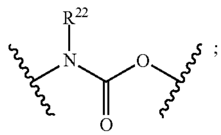

and $R^{22}$ is

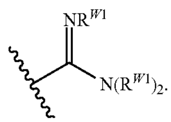

In certain embodiments, $X^1$ is

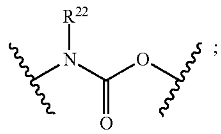

and $R^{22}$ is

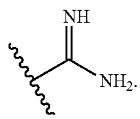 [SMILES: *C(=N)N]

In certain embodiments, $X^1$ is

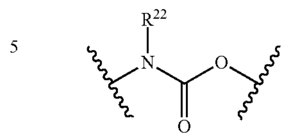

and $R^{22}$ is

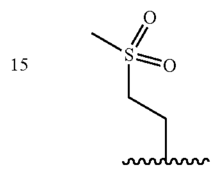

In certain embodiments, $X^1$ is

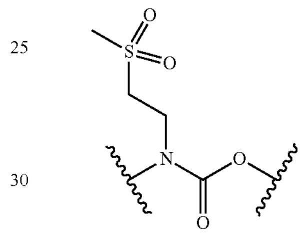

In certain embodiments, $X^1$ is heterocyclylene or heteroarylene. In certain embodiments, $X^1$ is heterocyclylene. In certain embodiments, $X^1$ is a 6-membered heterocyclylene. In certain embodiments, $X^1$ is a piperazinylene. In certain embodiments, $X^1$ is heteroarylene. In certain embodiments, $X^1$ is a 5-membered heteroarylene. In certain embodiments, $X^1$ is an imidazolylene.

In certain embodiments, Ar is substituted or unsubstituted arylene. In certain embodiments, Ar is substituted or unsubstituted phenylene. In certain embodiments, Ar is unsubstituted phenylene. In certain embodiments, Ar is substituted phenylene. In certain embodiments, Ar is phenylene substituted with —$OR^a$, wherein $R^a$ is a substituted or unsubstituted heterocycle. In certain embodiments, Ar is phenylene substituted with —$OR^a$, wherein $R^a$ is a substituted heterocycle. In certain embodiments, $R^a$ is a sugar moiety. In certain embodiments, Ar is

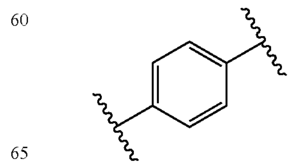

In certain embodiments, Ar is

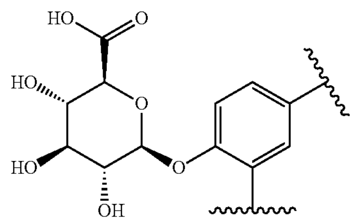

In certain embodiments, each occurrence of Z is independently an amino acid. In certain embodiments, Z is independently a naturally occurring amino acid. In certain embodiments, Z is independently a non-natural amino acid. In certain embodiments, Z is independently alanine, lysine, arginine, histidine, ornithine, or citrulline. In certain embodiments, Z is alanine, lysine, or citrulline. In certain embodiments, Z is alanine or citrulline. In certain embodiments, Z is citrulline. In certain embodiments, Z is alanine.

In certain embodiments, each occurrence of Y is independently an amino acid. In certain embodiments, Y is independently a naturally occurring amino acid. In certain embodiments, Y is independently a non-natural amino acid. In certain embodiments, Y is alanine, valine, leucine, isoleucine, methionine, phenylalanine, or tryptophan. In certain embodiments, Y is valine or phenylalanine. In certain embodiments, Y is valine.

In certain embodiments, each occurrence of m is 1, 2, or 3. In certain embodiments, each occurrence of m is 1 or 2. In certain embodiments, each occurrence of m is 1.

In certain embodiments, $—Z_m—Y_m—$ is -citrulline-valine-. In certain embodiments, $—Z_m—Y_m—$ is -alanine-valine-.

In certain embodiments, E is a bond or an amino acid. In certain embodiments, E is a bond or a naturally occurring amino acid. In certain embodiments, Z is independently a non-natural amino acid. In certain embodiments, E is a bond or a substituted naturally occurring amino acid. In certain embodiments, E is a bond. In certain embodiments, E is a naturally occurring amino acid. In certain embodiments, E is a substituted naturally occurring amino acid. In certain embodiments, E is a substituted lysine.

In certain embodiments, E is of the formula:

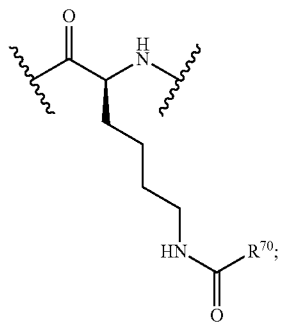

wherein $R^{70}$ is substituted or unsubstituted alkyl, or substituted or unsubstituted heteroalkyl.

In certain embodiments, E is of the formula:

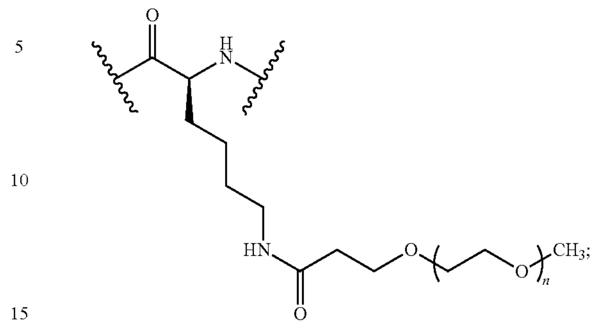

wherein n is 2-30.

In certain embodiments, E is of the formula:

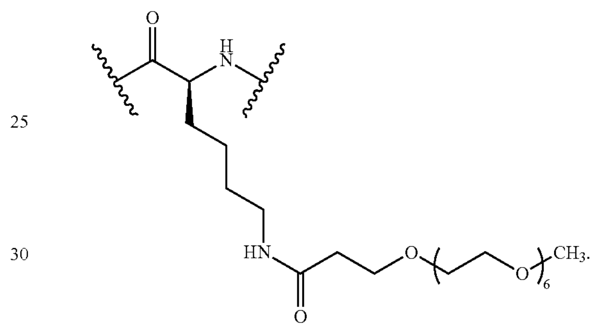

In certain embodiments, k is 0 or 1. In certain embodiments, k is 0. In certain embodiments, k is 1.

In certain embodiments, $Ar^1$ is a bond or substituted or unsubstituted heteroarylene. In certain embodiments, $Ar^1$ is a bond. In certain embodiments, $Ar^1$ is substituted or unsubstituted heteroarylene. In certain embodiments, $Ar^1$ is unsubstituted heteroarylene. In certain embodiments, $Ar^1$ is unsubstituted 5-6-membered heteroarylene. In certain embodiments, $Ar^1$ is unsubstituted 5-membered heteroarylene. In certain embodiments, $Ar^1$ is tetrazolene, triazolene, or imidazolene. In certain embodiments, $Ar^1$ is triazolene. In certain embodiments, $Ar^1$ is

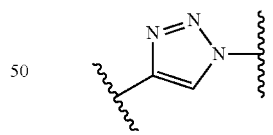

In certain embodiments, k is 1; and $Ar^1$ is a bond. In certain embodiments, k is 1; and $Ar^1$ is

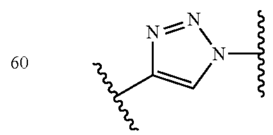

In certain embodiments, $R^{40}$ is substituted or unsubstituted alkylene; or substituted or unsubstituted heteroalkylene. In certain embodiments, $R^{40}$ is substituted or unsubstituted $C_{1-6}$ alkylene; or substituted or unsubstituted $C_{1-40}$ heteroalkylene. In certain embodiments, $R^{40}$ is substituted or unsubstituted alkylene. In certain embodiments, $R^{40}$ is substituted or unsubstituted $C_{1-6}$ alkylene. In certain embodiments, $R^{40}$ is substituted $C_{1-6}$ alkylene. In certain embodiments, $R^{40}$ is unsubstituted $C_{1-6}$ alkylene. In certain embodiments, $R^{40}$ is substituted or unsubstituted heteroalkylene. In certain embodiments, $R^{40}$ is substituted or unsubstituted $C_{1-40}$ heteroalkylene. In certain embodiments, $R^{40}$ is substituted $C_{1-40}$ heteroalkylene. In certain embodiments, $R^{40}$ is unsubstituted $C_{1-40}$ heteroalkylene. In certain embodiments, $R^{40}$ is

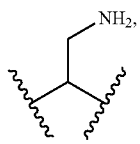 [SMILES: *C(*)CN]

$C_{1-6}$ unsubstituted alkylene,

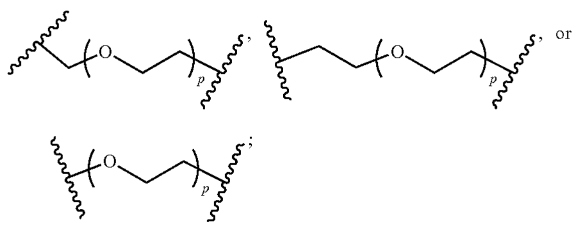

wherein p is 1-8. In certain embodiments, $R^{40}$ is

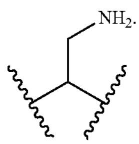 [SMILES: *C(*)CN]

In certain embodiments, $R^{40}$ is

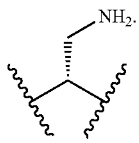

In certain embodiments, $R^{40}$ is

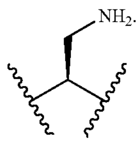

In certain embodiments, $R^{40}$ is $C_{1-6}$ unsubstituted alkylene. In certain embodiments, $R^{40}$ is

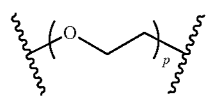

wherein p is 1-8. In certain embodiments, $R^{40}$ is

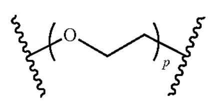

wherein p is 2-8. In certain embodiments, $R^{40}$ is

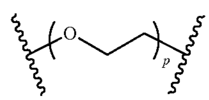

wherein p is 2, 4 or 8. In certain embodiments, $R^{40}$ is

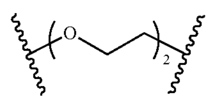

In certain embodiments, $R^{40}$ is

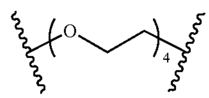

In certain embodiments, $R^{40}$ is

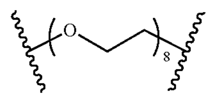

In certain embodiments, $R^{40}$ is

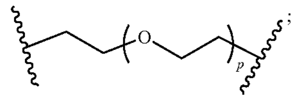

wherein p is 1-8. In certain embodiments $R^{40}$ is

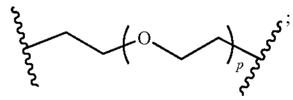

wherein p is 2-8. In certain embodiments, $R^{40}$ is

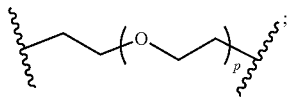

wherein p is 2, 4, or 8. In certain embodiments, $R^{40}$ is

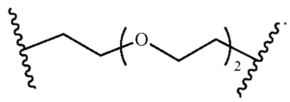

In certain embodiments, $R^{40}$ is

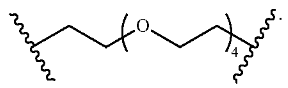

In certain embodiments, $R^{40}$ is

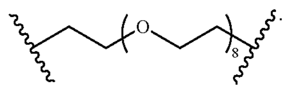

In certain embodiments, $R^{40}$ is

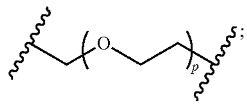

wherein p is 1-8. In certain embodiments, $R^{40}$ is

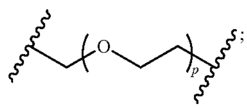

wherein p is 2-8. In certain embodiments, $R^{40}$ is

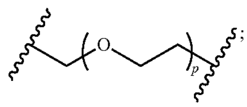

wherein p is 2, 4, or 8. In certain embodiments, $R^{40}$ is

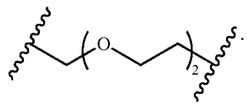

In certain embodiments, $R^{40}$ is

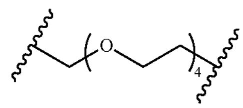

In certain embodiments, $R^{40}$ is

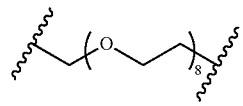

In certain embodiments, A is a group of the formula:

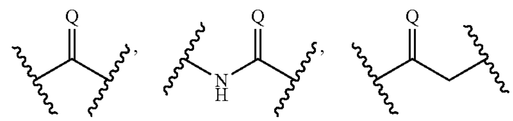

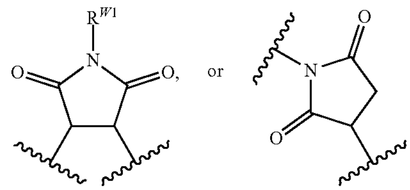

and

Q is —S—, or —O—; and $R^{W1}$ is hydrogen, substituted or unsubstituted alkyl; or a nitrogen protecting group.

In certain embodiments, A is a group of the formula:

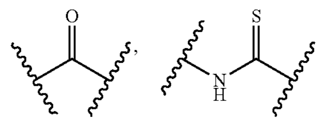

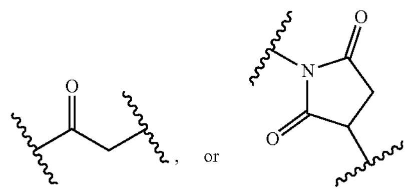

In certain embodiments, A is a group of the formula:

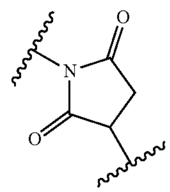

In certain embodiments, L is a group of Formula (L-1):

(L-1)

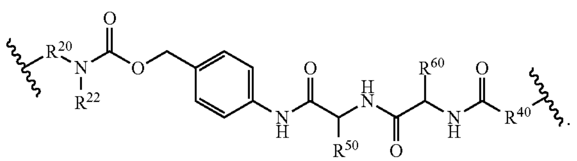

In certain embodiments of Formula (L-1), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of alanine, lysine, arginine, histidine, ornithine, or citrulline; and $R^{60}$ is the sidechain of alanine, valine, leucine, isoleucine, methionine, phenylalanine, or tryptophan.

In certain embodiments, L is a group of Formula (L-1-a):

(L-1-a)

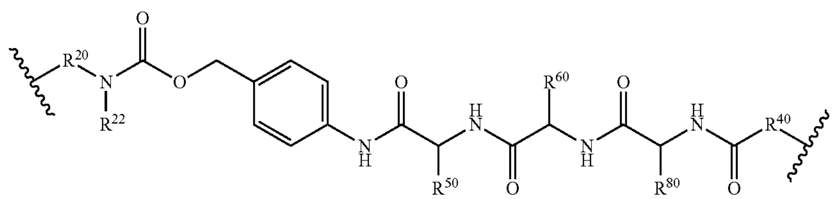

In certain embodiments of Formula (L-1-a), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of alanine, lysine, arginine, histidine, ornithine, or citrulline; $R^{60}$ is the sidechain of alanine, valine, leucine, isoleucine, methionine, phenylalanine, or tryptophan; and $R^{80}$ is a substituted sidechain of a lysine, arginine, histidine, ornithine, or citrulline.

In certain embodiments, L is a group of Formula (L-1-b):

(L-1-b)

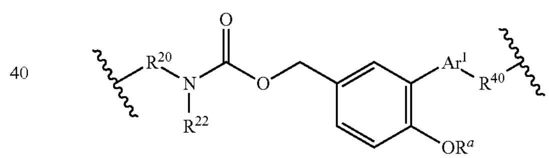

In certain embodiments of Formula (L-1-b), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted heterocycle; $Ar^1$ is substituted or unsubstituted heteroarylene; $R^a$ is a substituted heterocycle; and $R^{40}$ is substituted or unsubstituted $C_{1-6}$ alkylene, or substituted or unsubstituted $C_{1-40}$ heteroalkylene.

In certain embodiments, -L-A- is a group of Formula (L-2):

(L-2)

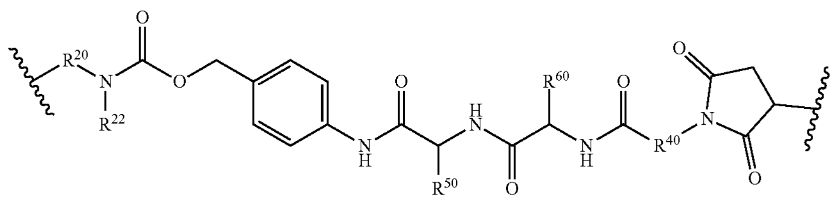

In certain embodiments of Formula (L-2), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of lysine, arginine, histidine, ornithine, or citrulline; and $R^{60}$ is the sidechain of alanine, valine, leucine, isoleucine, methionine, phenylalanine, or tryptophan.

In certain embodiments, -L-A- is a group of Formula (L-2-a):

(L-2-a)

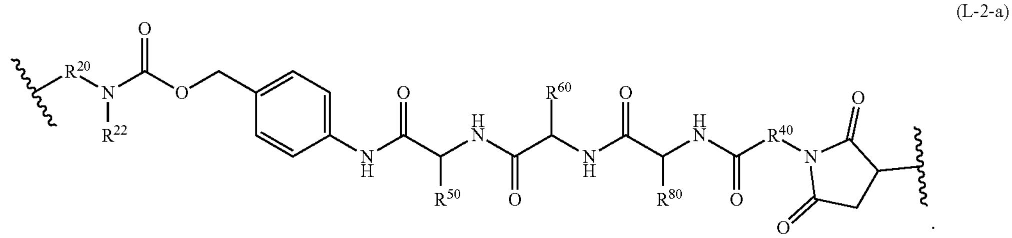

In certain embodiments of Formula (L-2-a), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of alanine, lysine, arginine, histidine, ornithine, or citrulline; $R^{60}$ is the sidechain of alanine, valine, leucine, isoleucine, methionine, phenylalanine, or tryptophan; and $R^{80}$ is a substituted sidechain of a lysine, arginine, histidine, ornithine, or citrulline.

In certain embodiments, -L-A- is a group of Formula (L-2-b):

(L-2-b)

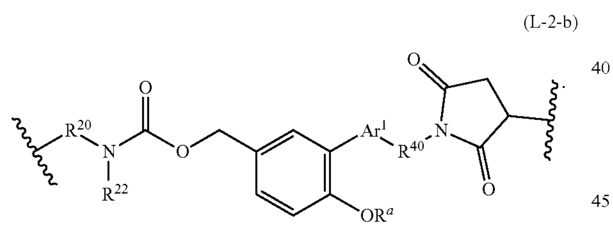

In certain embodiments of Formula (L-2-b), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted heterocycle; $R^a$ is a substituted heterocycle; $Ar^1$ is substituted or unsubstituted heteroarylene; and $R^{40}$ is substituted or unsubstituted $C_{1-6}$ alkylene, or substituted or unsubstituted $C_{1-40}$ heteroalkylene.

In certain embodiments, -L-A- is a group of Formula (L-3):

(L-3)

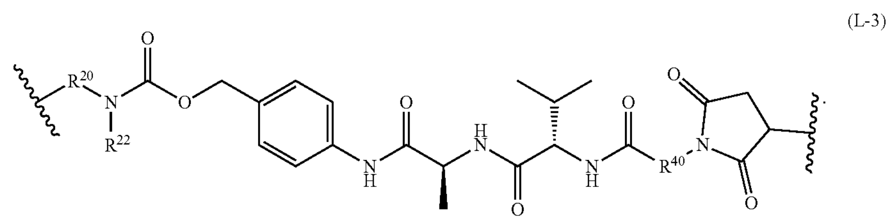

In certain embodiments of Formula (L-3), $R^{20}$ is substituted or unsubstituted $C_{1-6}$ alkylene; $R^{22}$ is hydrogen, or substituted or unsubstituted $C_{1-6}$ alkyl; and $R^{40}$ is substituted or unsubstituted $C_{1-6}$ alkylene, or substituted or unsubstituted $C_{1-40}$ heteroalkylene.

In certain embodiments, -L-A- is a group of Formula (L-3-a):

(L-3-a)

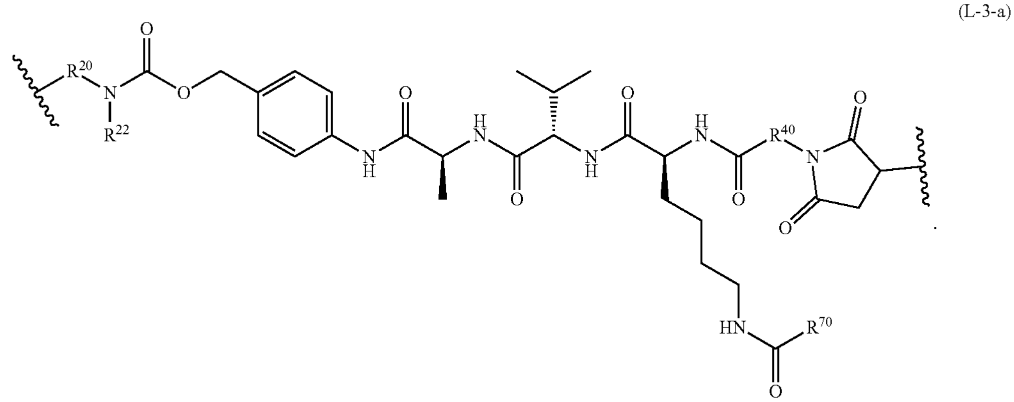

In certain embodiments of Formula (L-3-a), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; and $R^{70}$ is substituted or unsubstituted heteroalkyl.

In certain embodiments, -L-A- is a group of Formula (L-3-b):

(L-3-b)

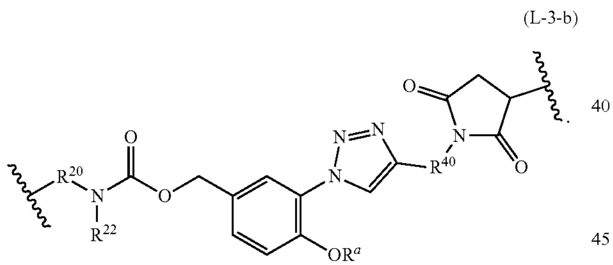

In certain embodiments of Formula (L-3-b), $R^{20}$ is substituted or unsubstituted $C_{1-6}$ alkylene; $R^{22}$ is hydrogen, or substituted or unsubstituted $C_{1-6}$ alkyl; $R^a$ is substituted or unsubstituted heterocycle; and $R^{40}$ is substituted or unsubstituted $C_{1-6}$ alkylene, or substituted or unsubstituted $C_{1-40}$ heteroalkylene.

In certain embodiments, -L-A- is a group of Formula (L-4):

(L-4)

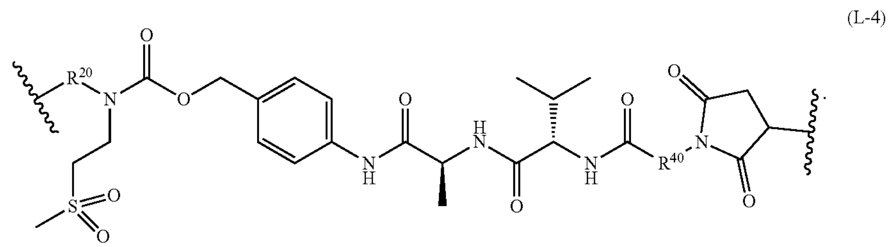

In certain embodiments of Formula (L-4), $R^{20}$ is substituted or unsubstituted $C_{1-6}$ alkylene; and $R^{40}$ is substituted or unsubstituted $C_{1-6}$ alkylene, or substituted or unsubstituted $C_{1-40}$ heteroalkylene.

In certain embodiments, -L-A- is a group of Formula (L-4-a):

(L-4-a)

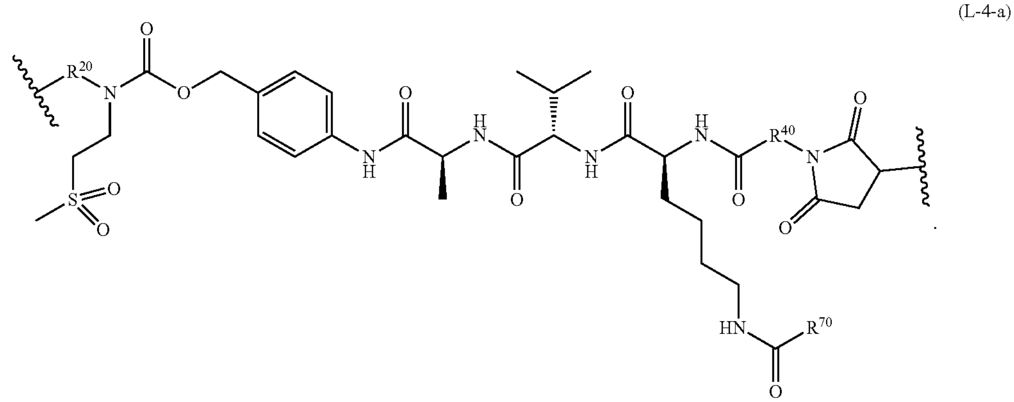

In certain embodiments of Formula (L-4-a), $R^{20}$ is substituted or unsubstituted $C_{1-6}$ alkylene; $R^{40}$ is substituted or unsubstituted $C_{1-6}$ alkylene, or substituted or unsubstituted $C_{1-40}$ heteroalkylene; and $R^{70}$ is substituted or unsubstituted heteroalkyl.

In certain embodiments, -L-A- is a group of Formula (L-4-b):

(L-4-b)

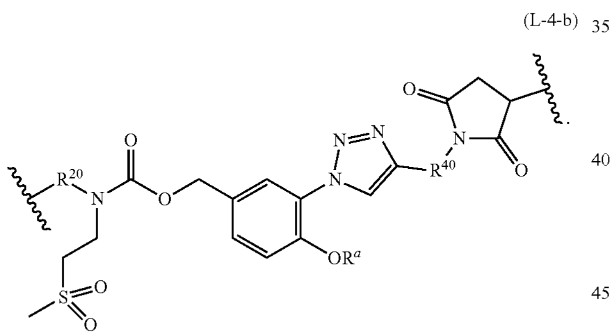

In certain embodiments of Formula (L-4-b), $R^{20}$ is substituted or unsubstituted $C_{1-6}$ alkylene; $R^a$ is substituted or unsubstituted heterocycle; and $R^{40}$ is substituted or unsubstituted $C_{1-6}$ alkylene, or substituted or unsubstituted $C_{1-40}$ heteroalkylene.

In certain embodiments, -L-A- is a group of Formula (L-5):

(L-5)

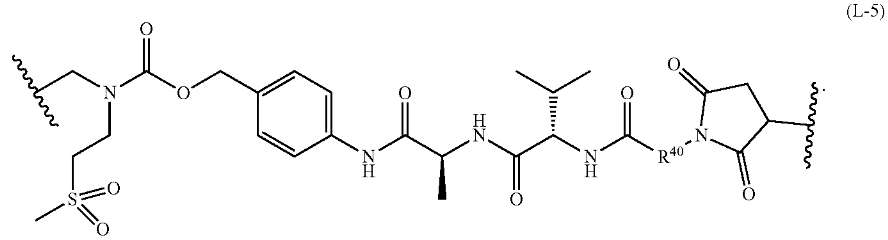

In certain embodiments of Formula (L-5), $R^{40}$ is substituted or unsubstituted $C_{1-6}$ alkylene, or substituted or unsubstituted $C_{1-40}$ heteroalkylene. In certain embodiments of Formula (L-5), $R^{40}$ is substituted or unsubstituted $C_{1-6}$ alkylene. In certain embodiments of Formula (L-5), $R^{40}$ is unsubstituted $C_{1-6}$ alkylene.

In certain embodiments, -L-A- is a group of Formula (L-5-a):

(L-5-a)

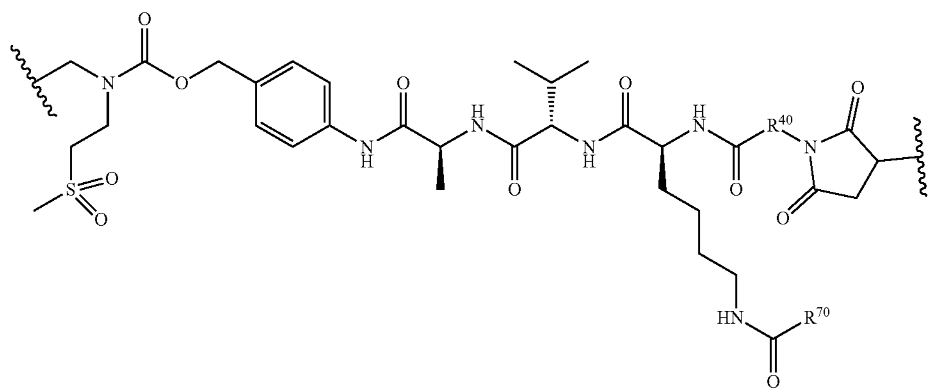

In certain embodiments of Formula (L-5-a), $R^{40}$ is substituted or unsubstituted $C_{1-6}$ alkylene, or substituted or unsubstituted $C_{1-40}$ heteroalkylene; and $R^{70}$ is substituted or unsubstituted heteroalkyl.

In certain embodiments, -L-A- is a group of Formula (L-5-a1):

(L-5-a1)

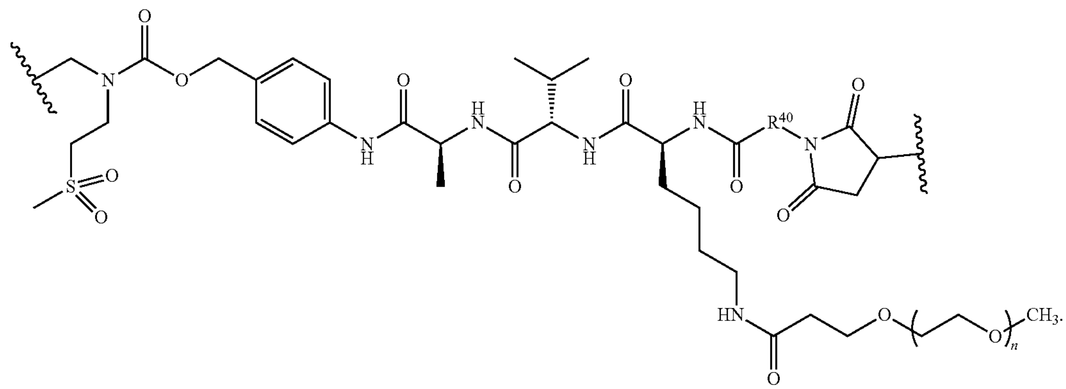

In certain embodiments of Formula (L-5-a1), $R^{40}$ is substituted or unsubstituted $C_{1-6}$ alkylene, or substituted or unsubstituted $C_{1-40}$ heteroalkylene; and n is 2-8.

In certain embodiments, -L-A- is a group of Formula (L-5-b):

(L-5-b)

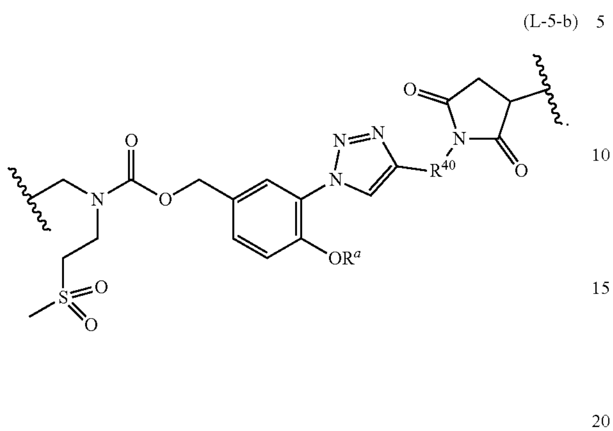

In certain embodiments of Formula (L-5-b), $R^a$ is substituted or unsubstituted heterocycle; and $R^{40}$ is substituted or unsubstituted $C_{1-6}$ alkylene, or substituted or unsubstituted $C_{1-40}$ heteroalkylene.

In certain embodiments, -L-A- is a group of Formula (L-5-b1):

(L-5-b1)

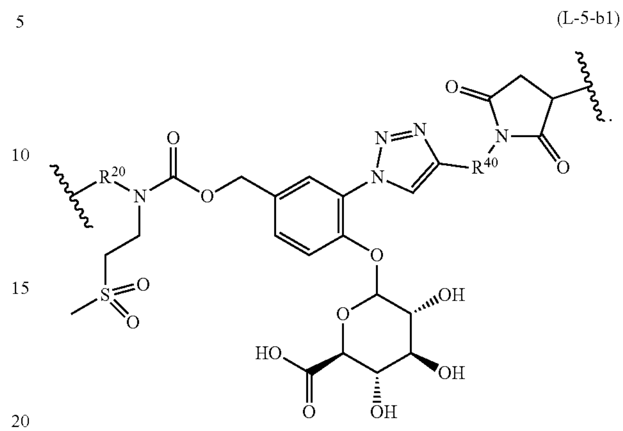

In certain embodiments of Formula (L-5-b), $R^{40}$ is substituted or unsubstituted $C_{1-6}$ alkylene, or substituted or unsubstituted $C_{1-40}$ heteroalkylene.

In certain embodiments, -L-A- is a group of Formula (L-6):

(L-6)

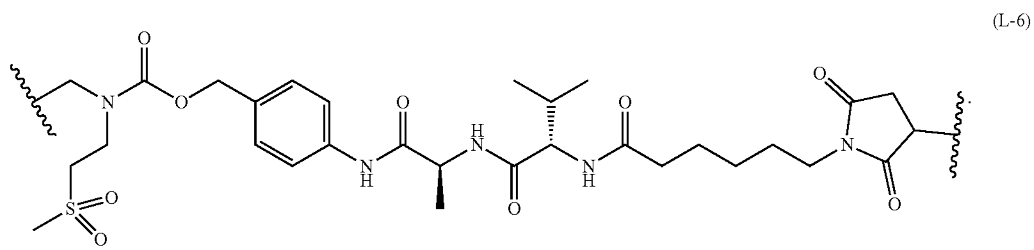 [SMILES: *CN(CCS(C)(=O)=O)C(=O)OCc1ccc(NC(=O)[C@H](C)NC(=O)[C@@H](NC(=O)CCCCCN2C(=O)CC(*)C2=O)C(C)C)cc1]

In certain embodiments, -L-A- is a group of Formula (L-6-a):

(L-6-a)

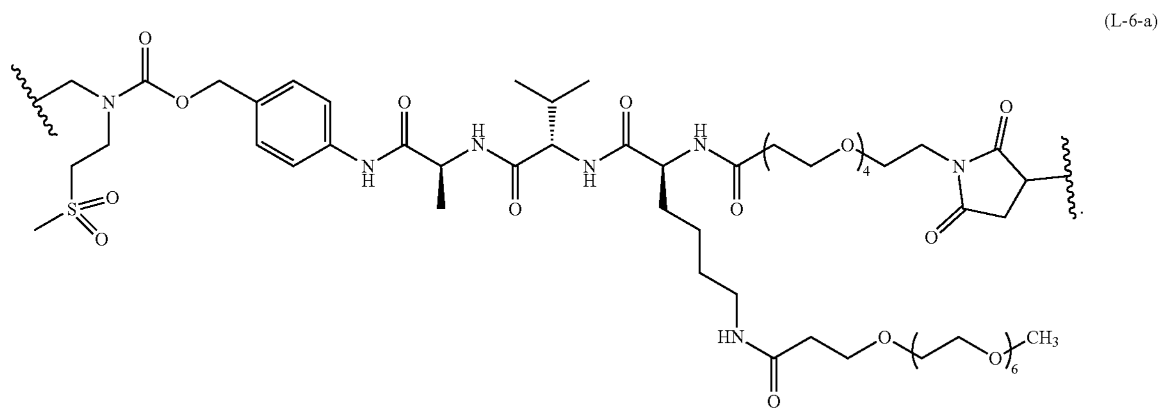

In certain embodiments, -L-A- is a group of Formula (L-6-b):

(L-6-b)

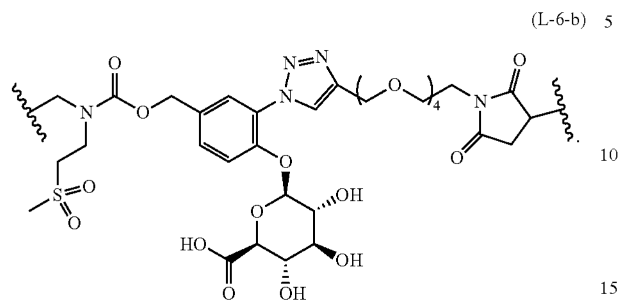

Group $R^7$—Compounds of Formula (III) and (IV)

As generally defined above for compounds of Formula (III) and (IV), $R^7$ is -L-T; wherein L is a bond or group of the formula:

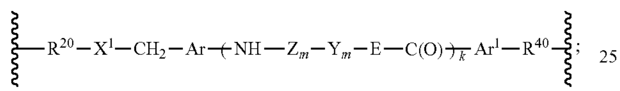

$R^{20}$ is substituted or unsubstituted alkylene; or substituted or unsubstituted heteroalkylene;

$X^1$ is

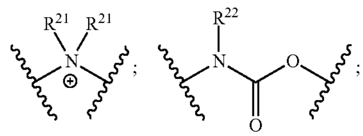

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

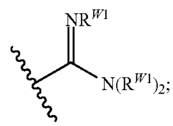

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene; and combinations thereof;

T is hydrogen, —N═C═S,

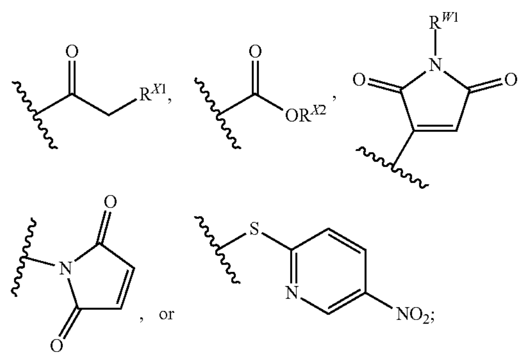

, or $R^{X1}$ is a leaving group (e.g., halogen, tosylate, mesylate, or triflate);

$R^{X2}$ is hydrogen, substituted or unsubstituted alkyl; substituted or unsubstituted heterocyclyl; substituted or unsubstituted aryl; substituted or unsubstituted heteroaryl; or an oxygen protecting group; and $R^{W1}$ is independently hydrogen, substituted or unsubstituted alkyl; or a nitrogen protecting group.

In certain embodiments, L is a bond or group of the formula:

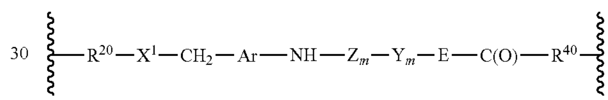

$R^{20}$ is substituted or unsubstituted alkylene; or substituted or unsubstituted heteroalkylene;

$X^1$ is

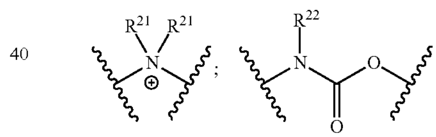

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

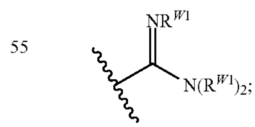

Ar is substituted or unsubstituted arylene;

each occurrence of Z is independently an amino acid;

each occurrence of Y is independently an amino acid;

E is a bond or an amino acid;

m is independently 1, 2, or 3;

$R^{40}$ is substituted or unsubstituted alkylene; or substituted or unsubstituted heteroalkylene; and combinations thereof;

T is hydrogen, —N═C═S,

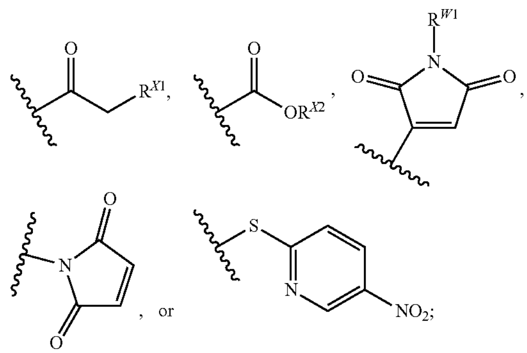

$R^{X1}$ is a leaving group (e.g., halogen, tosylate, mesylate, or triflate);

$R^{X2}$ is hydrogen, substituted or unsubstituted alkyl; substituted or unsubstituted heterocyclyl; substituted or unsubstituted aryl; substituted or unsubstituted heteroaryl; or an oxygen protecting group; and $R^{W1}$ is independently hydrogen, substituted or unsubstituted alkyl; or a nitrogen protecting group.

In certain embodiments, $R^{20}$ is substituted or unsubstituted alkylene. In certain embodiments, $R^{20}$ is unsubstituted alkylene. In certain embodiments, $R^{20}$ is unsubstituted $C_{1-6}$ alkylene. In certain embodiments, $R^{20}$ is unsubstituted $C_{1-5}$ alkylene. In certain embodiments, $R^{20}$ is unsubstituted $C_{1-4}$ alkylene. In certain embodiments, $R^{20}$ is unsubstituted $C_{2-6}$ alkylene. In certain embodiments, $R^{20}$ is unsubstituted $C_{2-5}$ alkylene. In certain embodiments, $R^{20}$ is unsubstituted $C_{2-4}$ alkylene. In certain embodiments, $R^{20}$ is unsubstituted $C_{2-3}$ alkylene. In certain embodiments, $R^{20}$ is unsubstituted methylene. In certain embodiments, $R^{20}$ is unsubstituted ethylene. In certain embodiments, $R^{20}$ is unsubstituted propylene. In certain embodiments, $R^{20}$ is unsubstituted butylene. In certain embodiments, $R^{20}$ is unsubstituted pentylene. In certain embodiments, $R^{20}$ is unsubstituted hexylene.

In certain embodiments, $X^1$ is

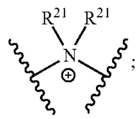

and $R^{21}$ is independently substituted or unsubstituted alkyl; or substituted or unsubstituted carbocyclyl; or two $R^{21}$ groups are joined to form an optionally substituted heterocyclyl ring. In certain embodiments, $X^1$ is

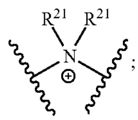

and $R^{21}$ is independently substituted or unsubstituted alkyl; or substituted or unsubstituted carbocyclyl. In certain embodiments, $X^1$ is

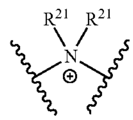

and $R^{21}$ is independently substituted or unsubstituted alkyl. In certain embodiments, $X^1$ is

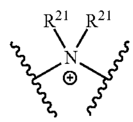

and $R^{21}$ is independently unsubstituted alkyl. In certain embodiments, $X^1$ is

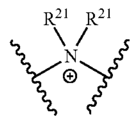

and $R^{21}$ is independently unsubstituted $C_{1-6}$ alkyl. In certain embodiments, $X^1$ is

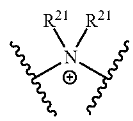

and $R^{21}$ is independently unsubstituted $C_{1-4}$ alkyl. In certain embodiments, $X^1$ is

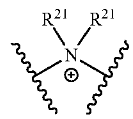

and $R^{21}$ is independently unsubstituted $C_{1-3}$ alkyl. In certain embodiments, $X^1$ is

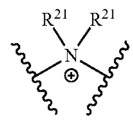

and $R^{21}$ is independently unsubstituted $C_{1-2}$ alkyl. In certain embodiments, $X^1$ is

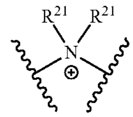

and two $R^{21}$ groups are joined to form an optionally substituted heterocyclyl ring. In certain embodiments, $X^1$ is

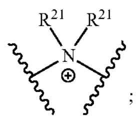

and two $R^{21}$ groups are optionally joined to form an optionally substituted 5-6 membered heterocyclyl ring. In certain embodiments, $X^1$ is

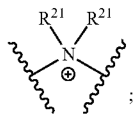

and two $R^{21}$ groups are joined to form an optionally substituted 6 membered heterocyclyl ring. In certain embodiments, $X^1$ is

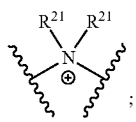

and two $R^{21}$ groups are joined to form an unsubstituted 6 membered heterocyclyl ring. In certain embodiments, $X^1$ is

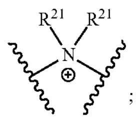

and two $R^{21}$ groups are joined to form an optionally substituted pyrrolidine, piperidine, piperazine, thiomorpholine 1,1-dioxide, or morpholine. In certain embodiments, $X^1$ is

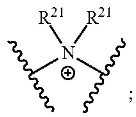

and two $R^{21}$ groups are joined to form an optionally substituted morpholine. In certain embodiments, $X^1$ is

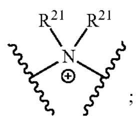

and two $R^{21}$ groups are joined to form an unsubstituted morpholine.

In certain embodiments, $X^1$ is

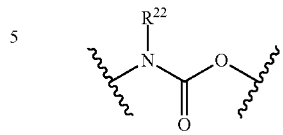

and $R^{22}$ is hydrogen; substituted or unsubstituted carbocyclyl; substituted or unsubstituted alkyl; or

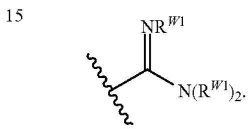

In certain embodiments, $X^1$ is

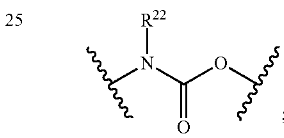

and $R^{22}$ is hydrogen; substituted or unsubstituted carbocyclyl, or substituted or unsubstituted alkyl. In certain embodiments, $X^1$ is

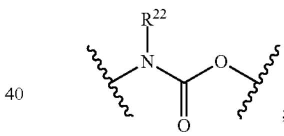

and $R^{22}$ is hydrogen; or substituted or unsubstituted alkyl. In certain embodiments, $X^1$ is

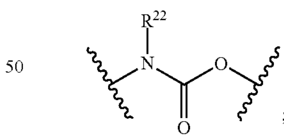

and $R^{22}$ is hydrogen; or substituted or unsubstituted $C_{1-6}$ alkyl. In certain embodiments, $X^1$ is

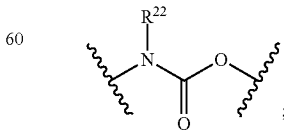

and $R^{22}$ is hydrogen; or substituted or unsubstituted $C_{1-2}$ alkyl. In certain embodiments, $X^1$ is

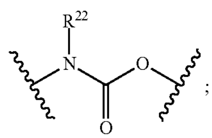

and $R^{22}$ is hydrogen; or substituted or unsubstituted $C_{1-2}$ alkyl. In certain embodiments, $X^1$ is

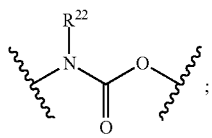

and $R^{22}$ is hydrogen; or substituted $C_{1-2}$ alkyl. In certain embodiments, $X^1$ is

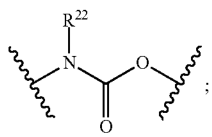

and $R^{22}$ is hydrogen; or unsubstituted $C_{1-2}$ alkyl. In certain embodiments, $X^1$ is

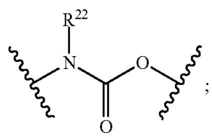

and $R^{22}$ is hydrogen. In certain embodiments, $X^1$ is

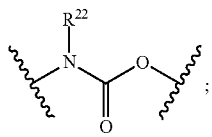

and $R^{22}$ is substituted or unsubstituted $C_{1-2}$ alkyl. In certain embodiments, $X^1$ is

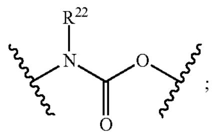

and $R^{22}$ is substituted $C_{1-2}$ alkyl (e.g., haloalkyl). In certain embodiments, $X^1$ is

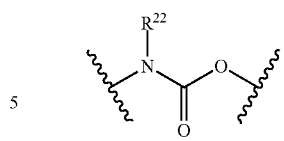

and $R^{22}$ is unsubstituted $C_{1-2}$ alkyl. In certain embodiments, $X^1$ is

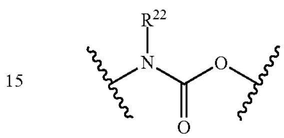

and $R^{22}$ is

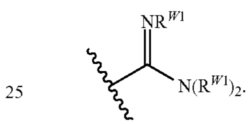

In certain embodiments, $X^1$ is

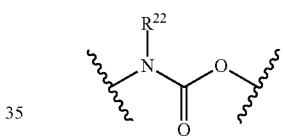

and $R^{22}$ is

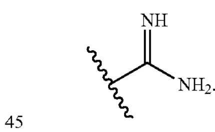

In certain embodiments, $X^1$ is

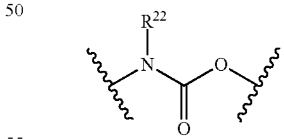

and $R^{22}$ is

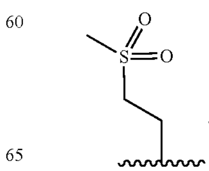

In certain embodiments, $X^1$ is

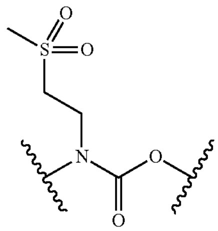

In certain embodiments, $X^1$ is heterocyclylene or heteroarylene. In certain embodiments, $X^1$ is heterocyclylene. In certain embodiments, $X^1$ is a 6-membered heterocyclylene. In certain embodiments, $X^1$ is a piperazinylene. In certain embodiments, $X^1$ is heteroarylene. In certain embodiments, $X^1$ is a 5-membered heteroarylene. In certain embodiments, $X^1$ is an imidazolylene.

In certain embodiments, Ar is substituted or unsubstituted arylene. In certain embodiments, Ar is substituted or unsubstituted phenylene. In certain embodiments, Ar is unsubstituted phenylene. In certain embodiments, Ar is substituted phenylene. In certain embodiments, Ar is phenylene substituted with —$OR^a$, wherein $R^a$ is a substituted or unsubstituted heterocycle. In certain embodiments, Ar is phenylene substituted with —$OR^a$, wherein $R^a$ is a substituted heterocycle. In certain embodiments, $R^a$ is a sugar moiety. In certain embodiments, Ar is

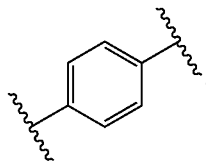

In certain embodiments, Ar is

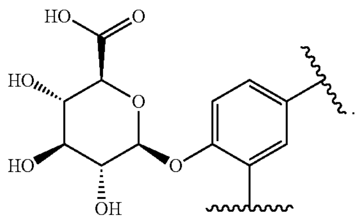 [SMILES: *c1ccc(O[C@@H]2O[C@H](C(=O)O)[C@@H](O)[C@H](O)[C@H]2O)c(*)c1]

In certain embodiments, each occurrence of Z is independently an amino acid. In certain embodiments, Z is independently a naturally occurring amino acid. In certain embodiments, Z is independently alanine, lysine, arginine, histidine, ornithine, or citrulline. In certain embodiments, Z is alanine, lysine, or citrulline. In certain embodiments, Z is alanine or citrulline. In certain embodiments, Z is citrulline. In certain embodiments, Z is alanine.

In certain embodiments, each occurrence of Y is independently an amino acid. In certain embodiments, Y is independently a naturally occurring amino acid. In certain embodiments, Y is alanine, valine, leucine, isoleucine, methionine, phenylalanine, or tryptophan. In certain embodiments, Y is valine or phenylalanine. In certain embodiments, Y is valine.

In certain embodiments, each occurrence of m is 1, 2, or 3. In certain embodiments, each occurrence of m is 1 or 2. In certain embodiments, each occurrence of m is 1.

In certain embodiments, —$Z_m$—$Y_m$— is -citrulline-valine-. In certain embodiments, —$Z_m$—$Y_m$— is -alanine-valine-.

In certain embodiments, E is a bond or an amino acid. In certain embodiments, E is a bond or a naturally occurring amino acid. In certain embodiments, E is a bond or a substituted naturally occurring amino acid. In certain embodiments, E is a bond. In certain embodiments, E is a naturally occurring amino acid. In certain embodiments, E is a substituted naturally occurring amino acid. In certain embodiments, E is a substituted lysine.

In certain embodiments, E is of the formula:

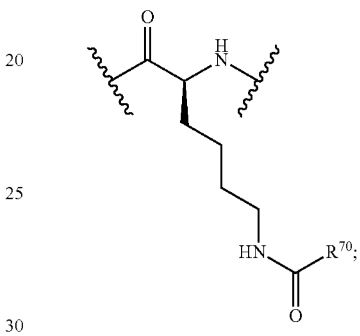

wherein $R^{70}$ is substituted or unsubstituted alkyl, or substituted or unsubstituted heteroalkyl.

In certain embodiments, E is of the formula:

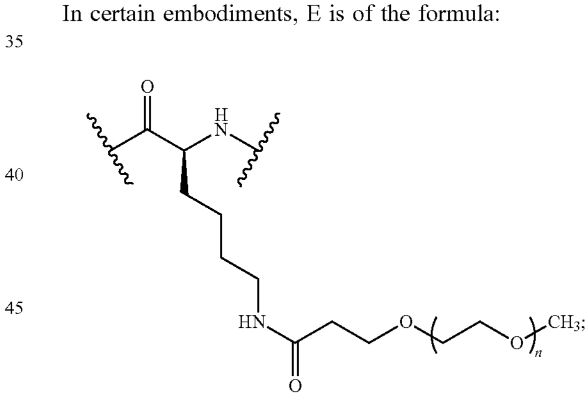

wherein n is 2-30.

In certain embodiments, E is of the formula:

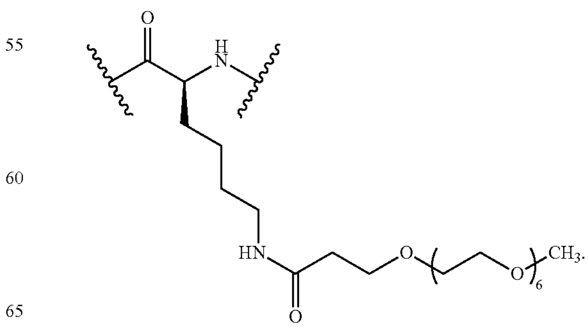

In certain embodiments, k is 0 or 1. In certain embodiments, k is 0. In certain embodiments, k is 1.

In certain embodiments, $Ar^1$ is a bond or substituted or unsubstituted heteroarylene. In certain embodiments, $Ar^1$ is a bond. In certain embodiments, $Ar^1$ is substituted or unsubstituted heteroarylene. In certain embodiments, $Ar^1$ is unsubstituted heteroarylene. In certain embodiments, $Ar^1$ is unsubstituted 5-6-membered heteroarylene. In certain embodiments, $Ar^1$ is unsubstituted 5-membered heteroarylene. In certain embodiments, $Ar^1$ is tetrazolene, triazolene, or imidazolene. In certain embodiments, $Ar^1$ is triazolene. In certain embodiments, $Ar^1$ is

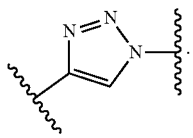 [SMILES: *c1cn(*)nn1]

In certain embodiments, k is 1; and $Ar^1$ is a bond. In certain embodiments, k is 1; and $Ar^1$ is

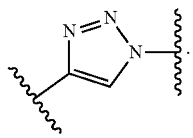 [SMILES: *c1cn(*)nn1]

In certain embodiments, $R^{40}$ is substituted or unsubstituted alkylene; or substituted or unsubstituted heteroalkylene. In certain embodiments, $R^{40}$ is substituted or unsubstituted $C_{1-6}$ alkylene; or substituted or unsubstituted $C_{1-40}$ heteroalkylene. In certain embodiments, $R^{40}$ is substituted or unsubstituted alkylene. In certain embodiments, $R^{40}$ is substituted or unsubstituted $C_{1-6}$ alkylene. In certain embodiments, $R^{40}$ is substituted $C_{1-6}$ alkylene. In certain embodiments, $R^{40}$ is unsubstituted $C_{1-6}$ alkylene. In certain embodiments, $R^{40}$ is substituted or unsubstituted heteroalkylene. In certain embodiments, $R^{40}$ is substituted or unsubstituted $C_{1-40}$ heteroalkylene. In certain embodiments, $R^{40}$ is substituted $C_{1-40}$ heteroalkylene. In certain embodiments, $R^{40}$ is unsubstituted $C_{1-40}$ heteroalkylene. In certain embodiments, $R^{40}$ is

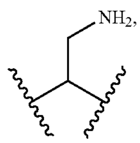 [SMILES: *C(*)CN]

$C_{1-6}$ unsubstituted alkylene,

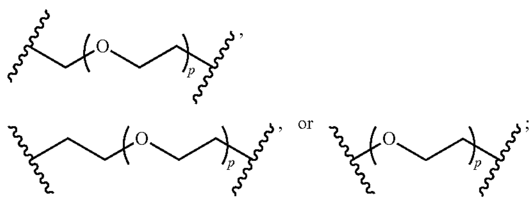

or wherein p is 1-8. In certain embodiments, $R^{40}$ is

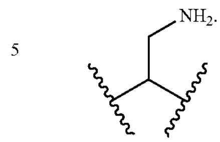

In certain embodiments, $R^{40}$ is

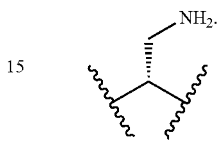

In certain embodiments, $R^{40}$ is

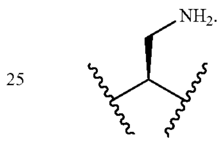

In certain embodiments, $R^{40}$ is $C_{1-6}$ unsubstituted alkylene. In certain embodiments, $R^{40}$ is unsubstituted hexylene. In certain embodiments, $R^{40}$ is unsubstituted pentylene. In certain embodiments, $R^{40}$ is unsubstituted butylene. In certain embodiments, $R^{40}$ is unsubstituted propylene. In certain embodiments, $R^{40}$ is unsubstituted ethylene. In certain embodiments, $R^{40}$ is unsubstituted methylene. In certain embodiments, $R^{40}$ is

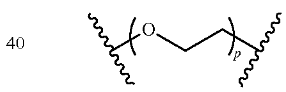

wherein p is 1-8. In certain embodiments, $R^{40}$ is

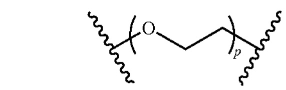

wherein p is 2-8. In certain embodiments, $R^{40}$ is

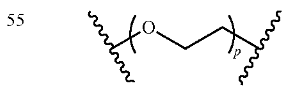

wherein p is 2, 4, or 8. In certain embodiments, $R^{40}$ is

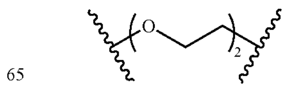

In certain embodiments, $R^{40}$ is

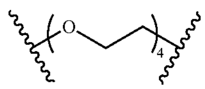

In certain embodiments, $R^{40}$ is

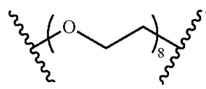

In certain embodiments, $R^{40}$ is

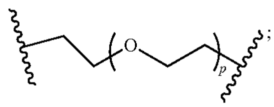

wherein p is 1-8. In certain embodiments, $R^{40}$ is

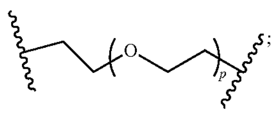

wherein p is 2-8. In certain embodiments, $R^{40}$ is

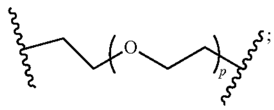

wherein p is 2, 4, or 8. In certain embodiments, $R^{40}$ is

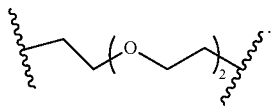

In certain embodiments, $R^{40}$ is

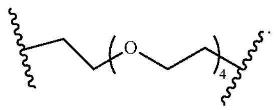

In certain embodiments, $R^{40}$ is

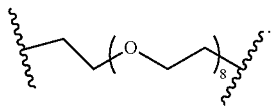

In certain embodiments, $R^{40}$ is

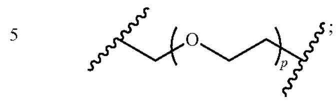

wherein p is 1-8. In certain embodiments, $R^{40}$ is

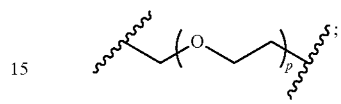

wherein p is 2-8. In certain embodiments, $R^{40}$ is

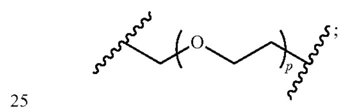

wherein p is 2, 4, or 8. In certain embodiments, $R^{40}$ is

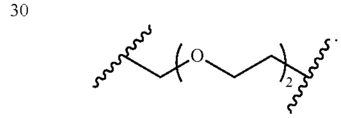

In certain embodiments, $R^{4}$ is

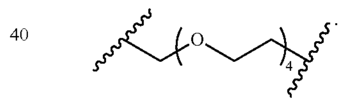

In certain embodiments, $R^{40}$ is

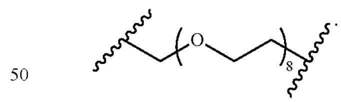

In certain embodiments, T is a group of the formula: —N═C═S,

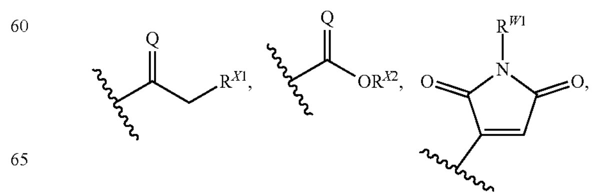

-continued

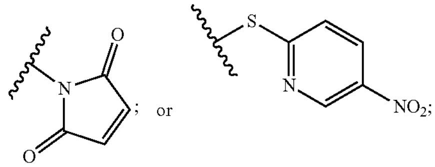

Q is —S—, or —O—; $R^{X1}$ is halogen; $R^{X2}$ is substituted or unsubstituted heterocyclyl; and $R^{W1}$ is hydrogen, substituted or unsubstituted alkyl; or a nitrogen protecting group.

($L^T$-1)

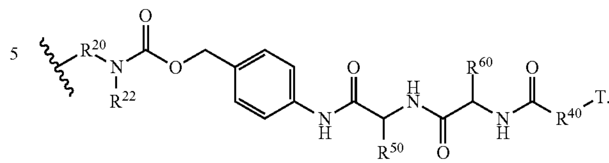

In certain embodiments of Formula ($L^T$-1), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of alanine, lysine, arginine, histidine, ornithine, or citrulline; and $R^{60}$ is the sidechain of alanine, valine, leucine, isoleucine, methionine, phenylalanine, or tryptophan.

In certain embodiments, -L-T is a group of Formula ($L^{T-1}$-a):

($L^T$-1-a)

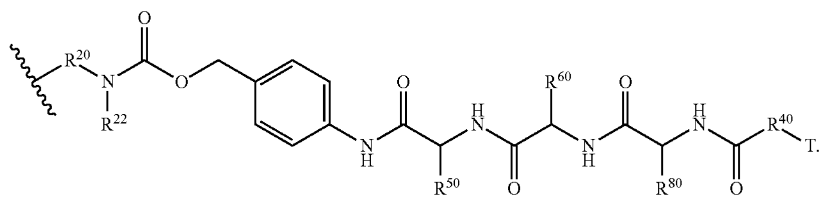

In certain embodiments, T is a group of the formula: —N═C═S,

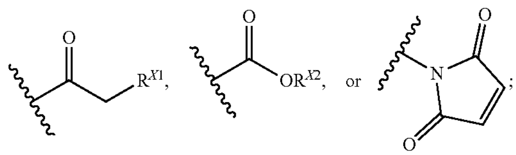

$R^{X1}$ is halogen; and $R^{X2}$ is substituted or unsubstituted heterocyclyl.

In certain embodiments, T is a group of the formula:

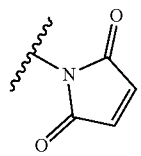

In certain embodiments, T is a group of the formula:

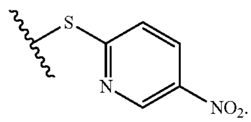 [SMILES: *Sc1ccc([N+](=O)[O-])cn1]

In certain embodiments, -L-T is a group of Formula ($L^T$-1):

In certain embodiments of Formula ($L^T$-1-a), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of alanine, lysine, arginine, histidine, ornithine, or citrulline; $R^{60}$ is the sidechain of alanine, valine, leucine, isoleucine, methionine, phenylalanine, or tryptophan; and $R^{80}$ is a substituted sidechain of a lysine, arginine, histidine, ornithine, or citrulline.

In certain embodiments, -L-T is a group of Formula ($L^{T-1}$-b):

($L^T$-1-b)

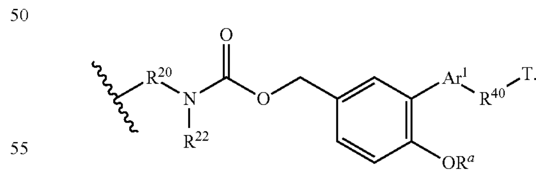

In certain embodiments of Formula ($L^T$-1-b), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted heterocycle; $Ar^1$ is substituted or unsubstituted heteroarylene; $R^a$ is a substituted heterocycle; and $R^{40}$ is substituted or unsubstituted $C_{1-6}$ alkylene, or substituted or unsubstituted $C_{1-40}$ heteroalkylene.

In certain embodiments, -L-T is a group of Formula ($L^T$-2):

($L^T$-2)

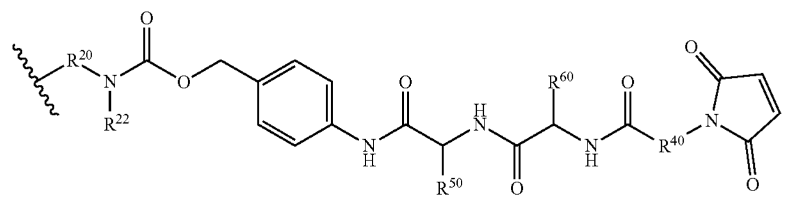

In certain embodiments of Formula ($L^T$-2), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of alanine, lysine, arginine, histidine, ornithine, or citrulline; and $R^{60}$ is the sidechain of alanine, valine, leucine, isoleucine, methionine, phenylalanine, or tryptophan.

In certain embodiments, -L-T is a group of Formula ($L^{T\text{-}2}$-a):

($L^T$-2-a)

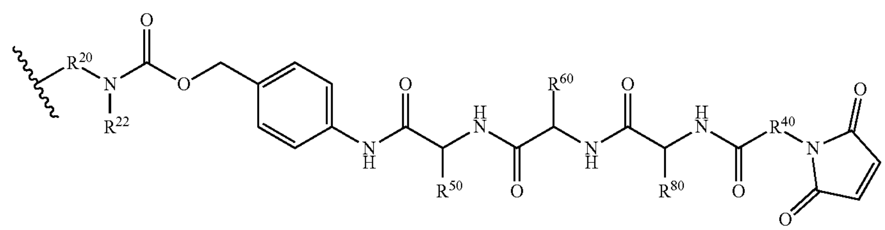

In certain embodiments of Formula ($L^T$-2-a), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; $R^{50}$ is the sidechain of alanine, lysine, arginine, histidine, ornithine, or citrulline; $R^{60}$ is the sidechain of alanine, valine, leucine, isoleucine, methionine, phenylalanine, or tryptophan; and $R^{80}$ is a substituted sidechain of a lysine, arginine, histidine, ornithine, or citrulline.

In certain embodiments, -L-T is a group of Formula (L-2-b):

($L^T$-2-b)

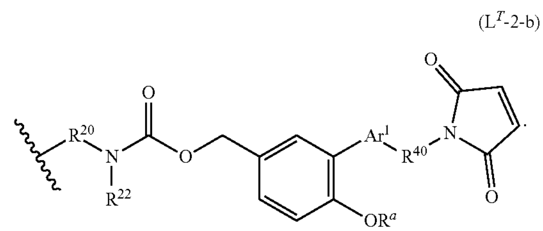

In certain embodiments of Formula ($L^{T\text{-}2}$-b), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted heterocycle; $R^a$ is a substituted heterocycle; $Ar^1$ is substituted or unsubstituted heteroarylene; and $R^{40}$ is substituted or unsubstituted $C_{1-6}$ alkylene, or substituted or unsubstituted $C_{1-40}$ heteroalkylene.

In certain embodiments, -L-T is a group of Formula ($L^T$-3):

($L^T$-3)

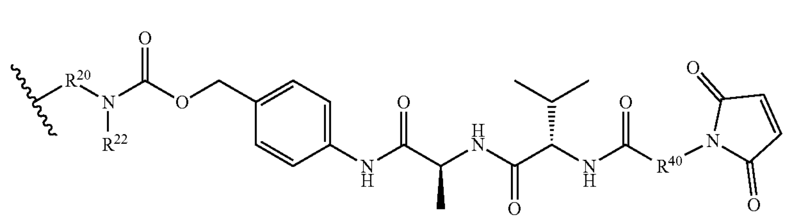

In certain embodiments of Formula ($L^T$-3), $R^{20}$ is substituted or unsubstituted $C_{1-6}$ alkylene; $R^{22}$ is hydrogen, or substituted or unsubstituted $C_{1\_}s$ alkyl; and $R^{40}$ is substituted or unsubstituted $C_{1-6}$ alkylene, or substituted or unsubstituted $C_{1-40}$ heteroalkylene.

In certain embodiments, -L-T is a group of Formula ($L^{T-3}$-a):

($L^T$-3-a)

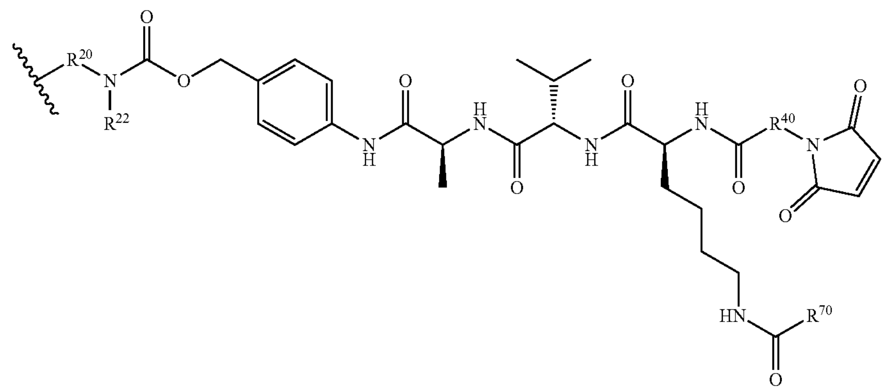

In certain embodiments of Formula ($L^T$-3-a), $R^{20}$ is substituted or unsubstituted $C_{1-6}$ alkylene; $R^{22}$ is hydrogen, or substituted or unsubstituted $C_{1-6}$ alkyl; $R^{40}$ is substituted or unsubstituted $C_{1-6}$ alkylene, or substituted or unsubstituted $C_{1-40}$ heteroalkylene; and $R^{70}$ is substituted or unsubstituted heteroalkyl.

In certain embodiments, -L-T is a group of Formula ($L^{T-3}$-b):

($L^T$-3-b)

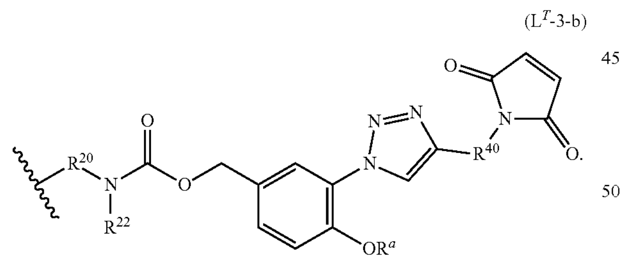

In certain embodiments of Formula ($L^T$-3-b), $R^{20}$ is substituted or unsubstituted $C_{1-6}$ alkylene; $R^{22}$ is hydrogen, or substituted or unsubstituted $C_{1-6}$ alkyl; $R^a$ is substituted or unsubstituted heterocycle; and $R^{40}$ is substituted or unsubstituted $C_{1-6}$ alkylene, or substituted or unsubstituted $C_{1-40}$ heteroalkylene.

In certain embodiments, $-L^1$-T is a group of Formula ($L^T$-4):

(L$^T$-4)

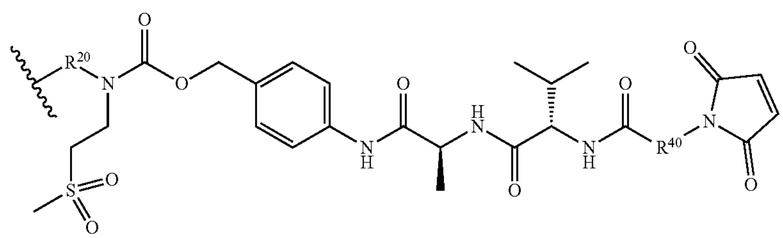

In certain embodiments of Formula (L$^T$-4), $R^{20}$ is substituted or unsubstituted $C_{1-6}$ alkylene; and $R^{40}$ is substituted or unsubstituted $C_{1-6}$ alkylene, or substituted or unsubstituted $C_{1-40}$ heteroalkylene. In certain embodiments of Formula (LT-4), $R^{20}$ is substituted or unsubstituted $C_{1-6}$ alkylene; and $R^{40}$ is substituted or unsubstituted $C_{1-6}$ alkylene.

In certain embodiments, -L-T is a group of Formula (L$^T$-4-a):

(L$^T$-4-a)

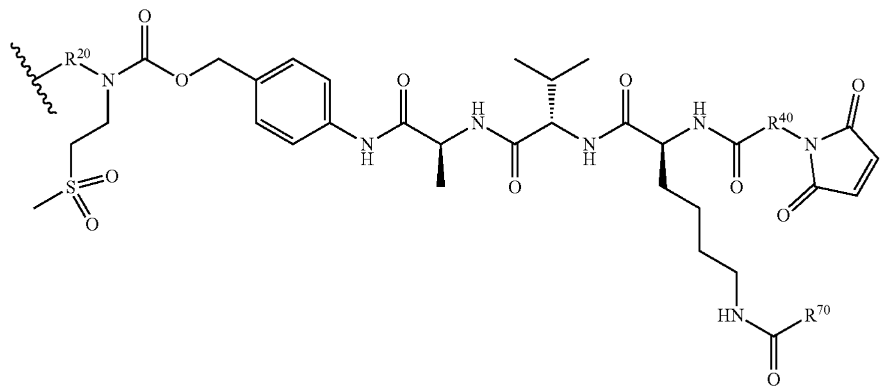

In certain embodiments of Formula (L$^T$-4-a), $R^{20}$ is substituted or unsubstituted $C_{1-6}$ alkylene; $R^{40}$ is substituted or unsubstituted $C_{1-6}$ alkylene, or substituted or unsubstituted $C_{1-40}$ heteroalkylene; and $R^{70}$ is substituted or unsubstituted heteroalkyl.

In certain embodiments, -L-T is a group of Formula (L$^T$-4-b):

(L$^T$-4-b)

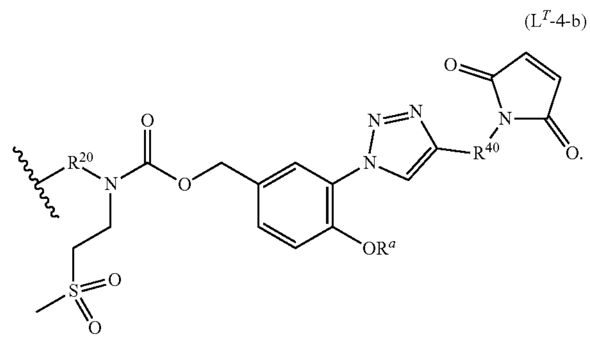

In certain embodiments of Formula (L$^T$-4-b), $R^{20}$ is substituted or unsubstituted $C_{1-6}$ alkylene; $R^a$ is substituted or unsubstituted heterocycle; and $R^{40}$ is substituted or unsubstituted $C_{1-6}$ alkylene, or substituted or unsubstituted $C_{1-40}$ heteroalkylene.

In certain embodiments, -L-T is a group of Formula (L$^T$-5):

(L$^T$-5)

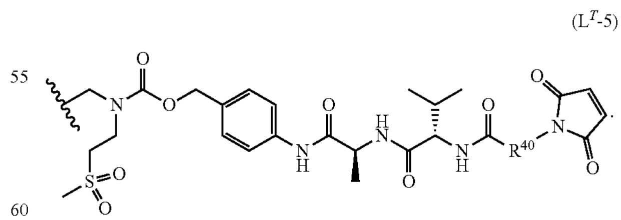

In certain embodiments of Formula (L$^T$-5), $R^{40}$ is substituted or unsubstituted $C_{1-6}$ alkylene. In certain embodiments of Formula (LT-5), $R^{40}$ is unsubstituted $C_{1-6}$ alkylene.

In certain embodiments, -L-T is a group of Formula (L$^T$-5-a):

($L^T$-5-a)

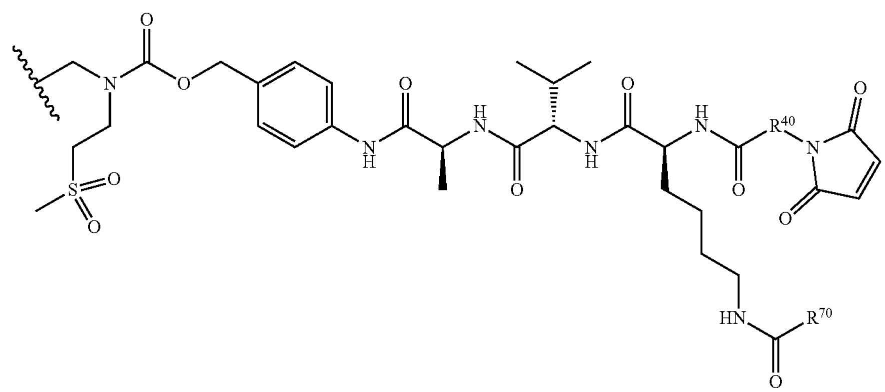

In certain embodiments of Formula ($L^T$-5-a), $R^{40}$ is substituted or unsubstituted $C_{1-6}$ alkylene, or substituted or unsubstituted $C_{1-40}$ heteroalkylene; and $R^{70}$ is substituted or unsubstituted heteroalkyl.

In certain embodiments, -L-T is a group of Formula ($L^T$-5-a1):

($L^T$-5-a1)

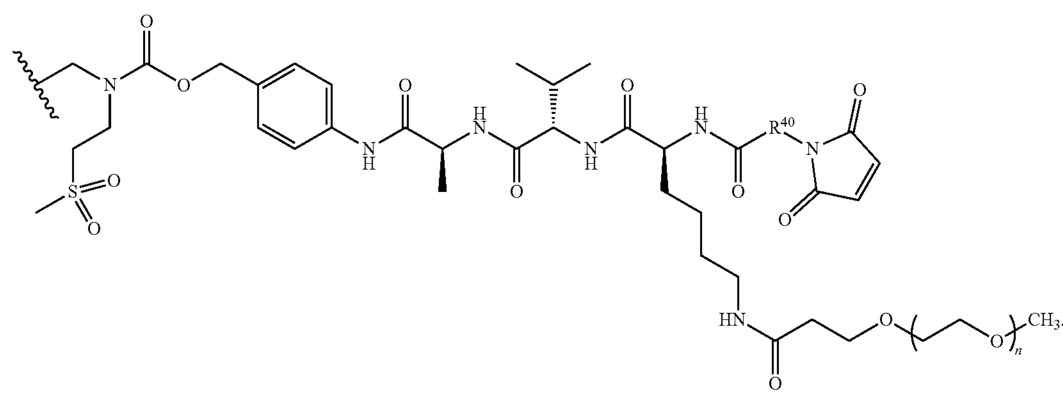

In certain embodiments of Formula ($L^T$-5-a1), $R^{40}$ is substituted or unsubstituted $C_{1-6}$ alkylene, or substituted or unsubstituted $C_{1-40}$ heteroalkylene; and n is 2-8.

In certain embodiments, -L-T is a group of Formula ($L^T$-5-b):

($L^T$-5-b)

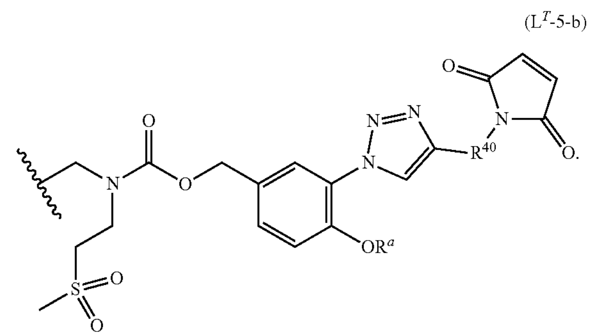

In certain embodiments of Formula ($L^T$-5-b), $R^a$ is substituted or unsubstituted heterocycle; and $R^{40}$ is substituted or unsubstituted $C_{1-6}$ alkylene, or substituted or unsubstituted $C_{1-40}$ heteroalkylene.

In certain embodiments, -L-T is a group of Formula ($L^T$-5-b1):

($L^T$-5-b1)

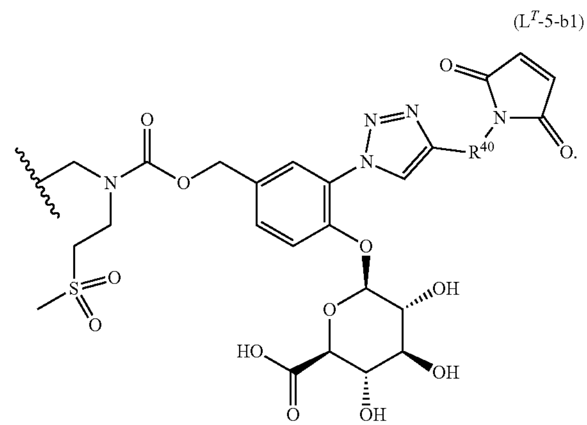

In certain embodiments of Formula (L T-5-b), $R^{40}$ is substituted or unsubstituted $C_{1-6}$ alkylene, or substituted or unsubstituted $C_{1-40}$ heteroalkylene.

In certain embodiments, -$L^1$-T is a group of Formula (LT-6):

($L^T$-6)

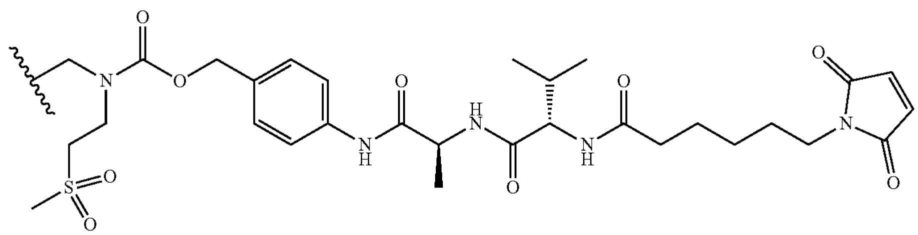

In certain embodiments, -L-T is a group of Formula ($L^T$-6-a):

($L^T$-6-a)

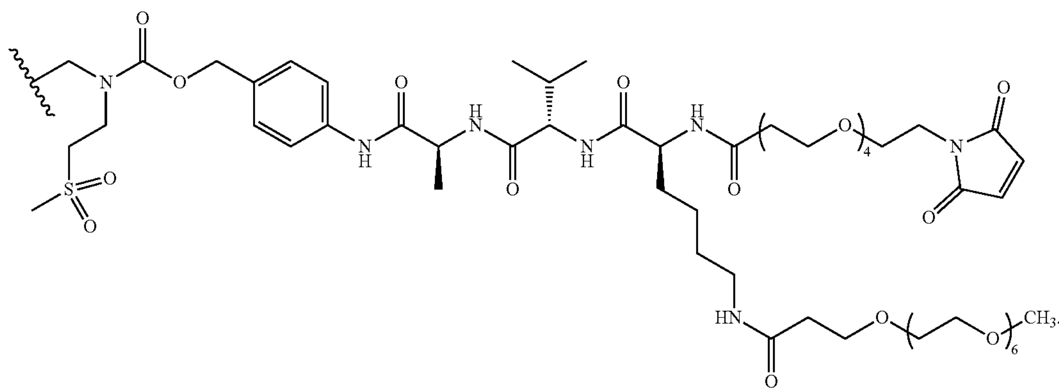

In certain embodiments, -L-T is a group of Formula ($L^T$-6-b):

($L^T$-6-b)

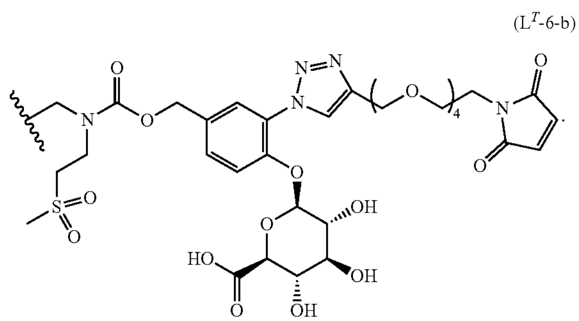

Group $R^8$

As generally defined above, $R^8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{I1}$; —C(═O)$R^{I2}$; —$CO_2R^{I1}$; —CN; —SCN; —$SR^{I1}$; —$SOR^{I1}$; —$SO_2R^{I2}$; —$NO_2$; —$N_3$; —$N(R^{I2})_2$; —$NR^{I2}$C(═O)$R^{I2}$; —$NR^{I2}$C(═O)$N(R^{I2})_2$; —OC(═O)$OR^{I1}$; —OC(═O)$R^{I2}$; —OC(═O)$N(R^{I2})_2$; —$NR^{I2}$C(═O)$OR^{I1}$; or —$C(R^{I2})_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{I2}$ groups are optionally joined to form a heterocyclyl or heteroaryl ring.

In certain embodiments, $R^8$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —$OR^{I1}$; —C(═O)$R^{I2}$; —$CO_2R^{I1}$; —CN; —SCN; —$SR^{I1}$; —$SOR^{I1}$; —$SO_2R^{I2}$; —$NO_2$; —$N_3$; —$N(R^{I2})_2$; —$NR^{I2}$C(═O)$R^{I2}$; —$NR^{I2}$C(═O)$N(R^{I2})_2$; —OC(═O)$OR^{I1}$; —OC(═O)$R^{I2}$; —OC(═O)$N(R^{I2})_2$; —$NR^{I2}$C(═O)$OR^{I1}$; —$CH_2(OR^{I1})$, —$CH(OR^{I1})_2$, —$CH_2OC$(═O)$R^{I2}$, or —$C(R^{I2})_3$.

In certain embodiments, $R^8$ is hydrogen.

In certain embodiments, $R^8$ is halogen, e.g., —F, —Cl, —Br, or —I.

In certain embodiments, $R^8$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl.

In certain embodiments, $R^8$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, $R^8$ is substituted or unsubstituted alkynyl, e.g., substituted or unsubstituted $C_{2-6}$ alkynyl, substituted or unsubstituted $C_{2-3}$alkynyl, substituted or unsubstituted $C_{3-4}$ alkynyl, substituted or unsubstituted $C_{4-5}$ alkynyl, or substituted or unsubstituted $C_{5-6}$ alkynyl.

In certain embodiments, $R^8$ is substituted or unsubstituted carbocyclyl, e.g., substituted or unsubstituted $C_{3-6}$ carbocyclyl, substituted or unsubstituted $C_{3-4}$ carbocyclyl, substituted or unsubstituted $C_{4-5}$ carbocyclyl, or substituted or unsubstituted $C_{5-6}$ carbocyclyl.

In certain embodiments, $R^8$ is substituted or unsubstituted heterocyclyl, e.g., substituted or unsubstituted 3-6 membered heterocyclyl, substituted or unsubstituted 3-4 membered heterocyclyl, or substituted or unsubstituted 4-5 membered heterocyclyl.

In certain embodiments, $R^8$ is substituted or unsubstituted aryl, e.g., substituted or unsubstituted phenyl.

In certain embodiments, $R^8$ is substituted or unsubstituted heteroaryl, e.g., substituted or unsubstituted 5-6 membered heteroaryl.

In certain embodiments, $R^8$ is $—OR^{I1}$. In certain embodiments, $R^8$ is $—C(=O)R^{I2}$. In certain embodiments, $R^8$ is $—CO_2R^{I1}$. In certain embodiments, $R^8$ is —CN. In certain embodiments, $R^8$ is —SCN. In certain embodiments, $R^8$ is $—SR^{I1}$. In certain embodiments, $R^8$ is $—SOR^{I1}$. In certain embodiments, $R^8$ is $—SO_2R^{I2}$. In certain embodiments, $R^8$ is $—NO_2$. In certain embodiments, $R^8$ is $—N_3$. In certain embodiments, $R^8$ is $—N(R^{I2})_2$. In certain embodiments, $R^8$ is $—NR^2C(=O)R^2$. In certain embodiments, $R^8$ is $—NR^{I2}C(=O)N(R^{I2})_2$. In certain embodiments, $R^8$ is $—OC(=O)OR^{I1}$. In certain embodiments, $R^8$ is $—OC(=O)R^{I2}$. In certain embodiments, $R^8$ is $—OC(=O)N(R^2)_2$. In certain embodiments, $R^8$ is $—NR^{I2}C(=O)OR^{I1}$. In certain embodiments, $R^8$ is $—CH_2(OR^{I1})$. In certain embodiments, $R^8$ is $—CH(OR^1)_2$. In certain embodiments, $R^8$ is $—CH_2OC(=O)R^2$. In certain embodiments, $R^8$ is $—C(R^{I2})_3$.

In certain embodiments, at least one instance of $R^{I1}$ is independently hydrogen.

In certain embodiments, at least one instance of $R^{I1}$ is an oxygen protecting group if attached to oxygen or a sulfur protecting group if attached to sulfur.

In certain embodiments, at least one instance of $R^{I1}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl.

In certain embodiments, at least one instance of $R^{I1}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, at least one instance of $R^{I1}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl.

In certain embodiments, at least one instance of $R^{I1}$ is substituted or unsubstituted carbocyclyl, e.g., substituted or unsubstituted $C_{3-6}$carbocyclyl, substituted or unsubstituted $C_{3-4}$ carbocyclyl, substituted or unsubstituted $C_{4-5}$ carbocyclyl, or substituted or unsubstituted $C_{5-6}$ carbocyclyl.

In certain embodiments, at least one instance of $R^{I1}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, at least one instance of $R^{I1}$ is substituted or unsubstituted aryl, e.g., substituted or unsubstituted phenyl.

In certain embodiments, at least one instance of $R^{I1}$ is substituted or unsubstituted heteroaryl, e.g., substituted or unsubstituted 5-6 membered heteroaryl.

In certain embodiments, at least one instance of $R^{I1}$ is acyl.

In certain embodiments, at least one instance of $R^{I2}$ is independently hydrogen.

In certain embodiments, at least one instance of $R^{I2}$ is a nitrogen protecting group if attached to nitrogen.

In certain embodiments, at least one instance of $R^{I2}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl.

In certain embodiments, at least one instance of $R^2$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, at least one instance of $R^{I2}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl.

In certain embodiments, at least one instance of $R^{I2}$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, at least one instance of $R^{I2}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, at least one instance of $R^{I2}$ is substituted or unsubstituted aryl, e.g., substituted or unsubstituted phenyl.

In certain embodiments, at least one instance of $R^{I2}$ is substituted or unsubstituted heteroaryl, e.g., substituted or unsubstituted 5-6 membered heteroaryl.

In certain embodiments, at least one instance of $R^{I2}$ is acyl.

In certain embodiments, at least one instance of $R^{I2}$ is hydroxyl; substituted hydroxyl; thiol; substituted thiol; amino; or substituted amino.

In certain embodiments, two $R^{I2}$ groups are optionally joined to form a heterocyclyl or heteroaryl ring.

Group $R^9$

As generally defined herein, $R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{G1}$; —C(═O)$R^{G2}$; —$CO_2R^{G1}$; —CN; —SCN; —$SR^{G1}$; —$SOR^{G1}$; —$SO_2R^{G2}$; —$NO_2$; —$N_3$; —$N(R^{G})_2$; —$NR^{G2}$C(═O)$R^{G2}$; —$NR^{G2}$C(═O)$N(R^{G2})_2$; —OC(═O)$OR^{G1}$; —OC(═O)$R^{G2}$; —OC(═O)$N(R^{G2})_2$; —$NR^{G2}$C(═O)$OR^{G1}$; or —$C(R^{G2})_3$; wherein each occurrence of $R^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{G2}$ groups are optionally joined to form a heterocyclyl or heteroaryl ring; or $R^4$ and $R^9$ are optionally taken together with the intervening carbon atoms to form an optionally substituted cyclic moiety; or $R^6$ and $R^9$ are optionally taken together with the intervening carbon atoms to form an optionally substituted cyclic moiety.

In certain embodiments, $R^4$ and $R^9$ are optionally taken together with the intervening carbon atoms to form an optionally substituted cyclic moiety. In certain embodiments, $R^6$ and $R^9$ are optionally taken together with the intervening carbon atoms to form an optionally substituted cyclic moiety.

In certain embodiments, $R^9$ is hydrogen.

Group $R^{10}$

As generally defined herein, $R^{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{B1}$; —C(═O)$R^{B2}$; —$CO_2R^{B2}$; —CN; —SCN; —$SR^{B1}$; —$SOR^{B1}$; $SO_2R^{B2}$; —$NO_2$; —$N_3$; ═O; ═$N(R^{B2})$; ═S; —$N(R^{B2})_2$; —$NR^{B2}$C(═O)$R^{B2}$; —$NR^{B2}$C(═O)N$(R^{B2})_2$; —OC(═O)$OR^{B1}$; —OC(═O)$R^{B2}$; —OC(═O)N$(R^{B2})_2$; —$NR^{B2}$C(═O)$OR^{B1}$; or —$C(R^{B2})_3$; wherein each occurrence of $R^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl; substituted thiol; amino; or substituted amino; or two $R^{B2}$ groups are optionally joined to form a heterocyclyl or heteroaryl ring; or $R^1$ and $R^{10}$ are optionally taken together with the intervening carbon atoms to form an optionally substituted cyclic moiety; or $R^{10}$ and $R^3$ are optionally taken together with the intervening carbon atoms to form an optionally substituted cyclic moiety.

In certain embodiments, $R^1$ and $R^{10}$ are optionally taken together with the intervening carbon atoms to form an optionally substituted cyclic moiety. In certain embodiments, $R^{10}$ and $R^3$ are optionally taken together with the intervening carbon atoms to form an optionally substituted cyclic moiety.

In certain embodiments, $R^{10}$ is hydrogen.

Group $R^{11}$

As generally defined herein, $R^{11}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or —C(═O)$R^{H1}$; wherein $R^{H1}$ is hydrogen, substituted or unsubstituted alkyl; —$OR^{H9}$; —OC(═O)$R^{H9}$; —$N(R^{H9})_2$; or —NHC(═O)$R^{H9}$; wherein each occurrence of $R^{H9}$ is independently hydrogen; substituted or unsubstituted alkyl; an oxygen protecting group when attached to an oxygen atom; a nitrogen protecting group when attached to a nitrogen atom; or two $R^{H9}$ groups are joined to form a substituted or unsubstituted heterocyclic or substituted or unsubstituted heteroaryl ring.

In certain embodiments, $R^{11}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl.

In certain embodiments, $R^{11}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, $R^{11}$ is substituted or unsubstituted alkynyl, e.g., substituted or unsubstituted $C_{2-6}$ alkynyl, substituted or unsubstituted $C_{2-3}$alkynyl, substituted or unsubstituted $C_{3-4}$ alkynyl, substituted or unsubstituted $C_{4-5}$ alkynyl, or substituted or unsubstituted $C_{5-6}$ alkynyl.

In certain embodiments, $R^{11}$ is substituted or unsubstituted carbocyclyl, e.g., substituted or unsubstituted $C_{3-6}$ carbocyclyl, substituted or unsubstituted $C_{3-4}$ carbocyclyl, substituted or unsubstituted $C_{4-5}$ carbocyclyl, or substituted or unsubstituted $C_{5-6}$ carbocyclyl.

In certain embodiments, $R^{11}$ is substituted or unsubstituted heterocyclyl, e.g., substituted or unsubstituted 3-6 membered heterocyclyl, substituted or unsubstituted 3-4 membered heterocyclyl, or substituted or unsubstituted 4-5 membered heterocyclyl.

In certain embodiments, $R^8$ is substituted or unsubstituted aryl, e.g., substituted or unsubstituted phenyl.

In certain embodiments, $R^{11}$ is substituted or unsubstituted heteroaryl, e.g., substituted or unsubstituted 5-6 membered heteroaryl.

In certain embodiments, $R^{11}$ is hydrogen; an oxygen protecting group; or substituted or unsubstituted alkyl. In certain embodiments, $R^{11}$ is —$CH_3$.

Additional Embodiments of Formula (I) and (II)

Various combinations of the above embodiments are further contemplated herein. One of skill in the art would appreciate that the various embodiments described herein may be combined in various ways and are contemplated by the inventors.

In certain embodiments of the compound of Formula (I) and (II), $R^1$ and $R^2$ are each hydrogen or together form ═O; and $R^{10}$ and $R^3$ are hydrogen; or $R^4$ and $R^9$ are optionally taken together with the intervening carbon atoms to form an optionally substituted cyclic moiety; or $R^6$ and $R^9$ are optionally taken together with the intervening carbon atoms to form an optionally substituted cyclic moiety.

In certain embodiments of the compound of Formula (I) and (II), $R^1$ is —$OR^{A1}$; wherein $R^{A1}$ is hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and $R^{10}$ and $R^3$ are hydrogen; or $R^1$ and $R^4$ are optionally taken together with the intervening carbon atoms to form an optionally substituted cyclic moiety; or $R^4$ and $R^9$ are optionally taken together with the intervening carbon atoms to form an optionally substituted cyclic moiety; or $R^6$ and $R^9$ are optionally taken together with the intervening carbon atoms to form an optionally substituted cyclic moiety.

In certain embodiments of the compound of Formula (I) and (II), $R^1$ is hydrogen or —$OR^{A1}$; $R^2$ is hydrogen; or $R^1$ and $R^2$ are joined to form ═O; $R^{A1}$ is hydrogen; an oxygen protecting group; or substituted or unsubstituted alkyl; or $R^{A1}$ is a group of Formula (i):

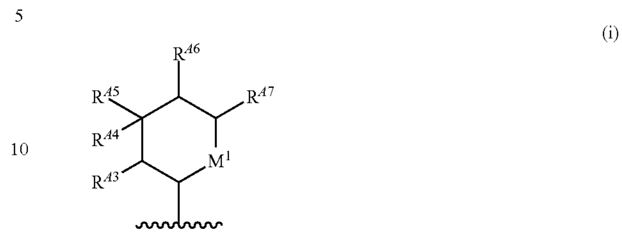

(i)

wherein each occurrence of $R^{A3}$, $R^{A4}$, $R^{A5}$, $R^{A6}$, and $R^{A7}$ is independently hydrogen, substituted or unsubstituted alkyl; —$OR^{A9}$; —OC(═O)$R^{A9}$; —N($R^{A9}$)$_2$; or —NHC(═O)$R^{A9}$; wherein each occurrence of $R^{A9}$ is independently hydrogen; substituted or unsubstituted alkyl; an oxygen protecting group when attached to an oxygen atom; or a nitrogen protecting group when attached to a nitrogen atom; or two $R^{A9}$ groups are joined to form a substituted or unsubstituted heterocyclic or substituted or unsubstituted heteroaryl ring; and $M^1$ is —O—;

$R^3$ is hydrogen or —$OR^{C1}$, wherein $R^{C1}$ is hydrogen; an oxygen protecting group; or substituted or unsubstituted alkyl; $R^4$ is hydrogen or —$OR^{D1}$, wherein $R^{D1}$ is hydrogen; an oxygen protecting group; or substituted or unsubstituted alkyl; $R^5$ is hydrogen or —$OR^{E1}$, wherein $R^{E1}$ is hydrogen; an oxygen protecting group; or substituted or unsubstituted alkyl; $R^6$ is substituted or unsubstituted alkyl; $R^8$ is —CH($OR^{11}$)$_2$; and each occurrence of $R^{11}$ is substituted or unsubstituted alkyl.

In certain embodiments, the compound of Formula (II) is

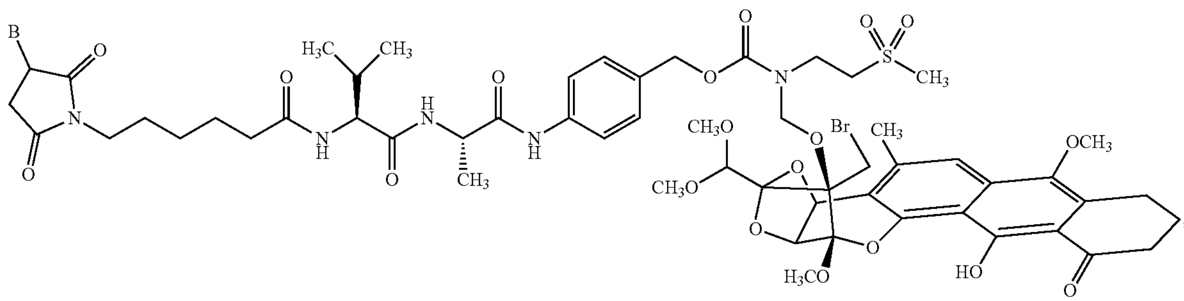

or a pharmaceutically acceptable salt thereof, wherein B is an antibody or an antibody fragment.

In certain embodiments, the compound of Formula (II) is

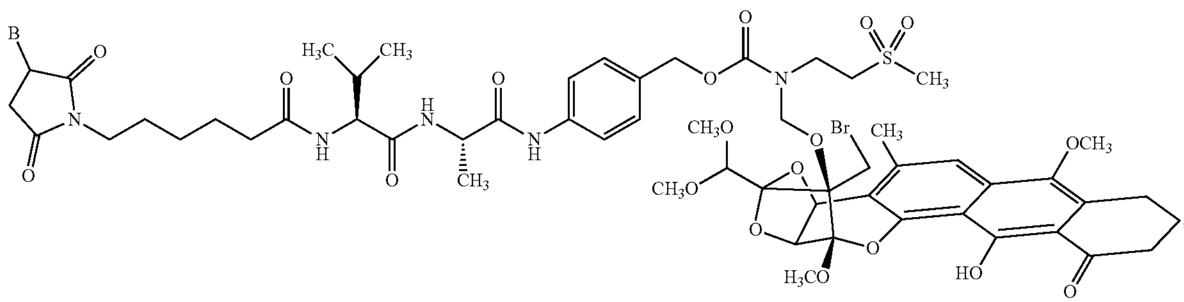

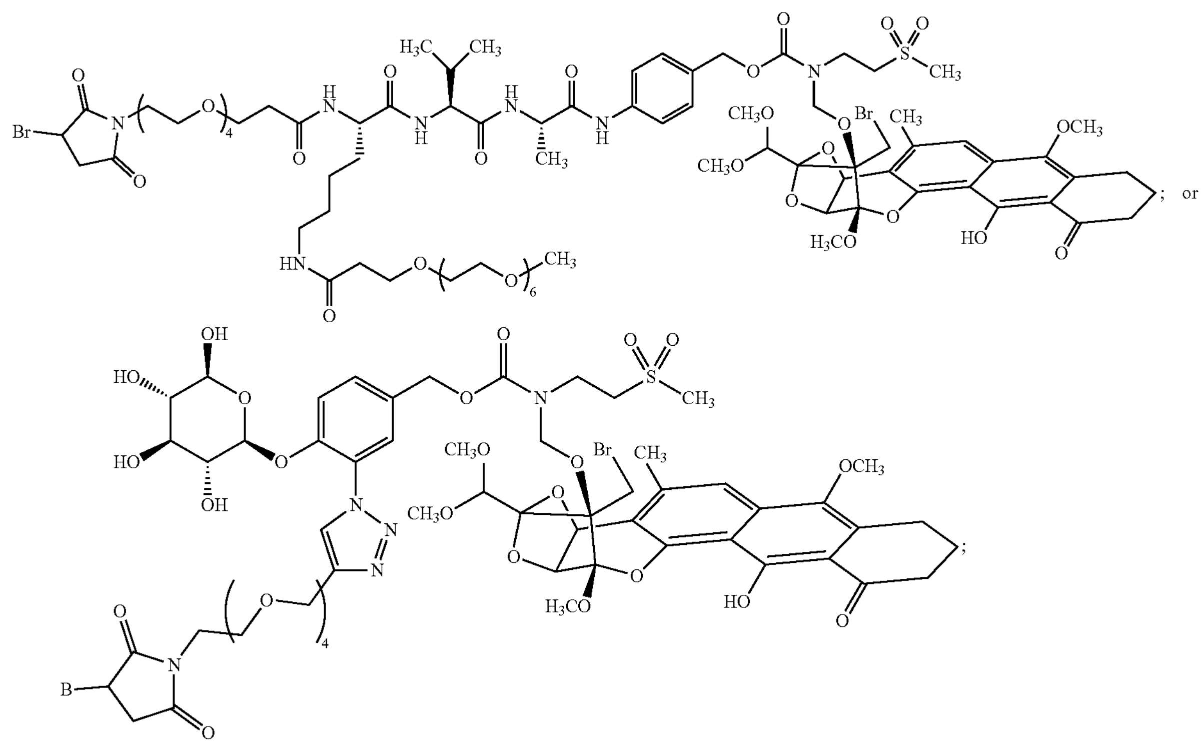

; or

;

or a pharmaceutically acceptable salt thereof, wherein B is an antibody or an antibody fragment.

Additional Embodiments of Formula (III) and (IV)

Various combinations of the above embodiments are further contemplated herein. One of skill in the art would appreciate that the various embodiments described herein may be combined in various ways and are contemplated by the inventors.

In certain embodiments of the compound of Formula (III) and (IV), $R^1$ and $R^2$ are each hydrogen or together form =O; and $R^{10}$ and $R^3$ are hydrogen; or $R^4$ and $R^9$ are optionally taken together with the intervening carbon atoms to form an optionally substituted cyclic moiety; or $R^6$ and $R^9$ are optionally taken together with the intervening carbon atoms to form an optionally substituted cyclic moiety.

In certain embodiments of the compound of Formula (III) and (IV), $R^1$ is —$OR^{A1}$; wherein $R^{A1}$ is hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and $R^{10}$ and $R^3$ are hydrogen; or $R^1$ and $R^4$ are optionally taken together with the intervening carbon atoms to form an optionally substituted cyclic moiety; or $R^4$ and $R^9$ are optionally taken together with the intervening carbon atoms to form an optionally substituted cyclic moiety; or $R^6$ and $R^9$ are optionally taken together with the intervening carbon atoms to form an optionally substituted cyclic moiety.

In certain embodiments of the compound of Formula (III) and (IV), $R^1$ is hydrogen or —$OR^{A1}$; $R^2$ is hydrogen; or $R^1$ and $R^2$ are joined to form =O; $R^{A1}$ is hydrogen; an oxygen protecting group; or substituted or unsubstituted alkyl; or $R^{A1}$ is a group of Formula (i):

(i)

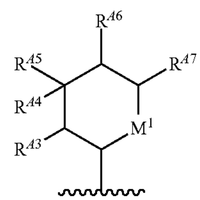

wherein each occurrence of $R^{A3}$, $R^{A4}$, $R^{A5}$, $R^{A6}$, and $R^{A7}$ is independently hydrogen, substituted or unsubstituted alkyl; —$OR^{A9}$; —OC(=O)$R^{A9}$; —$N(R^{A9})_2$; or —NHC(=O)$R^{A9}$; wherein each occurrence of $R^{A9}$ is independently hydrogen; substituted or unsubstituted alkyl; an oxygen protecting group when attached to an oxygen atom; or a nitrogen protecting group when attached to a nitrogen atom; or two $R^{A9}$ groups are joined to form a substituted or unsubstituted heterocyclic or substituted or unsubstituted heteroaryl ring; and $M^1$ is —O—;

$R^3$ is hydrogen or —$OR^{C1}$, wherein $R^{C1}$ is hydrogen; an oxygen protecting group; or substituted or unsubstituted alkyl; $R^4$ is hydrogen or —$OR^{D1}$, wherein $R^{D1}$ is hydrogen; an oxygen protecting group; or substituted or unsubstituted alkyl; $R^5$ is hydrogen or —$OR^{E1}$, wherein $R^{E1}$ is hydrogen; an oxygen protecting group; or substituted or unsubstituted alkyl; $R^6$ is substituted or unsubstituted alkyl; $R^8$ is —$CH(OR^{I1})_2$; and each occurrence of $R^{I1}$ is substituted or unsubstituted alkyl.

In certain embodiments, the compound of Formula (IV) is
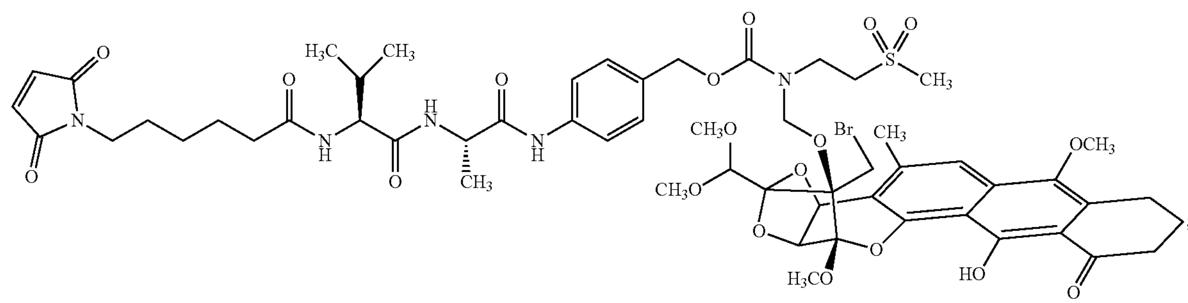
or a pharmaceutically acceptable salt thereof.
In certain embodiments, the compound of Formula (IV) is
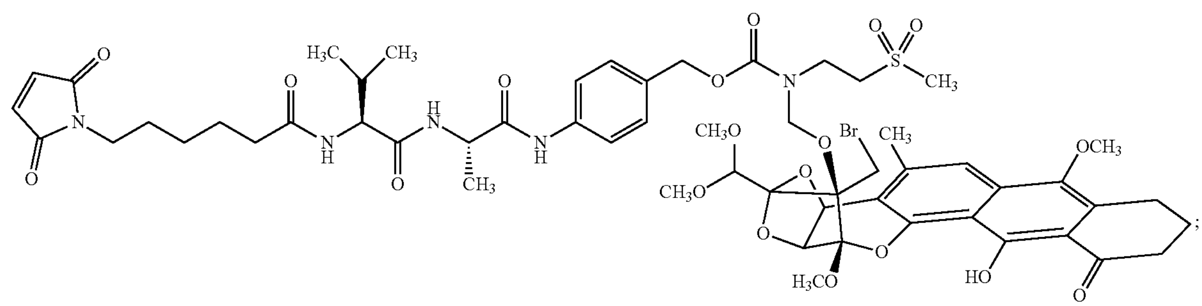
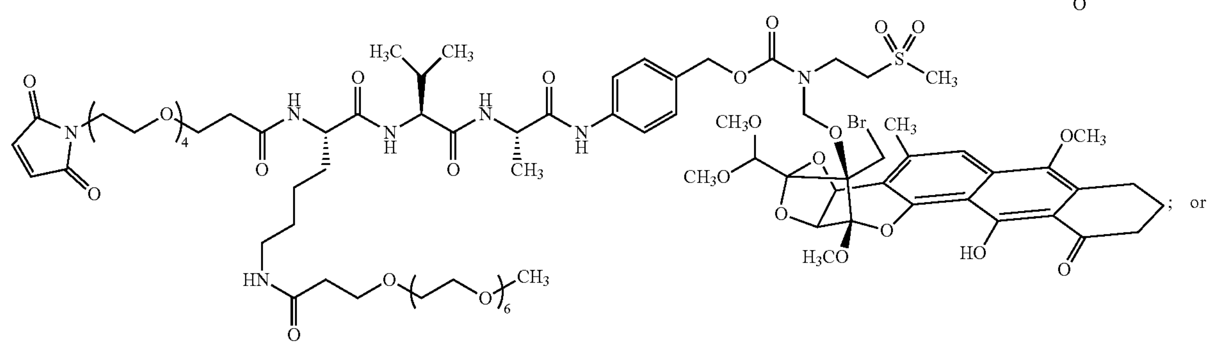
or
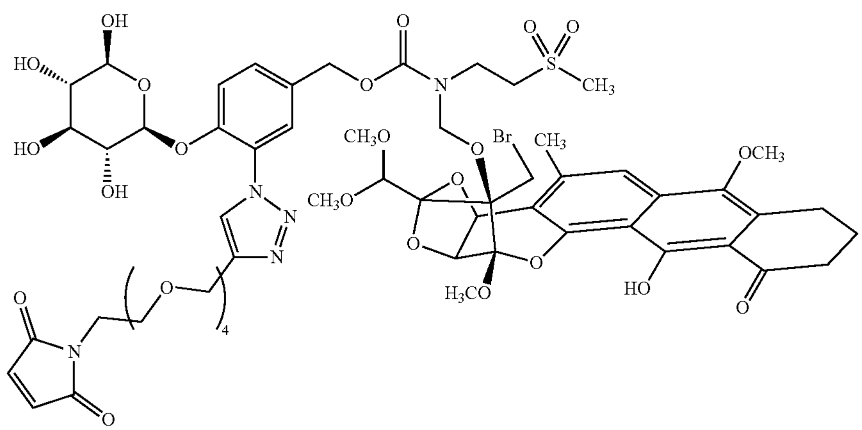
or a pharmaceutically acceptable salt thereof.

In certain embodiments, the compound of Formula (IV) is

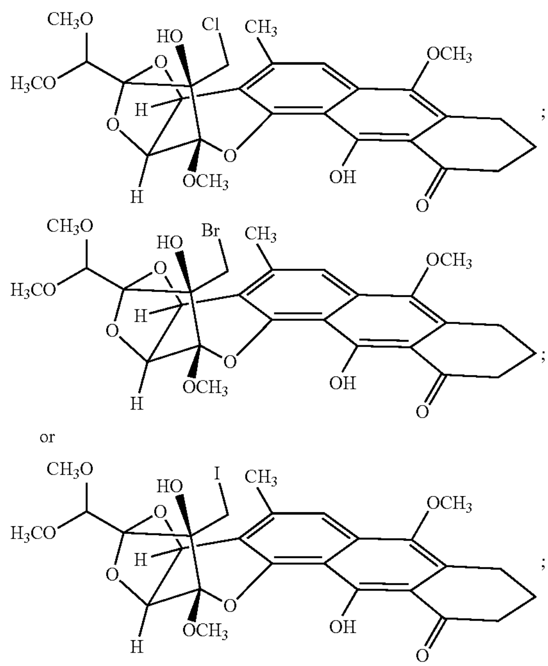

or or a pharmaceutically acceptable salt thereof.

Group B

As generally defined herein, B is an antibody or antibody fragment. It is generally understood that the antibody or antibody fragment B is a large molecule with many possible sites of attachment of the trioxacarcin-linker moiety, i.e., a [trioxacarcin-L-A-] moiety. In certain embodiments, the antibody or antibody fragment comprises 1 to 200 independent instances of a trioxacarcin-linker moiety attached thereto, inclusive, e.g., 1 to 150, 1 to 100, 1 to 75, 1 to 50, 1 to 25, 1 to 15, 1 to 10, inclusive, e.g., 1, 2, 3, 4, 5, 6, 7, 8, 9, or 10 independent instances.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three subdomains, $C_{H1}$, $C_{H2}$ and $C_{H3}$. Each light chain is comprised of a light chain variable region (abbreviated herein as $V_L$) and a light chain constant region. The light chain constant region is comprised of one subdomain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

As used herein, the term "monoclonal antibody" may refer to an antibody obtained from a single clonal population of immunoglobulins that bind to the same epitope of an antigen. Monoclonal antibodies have the same Ig gene rearrangement and thus demonstrate identical binding specificity. Methods for preparing monoclonal antibodies, as described herein, are known in the art. Monoclonal antibodies can be prepared by a variety of methods. For example, monoclonal antibodies may be made by a hybridoma method (see, e.g., Kohler et al., *Nature,* 1975, 256: 495), or may be made by recombinant DNA methods (see, e.g., U.S. Pat. No. 4,816,567). The monoclonal antibodies may also be isolated from phage antibody libraries. (See e.g., Clarkson et al., *Nature,* 1991, 352: 624-628 and Marks et al., *J. Mol. Biol.,* 1991, 222: 581-597).

Human monoclonal antibodies may be made by any of the methods known in the art, including those disclosed in U.S. Pat. Nos. 5,567,610, 5,565,354, 5,571,893, Kozber, *J. Immunol.,* 1984, 133: 3001, Brodeur, et al., Monoclonal Antibody Production Techniques and Applications, p. 51-63 (Marcel Dekker, Inc., new York, 1987), and Boerner et al., *J. Immunol.,* 1991, 147: 86-95. Human antibodies may be obtained by recovering antibody-producing lymphocytes from the blood or other tissues of humans producing antibody to an antigen of interest (e.g., CD20 or EGFR). These lymphocytes can be treated to produce cells that grow independently in the laboratory under appropriate culture conditions. The cell cultures can be screened for production of antibodies to the antigen of interest and then cloned. Clonal cultures can be used to produce human monoclonal antibodies to CD20 and/or EGFR, or the genetic elements encoding the variable portions of the heavy and light chain of the antibodies can be cloned and inserted into nucleic acid vectors for production of antibodies of different types. In addition to the conventional methods for preparing human monoclonal antibodies, such antibodies may also be prepared by immunizing transgenic animals that are capable of producing human antibodies (e.g., Jakobovits et al., *PNAS USA,* 1993, 90: 2551, Jakobovits et al., *Nature,* 1993, 362: 255-258, Bruggermann et al., *Year in Immunol.,* 1993, 7:33 and U.S. Pat. No. 5,569,825).

As used herein, "humanized monoclonal antibody" may refer to monoclonal antibodies having at least human constant regions and an antigen-binding region, such as one, two, or three CDRs, from a non-human species. Humanized antibodies specifically recognize antigens of interest, but will not evoke an immune response in humans against the antibody itself. As an example, murine CDRs may be grafted into the framework region of a human antibody to prepare the humanized antibody (e.g., Riechmann et al., *Nature,* 1988, 332, 323, and Neuberger et al., *Nature,* 1985, 314, 268). Alternatively, humanized monoclonal antibodies may be constructed by replacing the non-CDR regions of non-human antibodies with similar regions of human antibodies while retaining the epitopic specificity of the original antibodies. For example, non-human CDRs and optionally some of the framework regions may be covalently joined to human FR and/or Fc/pFc' regions to produce functional antibodies.

As used herein, the term "chimeric antibody" may refer to a monoclonal antibody comprising a variable region from one source (e.g., species) and at least a portion of a constant region derived from a different source. In some embodiments, chimeric antibodies are prepared by recombinant DNA techniques. In some embodiments, the chimeric antibodies comprise a murine variable region and a human constant region. Such chimeric antibodies may, in some embodiments, be the product of expressed immunoglobulin genes comprising DNA segments encoding murine immunoglobulin variable regions and DNA segments encoding human immunoglobulin constant regions. Methods for producing chimeric antibodies involve conventional recombinant DNA and gene transfection techniques (see, e.g., Morrison et al., *Proc. Natl. Acad. Sci. USA,* 1984, 81: 6851-6855; U.S. Pat. Nos. 5,202,238; and 5,204,244).

An antibody fragment is a portion of an antibody such as F(ab').sub.2, F(ab).sub.2, Fab', Fab, Fv, scFv (single chain Fv) and the like. Such fragments may be prepared by standard methods. See, e.g., Coligan et al. *Current Protocols in Immunology*, John Wiley & Sons, 1991-1997. Regardless of structure, an antibody fragment binds with the same antigen that is recognized by the intact antibody. An antibody fragment may comprise one or more proteolytic fragments (i.e., fragments produced by cleavage with papain), e.g., a Fab fragment, each containing a light chain domain and a heavy chain domain (designated herein as a "Fab heavy chain domain"), and/or Fc fragment containing two Fc domains. Each light chain domain contains a $V_L$ and a $C_L$ subdomain, each Fab heavy chain domain contains a $V_H$ and a $C_{H1}$ subdomain, and each Fc domain contains a $C_{H2}$ and $C_{H3}$ subdomain.

In certain embodiments, antigen-binding antibody fragments is only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. An isolated F(ab')2 fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Further, Fab fragments consist of a covalently bound antibody light chain and a portion of the antibody heavy chain denoted Fd (heavy chain variable region, referred to herein as Fab heavy chain domain). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')2 and Fv are employed with either standard immunological meanings (Klein, Immunology (John Wiley, New York, NY, 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)). Well-known functionally active antibody fragments include but are not limited to F(ab')2, Fab, Fv and Fd fragments of antibodies. These fragments, which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies may be constructed in accordance with the methods described in U.S. Pat. No. 4,946,778. Such single-chain antibodies include the variable regions of the light and heavy chains joined by a flexible linker moiety. Methods for obtaining a single domain antibody ("Fd") which comprises an isolated variable heavy chain single domain, also have been reported (see, e.g., Ward et al., *Nature,* 1989, 341:644-646, disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, (see, e.g., Moore et al., U.S. Pat. No. 4,462,334). Other references describing the use and generation of antibody fragments include, e.g., Fab fragments (Tijssen, Practice and Theory of Enzyme Immunoassays (Elsevieer, Amsterdam, 1985)), Fv fragments (Hochman et al., *Biochemistry,* 1973, 12: 1130; Sharon et al., *Biochemistry,* 1976, 15: 1591; Ehrilch et al., U.S. Pat. No. 4,355,023) and portions of antibody molecules (Audilore-Hargreaves, U.S. Pat. No. 4,470,925). Thus, antibody fragments may be constructed from intact antibodies without destroying the specificity of the antibodies for the CD20 or EGFR epitope.

In certain embodiments, the antibody fragment is a camelid antibody; e.g., a functional antibody devoid of light chains of which the single N-terminal domain is fully capable of antigen binding; i.e., a single-domain antibody fragment.

Exemplary antibodies and their cell markers (targets) contemplated for use include, but are not limited to, antibodies listed in Table A, and antibody fragments thereof.

TABLE A

| Antibody | Target |
|---|---|
| adecatumumab (MT201) | EpCAM - CD326 |
| afutuzumab | CD20 |
| alemtuzumab (CAMPATH) | CD52 |
| bavituximab | phosphatidylserine |
| belimumab | BAFF, BLyS |
| bevacizumab (AVASTIN) | VEGF-A |
| brentuximab (ADCETRIS) | CD30 |
| cantuzumab | MUC1 |
| cetuximab (ERBITUX) | EGF receptor |
| citatuzumab | TACSTD1 |
| cixutumumab | IGF-1 receptor |
| conatumumab | TRAIL-R2 (CD262) |
| dacetuzumab | CD40 |
| elotuzumab | SLAMF7 (CD319) |
| etaracizumab | alpha-v beta-3 integrin |
| farletuzumab | FR-alpha |
| figitumumab | IGF-1 receptor |
| gemtuzumab | CD33 |
| ibritumomab | CD20 |
| inotuzumab (CMC-533) | CD22 |
| ipilimumab (YERVOY) | CTLA-4 |
| iratumumab | CD30 |
| labetuzumab | carcinoembryonic antigen |
| lexatumumab | TRAIL-R2 |
| lintuzumab | CD33 |
| lucatumumab | CD40 |
| mapatumumab | TRAIL-receptor (death receptor 4) |
| matuzumab | EGFR |
| milatuzumab | CD74 |
| necitumumab | EGFR |
| nimotuzumab | EGFR |
| ofatumumab (ARZERRA) | CD20 |
| olaratumab | PDGF-R α |
| oportuzumab | EpCAM |
| panitumumab (VECTIBIX) | EGFR |
| pertuzumab (PERJETA) | HER2 |
| pritumumab | vimentin |
| rituximab (RITUXAN) | CD20 |

TABLE A-continued

| Antibody | Target |
|---|---|
| robatumumab | CD221 |
| sibrotuzumab | FAP |
| siltuximab | IL-6 |
| tacatuzumab | α-fetoprotein |
| tigatuzumab | TNFRSF10B (TRAIL-R2) |
| tositumomab (BEXXAR) | CD20 |
| trastuzumab (HERCEPTIN) | HER2/neu |
| tucotuzumab | EpCAM |
| veltuzumab | CD20 |
| votumumab | mor antigen CTAA16.88 |
| zalutumumab | EGFr |

In certain embodiments, the antibody is any antibody directed to any of the targets listed in table A.

Additional antibodies include, but are not limited to, pembrolizumab, nivolumab, pidilizumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDIO680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, Chi Lob 7/4, $R^{G6058}$, $R^{G7686}$, $R^{G7876}$, $R^{G7888}$, TRX518, MK-4166, MGA271, IMC-CS4, emactuzumab, obinutuzumab, cabiralizumab, margetuximab, enoblituzumab, mogamulizumab, carlumab, fresolimumab, FAZ053, TSR022, MBG453, REGN2810, REGN3767, MOXR0916, PF-04518600, R07009789, BMS986156, GWN323, JTX-2011, NKTR-214, GSK3174998, DS-8273a, NIS793, or BGB-A317

In certain embodiments, the antibody is trastuzumab (HERCEPTIN) or an antibody fragment thereof.

Methods of Preparation

As is generally understood from the above disclosure, the compound of Formula (II), comprising a group T, is coupled to an antibody to form an antibody-drug conjugate of Formula (I). See, e.g., Scheme 1. In certain embodiments, the coupling takes place between a nucleophilic sidechain of an amino acid residue (e.g., cysteine, lysine, serine) of the antibody and an electrophilic T group. Exemplary coupling reactions include, but are not limited to, formation of esters, thioesters, amides (e.g., such as peptide coupling) from activated acids or acyl halides; nucleophilic displacement reactions (e.g., such as nucleophilic displacement of a halide); and Michael additions (e.g., maleimide addition).

Scheme 1.

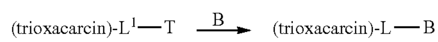

In certain embodiments, the method of preparing a compound of Formula (I) comprises coupling an antibody with a compound of Formula (II), wherein T is

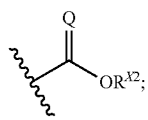

Q is —S—, or —O—; and Rx is hydrogen, substituted or unsubstituted alkyl; substituted or unsubstituted heterocyclyl (e.g., succinimide); substituted or unsubstituted aryl; substituted or unsubstituted heteroaryl; or an oxygen protecting group, to provide a corresponding compound of Formula (I). See, for example, Scheme 2.

Scheme 2.
Preparation of compounds of Formula (I) via amide, thioester, and ester formation

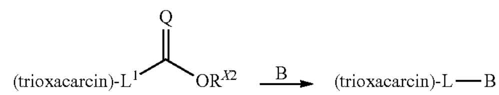

In certain embodiments, the method of preparing a compound of Formula (I) comprises coupling an antibody with a compound of Formula (II), wherein T is

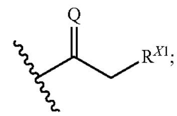

Q is —S—, or —O—; and $R^{X1}$ is a leaving group (e.g., halogen, tosylate, mesylate, or triflate), to provide a compound of Formula (I). See, for example, Scheme 3.

Scheme 3.
Nucleophilic displacement of a halide or other leaving group

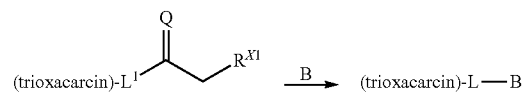

In certain embodiments, the method of preparing a compound of Formula (I) comprises coupling an antibody with a compound of Formula (II), wherein T is —N═C═S (i.e., isothiocyanate) to provide a compound of Formula (I). See, for example, Scheme 4.

Scheme 4.
Nucleophilic addition to isothiocyanate

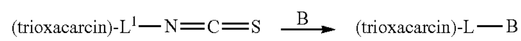

In certain embodiments, the method of preparing a compound of Formula (I) comprises coupling an antibody with a compound of Formula (II), wherein T is a maleimide group to provide a compound of Formula (I). See, for example, Scheme 5.

Scheme 5. Maleimide addition

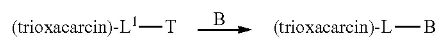

| T |
| --- |
| 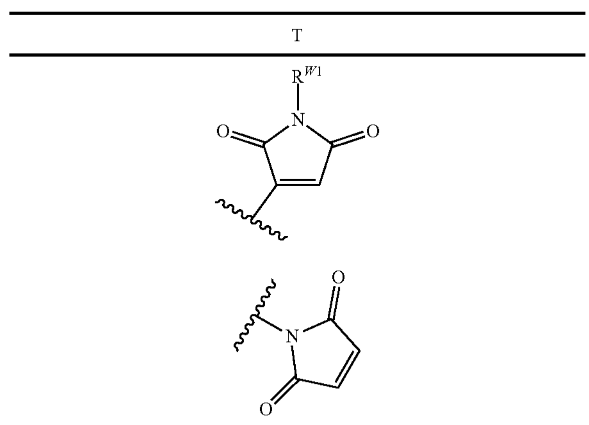 |

In certain embodiments, the method of preparing a compound of Formula (I) comprises coupling an antibody with a compound of Formula (II), wherein T is 4-nitrobenzenethiol (e.g., wherein the sulfur is attached to a sulfur atom of $L^1$) to provide a compound of Formula (I). See, for example, Scheme 6.

Scheme 6.
Nucleophilic displacement of a thiol

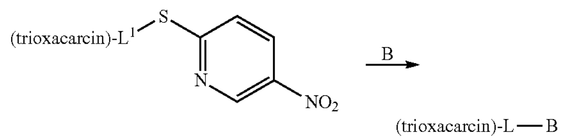

Pharmaceutical Compositions

The present disclosure provides pharmaceutical compositions comprising an active ingredient and, optionally, a pharmaceutically acceptable carrier. In certain embodiments, the active ingredient is present in an effective amount, e.g., a therapeutically effective amount or a prophylactically effective amount.

An "active ingredient," as used herein, refers to antibody drug conjugates of Formula (I), trioxacarcin-antibody conjugates of Formula (II), precursor compounds of Formula (III) and (IV), or novel trioxacarcin compounds without an antibody conjugated thereto, and pharmaceutically acceptable salts thereof.

A pharmaceutical composition of the present disclosure can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal, or other parenteral routes of administration, for example, by epidermal administration (e.g., by injection or infusion). The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion.

Alternatively, the pharmaceutical composition can be administered via a non-parenteral route, such as a topical, epidermal or mucosal route of administration, for example, intranasally, orally, vaginally, rectally, sublingually or topically.

Depending on the route of administration, the pharmaceutical composition or active ingredient may be coated in a material to protect the compound from the action of acids and other natural conditions that may inactivate the compound.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* $21^{st}$ Edition (Lippincott Williams & Wilkins, 2005).

Pharmaceutical compositions described herein can be prepared by any method known in the art of pharmacology. In general, such preparatory methods include the steps of bringing the active ingredient into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

The active ingredient can be prepared with carriers that will protect the active ingredient against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Pharmaceutical compositions can be administered with medical devices known in the art. For example, in a preferred embodiment, a pharmaceutical composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

The exact amount of the active ingredient required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an active ingredient for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of the active ingredient per unit dosage form.

In certain embodiments, the active ingredient may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that the active ingredient or composition, as described herein, can be administered in combination with one or more additional therapeutically active agents. The active ingredient or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-cancer agent, etc.), and/or it may achieve different effects (e.g., control of adverse side-effects, e.g., emesis controlled by an anti-emetic).

The active ingredient or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the active ingredient with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, cancer therapies, antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestant, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants/anti-epileptics (e.g., Neurontin, Lyrica, valproates (e.g., Depacon), and other neurostabilizing agents), muscle relaxants, anti-spasmodics, muscle contractants, channel blockers, miotic agents, anti-secretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g., cell growth inhibitors and anti-adhesion molecules), or inhibitors/intercalators of DNA, RNA, protein-protein interactions, protein-receptor interactions, etc. Therapeutically active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutic agent is a cancer therapy. Cancer therapies include, but are not limited to, surgery and surgical treatments, radiation therapy, and administration of additional therapeutic cancer agents (e.g., biotherapeutic and chemotherapeutic cancer agents).

Exemplary biotherapeutic cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic cancer agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g., 1-methyl-4-phenylpyridinium ion), cell cycle inhibitors (e.g. staurosporine), actinomycin (e.g., actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the additional pharmaceutical agent is an immunotherapy. In certain embodiments, the immunotherapy is useful in the treatment of a cancer. Exemplary immunotherapies include, but are not limited to, T-cell therapies, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In certain embodiments, the immunotherapy is an antibody. In certain embodiments, the antibody is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICB antibody, an anti- NKG2D antibody, an anti-NKG2A antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDIO680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, $R^{G6058}$, $R^{G7686}$, $R^{G7876}$, $R^{G7888}$, TRX518, MK-4166, MGA271, IMC-CS4, emactuzumab, trastuzumab, pertuzumab, obinutuzumab, cabiralizumab, margetuximab, enoblituzumab, mogamulizumab, panitumumab, carlumab, bevacizumab, rituximab, or cetuximab.

In certain embodiments, the compounds or pharmaceutical compositions described herein can be administered in combination with an anti-cancer therapy including, but not limited to, surgery, radiation therapy, and transplantation (e.g., stem cell transplantation, bone marrow transplantation).

In other embodiments, the additional therapeutically active agent is an anti-inflammatory agent. Exemplary anti-inflammatory agents include, but are not limited to, aspirin; ibuprofen; ketoprofen; naproxen; etodolac (LODINE®); COX-2 inhibitors such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl) cyclopenta-2,4-dien-3-yl)benzene, 4-(1,5-Dihydro-6-fluoro-7-methoxy-3-(trifluoromethyl)-(2)-benzothiopyrano(4,3-c) pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIAPED® prednisolone sodium phosphate oral solution, SOLU-MEDROL® methylprednisolone sodium succinate for injection, PRELONE® brand prednisolone syrup.

Further examples of anti-inflammatory agents include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-Tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

In certain embodiments, the additional therapeutically active agent is a pain-relieving agent. Exemplary pain relieving agents include, but are not limited to, analgesics such as non-narcotic analgesics [e.g., salicylates such as aspirin, ibuprofen (MOTRIN®, ADVIL®), ketoprofen (ORUDIS®), naproxen (NAPROSYN®), acetaminophen, indomethacin] or narcotic analgesics [e.g., opioid analgesics such as tramadol, fentenyl, sufentanil, morphine, hydromorphone, codeine, oxycodone, and buprenorphine]; non-steroidal anti-inflammatory agents (NSAIDs) [e.g., aspirin, acetaminophen, COX-2 inhibitors]; steroids or anti-rheumatic agents; migraine preparations such as beta adrenergic blocking agents, ergot derivatives; tricyclic antidepressants (e.g., amitryptyline, desipramine, imipramine); anti-epileptics (e.g., clonaxepam, valproic acid, phenobarbital, phenytoin, tiagaine, gabapentin, carbamazepine, topiramate, sodium valproate); $\alpha_2$ agonists; selective serotonin reuptake inhibitors (SSRIs), selective norepinepherine uptake inhibitors; benzodiazepines; mexiletine (MEXITIL); flecainide (TAMBOCOR); NMDA receptor antagonists (e.g., ketamine, detromethorphan, methadone); and topical agents (e.g., capsaicin (Zostrix), EMLA cream, lidocaine, prilocaine).

Kits

Still further contemplated herein are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration.

Still further, instructions may provide specialized instructions for use in conjunction and/or in combination with additional therapy.

Methods of Use and Treatment

Further provided are methods of using compounds as described herein (e.g., antibody drug conjugates of Formula (I), trioxacarcin-antibody conjugates of Formula (II) and precursor compounds of Formulae (III) and (IV), or novel trioxacarcin compounds which do not comprise an antibody conjugated thereto, and pharmaceutically acceptable salts thereof).

For example, in one aspect, provided is a method of treating a disease, disorder, or condition selected from the group consisting of cardiovascular disease, proliferative disease (e.g., cancer, benign tumors), diabetic retinopathy, inflammatory disease, autoimmune disease, and infectious disease (e.g., bacterial infections, fungal infections, parasitic infections) comprising administering an effective amount of a compound of the present disclosure to a subject in need thereof.

In certain embodiments, the compound of the present disclosure is useful in the treatment of cardiovascular disease. Exemplary cardiovascular diseases include, but are not limited to, coronary heart disease, cardiomyopathy, hypertensive heart disease, heart failure, inflammatory heart disease, valvular heart disease, stroke, cerebrovascular disease, and peripheral arterial disease.

In certain embodiments, the compound of the present disclosure is useful in the treatment of a proliferative disease. Exemplary proliferative diseases include, but are not limited to, cancers and benign neoplasms. In certain embodiments, the proliferative disease is cancer. Exemplary cancers include, but are not limited to, acoustic neuroma, adenocarcinoma, adrenal gland cancer, anal cancer, angiosarcoma (e.g., lymphangiosarcoma, lymphangio-endotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above, e.g., mixed leukemia lymphoma (MLL); and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Trioxacarcins are known to be useful in the treatment of various cancers, such as ovarian, colorectal, hepatocellular, pancreatic cancer, and andenocarcinomas. See, e.g., Cassidy et al., *Cancer Chemother. Pharmacol*. (1993) 31:395-400; Tomita et al., *J. Antibiot*. (1981) 34:1519-1524. It is contemplated that various compounds of Formula (I), (II), (III), and (IV) conjugated to an antibody, will have even higher efficacy against these and other cancers as described herein.

In certain embodiments, the compound of the present disclosure is useful in the treatment of diabetic retinopathy.

In certain embodiments, the compound of the present invention is useful in the treatment of an inflammatory disease. Exemplary inflammatory diseases include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis.

In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, the compound of the present disclosure is useful in the treatment of an autoimmune disease. Exemplary autoimmune diseases include, but are not limited to, arthritis (e.g., including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the inflammatory disorder and/or the immune disorder is a gastrointestinal disorder. In some embodiments, the gastrointestinal disorder is selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS).

In certain embodiments, the compound of the present disclosure is useful in the treatment of an infectious disease (e.g., bacterial infection, fungal infection, and/or parasitic infection). In certain embodiments, the compound is useful in treating a parasitic infection (e.g., malaria). In certain embodiments, the compound is useful in treating a bacterial infection. In certain embodiments, the compound is useful in treating a fungal infection.

Trioxacarcins are known to have antibiotic and antiparasitic (e.g., anti-malarial) activity. See, e.g., U.S. Pat. Nos. 4,459,291; 4,511,560; Fujimoto et al., *J. Antibiot*. (1983) 36:1216-1221; Maiese et al. *J. Antibiot*. (1990) 43:253-258; Tomita et al., *J. Antibiot*. (1981) 34:1519-1524; and Maskey et al. *J. Antibiot*. (2004) 57:771-779 (antibacterial and antimalarial activity). It is contemplated that various compounds of Formula (I), (II), (III), and (IV) conjugated to an antibody, will have even higher efficacy against an infectious disease, such as a bacterial infection, and other infectious diseases as described herein.

EXAMPLES

In order that the invention described herein may be more fully understood, the following examples are set forth. It should be understood that these examples are for illustrative purposes only and are not to be construed as limiting this invention in any manner.

In developing the compounds described herein, it was anticipated that reversible opening of the epoxide with a latent leaving group would reduce the reactivity of the warhead while attached to the antibody but would allow for reformation of the epoxide under appropriate conditions. After exploration of a variety of possible epoxide adducts using a potent analog (1, Me-ddx), it was discovered that halohydrin FSTs were not only readily synthesized under Lewis- or Brønsted-acid catalysis, but also reverted to the epoxide cleanly in pH 7.4 cell growth media at 37° C. (Scheme 7). Surprisingly, the bromo- and iodohydrin adducts exhibited no loss in cellular toxicity against H460 cells relative to the parent epoxide (3 $IC_{50}$=2 nM and 4 $IC_{50}$=4 nM respectively), indicating epoxide reversion occurred on a timescale sufficient for growth arrest. The chlorohydrin-FST 2 was an order of magnitude less potent than the bromohydrin, presumably due to slower reversion to the epoxide. The DNA-alkylating capability of the bromohydrin FST 3 in comparison to a set of FST analogs of varying potency by incubation with a self-complementary duplex DNA oligonucleotide d(AATTACGTAATT) for 4 h at 23° C. then analysis by gel electrophoresis and LC-MS was investigated. In general, more potent analogs exhibited greater DNA-alkylating efficiency. Notably, at this time scale and temperature the bromohydrin did not revert to the epoxide and itself did not alkylate DNA, indicating that the epoxide must be reformed before alkylation can occur.

In order to prevent premature reversion to the epoxide, a system in which the trioxacarcin prodrug would be linked through the tertiary alcohol of the halohydrin was envisioned. Therefore, epoxide formation could only occur once the payload had been released from the antibody upon delivery to the cellular target. Despite recent advances in the field, technology for linkage through alcohol functional groups is limited. Synthesis of benzyl ether, ester, carbonate, carbamate, diphosphate, and silyl linkers at the tertiary alcohol of 3 (bromohydrin) through previously reported methods all failed. Indeed, the electron withdrawing substituents surrounding the halohydrin alcohol (two β-acetals, a γ-acetal and a bromide) coupled with the steric encumbrance they impose prevented reaction of this alcohol with nearly all electrophiles evaluated. Quantitative deprotonation of the halohydrin alcohol to enhance its nucleophilicity naturally resulted in complete reversion to the epoxide. After significant experimentation, it was found that treatment of the Boc-protected bromohydrin 6 with isocyanate 7 in the presence of dibutyltin dilaurate catalyst furnished the FST-carbamate linkage 8 in good yield (Scheme 8). It was believed that this diamine spacer would release free bromohydrin after peptidase cleavage of the linker. Simultaneous Boc deprotection of both the phenol and amine with trifluoroacetic acid (TFA) provided the TFA salt of the amine 9

Scheme 7.

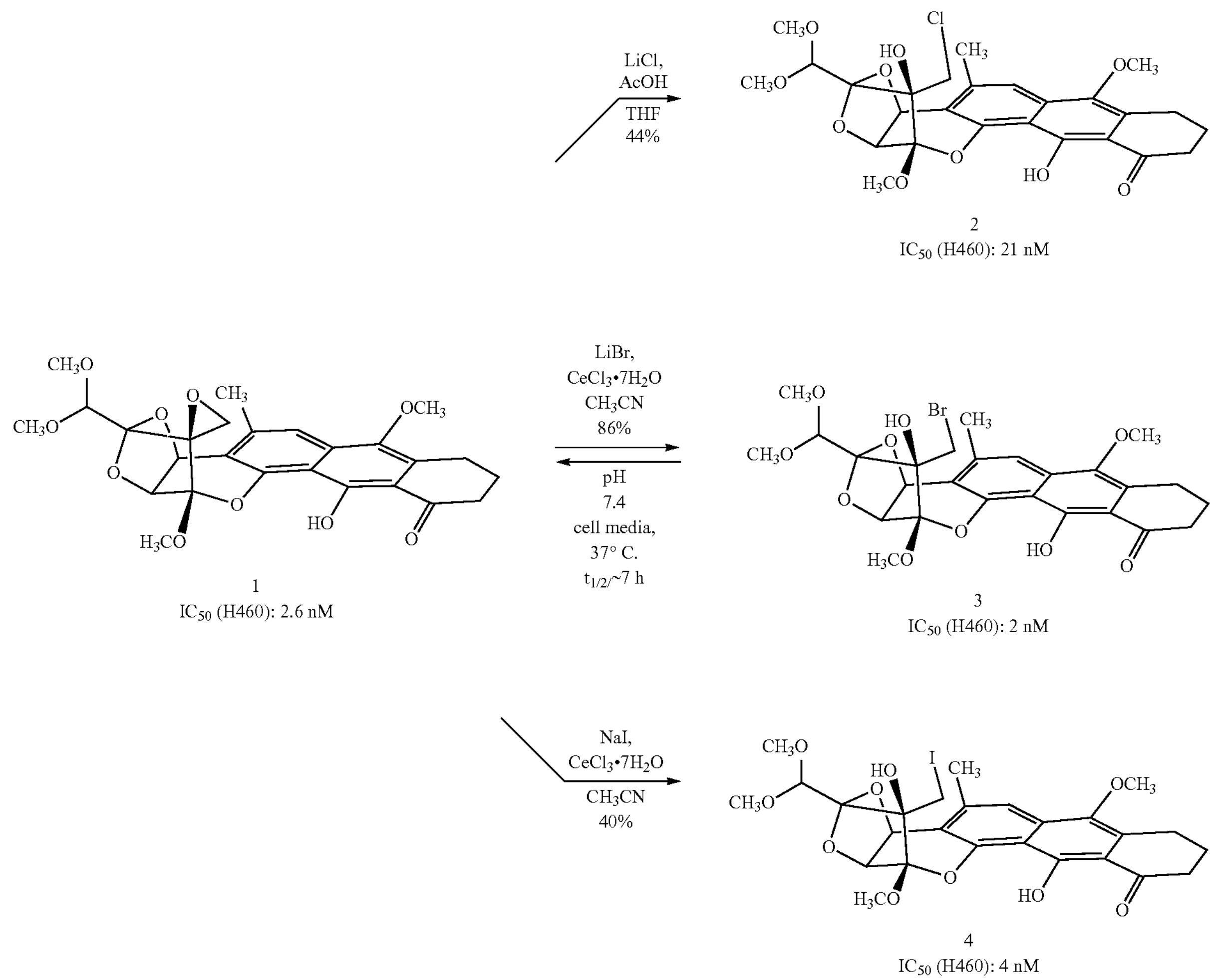

2
$IC_{50}$ (H460): 21 nM

1
$IC_{50}$ (H460): 2.6 nM

3
$IC_{50}$ (H460): 2 nM

4
$IC_{50}$ (H460): 4 nM after concentration, which was evaluated immediately for liberation of bromohydrin 3. Despite precedent for similar systems that release an alkyl alcohol through diamine spacer cyclization, no liberation of bromohydrin was observed when amine 9 was incubated at 37° C. in either pH 7.4 or 5.0 buffer (Scheme 8). Modifications of the diamine spacer unit to increase the rate of cyclization were unsuccessful.

Scheme 8.
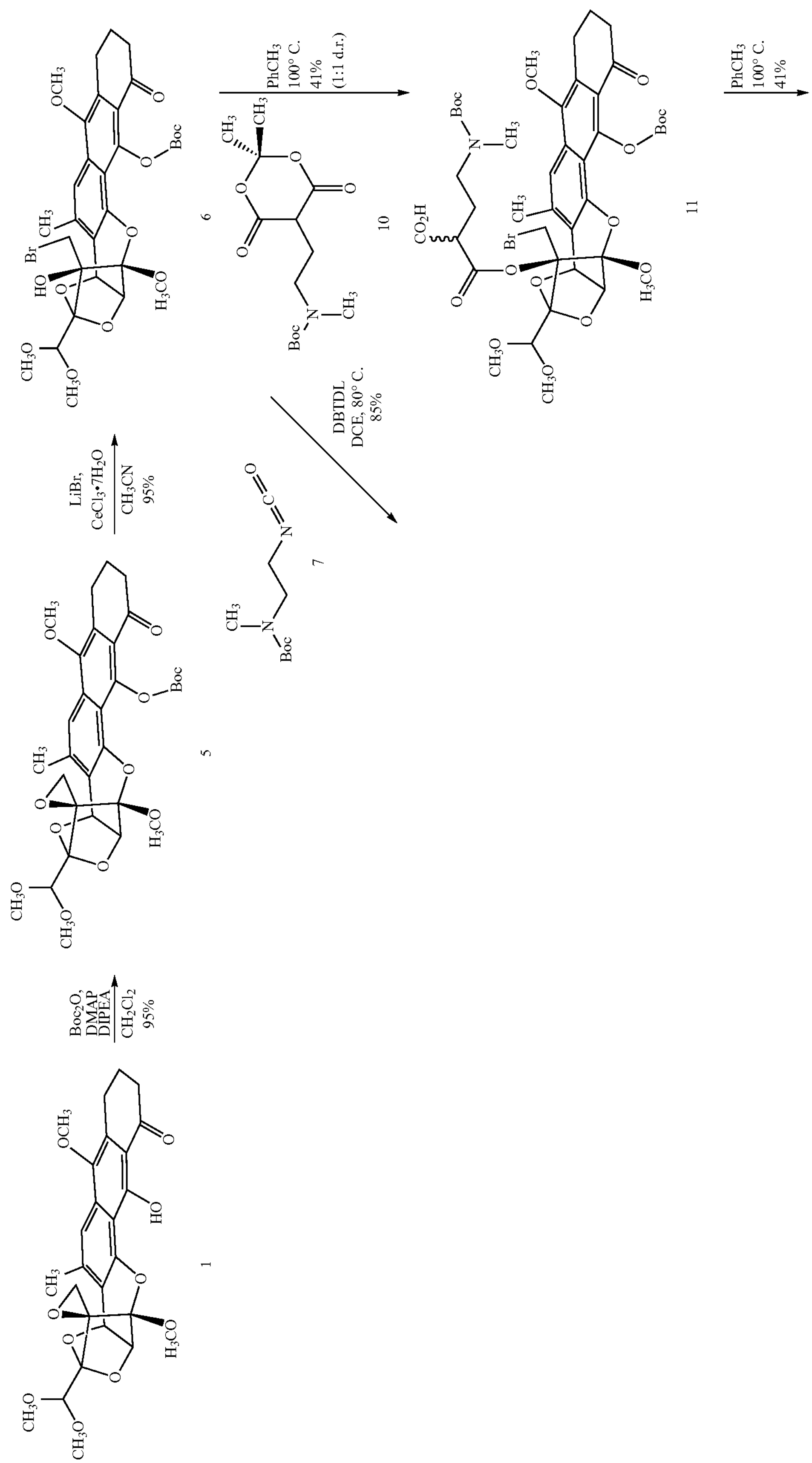
1
5
6
7
10
11

-continued
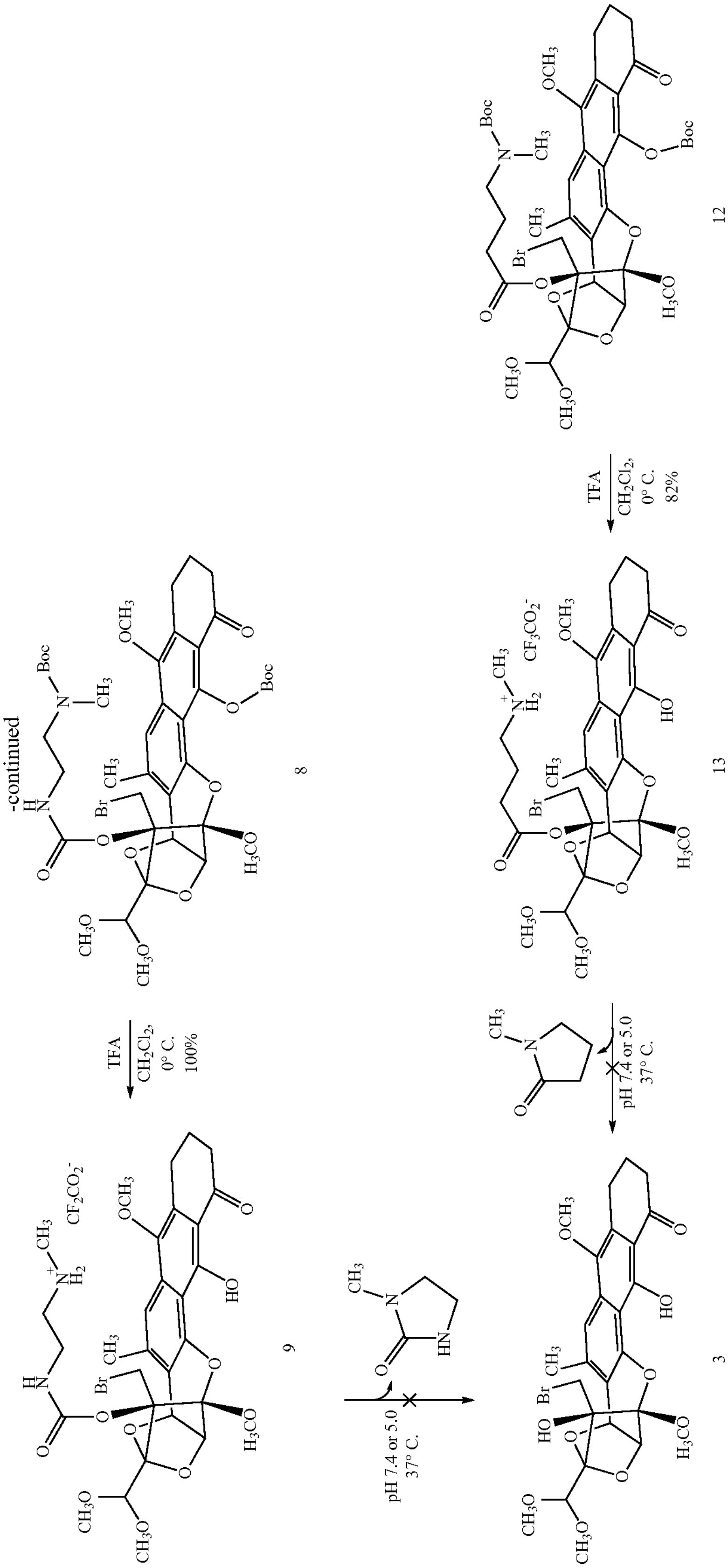
8
9
12
13
3

Recognizing that a carbamate linkage may have been too poorly electrophilic given the steric hindrance around the carbamate, the corresponding ester spacers were explored. While esters have generally been avoided for ADC linkage due to their sensitivity to hydrolysis and serum esterase activity, it was believed the uniquely hindered environment of the halohydrin may provide sufficient stability. As in the synthesis of carbamate spacer 8, it was useful to employ an sp-hybridized electrophile under essentially neutral conditions to functionalize the tertiary alcohol (Scheme 8). Treatment of bromohydrin 6 with the Meldrum's acid ketene precursor 10 at 100° C. yielded ester 11, presumably through the intermediacy of an acylketene via retro-hetero-Diels-Alder. The isolated product was a 1:1 diastereomeric mixture of the non-decarboxylated (3-carboxylic acid ester 12, which was further decarboxylated by extended reflux in toluene. Boc deprotection was accomplished with TFA and the free amine 13 evaluated for release of the bromohydrin as before. It was surprising to find that even the ester spacer failed to liberate the bromohydrin through cyclization at either pH 7.4 or 5.0 after extended incubation at 37° C. or 50° C., whereas similar 4-aminobutyric ester spacers are known to cyclize within seconds at 37° C. It was clear at this stage that the same challenge we were met with in functionalizing this tertiary alcohol was also precluding its release through immolative cyclization spacers; namely, formation of a tetrahedral intermediate at a carbon center adjacent to the bromohydrin was conformationally inaccessible.

A useful linker strategy arose from the use of a methylene alkoxy carbamate (MAC) spacer (Scheme 9). Coupling of the MAC spacer was achieved by treatment of FST-bromohydrin 6 with chloromethyl carbamate adduct 14 in the presence of lithium bromide and the bulky amine base pentamethylpiperidine (PMP) at 85° C. under rigorously anhydrous conditions, providing hemiaminal ether 15. This discovery was notable not only due to the extremely poor nucleophilicity of the bromohydrin alcohol, but also because it allowed for subsequent installation of a peptide unit, which would otherwise be incompatible with the chloromethyl carbamate chemistry. This development now expands the use of the MAC spacer from exclusively glucuronide linkers to the more broadly utilized peptide linkers. To achieve this transformation, aryl azide 15 was coupled using a "traceless" Staudinger ligation with phosphine ester 16. Direct formation of amide 17 without the intermediacy of the free aniline was useful as 1,6-elimination to liberate the carbamate is exceedingly fast ($t½=17$ s). Lithium methoxide cleavage of both the phenolic Boc group and terminal Fmoc group followed by installation of the maleimido caproyl unit yielded the completed FST-halohydrin MC-VA-PABC-MAC linker 19. This approach also allows for the synthesis of Val-Cit peptidic linkers, however we found Val-Ala to also be useful in this instance for its enhanced solubility. Gratifyingly, FST-linker 19 quenched with N-acetyl cysteine was stable for days at 37° C. and rapidly liberated FST-bromohydrin payload 3 upon exposure to cathepsin B at pH 5.0 (FIG. 1).

Scheme 9.
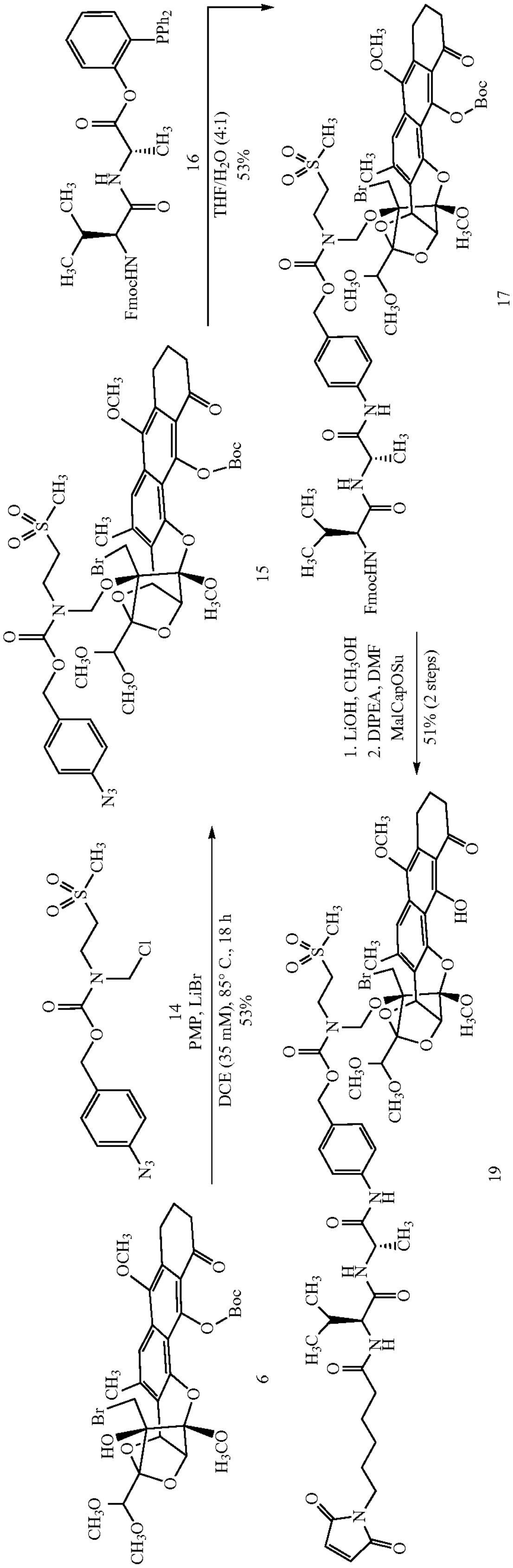
6
15
17
19

General Experimental Procedures: All reactions were performed in flame-dried glassware fitted with rubber septa under a positive pressure of argon, unless otherwise noted. Air- and moisture-sensitive liquids were transferred via syringe or stainless steel cannula. Solutions were concentrated by rotary evaporation at or below 40° C. Analytical thin-layer chromatography (TLC) was performed using glass plates pre-coated with silica gel (0.25-mm, 60-Å pore size, 230-400 mesh, Merck KGA) impregnated with a fluorescent indicator (254 nm). TLC plates were visualized by exposure to ultraviolet light (UV), then were stained by submersion in either an aqueous sulfuric acid solution of ceric ammonium molybdate (CAM), an acidic solution of p-anisaldehyde in ethanol (Anis), or an aqueous sodium hydroxide-potassium carbonate solution of potassium permanganate (KMnO4), followed by brief heating with a flameless heat gun. Flash column chromatography was performed as described by Still et al., employing silica gel (60 Å, standard grade) purchased from Dynamic Adsorbents.

Materials: Commercial solvents and reagents were used as received with the following exceptions: Dichloromethane, benzene, ether, dioxane, and tetrahydrofuran were purified by passage through $Al_2O_3$ under argon.

Instrumentation: Proton nuclear magnetic resonance ($^1H$ NMR) spectra and carbon nuclear magnetic resonance ($^{13}C$ NMR) spectra were recorded on Varian INOVA 500 (500 MHz/125 MHz) or Varian INOVA 600 (600 MHz/150 MHz) NMR spectrometers at 23° C. Proton chemical shifts are expressed in parts per million (ppm, 6 scale) and are referenced to residual protium in the NMR solvent ($CHCl_3$: δ 7.26). Carbon chemical shifts are expressed in parts per million (ppm, δ scale) and are referenced to the carbon resonance of the NMR solvent ($CHCl_3$: δ 77.0, $CH_3OD$: δ 49.0). Data are represented as follows: chemical shift, multiplicity (s=singlet, d=doublet, t=triplet, q=quartet, dd=doublet of doublets, dt=doublet of triplets, m=multiplet and/or multiple resonances, br=broad, app=apparent), integration, and coupling constant (J) in Hertz (Hz). Infrared (IR) spectra were obtained using a Shimadzu 8400S FT-IR spectrophotometer. Data are reported as follows: frequencies of absorption ($cm^{-1}$), intensity of absorption (s=strong, m=medium, w=weak, br=broad). High-resolution mass spectra were obtained at the Harvard University Mass Spectrometry Facility using a Bruker micrOTOF-QII or an Agilent 6220 LC-TOF mass spectrometer. Unless otherwise specified, diastereomeric ratios of products are reported as (major diastereomer):(sum of minor diastereomers). High performance liquid chromatography purifications were performed using an Agilent Technologies 1200 Series preparative HPLC system. LC-MS analysis was performed on an Agilent 6120 Single Quadrupole LC-MS interfaced to an Agilent 1260 Infinity HPLC instrument equipped with an Agilent Eclipse Plus C18, 1.8 μm, 2.1×50 mm reverse phase column, UV detection at 399 nm, 280 nm, 254 nm, 210 nm. The acidic eluent consisted of a linear gradient of acetonitrile from 10% to 90% in 0.1% aqueous formic acid over 8 min, followed by isocratic 90% acetonitrile for 2 min (flow rate=0.5 mL/min).

Synthesis of Trioxacarcin Halohydrin Analogs and Immolative Spacers

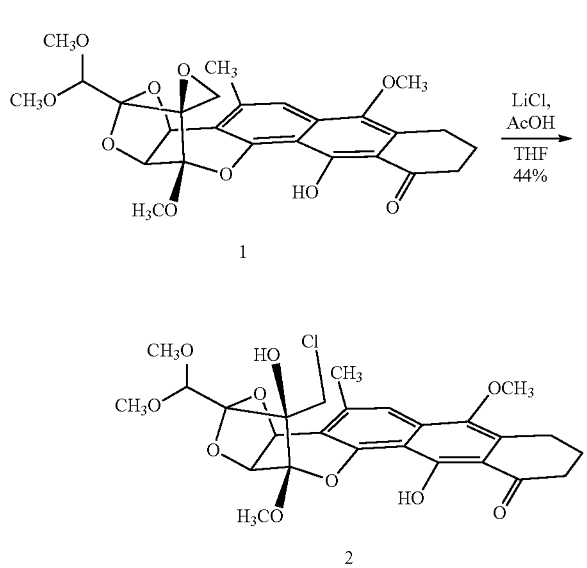

1

2

To a solution of epoxide 1 (1.5 mg, 0.003 mmol, 1 equiv) in tetrahydrofuran (60.0 μL) was added lithium chloride (8.9 mg, 0.210 mmol, 70 equiv) and glacial acetic acid (8.6 μL, 0.150 mmol, 50 equiv). The vessel was wrapped in foil to exclude light and the mixture was stirred at 23° C. for 24 h. The reaction mixture was partitioned between water (1 mL) and ethyl acetate (5 mL). The layers were separated and the aqueous layer was extracted with ethyl acetate (2×2 mL). The combined organic layers were washed with saturated aqueous sodium chloride solution (2 mL). The washed organic layer was dried over sodium sulfate. The dried solution was filtered and the filtrate was concentrated. The residue was purified by preparatory HPLC (Waters Prep-C18 SunFire® column, 5 μm, 19×250 mm, UV detection at 399 nm, gradient elution with 20→80% acetonitrile in water containing 0.1% formic acid over 25 min, flow rate: 15 mL/min) to provide chlorohydrin 2 as yellow film (0.7 mg, 44%). TLC (50% ethyl acetate-hexanes): $R_f$=0.22 (UV); $^1H$ NMR (600 MHz, $CDCl_3$) δ: 14.87 (s, 1H), 7.44 (d, J=0.9 Hz, 1H), 5.12 (d, J=3.8 Hz, 1H), 4.99 (s, 1H), 4.70 (d, J=3.8 Hz, 1H), 3.98 (s, 1H), 3.81 (s, 3H), 3.80 (d, J=12.6 Hz, 1H), 3.79 (s, 3H), 3.63 (s, 3H), 3.54 (s, 3H), 3.41 (d, J=12.4 Hz, 1H), 3.10-3.01 (m, 2H), 2.78-2.69 (m, 2H), 2.56 (d, J=1.0 Hz, 3H), 2.15-2.05 (m, 2H); FTIR (neat), $cm^{-1}$: 3508 (br w), 2956 (m), 1878 (m), 1621 (m), 1571 (m), 1389 (m), 1089 (s), 745 (w); HRMS (ESI): Calcd for $(C_{26}H_{29}ClO_{10}+H)^+$ 537.1522, found 537.1514.

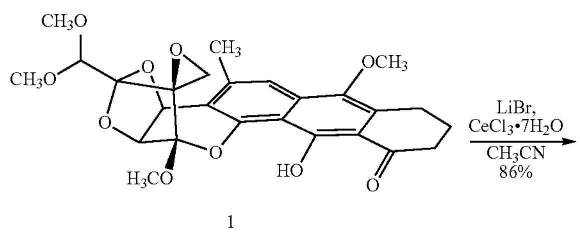

1

-continued

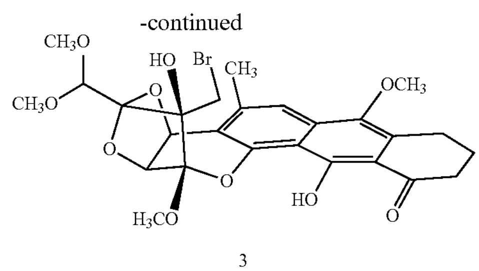

3

To a solution of epoxide 1 (23.6 mg, 0.047 mmol, 1 equiv) in acetonitrile (1.18 mL) was added lithium bromide (12.3 mg, 0.141 mmol, 3.0 equiv) and cerium(III) chloride heptahydrate (12.3 mg, 0.033 mmol, 0.7 equiv). The vessel was wrapped in foil to exclude light and the reaction mixture was stirred at 23° C. for 18 h at which time additional portions of lithium bromide (24.6 mg, 0.282 mmol, 6.0 eq) and cerium(III) chloride heptahydrate (12.3 mg, 0.033 mmol, 0.7 equiv) were added. The reaction mixture was stirred for an additional 9 h, then the mixture was partitioned between saturated aqueous sodium hydrogensulfite solution (2 mL) and ethyl acetate (10 mL). The layers were separated and the organic layer was washed with saturated aqueous sodium chloride solution (2 mL). The washed organic layer was dried over sodium sulfate. The dried solution was filtered and the filtrate was concentrated. The residue was purified by flash-column chromatography on silica gel (20%→50% ethyl acetate-hexanes) to provide bromohydrin 3 as a pale yellow-green solid (23.6 mg, 86%). TLC (75% ethyl acetate-hexanes): $R_f$=0.50 (UV); $^1$H NMR (600 MHz, $CDCl_3$) δ: 14.87 (s, 1H), 7.44 (d, J=1.1 Hz, 1H), 5.12 (d, J=3.8 Hz, 1H), 5.00 (s, 1H), 4.71 (d, J=3.8 Hz, 1H), 4.01 (s, 1H), 3.81 (s, 3H), 3.79 (s, 3H), 3.70 (d, J=11.6 Hz, 1H), 3.63 (s, 3H), 3.54 (s, 3H), 3.22 (d, J=11.6 Hz, 1H), 3.10-3.00 (m, 2H), 2.78-2.69 (m, 2H), 2.56 (d, J=0.9 Hz, 3H), 2.15-2.04 (m, 2H); $^{13}$C NMR (125 MHz, $CDCl_3$) δ: 204.6, 163.3, 152.6, 142.4, 141.4, 135.6, 130.8, 115.7, 112.8, 111.3, 108.5, 104.5, 100.4, 83.5, 71.1, 69.3, 61.0, 57.1, 56.8, 53.2, 39.0, 33.1, 23.8, 22.2, 20.2; FTIR (neat), $cm^{-1}$: 3525 (br w), 2923 (m), 2850 (m), 1620 (s), 1571 (m), 1445 (m), 1389 (s), 1095 (s), 1071 (s), 912 (m), 732 (m); HRMS (ESI): Calcd for $(C_{26}H_{29}BrO_{10}+H)^+$581.1017, found 581.1038.

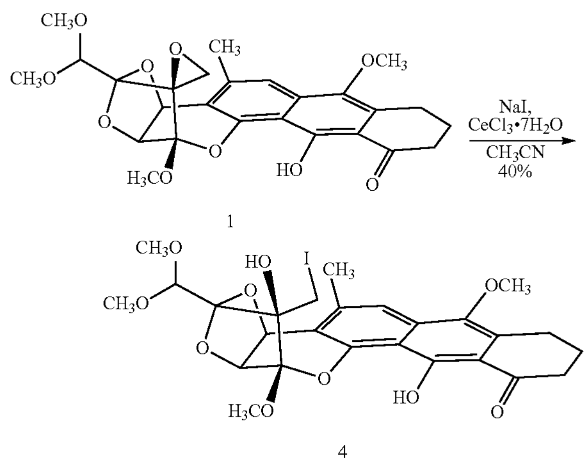

1

4

To a solution of epoxide 1 (2.0 mg, 0.004 mmol, 1 equiv) in acetonitrile (100 μL) was added sodium iodide (1.2 mg, 0.08 mmol, 2.0 equiv) and cerium(III) chloride heptahydrate (1.0 mg, 0.003 mmol, 0.7 equiv). The vessel was wrapped in foil to exclude light and the reaction mixture was stirred at 23° C. for 9 h. The mixture was partitioned between saturated aqueous sodium hydrogensulfite solution (0.5 mL) and ethyl acetate (1 mL). The layers were separated and the organic layer was washed with saturated aqueous sodium chloride solution (1 mL). The washed organic layer was dried over sodium sulfate. The dried solution was filtered and the filtrate was concentrated. The residue was purified by preparatory HPLC (Waters Prep-C18 SunFire® column, 5 μm, 19×250 mm, UV detection at 399 nm, gradient elution with 40-90% acetonitrile in water containing 0.1% formic acid over 25 min, flow rate: 15 mL/min) to provide iodohydrin 4 as yellow solid (1.0 mg, 40%). TLC (50% ethyl acetate-hexanes): $R_f$=0.27 (UV); $^1$H NMR (600 MHz, $CDCl_3$) δ: 14.85 (s, 1H), 7.44 (d, J=0.8 Hz, 1H), 5.12 (d, J=3.9 Hz, 1H), 5.00 (s, 1H), 4.71 (d, J=3.9 Hz, 1H), 4.01 (s, 1H), 3.80 (s, 3H), 3.80 (s, 3H), 3.64 (s, 3H), 3.59 (d, J=11.4 Hz, 1H), 3.54 (s, 3H), 3.10-3.01 (m, 2H), 2.95 (d, J=11.4 Hz, 1H), 2.79-2.69 (m, 2H), 2.56 (d, J=0.7 Hz, 3H), 2.15-2.06 (m, 2H); FTIR (neat), $cm^{-1}$: 3488 (br, w), 2926 (m), 2849 (w), 1620 (s), 1569 (m), 1445 (m), 1389 (s), 1095 (s), 1071 (s), 911 (m), 731 (m); HRMS (ESI): Calcd for $(C_{26}H_{29}IO_{10}+H)^+$629.0878, found 629.0906.

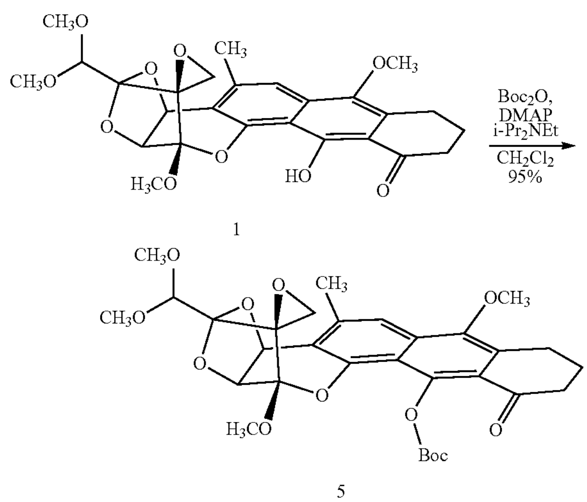

1

5

To a solution of methyl aglycone 1 (25 mg, 0.050 mmol, 1 equiv) in dichloromethane (1.00 mL) was added N,N-diisopropylethylamine (10.4 μL, 0.060 mmol, 1.2 equiv), di-tert-butyl dicarbonate (17.2 μL, 0.075 mmol, 1.5 equiv), and N,N-dimethylpyridine-4-amine (3.1 mg, 0.025 mmol, 0.5 equiv) in that order. The vessel was wrapped in foil to exclude light and the reaction mixture was stirred at 23° C. for 2 h. The reaction mixture was partitioned between dichloromethane (15 mL) and saturated aqueous ammonium chloride solution (10 mL). The layers were separated and the aqueous layer was extracted with dichloromethane (3×10 mL). The combined organic layers were dried over sodium sulfate. The dried solution was filtered and the filtrate was concentrated. The residue was purified first by flash-column chromatography on silica gel (35%→55% ethyl acetate-hexanes) to provide Boc-protected phenol 5 as a pale yellow foam (28.4 mg, 95%). TLC (50% ethyl acetate-hexanes): $R_f$=0.29 (UV); $^1$H NMR (500 MHz, $CDCl_3$) δ: 7.54 (d, J=1.1 Hz, 1H), 5.24 (d, J=4.2 Hz, 1H), 5.00 (d, J=4.2 Hz, 1H), 4.71

(s, 1H), 3.85 (s, 3H), 3.71 (s, 3H), 3.61 (s, 3H), 3.43 (s, 3H), 3.28-3.21 (m, 1H), 2.95 (d, J=5.7 Hz, 1H), 2.94-2.87 (m, 1H), 2.77 (d, J=5.6 Hz, 1H), 2.75-2.61 (m, 2H), 2.60 (d, J=1.0 Hz, 3H), 2.20-1.97 (m, 2H), 1.65 (s, 9H); $^{13}C$ NMR (125 MHz, $CDCl_3$) δ:197.0, 152.0, 149.9, 149.7, 144.6, 140.2, 133.2, 133.1, 122.8, 117.4, 115.8, 114.4, 104.7, 103.0, 100.0, 84.0, 77.4, 69.2, 68.9, 68.4, 61.4, 57.2, 56.9, 52.5, 47.5, 40.7, 29.8, 27.9, 24.0, 22.2, 20.6; FTIR (neat), $cm^{-1}$: 2926 (m), 2852 (w), 1752 (m), 1685 (m), 1623 (m), 1371 (m), 1258 (s), 1101 (s), 910 (s) 733 (s); HRMS (ESI): Caled for $(C_{31}H_{36}O_{12}+H)^+$601.2280, found 601.2280.

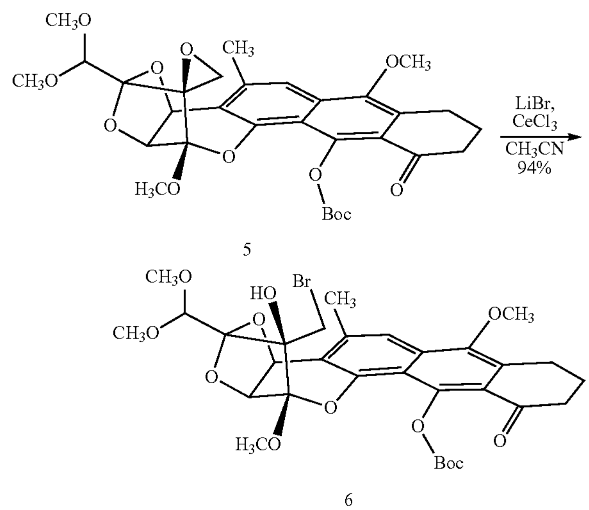

5

6

To a solution of epoxide 5 (59.6 mg, 0.099 mmol, 1 equiv) in acetonitrile (2.14 mL) was added lithium bromide (259 mg, 2.98 mmol, 30 equiv) and cerium(III) chloride heptahydrate (111 mg, 0.298 mmol, 3.0 equiv). The vessel was wrapped in foil to exclude light and the reaction mixture was stirred at 23° C. for 24 h. The reaction mixture was partitioned between saturated aqueous sodium hydrogensulfite solution (5 mL) and ethyl acetate (20 mL). The layers were separated and the organic layer was washed with saturated aqueous sodium chloride solution (5 mL). The washed organic layer was dried over sodium sulfate. The dried solution was filtered and the filtrate was concentrated. The residue was purified by flash-column chromatography on silica gel (45%→65% ethyl acetate-hexanes) to provide bromohydrin 6 as a pale yellow foam (63.3 mg, 94%). TLC (50% ethyl acetate-hexanes): $R_f$=0.25 (UV); $^1H$ NMR (600 MHz, $CDCl_3$) δ: 7.56 (d, J=1.2 Hz, 1H), 5.12 (d, J=3.8 Hz, 1H), 5.08 (s, 1H), 4.78 (d, J=3.8 Hz, 1H), 4.07 (br s, 1H), 3.87 (s, 3H), 3.78 (s, 3H), 3.61 (s, 3H), 3.56 (s, 3H), 3.48-3.35 (m, 2H), 3.25-2.93 (m, 2H), 2.69 (t, J=6.2 Hz, 2H), 2.58 (d, J=0.9 Hz, 3H), 2.19-2.02 (m, 2H), 1.65 (s, 9H); $^{13}C$ NMR (125 MHz, $CDCl_3$) δ: 197.1, 150.7, 149.6, 139.5, 133.4, 133.3, 122.9, 116.6, 115.9, 112.6, 108.5, 105.0, 100.1, 83.9, 77.4, 68.9, 61.4, 57.0, 56.0, 40.8, 32.8, 29.8, 28.2, 24.1, 22.1, 20.2; FTIR (neat), $cm^{-1}$: 3524 (br w), 2923 (m), 2852 (w), 1753 (m), 1685 (m), 1623 (m), 1446 (m), 1157 (s), 1058 (s), 910 (s) 733 (s); HRMS (ESI): Calcd for $(C_{31}H_{37}BrO_{12}+H)^+$681.1541, found 681.1535.

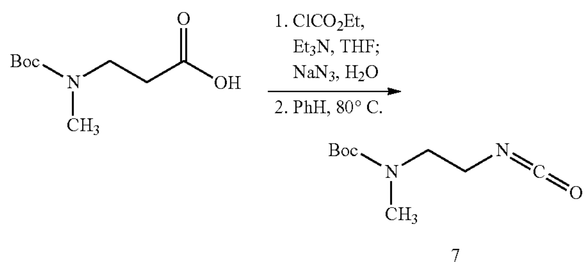

7

In a 25-mL flask, 3-((tertbutoxycarbonyl)(methyl)amino) propanoic acid (0.25 g, 1.23 mmol, 1 equiv) was dissolved in tetrahydrofuran (6.00 mL) and the solution was cooled to 0° C. in an ice-water bath. Triethylamine (343 μL, 2.46 mmol, 2.00 equiv) was added by syringe, followed by dropwise addition of ethyl chloroformate (235 μL, 2.46 mmol, 2.00 equiv) forming a white precipitate. The heterogeneous mixture was stirred vigorously at 0° C. for 20 min. Sodium azide (240 mg, 3.69 mmol, 3.00 equiv) was dissolved in water (4.20 mL) and added to the reaction mixture. The biphasic mixture was stirred vigorously at 0° C. for an additional 20 min, then the ice bath was removed and the mixture was allowed to warm to 23° C. for 10 min. The mixture was diluted with water (5 mL) and was extracted with ethyl acetate (3×5 mL). The combined organic layers were dried over sodium sulfate, filtered, and the filtrate concentrated not to dryness (CAUTION: acyl azides are known to be explosive when neat)! The resulting crude acyl azide containing residual ethyl acetate was taken up in benzene (7.00 mL) and heated to 80° C. for 30 min. The solution was cooled, concentrated, and dried under vacuum to provide crude isocyanate 7 as a pale brown oil that was taken forward without further purification. $^1H$ NMR (500 MHz, $CDCl_3$) δ: 3.44-3.39 (m, 4H), 2.92 (s, 3H), 1.47 (s, 9H); FTIR (neat), $cm^{-1}$: 2977 (w), 2932 (w), 2262 (s), 1690 (s), 1480 (m), 1391 (m), 1365 (m), 1232 (m), 1151 (s), 871 (w), 772 (w).

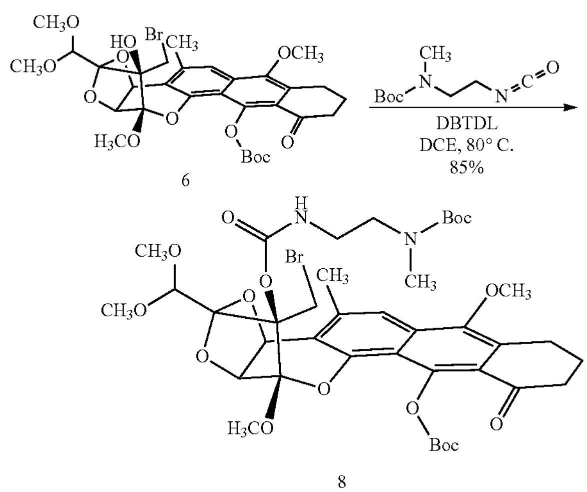

6

8

A conical microwave vial was charged with bromohydrin 6 (5.0 mg, 7.3 μmol, 1 equiv) as a solution in benzene. Solvent was removed by freezing then sublimation under high vacuum. The resulting pale-yellow residue was treated with a solution of isocyanate 7 (44.1 mg, 0.220 mmol, 30.0 equiv) in 1,2-dichloroethane (150 μL). Dibutyltin dilaurate (8.7 μL, 0.015 mmol, 2.0 equiv) was added and the reaction mixture was stirred at 23° C. for 10 min. The vial was sealed and the reaction was heated to 80° C. for 19 h. The reaction mixture was cooled to 23° C. and partitioned between ethyl acetate (5 mL) and 5% aqueous sodium bicarbonate solution (2 mL). The layers were separated and the organic layer was washed with saturated aqueous sodium chloride solution (2 mL). The washed organic layer was dried over sodium sulfate. The dried solution was filtered and the filtrate was concentrated. The residue was purified by preparatory HPLC (Waters Prep-C18 SunFire® column, 5 μm, 19×250 mm, UV detection at 399 nm, gradient elution with 40→90% acetonitrile in water containing 0.1% formic acid over 25 min, flow rate: 15 mL/min) to provide carbamate 8 as a white solid (5.5 mg, 85%). TLC (75% ethyl acetate-hexanes): $R_f$=0.31 (UV); $^1$H NMR (500 MHz, $CDCl_3$) δ: 7.55 (s, 1H), 5.20 (br s, 1H), 5.08 (s, 1H), 5.00 (s, 1H), 4.74 (s, 1H), 4.41 (br s, 1H), 3.85 (s, 3H), 3.70 (br s, 1H), 3.62 (s, 3H), 3.57 (s, 3H), 3.51 (s, 3H), 3.45-3.29 (m, 4H), 3.20-3.00 (m, 2H), 2.92 (s, 3H), 2.75-2.60 (m, 2H), 2.56 (s, 3H), 2.14-2.03 (m, 2H), 1.68 (s, 9H), 1.47 (s, 9H); HRMS (ESI): Calcd for $(C_{40}H_{53}BrN_2O_{15}+H)^+$898.2968, found 898.3009.

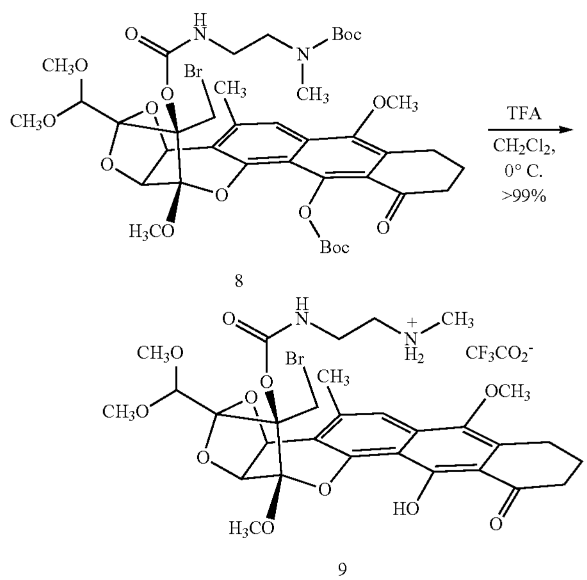

8

9

To a solution of N-Boc carbamate 8 (1.0 mg, 1.1 μmol, 1 equiv) in dichloromethane (113 μL) was added trifluoroacetic acid (8.7 μL, 110 μmol, 100 equiv) at 0° C. The resulting yellow solution was stirred at 0° C. for 1.5 h, after which an additional portion of trifluoroacetic acid (8.7 μL, 110 μmol, 100 equiv) was added. The reaction mixture was stirred at 0° C. for 1 h, then the solution was concentrated under reduced pressure. The residue was re-dissolved in a solution of dichloromethane and toluene (1:1) and concentrated again to remove residual trifluoroacetic acid. The crude product was dried under vacuum to provide the ammonium salt 9 as a bright yellow oil (0.9 mg, 99%). The material was used immediately in subsequent cyclization analysis without further purification. HRMS (ESI): Calcd for $(C_{30}H_{37}BrN_2O_{11}+H)^+$681.1653, found 681.1660.

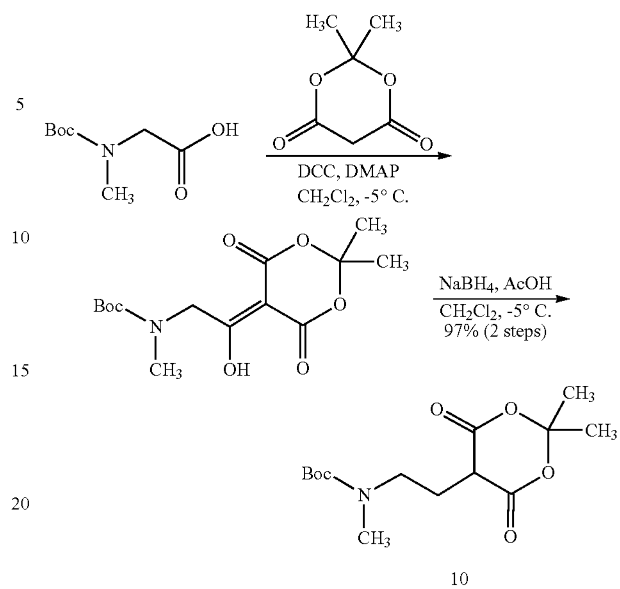

10

A 50-mL round bottom flask was charged with Boc-N-methylglycine (1.00 g, 5.29 mmol, 1 equiv), 2,2-dimethyl-1,3-dioxane-4,6-dione (0.838 g, 5.81 mmol, 1.10 equiv), and N,N-dimethylpyridine-4-amine (0.969 g, 7.93 mmol, 1.50 equiv). The solids were dissolved in dichloromethane (22.0 mL) and the resulting solution was cooled to 0° C. To the reaction mixture was added a solution of 1,3-dicyclohexylcarbodiimide (1.20 g, 5.81 mmol, 1.10 equiv) in dichloromethane (11.0 mL) by syringe pump over 1 h, then the reaction mixture was stirred at 4° C. for 17 h. Upon complete consumption of Boc-N-methylglycine as determined by TLC analysis (33% ethyl acetate-hexanes, UV, $KMnO_4$), the reaction mixture was warmed to 23° C. Suspended dicyclohexylurea was removed by filtration through a fritted glass funnel, then the filtrate was washed with 5% aqueous potassium bisulfate solution (4×10 mL) and saturated aqueous sodium chloride solution (10 mL). The washed organic solution was dried over sodium sulfate at 4° C. for 5 h. The dried solution was filtered and concentrated to approximately 20 mL, then the crude product solution was used directly in the next step without further purification assuming quantitative yield.

A 50-mL round bottom flask was charged with the crude keto ester as a solution in dichloromethane (20 mL) and the mixture was cooled to −5° C. in a salt/ice water bath. Acetic acid (3.33 mL, 58.2 mmol, 11.0 equiv) was added, followed by portion-wise addition of sodium borohydride (500 mg, 13.2 mmol, 2.5 equiv) over the course of 2.5 h (roughly 84 mg every 30 min). After complete addition of sodium borohydride, the reaction mixture was stirred at 4° C. for 15 h. The reaction was quenched by addition of water (10 mL) at 0° C., then the layers were separated. The organic layer was washed with water (2×10 mL) and saturated aqueous sodium chloride solution (2×10 mL). The washed organic solution was dried over sodium sulfate. The dried solution was filtered and the filtrate was concentrated. The residue was dissolved in diethyl ether (~8 mL) with brief heating, then was allowed to cool to 23° C. and subsequently stored at −15° C. for 30 min. Residual solid dicyclohexylurea was removed by filtration through a cotton plug, washing with additional 0° C. diethyl ether. The filtrate was concentrated and the residue was purified by flash-column chromatography (10-40% ethyl acetate-hexanes) to provide ketene precursor 10 as a clear, colorless oil (1.55 g, 97%). TLC (33% ethyl acetate-hexanes): $R_f$=0.30 (UV, $KMnO_4$); $^1H$ NMR (500 MHz, $CDCl_3$) δ: 4.02 (br s, 1H), 3.48 (t, J=6.0 Hz, 2H), 2.87 (s, 3H), 2.29 (q, J=5.8 Hz, 2H), 1.80 (s, 3H), 1.75 (s, 3H), 1.43 (s, 9H); HRMS (ESI): Calcd for $(C_{14}H_{23}NO_6+H)^+$302.1598, found 302.1590.

7.57 (s, 1H), 5.13-5.03 (m, 2H), 4.83 (s, 1H), 4.37 (br s, 1H), 3.85 (s, 3H), 3.60 (s, 6H), 3.55 (s, 3H), 3.52-3.37 (m, 4H), 3.29 (s, 1H), 3.05 (br s, 1H), 2.87 (s, 3H), 2.74-2.63 (m, 2H), 2.57 (s, 3H), 2.26-2.17 (m, 2H), 2.15-2.03 (m, 2H), 1.67 (s, 9H), 1.46 (s, 9H); HRMS (ESI): Caled for $(C_{41}H_{54}BrNO_{15}+Na)^+$946.2467, found 946.2492.

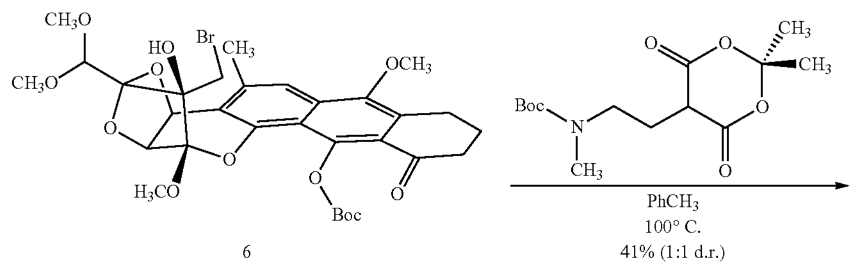

6

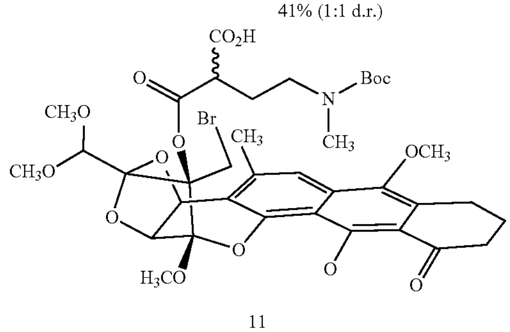

11

A microwave vial was charged with bromohydrin 6 (5.0 mg, 7.3 μmol, 1 equiv) as a solution in anhydrous benzene. Solvent was removed by freezing then sublimation under high vacuum. The resulting pale yellow residue was treated with 20 μL of a solution of ketene precursor 10 (11.1 mg, 37.0 μmol, 5.00 equiv) in anhydrous toluene (100 μL), then the vial was flushed with nitrogen, sealed, and heated to 110° C. in a pre-heated oil bath for 40 min. The subsequent 80 μL of ketene precursor 10 solution was added in four portions at intervals of 20 min beginning after the initial 40 min of heating. Once the final portion was added, the reaction mixture was stirred for an additional 20 min at 110° C. (2 h total reaction time), then the mixture was cooled to 23° C. and concentrated. $^1H$ NMR ($CDCl_3$) analysis of the crude residue indicated a 1:1 ratio of diastereomers at the carboxylic acid. The residue was purified by preparatory HPLC (Waters Prep-C18 SunFire® column, 5 μm, 19×250 mm, UV detection at 399 nm, gradient elution with 50-90% acetonitrile in water containing 0.1% formic acid over 25 min, flow rate: 15 mL/min) to provide ester 11 diastereomer 1 as a white solid (1.5 mg, 22%), and separately ester 11 diastereomer 2 as a white solid (1.3 mg, 19%). The absolute stereochemistry of each diastereomer was not determined.

Ester diastereomer 1—TLC (10% methanol-dichloromethane): $R_f$=0.37 (UV); $^1H$ NMR (600 MHz, $CDCl_3$) δ 7.57 (s, 1H), 5.11 (s, 1H), 5.04 (s, 1H), 4.81 (br s, 1H), 4.42 (br s, 1H), 3.85 (s, 3H), 3.59 (s, 6H), 3.53 (s, 3H), 3.52-3.39 (br m, 1H), 3.29 (s, 1H), 3.15 (br s, 2H), 2.92-2.84 (m, 5H), 2.75-2.63 (m, 2H), 2.57 (s, 3H), 2.21 (br m, 2H), 2.10 (br m, 2H), 1.67 (s, 9H), 1.46 (s, 9H); HRMS (ESI): Calcd for $(C_{41}H_{54}BrNO_{15}+Na)^+$946.2467, found 946.2495.

Ester diastereomer 2—TLC (10% methanol-dichloromethane): $R_f$=0.33 (UV); $^1H$ NMR (600 MHz, $CDCl_3$) δ

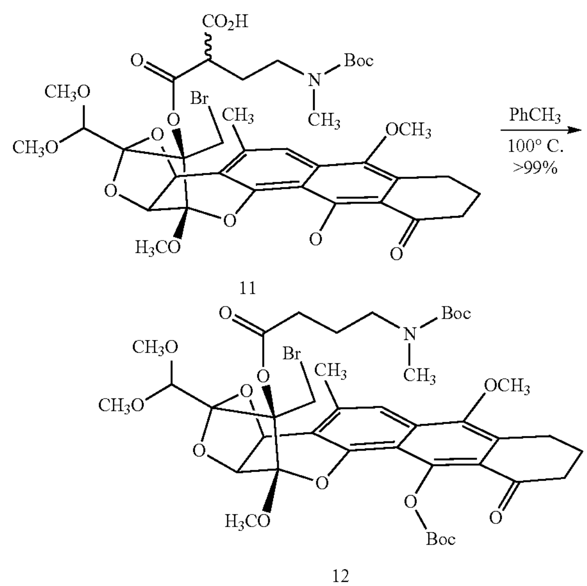

11

12

In a conical microwave vial, carboxylic acid 11 (0.4 mg, 0.4 μmol, 1 equiv) was dissolved in toluene (1 mL) and the vial was capped and vented with a 20-gauge needle. The solution was heated to 100° C. in an oil bath for 18 h, after which analysis by high resolution mass spectrometry indicated complete decarboxylation. The solution was cooled to 23° C. and concentrated to provide ester 12 as a colorless film (0.4 mg, >99%). This material was carried forward without further purification. HRMS (ESI): Calcd for $(C_{41}H_{54}BrNO_{15}+H)^+$902.2575, found 902.2619.

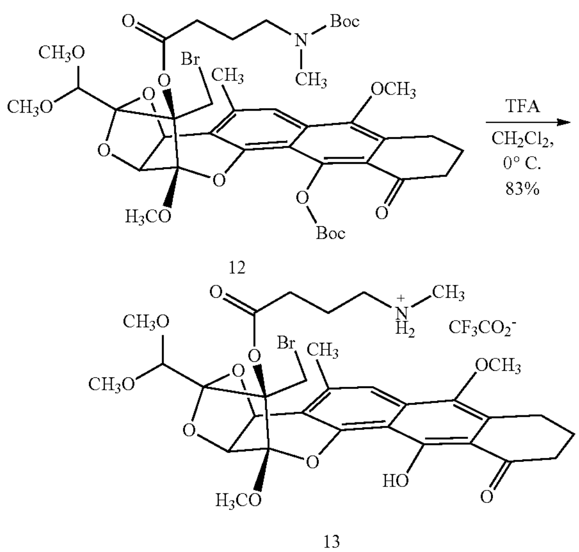

12

13

To a solution of N-Boc ester 12 (0.4 mg, 0.4 μmol, 1 equiv) in dichloromethane (45 L) was added trifluoroacetic acid (7.0 μL, 0.091 mmol, 200 equiv) at 0° C. The resulting yellow solution was stirred for 1 h, then the solution was concentrated under reduced pressure. The residue was re-dissolved in a solution of dichloromethane and toluene (1:1) and concentrated again to remove residual trifluoroacetic acid. The crude product was dried under vacuum to provide the ammonium salt 13 as a bright yellow film and determined to be 83% pure by liquid chromatography-mass spectrometry analysis (0.4 mg, 83%). The remaining fraction of the crude mixture was the free bromohydrin 3. The material was used immediately in subsequent cyclization analysis without further purification. HRMS (ESI): Calcd for $(C_{31}H_{38}BrNO_{11}+H)^+$680.1701, found 680.1750.

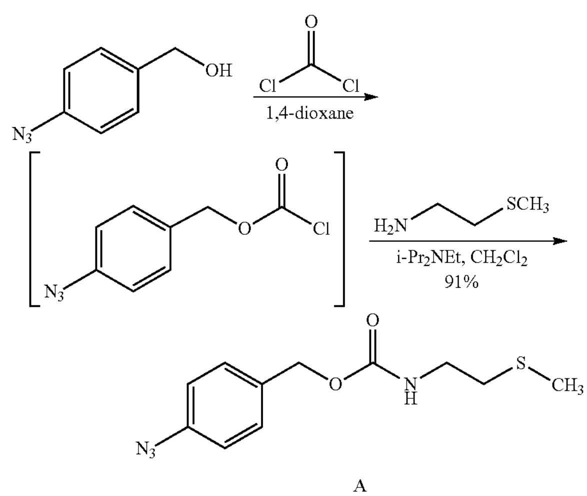

A

To an oven-dried, 250 mL round bottom flask containing 4-azidobenzyl alcohol[1] (1.25 g, 8.38 mmol, 1 equiv) and 1,4-dioxane (100 mL) was added phosgene as a 15% wt. solution in toluene (12.2 mL, 17.1 mmol, 2.04 equiv). Caution: phosgene is a poisonous gas. The resultant mixture was stirred at 23° C. for 24 h. Upon completion, the mixture was concentrated under reduced pressure. The crude yellow oil was resuspended in benzene (25 mL) and concentrated under reduced pressure. The 4-azidobenzyl chloroformate was resuspended in dichloromethane (100 mL) followed by addition of 2-(methylthio)ethan-1-amine (1.17 mL, 12.6 mmol, 1.50 equiv) and N,N-diisopropylethylamine (3 mL). The mixture was stirred at 23° C. for 16 h. Upon completion, the reaction was concentrated under reduced pressure. The residue was purified by flash-column chromatography (20% ethyl acetate-hexanes) to yield carbamate A as a white solid (2.03 g, 91% yield). TLC (30% ethyl acetate-hexanes): $R_f$=0.32; $^1$H NMR (500 MHz, $CDCl_3$) δ: 7.37-7.31 (m, 2H), 7.04-6.98 (m, 2H), 5.44 (s, 1H), 5.07 (s, 2H), 3.73 (q, J=6.0 Hz, 2H), 3.25 (t, J=5.9 Hz, 2H), 2.94 (s, 3H); $^{13}$C NMR (125 MHz, $CDCl_3$) δ: 156.3, 140.1, 133.3, 129.9, 119.2, 66.2, 39.5, 34.3, 15.1; FTIR (neat), $cm^{-1}$: 3331 (w), 3041 (w), 2918 (w), 2412 (w), 2255 (w), 2109 (s), 1697 (s), 1608 (s), 1508 (s), 1435 (s), 1362 (s), 1287 (w), 1248 (s), 1131 (s), 1056 (s); HRMS (ESI): Calcd for $(C_{11}H_{14}N_4O_2S+H)^+$ 267.0910, found 267.0912.

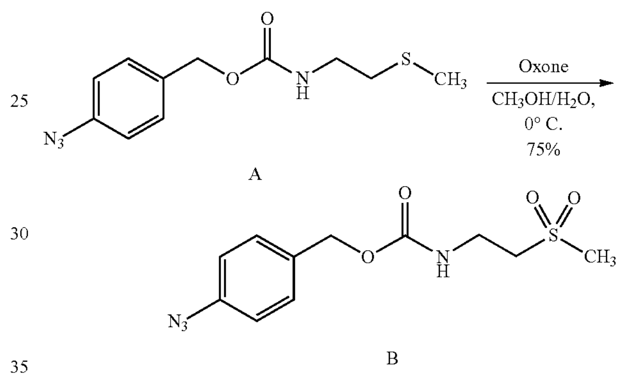

A

B

To a stirred solution of sulfide A (360 mg, 1.35 mmol, 1 equiv) in methanol (3.86 mL) at 0° C. was added Oxone (2.49 g, 4.06 mmol, 3.00 equiv). The resulting mixture was stirred at 0° C. for 3 h. Upon completion, solvent was removed under reduced pressure and the residue was partitioned between ethyl acetate (15 mL) and water (5 mL). The organic layer was separated and dried over sodium sulfate. The dried solution was filtered and the filtrate concentrated. The residue was purified by flash-column chromatography (20→50% ethyl acetate-hexanes) to provide sulfoxide carbamate B is a white, crystalline solid (318 mg, 79%). TLC (50% ethyl acetate-hexanes): $R_f$=0.13; $^1$H NMR (500 MHz, $CDCl_3$) δ: 7.37-7.31 (m, 2H), 7.04-6.98 (m, 2H), 5.44 (s, 1H), 5.07 (s, 2H), 3.73 (q, J=6.0 Hz, 2H), 3.25 (t, J=5.9 Hz, 2H), 2.94 (s, 3H); 13C NMR (125 MHz, $CDCl_3$) δ: 156.3, 140.2, 132.9, 123.0, 119.2, 66.5, 54.3, 41.8, 35.0; FTIR (neat), $cm^{-1}$: 3350 (w), 3018 (w), 2932 (w), 2413 (w), 2257 (w), 2113 (s), 1707 (s), 1608 (s), 1511 (s), 1456 (s), 1412 (s), 1371 (w), 1287 (s), 1254 (s), 1187 (s), 1128 (s), 1054 (s); HRMS (ESI): Calcd for $(C_{11}H_{14}N_4O_4S+NH_4)^+$316.1074, found 316.1074.

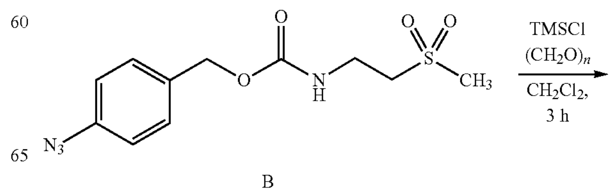

B

-continued

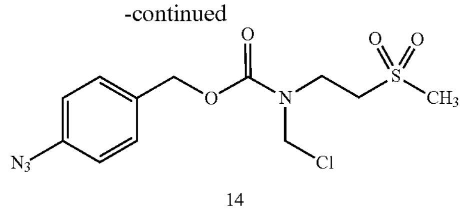

14

To a stirred solution of carbamate B (109 mg, 0.365 mmol, 1 equiv) in dichloromethane (1.75 mL) at 0° C. was added powdered paraformaldehyde (16.4 mg, 0.545 mmol, 1.50 equiv), followed by freshly distilled trimethylsilyl chloride (87.6 μL, 0.730 mmol, 2.00 equiv). The reaction mixture was allowed to warm to 23° C. and stirred for 3 h, monitoring by quenching an aliquot with methanol and observation of the methoxymethyl adduct by TLC (75% ethyl acetate-hexanes, UV) and LC-MS analysis. The reaction mixture was taken up in a syringe and passed through a 0.45 m syringe filter into a fresh, flame-dried flask. The filtered solution was diluted with anhydrous toluene (1.0 mL) and concentrated under reduced pressure while maintaining a nitrogen atmosphere. The residue was dried further by concentration from an additional 1.0 mL of anhydrous toluene to yield a pale, yellow oil. The crude chloromethyl carbamate 14 was dried for a minimum of 30 min under high vacuum and then was used in the following step without further purification.

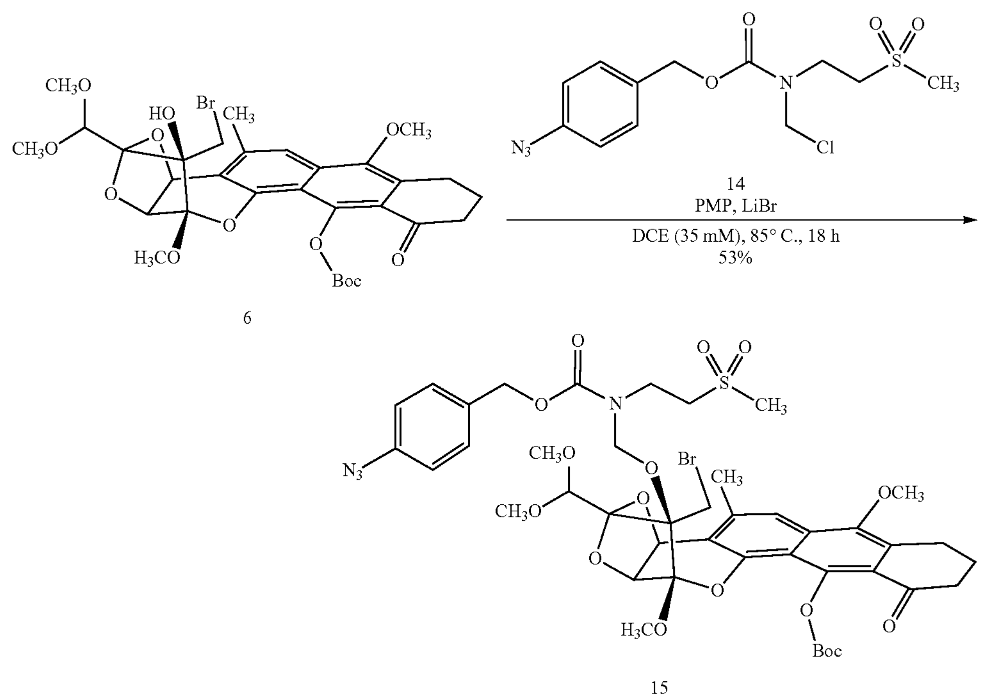

6

15

To an oven dried, 5-mL round bottom flask was added bromohydrin 6 (25.0 mg, 37 mol, 1 equiv), lithium bromide (16.0 mg, 0.185 mmol, 5.00 equiv), and 1,2-dichloroethane (520 L). The vessel was degassed with nitrogen for 1 min. To this was added a portion of chloromethyl carbamate 14 (42.7 mg, 0.123 mmol, 3.33 equiv) as a solution in 1,2-dichloroethane (173 μL) followed by a portion of the pentamethyl piperidine (33.0 μL, 0.185 mmol 5.00 equiv). The reaction mixture was transferred to an oil bath pre-heated to 85° C. After 2 h, an additional portion of chloromethyl carbamate 14 (42.7 mg, 0.123 mmol, 3.33 equiv) as a solution in 1,2-dichloroethane (173 μL) followed by a portion of the pentamethyl piperidine (33.0 μL, 0.185 mmol 5.00 equiv) were added. The mixture was purged with nitrogen for 30 s before being heated to 85° C. again. After an additional 2 h, the final portion of chloromethyl carbamate 14 (42.7 mg, 0.123 mmol, 3.33 equiv) as a solution in 1,2-dichloroethane (173 μL) followed by a portion of the pentamethyl piperidine (33.0 μL, 0.185 mmol 5.00 equiv) were added. The mixture was purged with nitrogen for 30 s before being heated to 85° C. for an additional 18 h (total: 22 h). The crude reaction mixture was allowed to cool to room temperature then transferred to a separatory funnel containing dichloromethane (15 mL) and water (5 mL). The round bottom flask was rinsed with dichloromethane (2×5 mL). The organic layer was separated and the aqueous layer was extracted with dichloromethane (2×15 mL). The combined organic layers were dried over sodium sulfate. The dried solution was filtered and the filtrate concentrated. The residue was purified by preparatory HPLC (Waters Prep-C18 SunFire® column, 5 μm, 19×250 mm, UV detection at 399 nm, gradient elution with 40→90% acetonitrile in water containing 0.1% formic acid over 25 min, flow rate: 15 mL/min) to provide hemiaminal ether 15 as a light yellow solid (19.3 mg, 53%). TLC (75% ethyl acetate-hexanes): $R_f$=0.16; $^1$H NMR (pairs of signals in a 2:1 ratio due to carbamate rotamers are denoted by an * and integration is provided as seen, 600 MHz, $CDCl_3$) δ: 7.55 (d, J=1.2 Hz, 1H), 7.39 (d, J=8.1 Hz, 2H), *7.03 (d, J=8.1 Hz, 0.77H), *6.97 (d, J=8.0 Hz, 1.23H), *5.59 (d, J=7.6 Hz, 0.33H), *5.50 (br s, 0.63H), 5.23 (d, J=8.3 Hz, 1H), *5.16 (s, 1.39H), 5.14 (d, J=12.4 Hz, 1H), 5.10-5.06 (m, 1H), *4.98 (s, 0.64H), 4.84-4.81 (m, 1H), 4.13-4.02 (m, 1H), 3.86 (s, 3H), 3.80-3.70 (m, 1H), 3.67 (ddd, J=14.8, 10.2, 5.0 Hz, 2H), 3.62-3.55 (m, 2H), 3.51 (s, 3H), 3.46 (s, 3H), 3.41 (s, 3H), 3.06 (br s, 2H), *2.97 (s, 2.23H), 2.85 (s, 1.10H), 2.69 (t, J=6.5 Hz, 2H), 2.57 (s, 3H), 2.11 (br s, 2H), 1.63 (s, 9H); $^{13}C$ NMR (125 MHz, $CDCl_3$) δ: 197.0, 155.6, 151.6, 150.8, 149.7, 144.5, 140.3, 139.5, 133.5, 133.3, 132.7, 130.2, 122.7, 119.4, 119.2, 116.5, 116.1, 112.6, 112.6, 108.9, 107.9, 99.5, 99.2, 87.5, 84.0, 75.9, 68.8, 67.5, 61.4, 56.1, 55.5, 54.9, 53.8, 53.0, 52.5, 42.4, 41.5, 41.2, 40.8, 29.8, 28.3, 26.2, 24.2, 22.1, 20.3; FTIR (neat), $cm^{-1}$: 2942 (s) 2838 (w) 2112 (s) 1757 (s) 1710 (s) 1686 (s) 1139 (s) 731.11 (s); HRMS (ESI): Calcd for $(C_{43}H_{51}BrN_4O_{16}S+NH_4)^+$1008.2542, found 1008.2526.

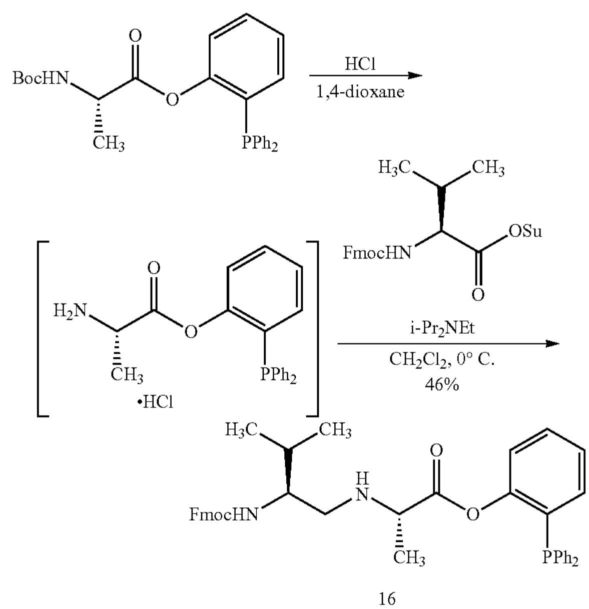

16

In a 10-mL round bottom flask, N-Boc alanine phosphine ester (100 mg, 0.222 mmol, 1 equiv) was taken up in a solution of 4.0 M hydrogen chloride in dioxane (2.78 mL, 11.2 mmol, 50.0 equiv) at 0° C. After 5 min, the ice bath was removed and the solution was stirred at 23° C. for 1 h. The reaction mixture was concentrated under reduced pressure, and the residue was triturated with diethyl ether (3×5 mL). Residual diethyl ether was removed under reduced pressure to provide the crude ammonium salt as a white foam. The product was taken forward without further purification after confirming quantitative conversion by $^1H$ NMR ($CDCl_3$) analysis.

The crude ammonium salt intermediate was dissolved in dichloromethane (1.10 mL) and cooled to 0° C. Fmoc-L-Val-OSu (102 mg, 0.234 mmol, 1.05 equiv) was added to the solution, followed by dropwise addition of N,N-diisopropylethylamine (58.2 μL, 0.334 mmol, 1.50 equiv). The cooling bath was allowed to warm to 23° C. and the reaction mixture was stirred for 5 h. The mixture was diluted with dichloromethane (15 mL) and the organic layer was washed with 0.5 M aqueous citric acid solution (5 mL), saturated aqueous sodium bicarbonate solution (5 mL), and water (5 mL). The washed organic layer was dried over sodium sulfate. The dried solution was filtered and the filtrate was concentrated. The residue was purified by flash-column chromatography (15-30% ethyl acetate-hexanes) to provide dipeptide 16 as a white foam (69.0 mg, 46%). TLC (33% ethyl acetate-hexanes): $R_f$=0.33 (UV); $^1H$ NMR (600 MHz, $CDCl_3$) δ: 7.76 (d, J=7.6 Hz, 2H), 7.59 (d, J=7.5 Hz, 2H), 7.42-7.26 (m, 15H), 7.16 (t, J=7.2 Hz, 2H), 6.83-6.78 (m, 1H), 6.15 (d, J=7.4 Hz, 1H), 5.42 (d, J=8.9 Hz, 1H), 4.63 (p, J=7.3 Hz, 1H), 4.43 (dd, J=10.6, 7.3 Hz, 1H), 4.35 (dd, J=10.7, 7.1 Hz, 1H), 4.22 (t, J=7.0 Hz, 1H), 3.97 (dd, J=8.9, 6.1 Hz, 1H), 2.11-2.02 (m, J=6.9 Hz, 1H), 1.32 (d, J=7.2 Hz, 3H), 0.94 (d, J=6.8 Hz, 3H), 0.92 (d, J=6.9 Hz, 3H); $^{13}C$ NMR (125 MHz, $CDCl_3$) δ 170.8, 170.6, 156.5, 152.7, 152.6, 144.0, 143.9, 141.4, 135.5, 135.4, 135.4, 135.3, 134.2, 134.1, 134.0, 134.0, 133.9, 130.3, 130.2, 130.1, 129.3, 128.9, 128.8, 127.9, 127.2, 126.7, 125.3, 125.2, 122.3, 120.1, 120.1, 67.2, 60.2, 48.5, 47.3, 31.6, 19.3, 17.9; FTIR (neat), $cm^{-1}$: 3296 (br, m), 3068 (w), 2963 (w), 1696 (m), 1654 (s), 1535 (s), 1245 (m), 1181 (m), 1132 (s), 1028 (m), 908 (s), 729 (s), 697 (s); HRMS (ESI): Calcd for $(C_{41}H_{39}N_2O_5P+H)^+$ 671.2699, found 671.2667.

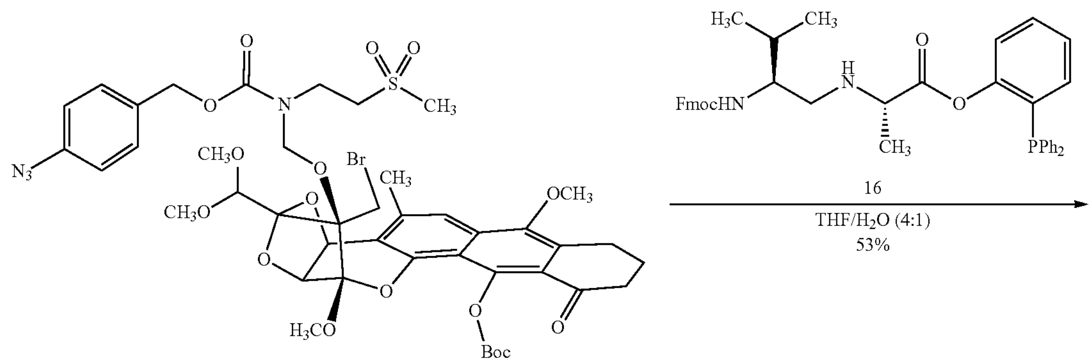

15

-continued

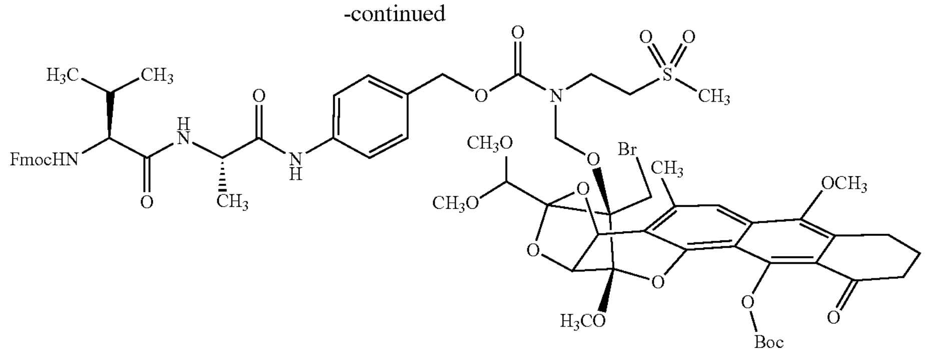

17

A 10-mL round bottom flask containing was charged with the p-azidobenzyl carbamate 15 (19.3 mg, 0.020 mmol, 1 equiv) and dipeptide ester 16 (33.0 mg, 0.050 mmol, 2.50 equiv). The solids were degassed with nitrogen for 5 minutes then tetrahydrofuran (775 μL) and water (194 μL) were added. The reaction was stirred for 24 h at 23° C. Upon completion, the reaction was diluted with water (600 μL) and then concentrated under reduced pressure in a 40° C. water bath. The residue was purified by preparatory HPLC (Waters Prep-C18 SunFire® column, 5 μm, 19×250 mm, UV detection at 399 nm, gradient elution with 50-80% acetonitrile in water containing 0.1% formic acid over 25 min, flow rate: 15 mL/min) to provide protected Val-Ala-PABO-carbamate 17 as a white solid (14.1 mg, 53%). FTIR (neat), $cm^{-1}$: 3309 (w), 3131 (w), 3063 (w), 2961 (w), 2939 (w), 2845 (w), 2255 (w), 1758 (s), 1697 (s), 1648 (s), 1531 (s), 1449 (s), 1413 (s), 1373 (s), 1334 (s), 1307 (s), 1247 (s), 1138 (s), 1089 (s), 1062 (s), 1021 (s); HRMS (ESI) Calcd for $(C_{66}H_{77}BrN_4O_{20}S+NH_4)^+$1374.4374, found 1374.4476.

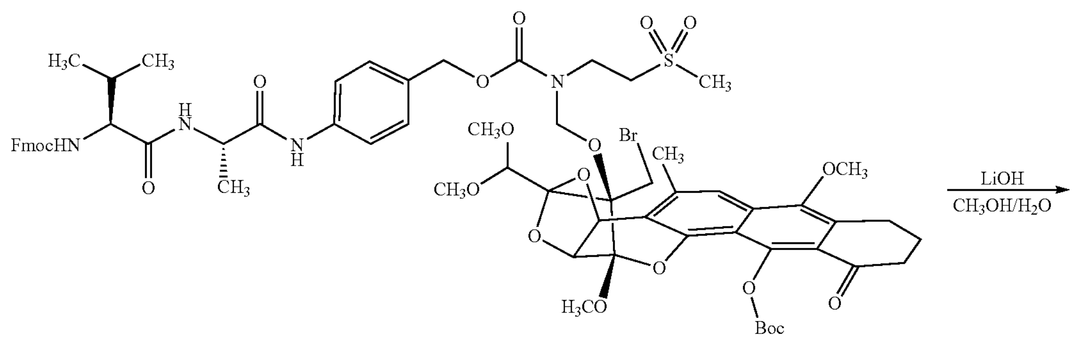

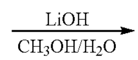

17

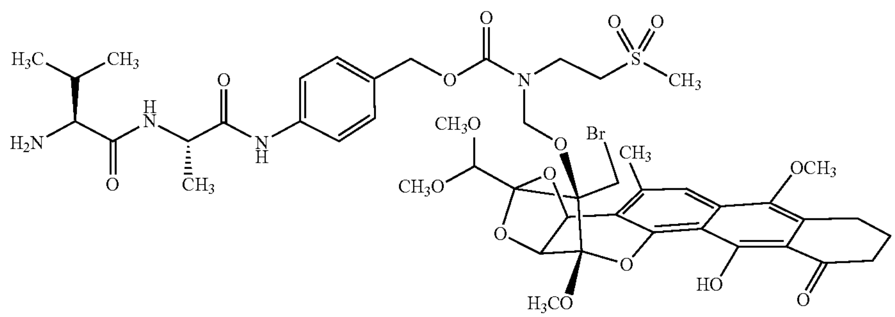

18

In a 10-mL round bottom flask, protected Val-Ala-PABO-carbamate 17 (5.0 mg, 0.004 mmol, 1 equiv) was dissolved in a methanol/water solution (1.75 mL, 1:1 v/v). To this was added lithium hydroxide (10.0 mg, 0.400 mmol, 100 equiv) and the reaction was stirred at 23° C. Reaction progression, i.e., removal of the Fmoc (first) then Boc (second) protecting groups, was monitored by LCMS. After 5 h, a second portion of lithium hydroxide (5.0 mg, 0.200 mmol, 50.0 equiv) was added. After an additional 2 h, LCMS indicated complete conversion to product and the mixture was concentrated under reduced pressure. The residue was purified by preparatory HPLC (Waters Prep-C18 SunFire® column, 5 μm, 19×250 mm, UV detection at 399 nm, gradient elution with 5→25% acetonitrile in water containing 0.1% formic acid over 25 min, flow rate: 15 mL/min) to provide deprotected Val-Ala-PABO-carbamate 18 as a light yellow solid. The product was carried immediately to the next step. HRMS (ESI): Calcd for $(C_{46}H_{59}BrN_4O_{16}S+Na)^+$ 1057.2722, found 1057.2704.

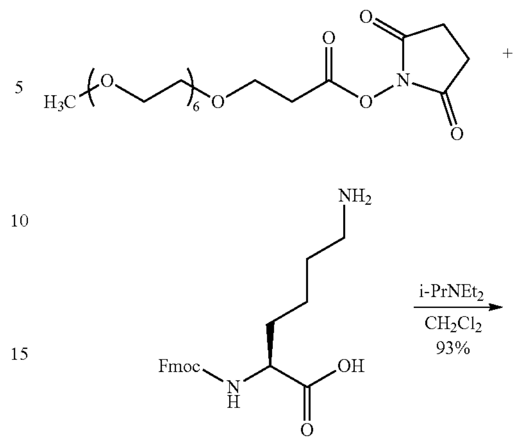

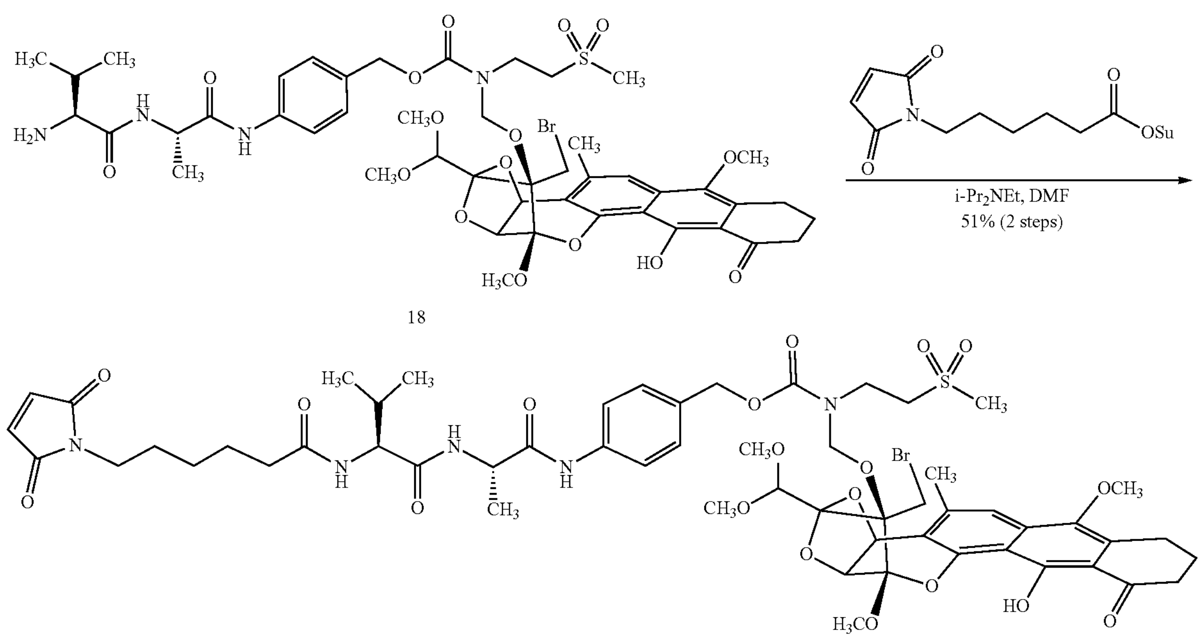

18

19

An oven-dried 5 mL round bottom flask was charged with deprotected Val-Ala-PABO-carbamate 18 and 6-maleimidohexanoic acid N-hydroxysuccinimide ester (15.0 mg, 0.050 mmol, 12.5 equiv). The solids were degassed with nitrogen for 1 min then dissolved in dimethylformamide (500 μL) followed by addition of N,N-diisopropylethylamine (131 μL, 0.100 mmol, 25 equiv). The mixture was stirred at 23° C. for 2 h then purified directly by by preparatory HPLC (Waters Prep-C18 SunFire® column, 5 μm, 19×250 mm, UV detection at 399 nm, gradient elution with 50→80% acetonitrile in water containing 0.1% formic acid over 25 min, flow rate: 15 mL/min) to provide maleimido trioxacarcin drug-linker 19 as a fluorescent yellow film (2.3 mg, 51% over 2 steps). FTIR (neat), $cm^{-1}$: 3273 (w), 3702 (w), 2934 (w), 2863 (w), 1706 (s), 1630 (s), 1539 (s), 1446 (s), 1390 (s), 1307 (s), 1245 (s), 1180 (s), 1116 (s), 1066 (s), 1019 (s); HRMS (ESI): Calcd for $(C_{56}H_{70}BrN_5O_{19}S+NH_4)^+$ 1245.3907, found 1245.3909.

-continued

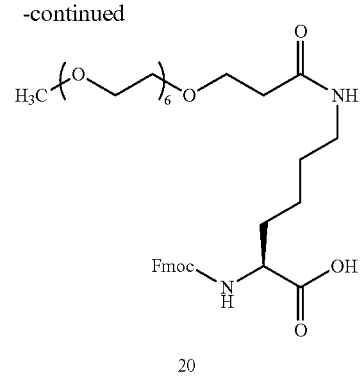

20

To a flame-dried 25 mL flask was added Fmoc-L-lysine (235 mg, 0.638 mmol, 1 equiv) under argon atmosphere. mPEG6-NHS ester (297 mg, 0.638 mmol, 1 equiv) was then added as a solution in dichloromethane (12.8 mL), followed by the addition of N,N-diisopropylethylamine (556 μl, 3.19 mmol, 5.0 equiv) at 23° C. After 20 h, the reaction mixture was partitioned between dichloromethane (30 mL) and water (10 mL). The aqueous layer was extracted with dichloromethane (3×30 mL). The organic layers were combined, and the combined solution was dried over sodium sulfate. The dried solution was filtered, and the filtrate was concentrated. The residue was purified by flash-column chromatography (0%→15% methanol-dichloromethane) to provide Fmoc-(PEG7)-L-Lys 20 as a clear, colorless oil (425 mg, 93%). TLC (15% methanol-dichloromethane): $R_f$=0.20 (UV, $KMnO_4$); $^1H$ NMR (500 MHz, $CDCl_3$) δ: 7.75 (d, J=7.5 Hz, 2H), 7.60 (t, J=6.9 Hz, 2H), 7.39 (t, J=7.5 Hz, 2H), 7.30 (t, J=7.6 Hz, 2H), 6.81 (t, J=5.9 Hz, 1H), 5.76 (d, J=7.8 Hz, 1H), 4.42-4.35 (m, 3H), 4.20 (t, J=7.0 Hz, 1H), 3.70-3.66 (m, 2H), 3.66-3.57 (m, 22H), 3.55-3.52 (m, 2H), 3.37 (s, 3H), 3.32-3.20 (m, 2H), 2.46 (t, J=5.5 Hz, 2H), 1.94-1.76 (m, 2H), 1.61-1.31 (m, 4H); $^{13}C$ NMR (125 MHz, $CDCl_3$) δ: 173.8, 172.4, 156.2, 144.1, 144.0, 141.4, 127.8, 127.2, 125.3, 120.1, 72.0, 70.7, 70.6, 70.6, 70.6, 70.6, 70.5, 70.4, 70.2, 67.4, 66.9, 59.1, 53.7, 47.4, 38.9, 37.0, 31.8, 29.0, 22.1; FTIR (neat), $cm^{-1}$: 3324 (br w), 2869 (s), 1716 (s), 1648 (m), 1535 (m), 1248 (m), 1102 (s), 741 (m); HRMS (ESI): Calcd for $(C_{37}H_{54}N_2O_{12}+H)^+$719.3750, found 719.3744.

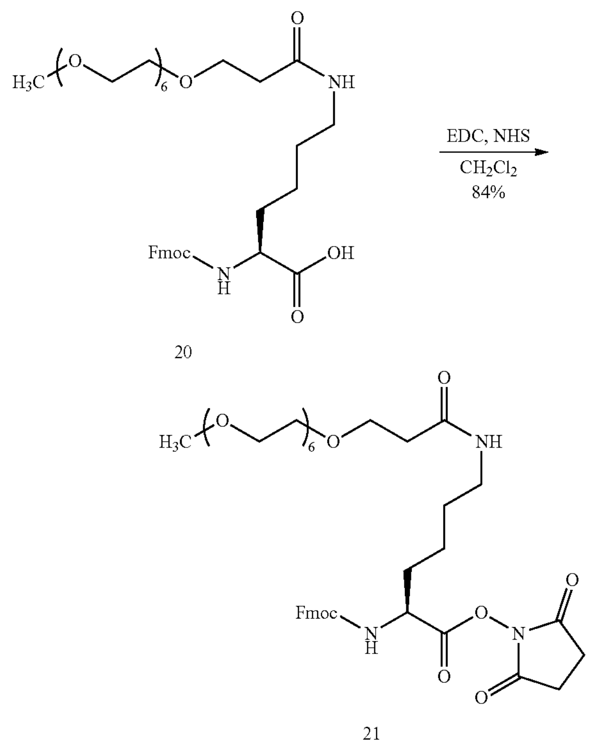

20

21

A vial containing Fmoc-(PEG7)-L-Lys 20 (161 mg, 0.224 mmol, 1 equiv) was charged with N-hydroxysuccinimide (30.9 mg, 0.269 mmol, 1.2 equiv) and N-ethyl-N'-(3-dimethylaminopropyl)carbodiimide hydrochloride (64.4 mg, 0.336 mmol, 1.5 equiv). The solids were dissolved in dichloromethane (2.24 mL) and stirred at 23° C. After 18 h, the reaction was quenched with water (9 mL). The layers were separated and the aqueous layer was extracted with dichloromethane (3×30 mL). The organic layers were combined and the combined solution was dried over sodium sulfate. The dried solution was filtered and the filtrate was concentrated to provide succinimide ester 21 as a clear, colorless oil (153 mg, 84%). The product was taken forward without further purification. TLC (15% methanol-dichloromethane): $R_f$=0.63 (UV, $KMnO_4$); $^1H$ NMR (600 MHz, $CDCl_3$) δ: 7.75 (d, J=7.6 Hz, 2H), 7.61 (t, J=6.7 Hz, 2H), 7.39 (t, J=7.4 Hz, 2H), 7.34-7.27 (m, 2H), 6.68 (s, 1H), 6.17 (t, J=6.1 Hz, 1H), 5.90 (d, J=7.8 Hz, 1H), 4.69-4.64 (m, 1H), 4.52-4.42 (m, 2H), 4.22 (t, J=6.8 Hz, 1H), 3.68 (td, J=6.1, 1.8 Hz, 2H), 3.65-3.51 (m, 22H), 3.36 (s, 3H), 3.33-3.20 (m, 2H), 2.87-2.83 (m, 6H), 2.47-2.42 (m, 2H), 2.03-1.85 (m, 2H), 1.61-1.45 (m, 4H); Calcd for $(C_{41}H_{57}N_3O_{14}+H)^+$ 816.3913, found 816.3904.

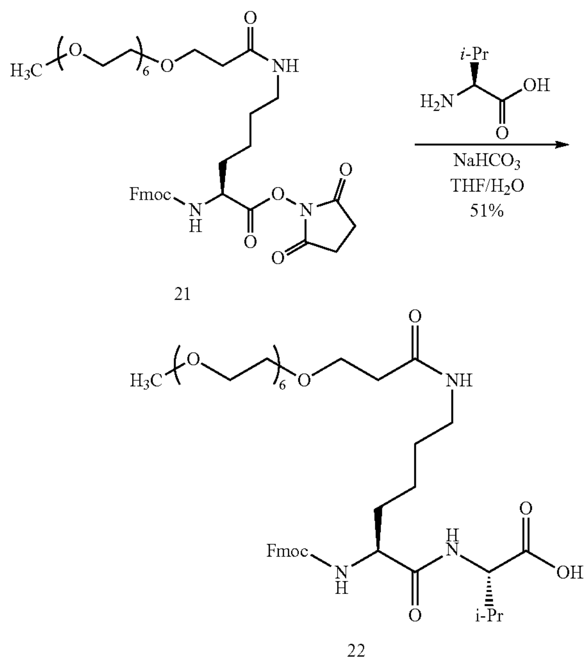

21

22

In a 1-dram vial, L-valine (7.5 mg, 0.064 mmol, 1.05 equiv) and sodium bicarbonate (5.7 mg, 0.067 mmol, 1.10 equiv) were suspended in a mixture of tetrahydrofuran (123 μL) and water (123 μL). To this mixture was added NHS ester 21 (50.0 mg, 0.061 mmol, 1 equiv) as a solution in tetrahydrofuran (123 μL). The resulting heterogeneous mixture was stirred vigorously at 23° C. for 24 h. The reaction mixture was concentrated under reduced pressure to remove tetrahydrofuran and the remaining aqueous mixture was diluted with water (1 mL). The solution was adjusted to pH 3 by addition of 1.0 M aqueous hydrochloric acid solution. The aqueous layer was extracted with ethyl acetate (6×2 mL) and the combined organic layers were washed with water (2 mL) and saturated aqueous sodium chloride solution (2 mL). The washed organic layer was dried over sodium sulfate. The dried solution was filtered, and the filtrate was concentrated. The residue was purified by preparatory HPLC (Waters Prep-C18 SunFire® column, 5 μm, 19×250 mm, UV detection at 280 nm, gradient elution with 20→90% acetonitrile in water containing 0.1% formic acid over 25 min, flow rate: 15 mL/min) to provide Fmoc-Lys(PEG7)-Val-OH 22 as a clear, colorless oil (25.3 mg, 51%). TLC (10% methanol-dichloromethane): $R_f$=0.12 (UV); $^1H$ NMR (600 MHz, $CDCl_3$) δ: 7.73 (d, J=7.5 Hz, 2H), 7.58 (dd, J=7.6, 2.8 Hz, 2H), 7.37 (t, J=7.5 Hz, 2H), 7.28 (t, J=7.5 Hz, 2H), 6.91 (t, J=5.9 Hz, 1H), 6.84 (d, J=8.6 Hz, 1H), 6.01 (d, J=8.1 Hz, 1H), 4.50 (dd, J=8.7, 4.9 Hz, 1H), 4.39-4.30 (m, 2H), 4.26 (q, J=7.1 Hz, 1H), 4.18 (t, J=7.2 Hz, 1H), 3.67 (t, J=5.9 Hz, 2H), 3.63-3.56 (m, 22H), 3.55-3.51 (m, 2H), 3.36 (s, 3H), 3.21 (q, J=6.5 Hz, 2H), 2.45 (q, J=5.9 Hz, 2H), 2.23 (dq, J=13.9, 6.9 Hz, 1H), 1.86-1.78 (m, 1H), 1.74-1.66 (m, 1H), 1.52-1.46 (m, 2H), 1.41-1.31 (m, 2H), 0.95 (d, J=6.8 Hz, 2H), 0.93 (d, J=6.9 Hz, 3H); $^{13}C$ NMR (125 MHz, $CDCl_3$) δ 173.7, 172.4, 172.2, 156.3, 144.1, 143.9, 141.4, 127.8, 127.2, 127.2, 125.3, 120.0, 72.0, 70.6, 70.6, 70.6, 70.5, 70.4, 70.2, 70.1, 67.4, 67.1, 59.1, 57.7, 54.9, 47.2, 38.9, 36.8, 32.3, 30.8, 29.0, 22.3, 19.3, 17.9; FTIR (neat), $cm^{-1}$: 3318 (br s), 2872 (br s), 1719 (s) 1654 (s), 1541 (s), 1450 (m), 1247 (s), 1106 (s), 742 (w); HRMS (ESI): Calcd for $(C_{42}H_{63}N_3O_{13}+H)^+$ 818.4434, found 818.4425.

preparatory HPLC (Waters Prep-C18 SunFire® column, 5 μm, 19×250 mm, UV detection at 280 nm, gradient elution with 50→90% acetonitrile in water containing 0.1% formic acid over 25 min, flow rate: 15 mL/min) to provide deprotected Fmoc-Lys(PEG7)-Val-Ala-$PPh_3$ 24 as a white solid (20.0 mg, 56%). TLC (10% methanol-dichloromethane): $R_f$=0.47 (UV); $^1H$ NMR (500 MHz, $CDCl_3$) δ: 7.75 (d, J=7.5 Hz, 2H), 7.60 (dd, J=7.8, 2.8 Hz, 2H), 7.42-7.22 (m, 15H), 7.18-7.11 (m, 2H), 6.81 (d, J=8.3 Hz, 1H), 6.78 (ddd, J=7.8, 4.1, 1.6 Hz, 1H), 6.72 (s, 1H), 6.52 (d, J=7.1 Hz, 1H), 5.88 (d, J=7.5 Hz, 1H), 4.55 (p, J=7.3 Hz, 1H), 4.42-4.35 (m, 2H), 4.25 (dd, J=8.7, 6.1 Hz, 1H), 4.20 (t, J=7.0 Hz, 1H), 4.18-4.13 (m, 1H), 3.68 (t, J=5.8 Hz, 2H), 3.65-3.56 (m, 22H), 3.55-3.51 (m, 2H), 3.36 (s, 3H), 3.23 (q, J=6.4 Hz, 2H), 2.43 (t, J=5.7 Hz, 2H), 2.16-2.07 (m, 1H), 1.86 (q, J=6.3 Hz, 1H), 1.71 (dq, J=15.3, 8.0 Hz, 1H), 1.50 (dq, J=6.8

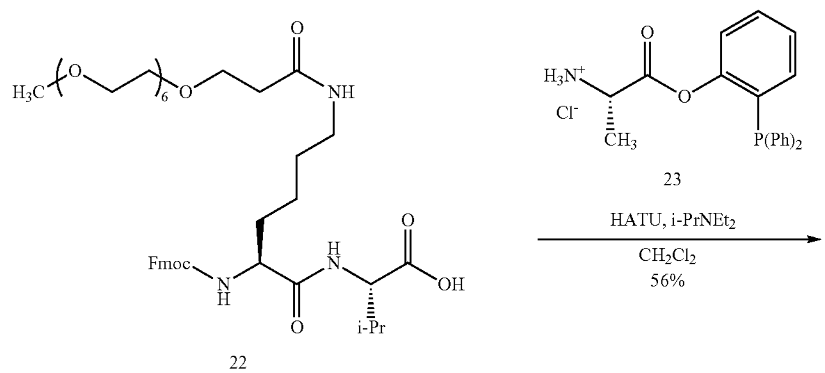

22

23

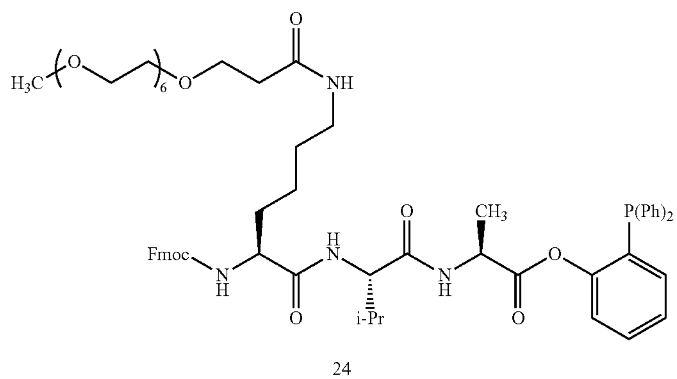

24

A solution of Fmoc-Lys(7PEG)-Val-OH 22 (25.3 mg, 0.031 mmol, 1 equiv), alanine ester 23 (14.3 mg, 0.037 mmol, 1.20 equiv), and HATU (14.7 mg, 0.039 mmol, 1.25 equiv) in dichloromethane was treated with N,N-diisopropylethylamine (16.2 μL, 0.093 mmol, 3.00 equiv) at 0° C. The cooling bath was removed, and the resulting solution was stirred at 23° C. for 4 h. The reaction mixture was diluted with dichloromethane (5 mL) and the organic solution was washed with water (6×2 mL) and saturated aqueous sodium chloride solution (2 mL). The organic layer was dried over sodium sulfate. The dried solution was filtered, and the filtrate concentrated. The residue was purified by Hz, 2H), 1.37 (p, J=7.3 Hz, 2H), 1.30-1.23 (m, 3H), 0.90 (d, J=6.8 Hz, 3H), 0.88 (d, J=6.8 Hz, 3H); $^{13}C$ NMR (125 MHz, $CDCl_3$) δ: 172.1, 172.1, 170.6, 170.6, 156.7, 152.8, 152.6, 144.0, 143.9, 141.4, 135.6, 135.5, 135.4, 135.3, 134.1, 134.1, 134.0, 133.9, 130.3, 130.1, 130.0, 129.3, 129.2, 128.8, 128.8, 127.8, 127.2, 126.6, 125.2, 122.4, 120.1, 120.1, 72.0, 70.7, 70.7, 70.6, 70.6, 70.6, 70.4, 70.3, 67.4, 67.1, 59.1, 58.4, 55.2, 48.5, 47.3, 38.4, 37.1, 31.5, 31.0, 29.0, 22.4, 19.4, 17.9, 17.6; FTIR (neat), $cm^{-1}$: 3286 (br m), 3068 (w), 2872 (m), 1639 (s), 1535 (s), 1183 (m), 1102 (s), 739 (s), 697 (m); HRMS (ESI): Calcd for $(C_{63}H_{81}N_4O_{14}+H)^+$ 1149.5560, found 1149.5565.

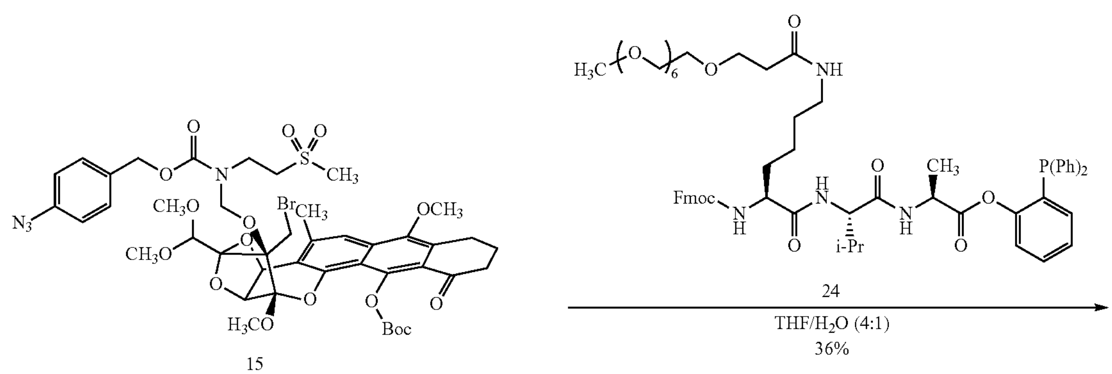

15

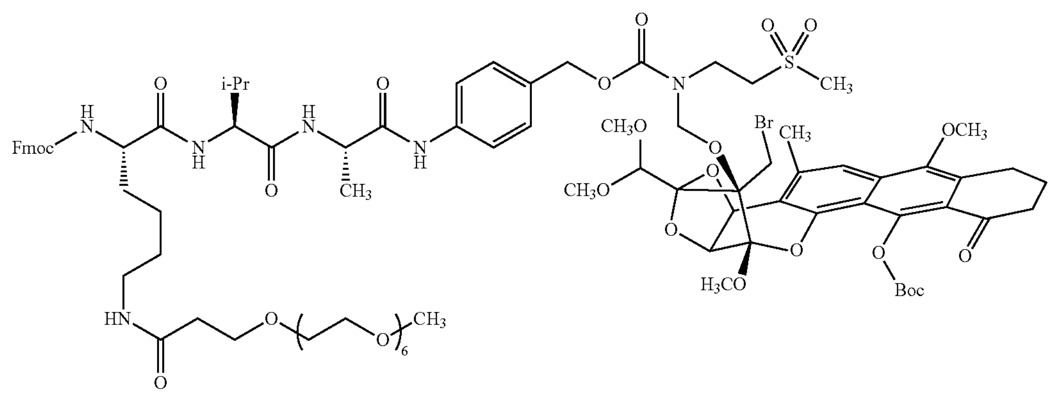

25

In a 1-dram vial, p-azidobenzyl carbamate 15 (8.6 mg, 8.67 μmol, 1 equiv) and tripeptide 24 (19.9 mg, 17.0 μmol, 2.0 equiv) were dissolved in a solution of 4:1 tetrahydrofuran/water (434 μL). The reaction mixture was stirred at 23° C. for 16 h. The mixture was diluted with saturated aqueous sodium chloride solution (2 mL) and the aqueous mixture was extracted with ethyl acetate (4×3 mL). The combined organic layers were washed with saturated aqueous sodium chloride solution (5 mL). The washed organic layer was dried over sodium sulfate. The dried solution was filtered and the filtrate concentrated. The residue was purified by preparatory HPLC (Waters Prep-C18 SunFire® column, 5 μm, 19×250 mm, UV detection at 399 nm, gradient elution with 60→80% acetonitrile in water containing 0.1% formic acid over 25 min, flow rate: 15 mL/min) to provide Fmoc-Lys(PEG7)-Val-Ala-PABO-carbamate 25 as a white solid (5.8 mg, 36%). TLC (10% methanol-dichloromethane): $R_f$=0.41 (UV); $^1$H NMR (pairs of signals in a 1.5:1 ratio due to carbamate rotamers are denoted by an * and integration is provided as seen, 500 MHz, $CDCl_3$) δ: *8.83 (s, 0.31H), *8.77 (s, 0.44H), 7.81-7.70 (m, 4H), 7.61 (dd, J=12.7, 7.1 Hz, 2H), 7.57-7.47 (m, 2H), 7.39 (t, J=7.7 Hz, 4H), 7.34-7.27 (m, 4H), 7.05 (s, 1H), *5.58 (d, J=7.7 Hz, 0.37H), *5.48 (d, J=8.1 Hz, 0.52H), *5.24 (d, J=8.0 Hz, 0.59H), *5.20 (d, J=7.6 Hz, 0.41H), *5.14-5.09 (m, 2.48H), 5.07 (s, 1H), *4.95 (s, 0.50H), 4.82 (d, J=3.6 Hz, 1H), 4.65-4.55 (m, 1H), 4.42-4.32 (m, 2H), 4.18 (d, J=6.0 Hz, 2H), 4.11-3.96 (m, 2H), 3.85 (s, 3H), 3.75-3.55 (m, 29H), 3.54-3.49 (m, 5H), 3.46 (s, 2H), 3.41 (s, 2H), 3.35 (s, 3H), 3.27-3.22 (m, 2H), 3.13-3.00 (m, 5H), 2.97 (s, 2H), 2.78 (s, 1H), 2.68 (t, J=6.5 Hz, 2H), 2.60-2.54 (m, 3H), 2.53-2.49 (m, 2H), 2.36-2.28 (m, 1H), 2.18-2.03 (m, 2H), 1.93-1.78 (m, 2H), 1.67-1.60 (m, 9H), 1.50-1.43 (m, 6H), 1.01-0.92 (m, 3H), 0.92-0.86 (m, 3H); HRMS (ESI): Calcd for $(C_{88}H_{119}BrN_6O_{29}S+H)^+$1835.6998, found 1835.6944.

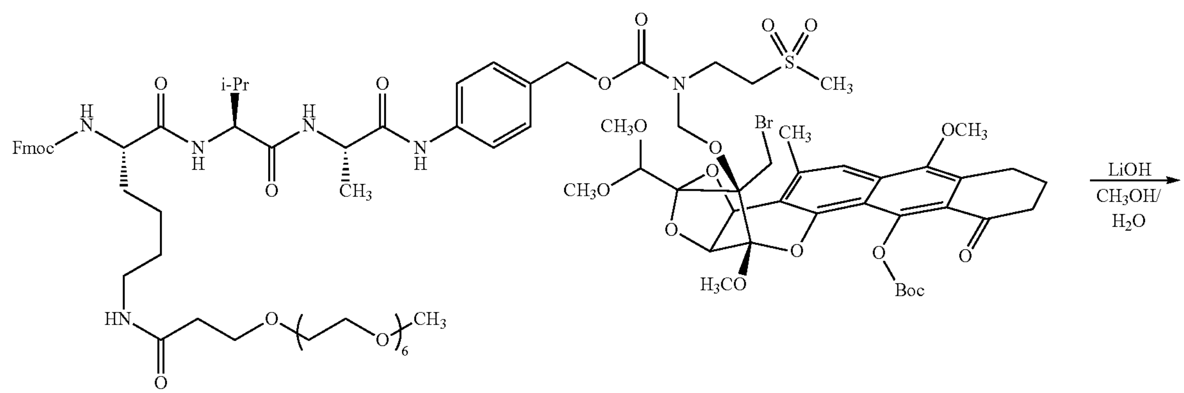

25

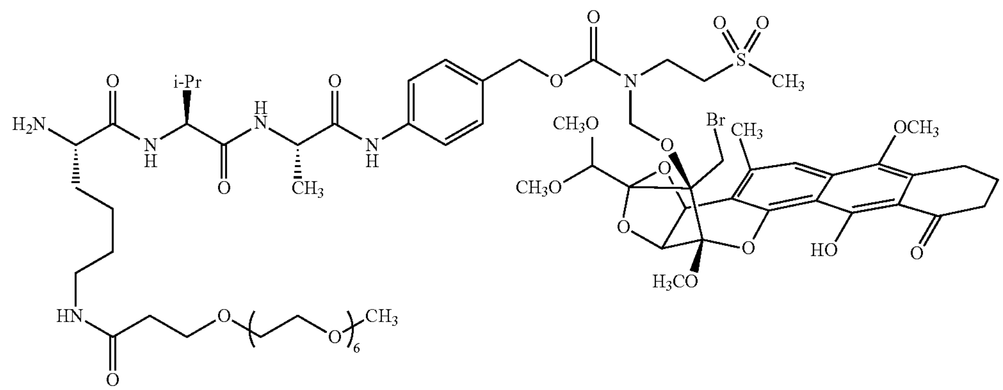

26

In a 20-mL vial, Fmoc-Lys(PEG7)-Val-Ala-PABO-carbamate 25 (5.8 mg, 3.16 μmol, 1 equiv) was dissolved in methanol (1.05 mL) at 23° C. under nitrogen atmosphere. A 0.5 M aqueous lithium hydroxide solution (631 μL, 0.316 mmol, 100 equiv) was added dropwise and the resulting yellow-green mixture was stirred vigorously at 23° C. for 2 h. The reaction mixture was then diluted with dichloromethane (3 mL) and water (2 mL) and quenched by the addition of formic acid (11.9 μL, 0.316 mmol, 100 equiv). The biphasic mixture was transferred to a separatory funnel and additional dichloromethane (3 mL) and saturated aqueous sodium chloride solution (2 mL) were added. The funnel was shaken vigorously, and the layers were separated. The aqueous layer was extracted with dichloromethane (3×1 mL). The combined organic layers were dried by filtration through a plug of sodium sulfate. The filtrate was concentrated to provide crude Amino-Lys(PEG7)-Val-Ala-PABO-carbamate 26 as a bright yellow film. The crude material was taken forward without further purification. TLC (10% methanol-dichloromethane): $R_f$=0.22 (UV); HRMS (ESI): Calcd for $(C_{68}H_{101}BrN_6O_{25}S+H)^+$1513.5793, found 1513.5751.

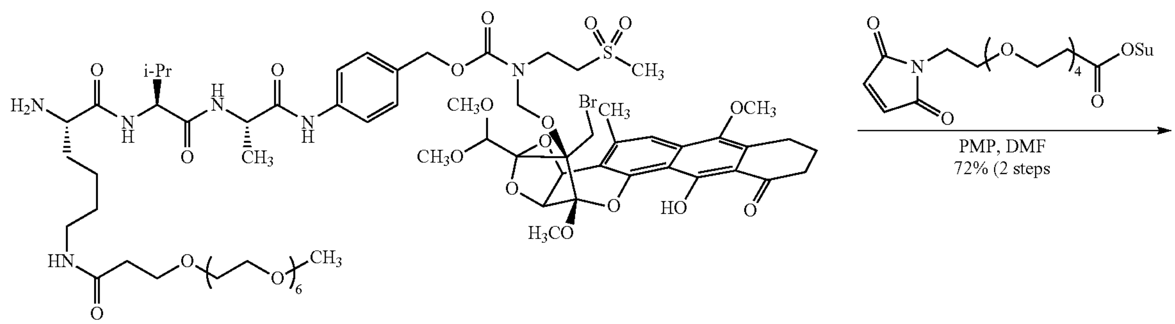

26

-continued

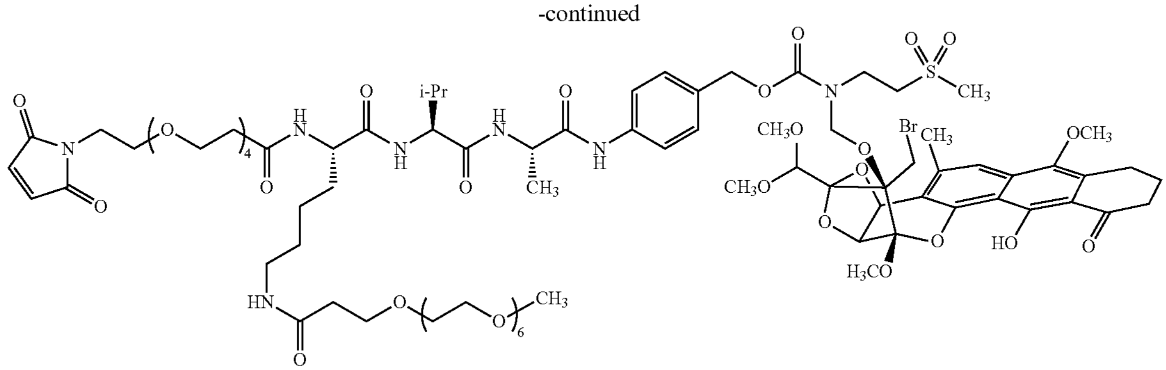

27

In a 0.5-dram vial, crude amine 26 (assuming quantitative conversion from the previous step) and Mal-PEG4-NHS ester (8.41 mg, 19.0 μmol, 6.00 equiv) were dissolved in dimethylformamide (317 μL) at 23° C. 1,2,2,6,6-pentamethylpiperidine dried over calcium hydride (3.44 μL, 19.0 μmol, 6.00 equiv) was added and the reaction mixture was stirred for 2 h. Upon completion, the reaction mixture was diluted with additional dimethylformamide to a total volume of 800 μL and the crude product solution was purified directly by preparatory HPLC (Waters Prep-C18 SunFire® column, 5 μm, 19×250 mm, UV detection at 399 nm, gradient elution with 40→90% acetonitrile in water containing 0.1% formic acid over 35 min, flow rate: 15 mL/min) to provide trioxacarcin drug-linker 27 (4.2 mg, 72%) as a yellow solid. TLC (10% methanol-dichloromethane): $R_f$=0.22 (UV); $^1$H NMR (pairs of signals in a 1.5:1 ratio due to carbamate rotamers are denoted by an * and integration is provided as seen, 400 MHz, $CDCl_3$) δ: 14.81 (d, J=6.9 Hz, 1H), 8.66 (d, J=19.7 Hz, 1H), 7.82-7.70 (m, 3H), 7.47-7.38 (m, 2H), 7.32 (d, J=8.1 Hz, 2H), 6.93 (d, J=7.3 Hz, 1H), 6.70 (s, 2H), 6.65 (d, J=6.7 Hz, 1H), 5.47 (t, J=9.9 Hz, 1H), 5.29 (t, J=7.2 Hz, 1H), *5.16 (s, 0.63H), 5.13 (d, J=3.0 Hz, 2H), 5.04 (t, J=4.5 Hz, 1H), *4.86 (s, 0.44H), 4.71 (d, J=3.6 Hz, 1H), 4.62 (h, J=4.4 Hz, 1H), 4.21-4.15 (m, 1H), 4.08 (s, 1H), 3.92-3.80 (m, 2H), 3.78 (s, 3H), 3.77-3.68 (m, 7H), 3.67-3.56 (m, 44H), 3.56-3.50 (m, 6H), 3.48 (s, 3H), 3.37 (s, 4H), 3.36-3.30 (m, 1H), 3.23-3.14 (m, 1H), 3.08-3.01 (m, 2H), *2.99 (s, 1.72H), *2.81 (s, 1.14H), 2.77-2.70 (m, 2H), 2.71-2.63 (m, 1H), 2.55 (d, J=2.4 Hz, 3H), 2.52-2.42 (m, 3H), 2.38-2.29 (m, 1H), 2.09 (p, J=7.6, 7.1 Hz, 2H), 1.97-1.87 (m, 1H), 1.86-1.77 (m, 1H), 1.55-1.47 (m, 4H), 1.45-1.29 (m, 1H), 0.99 (t, J=5.8 Hz, 3H), 0.94 (t, J=5.5 Hz, 3H); FTIR (neat), $cm^{-1}$: 3305 (br m), 2927 (br m), 1709 (s), 1648 (s), 1538 (m), 1259 (m), 1117 (s), 742 (m); HRMS (ESI): Calcd for $(C_{83}H_{122}BrN_7O_{32}S+Na)^+$1862.6931, found 1862.6862.

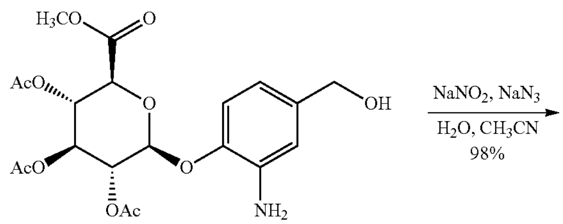

28

-continued

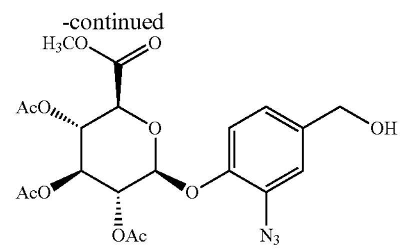

29

In a 25-mL flask, aniline 28 (1.00 g, 2.20 mmol, 1 equiv) was dissolved in acetonitrile (2.81 mL) and water (5.62 mL) then cooled to 0° C. in an ice bath. A 12 M aqueous hydrochloric acid solution (0.549 mL, 6.59 mmol, 3.00 equiv) was added and the mixture was stirred at 0° C. for 10 min. A solution of sodium nitrite (0.167 g, 2.42 mmol, 1.10 equiv) in water (0.562 mL) was then added dropwise by syringe. After an additional 10 minutes of stirring, the flask septum was pierced with a gas outlet needle and a solution of sodium azide (0.186 g, 2.85 mmol, 1.30 equiv) in water (0.562 mL) was added dropwise. The ice bath was removed, and the reaction mixture was stirred at 23° C. for 1 h. Upon complete consumption of starting material according to TLC, the reaction was diluted with water (40 mL) and extracted with ethyl acetate (3×75 mL). The combined organic fractions were washed with saturated aqueous sodium bicarbonate solution (50 mL) and saturated aqueous sodium chloride solution (50 mL). The organic layer was dried over sodium sulfate. The dried solution was filtered, and the filtrate concentrated to provide aryl azide 29 (1.03 g, 98% yield) as a pale yellow foam. TLC (100% ethyl acetate): $R_f$=0.52 (UV, $KMnO_4$); $^1$H NMR (400 MHz, $CDCl_3$) δ: 7.12 (d, J=8.2 Hz, 1H), 7.10-7.05 (m, 2H), 5.39-5.22 (m, 3H), 5.07 (d, J=7.0 Hz, 1H), 4.65 (d, J=5.8 Hz, 2H), 4.18-4.07 (m, 1H), 3.75 (s, 3H), 2.10 (s, 3H), 2.05 (s, 3H), 2.04 (s, 3H), 1.66 (t, J=5.8 Hz, 1H); $^{13}$C NMR (100 MHz, $CDCl_3$) δ: 170.3, 169.5, 169.4, 166.9, 147.7, 138.0, 130.8, 124.1, 119.4, 119.2, 100.3, 72.7, 71.9, 71.0, 69.2, 64.4, 53.1, 20.8, 20.7, 20.6; FTIR (neat), $cm^{-1}$: 3502 (br w), 2956 (w), 2110 (s), 1748 (s), 1506 (m), 1375 (m), 1209 (s), 1035 (s), 902 (m), 732 (m); HRMS (ESI): Calcd for $(C_{20}H_{23}N_3O_{11}+Na)^+$504.1225, found 504.1210.

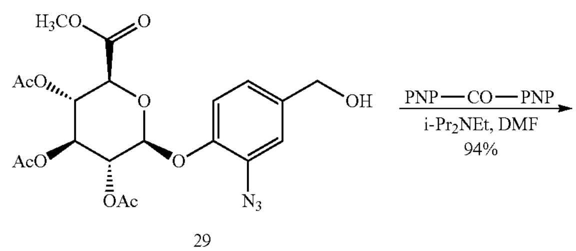

29

-continued

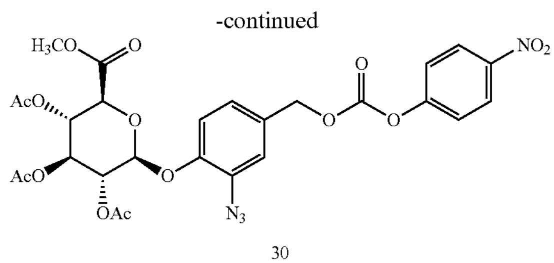

30

Benzylic alcohol 29 (1.03 g, 2.13 mmol, 1 equiv) was dissolved in dimethylformamide (21.3 mL) and cooled to 0° C. in an ice bath. Bis(4-nitrophenyl) carbonate (1.30 g, 4.27 mmol, 2.00 equiv) was added, followed by N,N-diisopropylethylamine (0.557 mL, 3.20 mmol, 1.50 equiv) and the resulting solution was stirred at 4° C. for 18 h. The reaction mixture was diluted with ethyl acetate (250 mL) and water (250 mL), transferred to a separatory funnel, and shaken vigorously. The layers were separated, and the organic layer was washed with saturated aqueous sodium bicarbonate solution (2×100 mL) and saturated aqueous sodium chloride solution (2×100 mL). The washed organic layer was dried over sodium sulfite. The dried solution was filtered, and the filtrate concentrated. The residue was purified by flash-column chromatography (10→50% ethyl acetate-hexanes) to provide p-nitrophenyl carbonate 30 (1.30 g, 94%) as a white foam. TLC (50% ethyl acetate-hexanes): $R_f$=0.33 (UV, $KMnO_4$); $^1H$ NMR (400 MHz, $CDCl_3$) δ: 8.32-8.24 (m, 2H), 7.42-7.34 (m, 2H), 7.18-7.14 (m, 2H), 7.12 (s, 1H), 5.38-5.32 (m, 2H), 5.32-5.26 (m, 1H), 5.22 (s, 2H), 5.14 (d, J=7.0 Hz, 1H), 4.20-4.12 (m, 1H), 3.75 (s, 3H), 2.10 (s, 3H), 2.06 (s, 4H), 2.05 (s, 3H); $^{13}C$ NMR (100 MHz, $CDCl_3$) δ:170.1, 169.3, 169.2, 166.7, 155.4, 152.4, 148.9, 145.5, 130.9, 130.9, 126.1, 125.4, 121.8, 121.2, 118.8, 99.8, 72.7, 71.7, 70.9, 69.9, 68.9, 53.1, 20.7, 20.6, 20.5; FTIR (neat), $cm^{-1}$: 2959 (w), 2119 (s), 1758 (s), 1525 (m), 1212 (s), 1040 (m); HRMS (ESI): Calcd for $(C_{27}H_{26}N_4O_{15}+NH_4)^+$664.1733, found 664.1732.

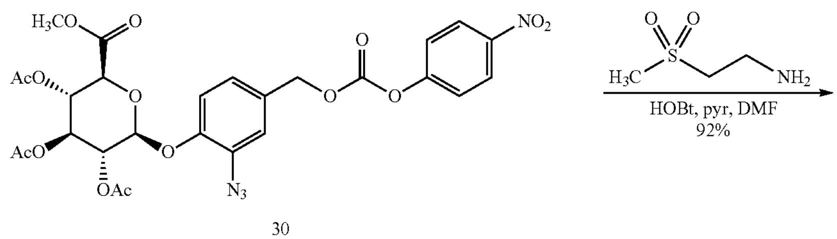

30

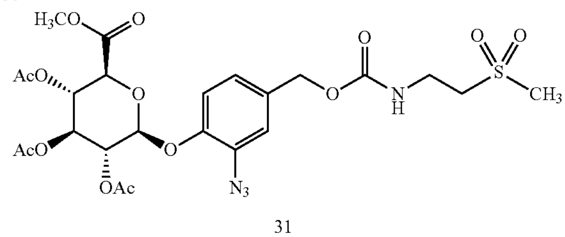

31

In a 50-mL round-bottom flask, p-nitrophenyl carbonate 30 (500 mg, 0.773 mmol, 1 equiv) was dissolved in dimethylformamide (15.5 mL). 2-(methylsulfonyl)-ethanamine (191 mg, 1.55 mmol, 2.00 equiv) was added to the solution, followed by 1-hydroxybenzotriazole hydrate (118 mg, 0.773 mmol, 1.00 equiv) and pyridine (62.0 μL, 0.773 mmol, 1.00 equiv). The resulting solution was stirred at 23° C. for 24 h. Upon completion, the reaction mixture was concentrated under reduced pressure to remove dimethylformamide and pyridine. The residue was dissolved in ethyl acetate (150 mL) and washed with 1 M aqueous hydrochloric acid solution (2×50 mL), saturated aqueous sodium bicarbonate solution (2×50 mL), and saturated aqueous sodium chloride solution (50 mL). The washed organic solution was dried over sodium sulfate. The dried solution was filtered and the filtrate concentrated. The residue was purified by flash-column chromatography (50→90% ethyl acetate-hexanes) to provide sulfonylethyl carbamate 31 (447 mg, 92%) as a white foam. TLC (50% ethyl acetate-hexanes): $R_f$=0.35 (UV, $KMnO_4$); $^1H$ NMR (400 MHz, $CDCl_3$) δ: 7.13-7.05 (m, 2H), 7.03 (d, J=1.9 Hz, 1H), 5.43 (t, J=5.3 Hz, 1H), 5.36-5.32 (m, 2H), 5.32-5.26 (m, 1H), 5.09 (d, J=7.1 Hz, 1H), 5.03 (s, 2H), 4.17-4.10 (m, 1H), 3.75 (s, 3H), 3.72 (q, J=6.2 Hz, 2H), 3.25 (t, J=6.0 Hz, 2H), 2.95 (s, 3H), 2.09 (s, 3H), 2.05 (s, 3H), 2.04 (s, 3H); $^{13}C$ NMR (100 MHz, $CDCl_3$) δ: 170.1, 169.3, 169.2, 166.7, 156.0, 133.9, 132.9, 130.7, 125.4, 120.5, 118.9, 100.0, 72.7, 71.8, 70.9, 69.0, 65.9, 54.2, 53.0, 41.7, 34.9, 20.7, 20.6, 20.5; FTIR (neat), $cm^{-1}$: 3369 (w), 2956 (w), 2119 (s), 1756 (s), 1720 (s), 1510 (m), 1375 (m), 1297 (m), 1225 (s), 1127 (m), 1040 (s); HRMS (ESI): Calcd for $(C_{24}H_{30}N_4O_{14}S+NH_4)^+$648.1817, found 648.1819.

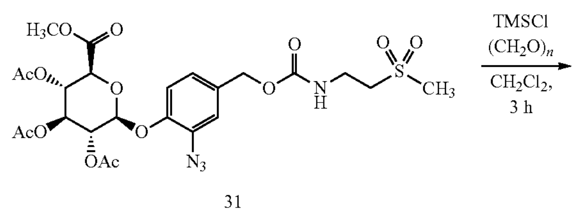

31

-continued

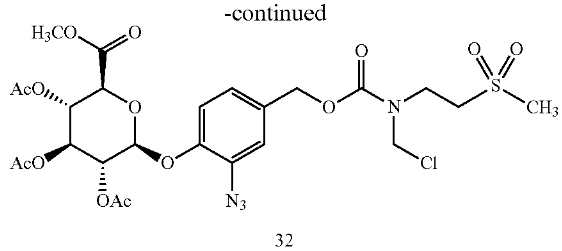

32

To a stirred solution of sulfonylethyl carbamate 31 (0.231 g, 0.366 mmol, 1 equiv) in dichloromethane (1.47 mL) at 0° C. was added paraformaldehyde (16.0 mg, 0.549 mmol, 1.50 equiv) followed by freshly distilled trimethylsilyl chloride (93.0 μL, 0.733 mmol, 2.00 equiv). The reaction mixture was allowed to warm to 23° C. and stirred for 3 h, monitoring by quenching an aliquot with methanol and observation of the methoxymethyl adduct by TLC and LCMS. Upon complete conversion to the chloromethyl carbamate, the reaction mixture was taken up in a syringe and passed through a 0.45 m PTFE syringe filter into a fresh flame-dried 5-mL flask, rinsing with addition dichloromethane (0.5 mL). The filtrate was diluted with anhydrous toluene (1 mL) and concentrated on a rotary evaporator flushed with nitrogen. The residue was dissolved in anhydrous toluene (1 mL) and concentrated again in the same manner to remove residual trimethylsilyl chloride. The crude chloromethyl carbamate 32 was isolated as a hazy colorless oil and was dried under high vacuum for 30 min before subsequent manipulations. The material was used in the next reaction immediately following drying assuming quantitative conversion.

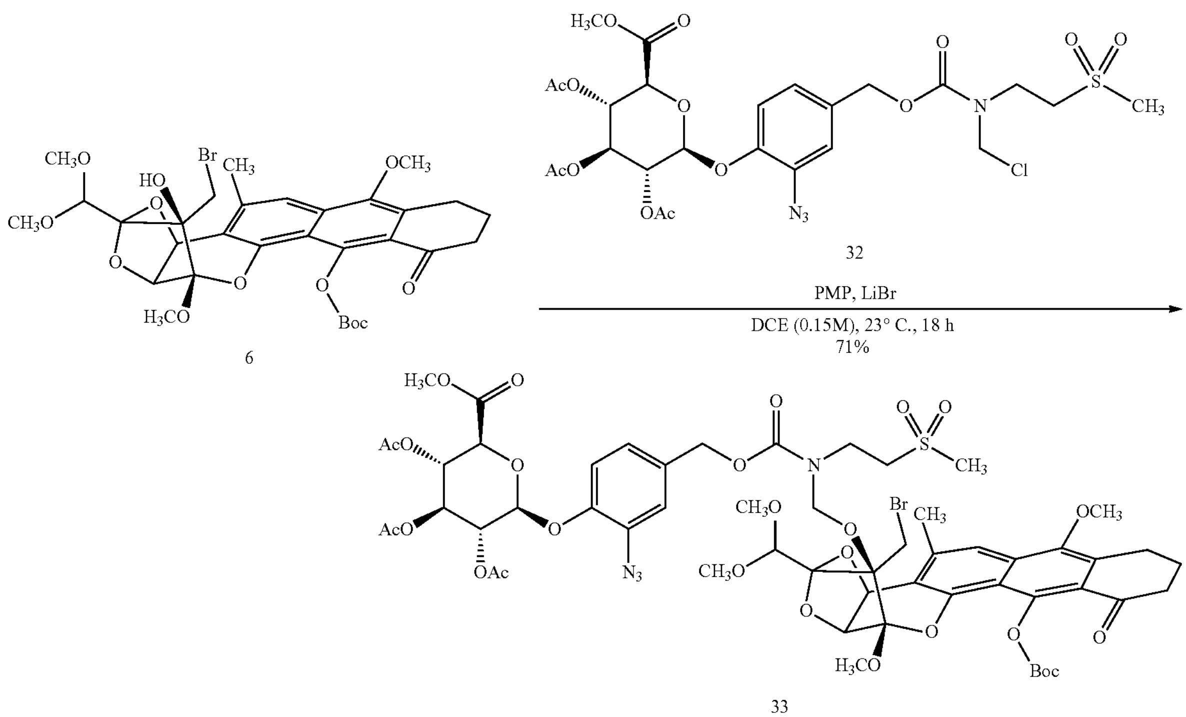

6

32

33

Lithium bromide (19.1 mg, 0.220 mmol, 3.00 equiv) and a stir bar were exhaustively flame-dried in a 0.5-dram vial. After cooling to 23° C., bromohydrin 6 (50.0 mg, 73.0 μmol, 1 equiv) was added to the vial as a solution in anhydrous benzene. Solvent was removed by freezing then sublimation under high vacuum for 18 h. The residue was taken up in 1,2-dichloroethane (245 μL), and the resulting mixture was treated with a solution of chloromethyl carbamate 32 (crude from previous reaction, approximately 249 mg, 0.367 mmol, 5.00 equiv) in 1,2-dichloroethane (245 μL) and 1,2,2,6,6-pentamethylipieridine (66.4 μL, 0.367 mmol, 5.00 equiv) simultaneously. The mixture was heated to 40° C. for 2 h, then was stirred at 23° C. for 16 h. The reaction mixture was partitioned between 2:1 dichloromethane/methanol (5 mL) and half-saturated aqueous sodium bicarbonate solution (5 mL). The layers were separated, and the aqueous layer was extracted with 2:1 dichloromethane/methanol (3×5 mL). The combined organic layers were concentrated to give the crude hemiaminal ether. The residue was purified by preparatory HPLC (Waters Prep-C18 SunFire® column, 5 μm, 19×250 mm, UV detection at 399 nm, gradient elution with 50→80% acetonitrile in water containing 0.1% formic acid over 25 min, flow rate: 15 mL/min) to provide methylene alkoxy carbamate 33 (62.9 mg, 71%) as a pale yellow oily solid. $^1$H NMR (pairs of signals in a 1.5:1 ratio due to carbamate rotamers are denoted by an * and integration is provided as seen, 400 MHz, $CDCl_3$) δ: 7.55 (s, 1H), 7.14-7.02 (m, 3H), 5.53 (dd, J=28.9, 8.0 Hz, 1H), 5.35-5.23 (m, 3H), 5.20 (d, J=8.2 Hz, 1H), 5.15-5.05 (m, 4H), 4.98 (s, 1H), 4.83 (d, J=4.0 Hz, 1H), 4.18-4.12 (m, 1H), 4.07 (ddd, J=15.9, 11.0, 4.3 Hz, 1H), 3.85 (s, 3H), 3.77-3.56 (m, 9H), 3.54-3.40 (m, 8H), 3.09 (s, 2H), *2.97 (s, 1.74H), *2.88 (s, 1.15H), 2.68 (t, J=6.6 Hz, 2H), 2.56 (s, 3H), 2.08 (d, J=10.2 Hz, 11H), 1.62 (d, J=5.4 Hz, 9H); $^{13}C$ NMR (100 MHz, $CDCl_3$) δ: 195.0, 168.2, 167.4, 167.3, 164.8, 153.5, 149.6, 148.8, 147.7, 146.6, 142.4, 137.5, 131.4, 131.3, 130.7, 128.6, 123.8, 120.7, 119.0, 116.9, 116.6, 114.5, 114.1, 110.6, 106.4, 105.9, 97.9, 97.4, 97.2, 85.5, 82.0, 73.9, 70.7, 69.9, 68.9, 67.1, 66.7, 65.0, 59.4, 54.0, 53.1, 52.8, 51.5, 51.1, 50.9, 50.5, 40.3, 39.2, 38.8, 27.6, 26.3, 22.1, 20.0, 18.7, 18.7, 18.6, 18.2; FTIR (neat), $cm^{-1}$: 2944 (w), 2256 (w), 2117 (m), 1753 (s), 1711 (m), 1685 (m), 1371 (m), 1224 (s), 1137 (s), 1089 (s), 1064 (s), 1037 (s), 912 (m), 729 (s); HRMS (ESI): Calcd for $(C_{56}H_{67}BrN_4O_{26}S+NH_4)^+$1340.3286, found 1340.3294.

solution was purged with nitrogen for 5 min. The solution was cooled to 0° C. in an ice bath and a 0.4 M aqueous lithium hydroxide solution (6.53 mL, 2.61 mmol, 100 equiv) was added dropwise. The yellow reaction mixture was stirred vigorously at 0° C. for 2 h. Upon complete saponification of the glucuronide esters and cleavage of the phenolic Boc group, the reaction was diluted with 2:1 dichloromethane/methanol (10 mL) and saturated aqueous sodium chloride solution (6 mL) then quenched by the addition of formic acid (0.148 mL, 3.92 mmol, 150 equiv) at 0° C. The mixture was stirred for 5 min, then transferred to a separatory funnel. The funnel was shaken vigorously, and the layers were separated. The aqueous layer (now pH ~4.5-5 or adjusted to this pH by further addition of formic acid) was extracted with 2:1 dichloromethane/methanol (4×3 mL). The combined organic layers were dried by filtration through a plug of sodium sulfate and the filtrate was concentrated to provide glucuronic acid 34 as a yellow solid. The crude material was taken forward without further purification assuming quantitative conversion. HRMS (ESI): Calcd for $(C_{44}H_{51}BrN_4O_{21}S+NH_4)^+$1100.2288, found 1100.2298.

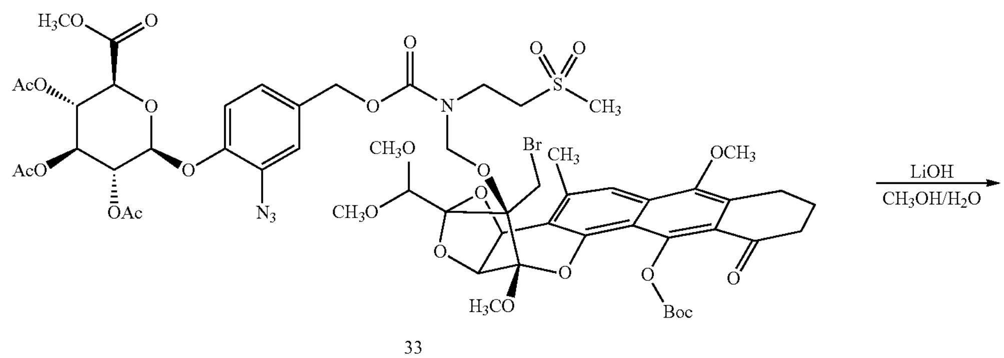

33

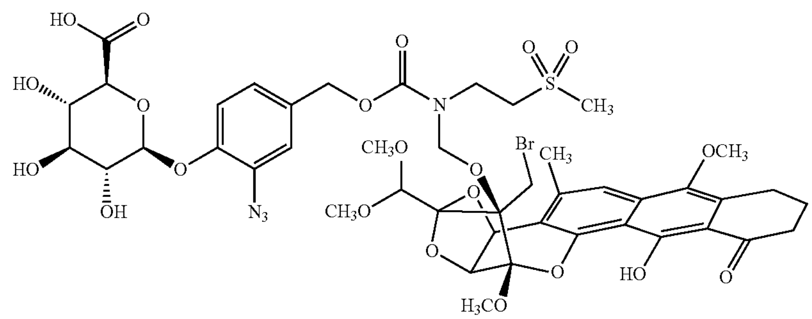

34

In a 50-mL flask, protected glucuronic ester linker 33 (34.6 mg, 26.0 μmol, 1 equiv) was dissolved in methanol (6.54 mL) and acetonitrile (2.18 mL) at 23° C. and the

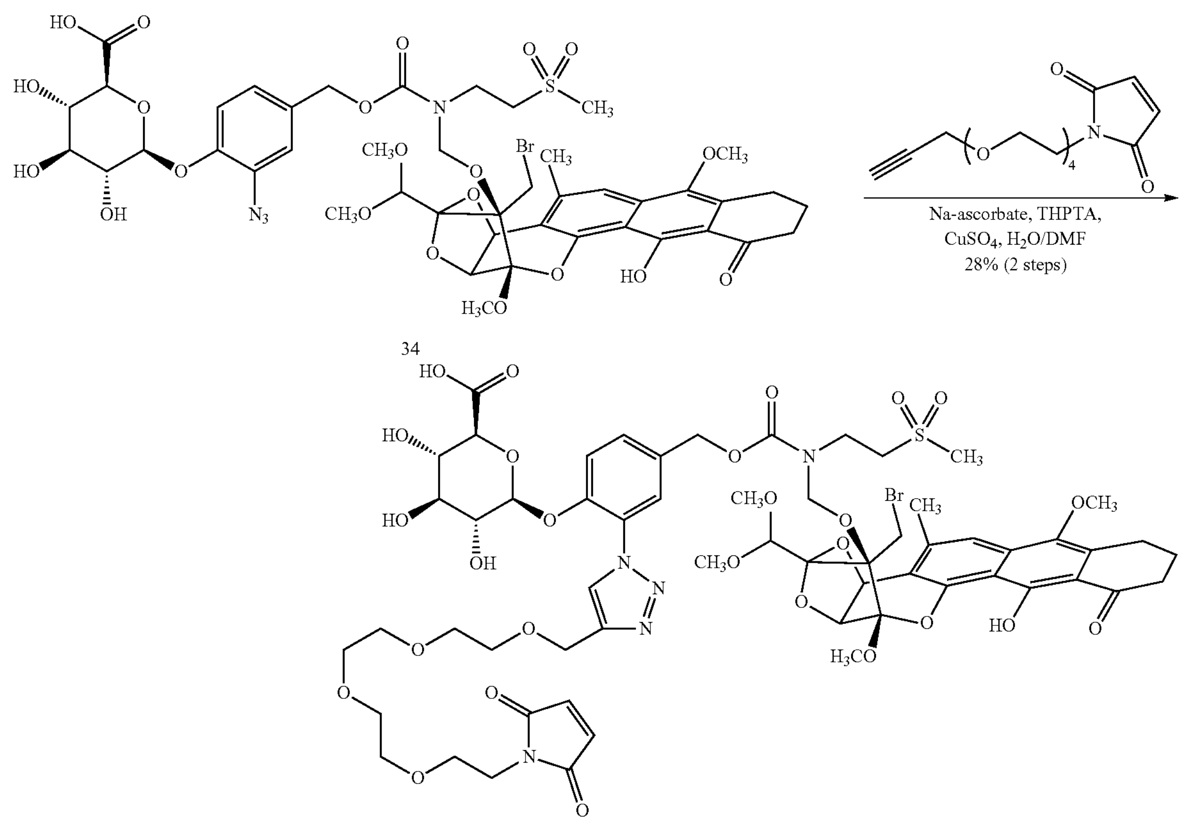

34

35

In a 50-mL flask, aryl azide 34 (crude from previous reaction, assuming 28.3 mg, 26.0 mol, 1 equiv) and Mal-PEG4-alkyne (15.8 μL, 78.0 μmol, 3.00 equiv) were dissolved in 4:1 water/DMSO (8.70 mL) at 23° C. A pre-mixed solution of 0.1 M aqueous cupric sulfate (65.3 L, 6.53 μmol, 0.250 equiv) and 0.05 M THPTA (653 μL, 0.033 mmol, 1.250 equiv) was added, followed by a 2.0 M aqueous sodium ascorbate solution (65.3 μL, 0.131 mmol, 5.00 equiv). The reaction mixture was stirred vigorously for 7 h, at which point LCMS analysis indicated complete conversion to product. The reaction mixture was diluted with 2:1 dichloromethane/methanol (10 mL) and saturated aqueous sodium chloride solution (5 mL). The pH of the aqueous layer was adjusted to ~4.5-5 by addition of formic acid, then the layers were shaken and separated. The aqueous layer was extracted with 2:1 dichloromethane/methanol (4×5 mL) and the combined organic layers were dried over sodium sulfate. The dried solution was filtered and the filtrate concentrated. The residue was purified by preparatory HPLC (Waters Prep-C18 SunFire® column, 5 μm, 19×250 mm, UV detection at 399 nm, gradient elution with 40→70% acetonitrile in water containing 0.1% formic acid over 25 min, flow rate: 15 mL/min) to provide glucuronide drug-linker 35 (10.3 mg, 28% over 2 steps) as a yellow solid. $^1$H NMR (pairs of signals in a 2:1 ratio due to carbamate rotamers are denoted by an * and integration is provided as seen, 400 MHz, $CD_3OD$) δ: *8.65 (s, 0.33H), *8.61 (s, 0.61H), *7.86 (s, 0.33H), 7.83 (s, 0.67H), 7.61-7.54 (m, 1H), 7.49 (d, J=1.0 Hz, 1H), 7.45 (app t, J=9.0 Hz, 1H), 6.78 (s, 2H), 5.47 (t, J=8.2 Hz, 1H), 5.35-5.28 (m, 1H), 5.26 (d, J=3.9 Hz, 1H), 5.23-5.15 (m, 2H), *5.13 (s, 0.30H), 5.12-5.05 (m, 1H), 4.96 (d, J=3.7 Hz, 1H), *4.87 (s, 0.84H), *4.73 (s, 0.79H), *4.70 (s, 1.28H), 3.99 (d, J=9.3 Hz, 2H), 3.93-3.82 (m, 1H), 3.80 (s, 3H), 3.75-3.45 (m, 28H), 3.44-3.40 (m, 3H), 3.32 (s, 1H), 3.11-3.03 (m, 2H), *3.04 (s, 2.09H), *2.97 (s, 0.96H), 2.78-2.70 (m, 2H), 2.55 (s, 3H), 2.08 (p, J=6.4 Hz, 2H); $^{13}$C NMR (100 MHz, $CD_3OD$) δ: 206.6, 172.4, 163.4, 157.0, 153.7, 150.4, 145.6, 143.9, 142.7, 136.7, 135.4, 133.0, 132.2, 131.9, 128.5, 127.7, 126.9, 118.4, 116.7, 113.6, 112.9, 112.2, 109.9, 108.3, 102.8, 101.7, 88.7, 77.5, 77.0, 76.6, 74.4, 72.9, 71.5, 71.5, 71.1, 70.7, 70.2, 68.8, 67.9, 64.9, 61.3, 56.5, 54.1, 53.7, 52.7, 42.9, 41.4, 39.8, 38.1, 30.5, 24.6, 23.2, 19.9; FTIR (neat), $cm^{-1}$: 3294 (br, m), 2961 (m), 2926 (m), 1712 (m), 1639 (s), 1514 (w), 1457 (m), 1268 (m), 1161 (s), 1024 (s), 735 (m); HRMS (ESI): Caled for $(C_{59}H_{72}BrN_5O_{27}S+H)^+$1394.3392, found 1394.3395.

Preparation of Trioxacarcin-Antibody Conjugates

Exemplary trioxacarcin-antibody conjugates are prepared from the anti-HER2 monoclonal antibody trastuzumab and the trioxacarcin-linker species 19. The methods for preparing and characterizing the antibody-drug conjugates are described below.

Partial reduction of interchain disulfides: To a solution of trastuzumab (500 μg, 25 μL of 20 mg/mL in PBS) is added a solution of tris(2-carboxyethyl)phosphine hydrochloride (1.7 μL, 5 mM in water, 2.5 equiv) and diluted to 15 mg/mL final antibody concentration using DPBS pH 7.4 containing ethylenediaminetetraacetic acid (5 mM, 8.3 μL). The reaction is incubated at 37° C. for 2 h and then cooled to 23° C.

Conjugation of maleimide containing trioxacarcin-linker: To a solution of partially reduced trastuzumab is added the trioxacarcin-linker species (6.9 μL, 5 mM in DMSO, 10 equiv). DPBS pH 7.4 containing ethylenediaminetetraacetic acid (5 mM, 8.3 μL) is added to achieve 10 mg/mL final antibody concentration. DMSO (1 μL) is added to achieve 15% (v/v) total organic solvent component in the final reaction mixture. The reaction is incubated for 2 h at 23° C. with agitation at 500 rpm. After conjugation, the antibody solution is desalted into DPBS by three rounds of dilution and centrifugation at 4,000×g through a 10 kDa MWCO filter. The resulting antibody-drug conjugate is analyzed by LC-MS, and stored at −80° C.

LC-MS analysis: Trioxacarcin-antibody conjugates (50 μg, 20 μL solution in DPBS) are optionally deglycosylated before analysis by addition of PNGase F (0.5 μL, New England Biolabs) and PNGase F 10× buffer (2 μL, New England Biolabs). The solution is incubated at 27° C. for 16 h. Antibody is fully reduced by addition of tris(2-carboxyethyl)phosphine hydrochloride solution (20 μL of 20 mM in water) immediately before analysis. LC-MS analysis is performed at the Harvard University Mass Spectrometry Facility using a Bruker Impact II q-TOF mass spectrometer.

Antiproliferative Assays

Cell Culture: Cell line NCI-H460, was purchased from American Type Culture Collection (ATCC). H460 cells were maintained in RPMI-1640 medium and HT-29 cells were maintained in McCoy's 5A medium, supplemented with 10% fetal bovine serum (Life Technologies, UK).

Cell Proliferation Assay: Cells were plated in black-walled 96-well plates (3000-4000 cells per well). Stock solutions of each compound were diluted serially and the resulting solutions were administrated to cells to achieve final concentrations of 1.1 nM to 2.5 μM in 100 μL total volume. After incubating at 37° C. (5% $CO_2$) for 2 days (H460), 20 μL of resazurin solution (Promega CellTiter-Blue® Cell Viability Assay) was added to each well. After incubating at 37° C. for 4.0 h, the fluorescence (560 nm excitation/590 nm emission) was recorded using a microplate reader (SpectraMax i3) as a measure of viable cells. $IC_{50}$ values, determined in triplicate, were calculated using a four-parameter logistic equation.

Table 1 reports the $IC_{50}$ values of exemplary trioxacarcin ADC precursors evaluated in H460, HT-29, SK-BR-3, and NCI-$N_{87}$ cell lines, exhibiting low nanomolar $IC_{50}$ values.

TABLE 1

| | $IC_{50}$ (nM) | | | |
|---|---|---|---|---|
| Compound | H460 | HT-29 (HER2−) | SK-BR-3 (HER2+) | NCI-N87 (HER2+) |
| 1 | 2 | 4 | 2 | 0.8 |
| 2 | 21 | | | |
| 3 | 2 | | | |
| 4 | 4 | 7 | 4 | 1 |

Stability of the Trioxacarcin-linker Species

To determine the stability of exemplary trioxacarcin-linker species 19 under physiological pH and temperature, the compound was incubated at 37° C. in pH 7.4 buffer. The trioxacarcin-linker species was stable as shown in FIG. 1.

Figure 2:
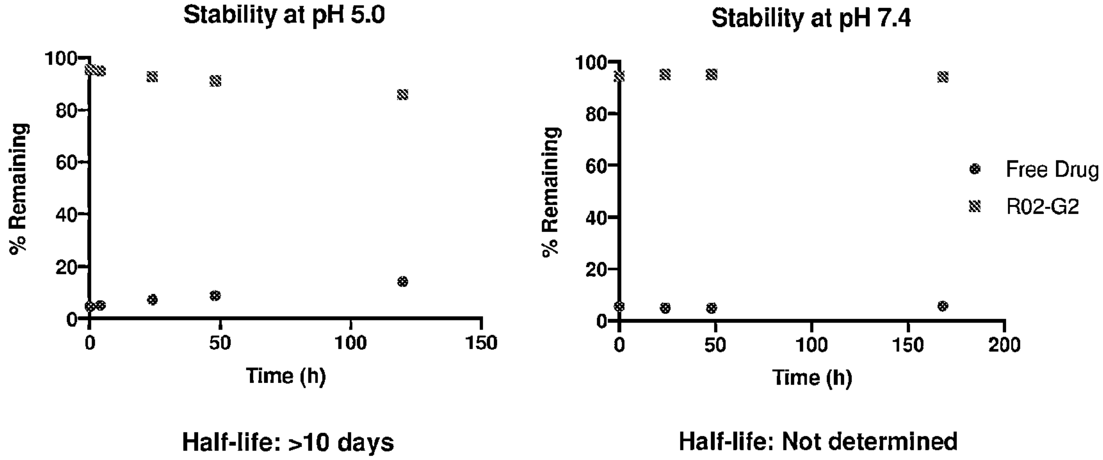
FIG. 2 is a series of graphs showing the stability of exemplary trioxacarcin-linker species 27 and its release kinetics upon exposure to cathepsin B at 37° C.
Figure 2:
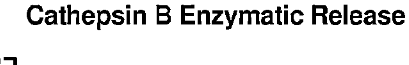
Figure 2:
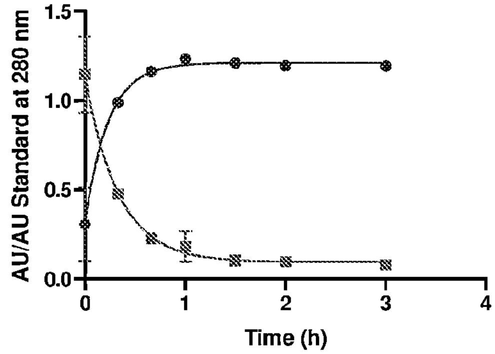

The stability of trioxacarcin-linker species 27 was also evaluated at pH 5 and 7.4. It was exceptionally stable at both pH 5.0 and 7.4, with no detectable free drug released after 1 week at pH 7.4 as shown in FIG. 2 (R02-G2=compound 27).

Compound Stability Assay: In a 1.5 mL screw-top conical plastic vial, the desired compound as a solution in DMSO (5 mM, 6 μL, 30 nmol) was mixed with a solution of N-acetylcysteine in DMSO (10 mM, 6 μL, 30 nmol, 2 equiv) to quench the maleimide. The mixture was diluted with either pH 5.0 sodium acetate or pH 7.4 phosphate buffer containing 8 mM N-acetylcysteine (282 μL). 1-naphthalene acetic acid in DMSO (5 mM, 6 μL, 30 nmol) was added as an internal standard. In the case of testing free drug stability, no N-acetylcysteine solution was added and instead the amount of buffer added was increased an equivalent amount to compensate (288 μL total buffer). The vial was placed in a heating block at 37° C. and protected from direct light. 25 μL aliquots of the reaction mixture were removed at various time points and analyzed by LC-MS. LC-MS peaks were integrated within the Agilent LC-MS software and the areas of each peak were normalized to 1-napthalene acetic acid at 280 nm. Percent compound remaining is defined as the normalized peak area at a given time point divided by the normalized peak area at 0 hours×100%. The results are shown in FIGS. 1 and 2.

Release Kinetics of the Trioxacarcin-linker Species

To determine whether free drug would be effectively released upon exposure to Cathepsin B, the enzyme most responsible for intracellular cleavage of the linker, exemplary trioxacarcin-linker species 19 was incubated with Cathepsin B at pH 5.0 at 37° C. These conditions simulate the environment of the lysosome. The linker exhibited excellent release kinetics. The results are shown in FIG. 1.

Trioxacarcin-linker species 27 was also evaluated under the same release conditions on exposure to Cathepsin B. FIG. 2 shows that the drug-linker species rapidly releases payload upon exposure to Cathepsin B.

Release Kinetics Assay: In a 1.5 mL screw-top conical plastic vial, the desired compound as a solution in DMSO (5 mM, 6 μL, 30 nmol) was mixed with a solution of N-acetylcysteine in DMSO (10 mM, 6 μL, 30 nmol, 2 equiv) to quench the maleimide. The mixture was diluted with pH 5.0 sodium acetate buffer containing 8 mM N-acetylcysteine (255 μL). 1-napthalene acetic acid in DMSO (5 mM, 6 μL, 30 nmol) was added as an internal standard. A 9.2 U/mL solution of Cathepsin B in pH 5.0 buffer was added. The vial was placed in a heating block at 37° C. and protected from direct light. 25 μL aliquots of the reaction mixture were removed at various time points and analyzed by LC-MS. LC-MS peaks were integrated within the Agilent LC-MS software and the areas of each peak were normalized to 1-napthalene acetic acid at 280 nm. Percent drug-linker remaining is defined as the normalized peak area at a given time point divided by the normalized peak area at 0 hours×100%.

Preparation of Stabilized Trioxacarcin-Antibody Conjugates

An exemplary stabilized trioxacarcin-antibody conjugates was prepared from the anti-HER2 monoclonal antibody trastuzumab and trioxacarcin-linker species 27. A drug-antibody ratio (DAR) of 3.37 and low aggregation was observed. The conjugate was entirely stable.

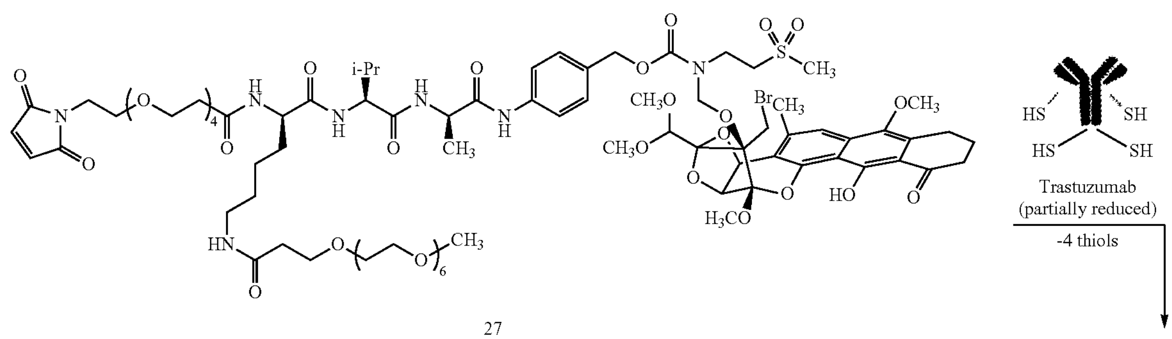
27
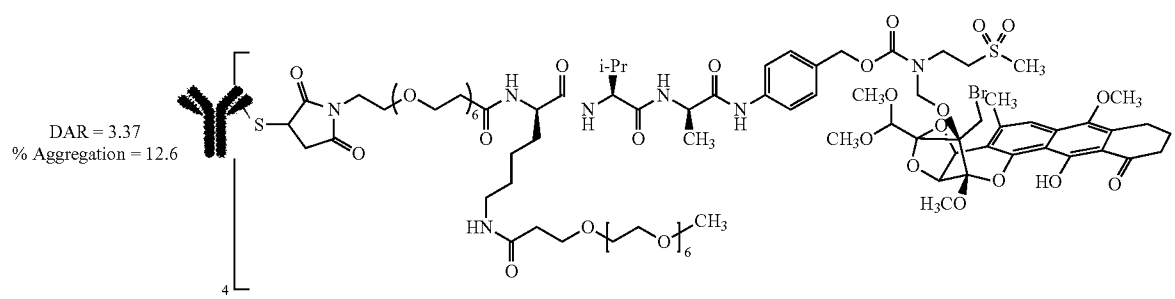
In contrast, trioxacarcin-antibody conjugates incorporating trioxacarcin warheads with an intact epoxide (prepared from R02-B5, R02-C10, and R02-D2 shown below) all decompose by self-alkylation within 6 hours in pH 7.4 buffer at 37° C.
R02-B5
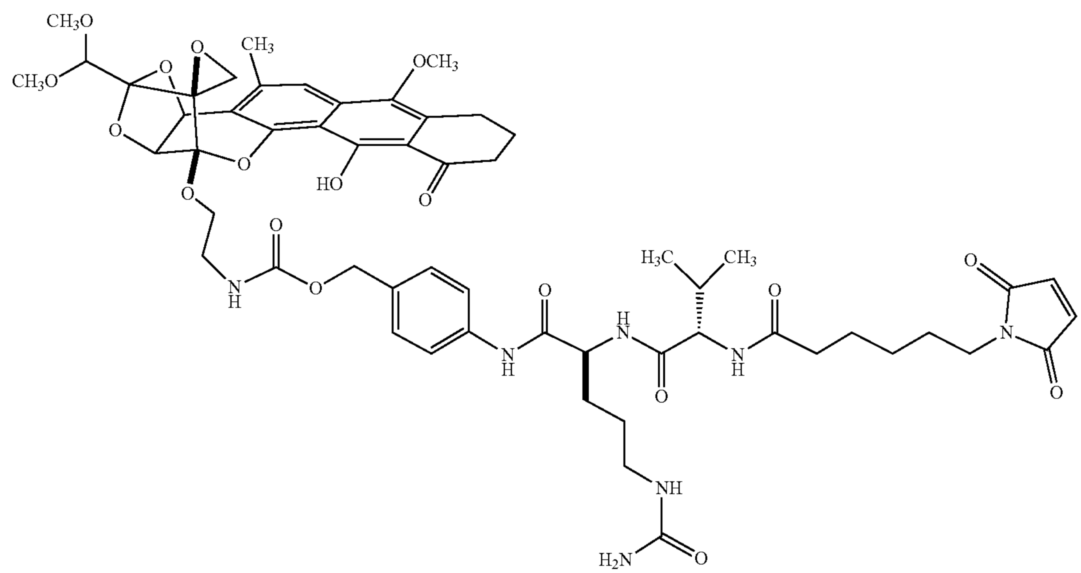

-continued

R02-C10

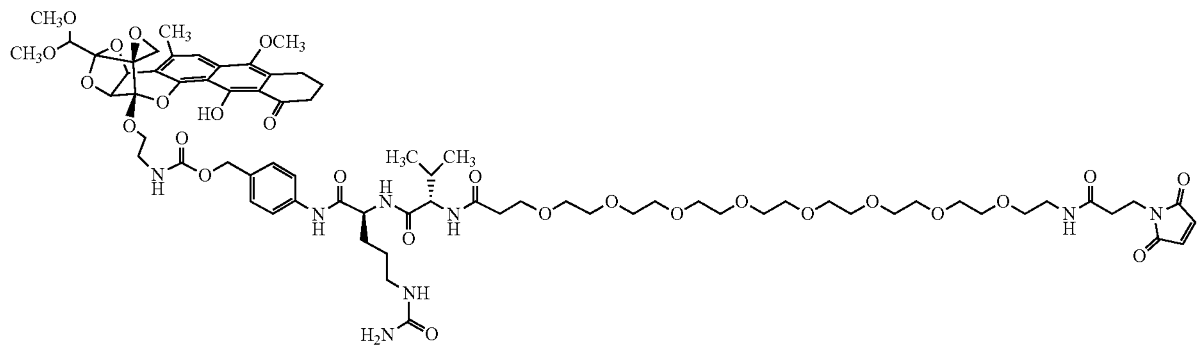

R02-D2

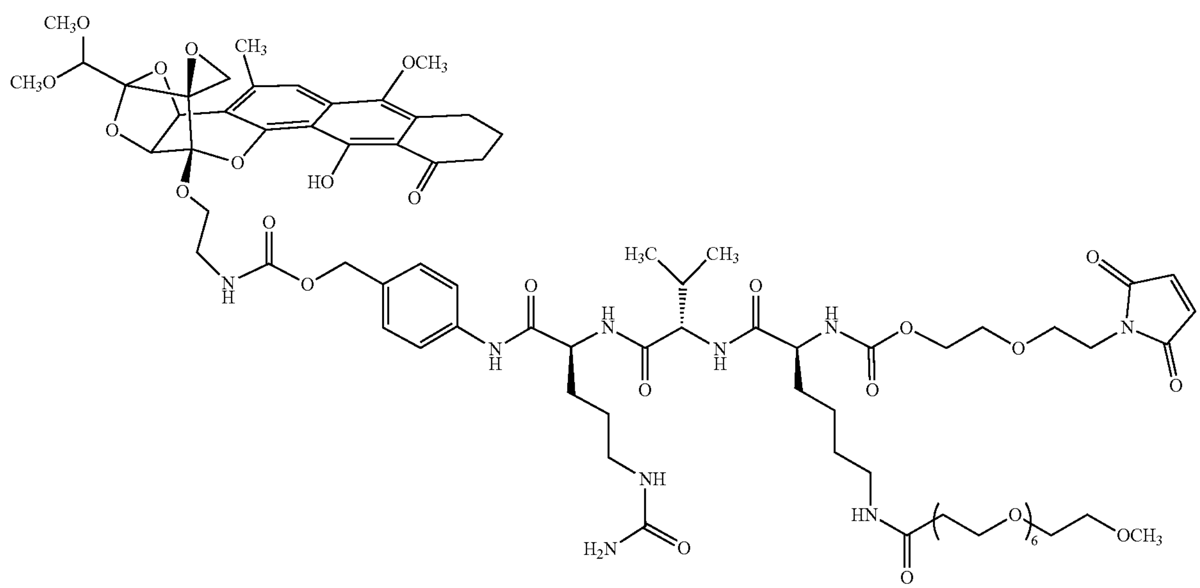

The methods used for preparing and characterizing the antibody-drug conjugate is described below.

Partial reduction of interchain disulfides: To a solution of trastuzumab (500 μg, 25 μL of 20 mg/mL in PBS) was added a solution of tris(2-carboxyethyl)phosphine hydrochloride (1.7 μL, 5 mM in water, 2.5 equiv) and diluted to 15 mg/mL final antibody concentration using DPBS pH 7.4 containing ethylenediaminetetraacetic acid (5 mM, 8.3 μL). The reaction was incubated at 37° C. for 2 h and then cooled to 23° C.

Conjugation of maleimide containing trioxacarcin-linker: To a solution of partially reduced trastuzumab was added the trioxacarcin-linker species (6.9 μL, 5 mM in DMSO, 10 equiv). DPBS pH 7.4 containing ethylenediaminetetraacetic acid (5 mM, 8.3 μL) was added to achieve 10 mg/mL final antibody concentration. DMSO (1 μL) was added to achieve 15% (v/v) total organic solvent component in the final reaction mixture. The reaction was incubated for 2 h at 23° C. with agitation at 500 rpm. After conjugation, the antibody solution was desalted into DPBS by three rounds of dilution and centrifugation at 4,000×g through a 10 kDa MWCO filter. The resulting antibody-drug conjugate was analyzed by LC-MS, and stored at −80° C.

LC-MS analysis: Trioxacarcin-antibody conjugates (50 μg, 20 μL solution in DPBS) were optionally deglycosylated before analysis by addition of PNGase F (0.5 μL, New England Biolabs) and PNGase F 10× buffer (2 μL, New England Biolabs). The solution was incubated at 27° C. for 16 h. Antibody was fully reduced by addition of tris(2-carboxyethyl)phosphine hydrochloride solution (20 μL of 20 mM in water) immediately before analysis. LC-MS analysis was performed at the Harvard University Mass Spectrometry Facility using a Bruker Impact II q-TOF mass spectrometer.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (II):

(II)

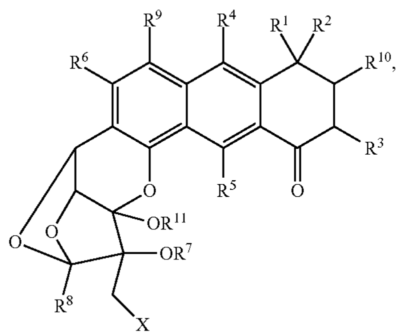

or a pharmaceutically acceptable salt thereof; wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{A1}$; $—C(=O)\ R^{A2}$; $—CO_2R^{A2}$; $—CN$; $—SCN$; $—SR^{A1}$; $—SOR^{A1}$; $—SO_2R^{A1}$; $—NO_2$; $—N_3$; $—N(R^{A2})_2$; $—NR^{A2}C(=O)R^{A2}$; $—NR^{A2}C(=O)N(R^{A2})_2$; $—OC(=O)OR^{A1}$; $—OC(=O)R^{A2}$; $—OC(=O)N(R^{A2})_2$; $—NR^{A}C(=O)OR^{A1}$; or $—C(R^{A2})_3$; wherein each occurrence of $R^{A1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{A2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino, or two $R^{A2}$ groups are optionally joined to form a heterocyclyl or heteroaryl ring;

$R^2$ is hydrogen; or $R^1$ and $R^2$ are joined to form $=O$; $=N(R^{A2})$; or $=S$;

$R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{C1}$; $—C(=O)R^{C2}$; $—CO_2R^{C1}$; $—CN$; $—SCN$; $—SR^{C1}$; $—SOR^{C1}$; $—SO_2R^{C2}$; $—NO_2$; $—N_3$; $=O$; $=N(R^{C2})$; $=S$; $—N(R^{C2})_2$; $—NHC(=O)R^{C2}$; $—NR^{C2}C(=O)N(R^{C2})_2$; $—OC(=O)OR^{C1}$; $—OC(=O)R^{C2}$; $—OC(=O)N(R^{C2})_2$; $—NRC^{2C}(=O)OR^{C1}$; or $—C(R^{C2})_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{C2}$ groups are optionally joined to form a heterocyclyl or heteroaryl ring;

$R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{D1}$; $—C(=O)R^{D2}$; $—CO_2R^{D2}$; $—CN$; $—SCN$; $—SR^{D1}$; $—SOR^{D1}$; $—SO_2R^{D2}$; $—NO_2$; $—N_3$; $—N(R^{D2})_2$; $—NR^{D2}C(=O)R^{D2}$; $—NR^{D2}C(=O)N(R^{D2})_2$; $—OC(=O)OR^{D1}$; $—OC$ (=O)$R^{D2}$; —OC(=O)N($R^{D2}$)$_2$; —$NR^{D2}$C(=O)$OR^{D1}$; or —C($R^{D2}$)$_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{D2}$ groups are optionally joined to form a heterocyclyl or heteroaryl ring;

R5 is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —ORE1; —C(=O)$R^{E2}$; —$CO_2R^{B1}$; —CN; —SCN; —$SR^{B1}$; —$SOR^{B1}$; —$SO_2R^{B2}$; —$NO_2$; —$N_3$; —N($R^{E2}$)$_2$; —$NR^{F2}$C(=O)$R^{E2}$; —$NR^{F2}$C(=O)N($R^{E2}$)$_2$; —OC(=O)$OR^{E1}$; —OC(=O)$R^{E2}$; —OC(=O)N($R^{E2}$)$_2$; —$NR^{E2}$C(=O)$OR_{E1}$; or —C($R_{E2}$) 3; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{F1}$; —C(=O)$R^{F2}$; —$CO_2R^{F1}$; —CN; —SCN; —$SR^{F1}$; —$SOR^{F1}$; —$SO_2R^{F2}$; —$NO_2$; —$N_3$; —N($R^{F2}$)$_2$; —$NR^{F2}$C(=O)$R^{F2}$; —$NR^{F2}$C(=O)N($R^{F2}$)$_2$; —OC(=O)$OR^{F1}$; —OC(=O)$R^{F2}$; —OC(=O)N($R^{F2}$)$_2$; —$NR^{F2}$C(=O)$OR^{F1}$; or —C($R^{F2}$)$_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{F2}$ groups are optionally joined to form a heterocyclyl or heteroaryl ring;

$R^7$ is -L-A-B;

X is a halogen;

$R^8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{I1}$; —C(=O)$R^{I2}$; —$CO_2R^{I1}$; —CN; —SCN; —$SR^{I1}$; —$SOR^{I1}$; —$SO_2R^{I2}$; —$NO_2$; —$N_3$; —N($R^{I2}$)$_2$; —$NR^{I2}$C(=O)$R^{I2}$; —$NR^{I2}$C(=O)N($R^{I2}$)$_2$; —OC(=O)$OR^{I1}$; —OC(=O)$R^{I2}$; —OC(=O)N($R^{I2}$)$_2$; —$NR^{I2}$C(=O)$OR^{I1}$; or —C($R^{I2}$)$_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{I2}$ groups are optionally joined to form a heterocyclyl or heteroaryl ring;

$R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{G1}$; —C(=O)$R^{G2}$; —$CO_2R^{G1}$; —CN; —SCN; —$SR^{G1}$; —$SOR^{G1}$; —$SO_2R^{G2}$; —$NO_2$; —$N_3$; —N($R^{G}$)$_2$; —$NR^{G2}$C(=O)$R^{G2}$; —$NR^{G2}$C(=O)N($R^{G2}$)$_2$; —OC(=O)$OR^{G1}$; —OC(=O)$R^{G2}$; —OC(=O)N($R^{G2}$)$_2$; —$NR^{G2}$C(=O)$OR^{G1}$; or —C($R^{G2}$)$_3$; wherein each occurrence of $R^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{G2}$ groups are optionally joined to form a heterocyclyl or heteroaryl ring;

$R^{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{B1}$; —C(=O)$R^{B2}$; —$CO_2R^{B2}$;

—CN; —SCN; —$SR^{B1}$; —$SOR^{B1}$; —$SO_2R^{B2}$; —$NO_2$; —$N_3$; ═O; ═$N(R^{B2})$; ═S; —$N(R^{B2})_2$; —$NR^{B2}C(═O)R^{B2}$; —$NR^{B2}C(═O)N(R^{B2})_2$; —$OC(═O)OR^{B1}$; —$OC(═O)R^{B2}$; —$OC(═O)N(R^{B2})_2$; —$NR^{B2}C(═O)OR^{B1}$; or —$C(R^{B2})_3$; wherein each occurrence of $R^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{B2}$ groups are optionally joined to form a heterocyclyl or heteroaryl ring;

$R^{11}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or —$C(═O)R^{H1}$; wherein $R^{H1}$ is hydrogen, substituted or unsubstituted alkyl; —$OR^{H9}$; —$OC(═O)R^{H9}$; —$N(R^{H9})_2$; or —$NHC(═O)R^{H9}$; wherein each occurrence of $R^{H9}$ is independently hydrogen; substituted or unsubstituted alkyl; an oxygen protecting group when attached to an oxygen atom; or a nitrogen protecting group when attached to a nitrogen atom; or two $R^{H9}$ groups are joined to form a substituted or unsubstituted heterocyclic or substituted or unsubstituted heteroaryl ring;

or $R^1$ and $R^{10}$ are optionally taken together with the intervening carbon atoms to form an optionally substituted cyclic moiety;

or $R^{10}$ and $R^3$ are optionally taken together with the intervening carbon atoms to form an optionally substituted cyclic moiety;

or $R^1$ and $R^4$ are optionally taken together with the intervening carbon atoms to form an optionally substituted cyclic moiety;

or $R^4$ and $R^9$ are optionally taken together with the intervening carbon atoms to form an optionally substituted cyclic moiety;

or $R^6$ and $R^9$ are optionally taken together with the intervening carbon atoms to form an optionally substituted cyclic moiety;

L is of the formula:

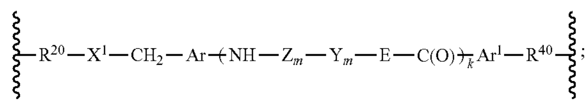

$R^{20}$ is substituted or unsubstituted alkylene; or substituted or unsubstituted heteroalkylene;

$X^1$ is

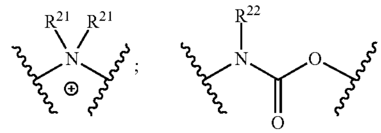

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

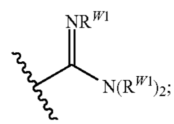

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene;

A is a group of the formula:

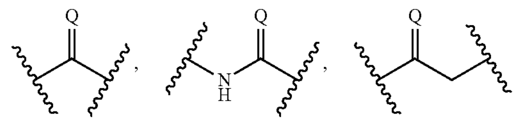

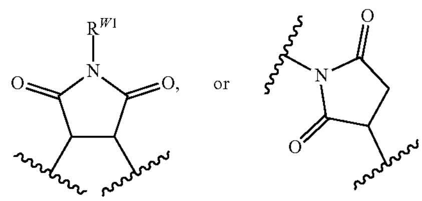

Q is —S— or —O—;

$R^{W1}$ is independently hydrogen, substituted or unsubstituted alkyl; or a nitrogen protecting group; and B is an antibody or an antibody fragment.

2. A compound of Formula (IV):

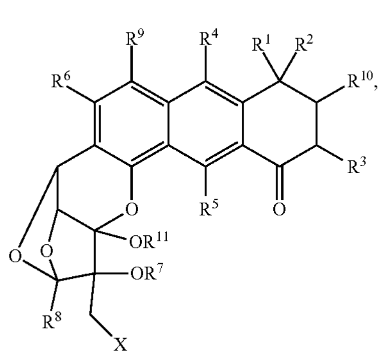

(IV)

or a pharmaceutically acceptable salt thereof;

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{A1}$; $—C(=O)R^{A2}$; $—CO_2R^{A2}$; —CN; —SCN; $—SR^{A1}$; $—SOR^{A1}$; $—SO_2R^{A}$; $—NO_2$; $—N_3$; =O; $=N(R^{A2})$; =S; $—N(R^{A2})_2$; $—NR^{A2}C(=O)R^{A2}$; $—NR^{A2}C(=O)N(R^{A2})_2$; $—OC(=O)OR^{A1}$; $—OC(=O)R^{A2}$; $—OC(=O)N(R^{A2})_2$; $—NR^{A}C(=O)OR^{A1}$; or $—C(R^{A2})_3$; wherein each occurrence of $R^{A1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{A2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino, or two $R^{A2}$ groups are optionally joined to form a heterocyclyl or heteroaryl ring;

$R^2$ is hydrogen; or $R^1$ and $R^2$ are joined to form =O; $=N(R^{A2})$; or =S;

$R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{C1}$; $—C(=O)R^{C2}$; $—CO_2R^{C1}$; —CN; —SCN; $—SR^{C1}$; $—SOR^{C1}$; $—SO_2R^{C2}$; $—NO_2$; $—N_3$; =O; $=N(R^{C2})$; =S; $—N(R^{C2})_2$; $—NHC(=O)R^{C2}$; $—NR^{C2}C(=O)N(R^{C2})_2$; $—OC(=O)OR^{C1}$; $—OC(=O)R^{C2}$; $—OC(=O)N(R^{C2})_2$; $—NR^{C2}C(=O)OR^{C1}$; or $—C(R^{C2})_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{C2}$ groups are optionally joined to form a heterocyclyl or heteroaryl ring;

$R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{D1}$; $—C(=O)R^{D2}$; $—CO_2R^{D2}$; —CN; —SCN; $—SR^{D1}$; $—SOR^{D1}$; $—SO_2R^{D2}$; $—NO_2$; $—N_3$; $—N(R^{D2})_2$; $—NR^{D2}C(=O)R^{D2}$; $—NR^{D2}C(=O)N(R^{D2})_2$; $—OC(=O)OR^{D1}$; $—OC(=O)R^{D2}$; $—OC(=O)N(R^{D2})_2$; $—NR^{D2}C(=O)OR^{D1}$; or $C(R^{D2})_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{D2}$ groups are optionally joined to form a heterocyclyl or heteroaryl ring;

$R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $—OR^{E1}$; $—C(=O)R^{E2}$; $—CO_2R^{E1}$; —CN; —SCN; $—SR^{E1}$; $—SOR^{E1}$; $—SO_2R^{E2}$; $—NO_2$; $—N_3$; $—N(R^{E2})_2$; $—NR^{E2}C(=O)R^{E2}$; $—NR^{E2}C(=O)N(R^{E2})_2$; $—OC(=O)OR^{E1}$; $—OC(=O)R^{E2}$; $—OC(=O)N(R^{E2})_2$; $—NR^{E2}C(=O)OR^{E1}$; or $—C(R^{E2})_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic;

cyclic or acyclic, substituted or unsubstituted, branched or unbranched heteroaliphatic; substituted or unsubstituted aryl; substituted or unsubstituted heteroaryl; —OR$^{F1}$; —C(═O)R$^{F2}$; —CO$_2$R$^{F1}$; —CN; —SCN; —SR$^{F1}$; —SOR$^{F1}$; —SO$_2$R$^{F2}$; —NO$_2$; —N$_3$; —N(R$^{F2}$)$_2$; —NR$^{F2}$C(═O)R$^{F2}$; —NR$^{F2}$C(═O)N(R$^{F2}$)$_2$; —OC(═O)OR$^{F1}$; —OC(═O)R$^{F2}$; —OC(═O)N(R$^{F2}$)$_2$; —NR$^{F2}$C(═O)OR$^{F1}$; or —C(R$^{F2}$)$_3$; wherein each occurrence of R$^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of R$^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two R$^{F2}$ groups are optionally joined to form a heterocyclyl or heteroaryl ring;

R$^7$ is -L-T;

X is a halogen;

R$^8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^{I1}$; —C(═O) R$^{I2}$; —CO$_2$R$^{11}$; —CN; —SCN; —SR$^{I1}$; —SOR$^{I1}$; —SO$_2$R$^{I2}$; —NO$_2$; —N$_3$; —N(R$^{I2}$)$_2$; —NR$^{I2}$C(═O) R$^{I2}$; —NR$^{I2}$C(═O) N(R$^{I2}$)$_2$; —OC(═O)OR$^{I1}$; —OC(═O)R$^{I2}$; —OC(═O)N(R$^{I2}$)$_2$; —NR$^{I2}$C(═O)OR$^{I1}$; or —C(R$^{I2}$)$_3$; wherein each occurrence of R$^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of R$^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two R$^{I2}$ groups are optionally joined to form a heterocyclyl or heteroaryl ring;

R$^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^{G1}$; —C(═O)R$^{G2}$; —CO$_2$R$^{G1}$; —CN; —SCN; —SR$^{G1}$; —SOR$^{G1}$; —SO$_2$R$^{G2}$; —NO$_2$; —N$_3$; —N(R$^{G}$)$_2$; —NR$^{G2}$C(═O)R$^{G2}$; —NR$^{G2}$C(═O)N(R$^{G2}$)$_2$; —OC(═O)OR$^{G1}$; —OC(═O)R$^{G2}$; —OC(═O)N(R$^{G2}$)$_2$; —NR$^{G2}$C(═O)OR$^{G1}$; or —C(R$^{G2}$)$_3$; wherein each occurrence of R$^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of R$^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two R$^{G2}$ groups are optionally joined to form a heterocyclyl or heteroaryl ring;

R$^{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^{B1}$; —C(═O)R$^{B2}$; —CO$_2$R$^{B2}$; —CN; —SCN; —SR$^{B1}$; —SOR$^{B1}$; —SO$_2$R$^{B2}$; —NO$_2$; —N$_3$; ═O; ═N(R$^{B2}$); ═S; —N(R$^{B2}$)$_2$; —NR$^{B2}$C(═O)R$^{B2}$; —NR$^{B2}$C(═O)N(R$^{B2}$)$_2$; —OC(═O)OR$^{B1}$; —OC(═O)R$^{B2}$; —OC(═O)N(R$^{B2}$)$_2$; —NR$^{B2}$C(═O)OR$^{B1}$; or —C(R$^{B2}$)$_3$; wherein each occurrence of R$^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of R$^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two R$^{B2}$ groups are optionally joined to form a heterocyclyl or heteroaryl ring;

R$^{11}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or —C(═O)R$^{H1}$; wherein R$^{H1}$ is hydrogen, substituted or unsubstituted alkyl; —OR$^{H9}$; —OC(═O)R$^{H9}$; —N(R$^{H9}$)$_2$; or —NHC(═O)R$^{H9}$; wherein each occurrence of R$^{H9}$ is independently hydrogen; substituted or unsubstituted alkyl; an oxygen protecting group when attached to an oxygen atom; or a nitrogen protecting group when attached to a nitrogen atom; or two R$^{H9}$ groups are joined to form a substituted or unsubstituted heterocyclic or substituted or unsubstituted heteroaryl ring;

or R$^1$ and R$^{10}$ are optionally taken together with the intervening carbon atoms to form an optionally substituted cyclic moiety;

or R$^{10}$ and R$^3$ are optionally taken together with the intervening carbon atoms to form an optionally substituted cyclic moiety;

or R$^1$ and R$^4$ are optionally taken together with the intervening carbon atoms to form an optionally substituted cyclic moiety;

or $R^4$ and $R^9$ are optionally taken together with the intervening carbon atoms to form an optionally substituted cyclic moiety;

or $R^6$ and $R^9$ are optionally taken together with the intervening carbon atoms to form an optionally substituted cyclic moiety;

L is a bond, or of the formula:

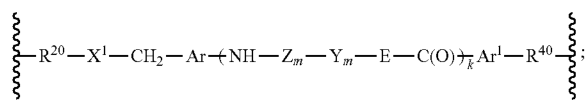

$R^{20}$ is substituted or unsubstituted alkylene; or substituted or unsubstituted heteroalkylene;

$X^1$ is

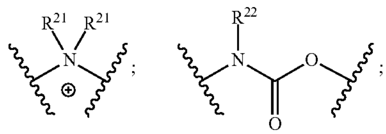

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl;

or

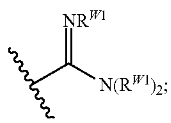

Ar is substituted or unsubstituted arylene;

each occurrence of Z is independently an amino acid;

each occurrence of Y is independently an amino acid;

E is a bond or an amino acid;

m is independently 1, 2, or 3;

k is 0 or 1;

$Ar^1$ is a bond or substituted or unsubstituted heteroarylene;

$R^{40}$ is substituted or unsubstituted alkylene; or substituted or unsubstituted heteroalkylene; and combinations thereof;

T is hydrogen, —N═C═S,

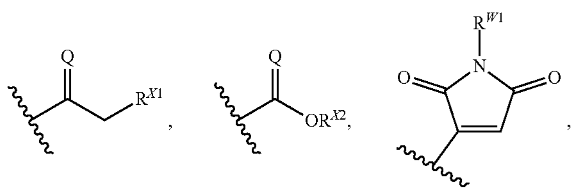

-continued

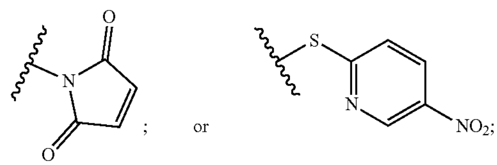

Q is —S— or —O—;

$R^{X1}$ is a leaving group;

$R^{X2}$ is hydrogen; substituted or unsubstituted alkyl; substituted or unsubstituted heterocyclyl; substituted or unsubstituted aryl; substituted or unsubstituted heteroaryl; or an oxygen protecting group; and $R^{W1}$ is independently hydrogen; substituted or unsubstituted alkyl; or a nitrogen protecting group.

3. The compound of claim 1, wherein the compound is of the formula:

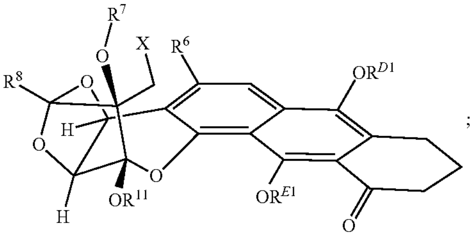

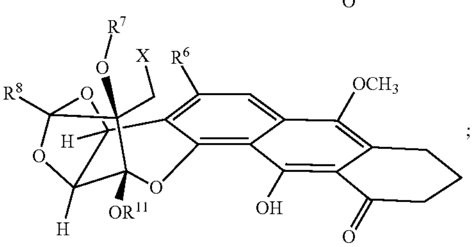

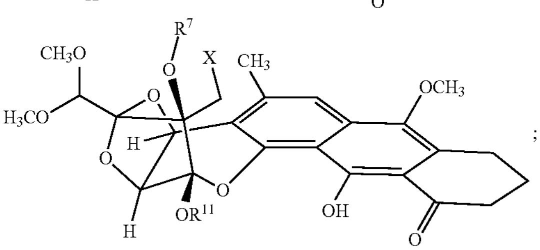

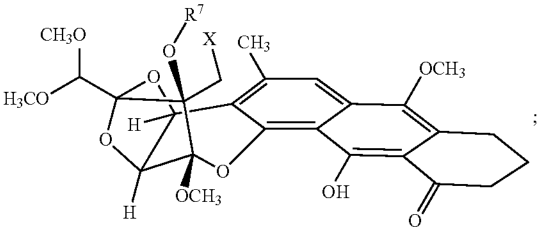

or

-continued

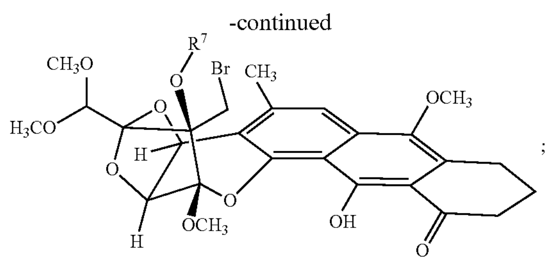

or a pharmaceutically acceptable salt thereof.

4. The compound of claim 1, or a pharmaceutically acceptable salt thereof, wherein X is —Cl, —Br, or —I.

5. The compound of claim 1, or a pharmaceutically acceptable salt thereof, wherein:

$X^1$ is

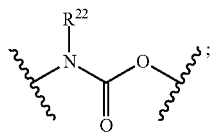

and $R^{22}$ is hydrogen; substituted or unsubstituted alkyl; or substituted or unsubstituted carbocyclyl.

6. The compound of claim 1, or a pharmaceutically acceptable salt thereof, wherein Z is alanine, lysine, arginine, histidine, ornithine, or citrulline.

7. The compound of claim 1, or a pharmaceutically acceptable salt thereof, wherein Y is alanine, valine, leucine, isoleucine, methionine, phenylalanine, or tryptophan.

8. The compound of claim 1, or a pharmaceutically acceptable salt thereof, wherein L is of the formula:

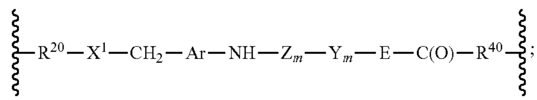

$R^{20}$ is substituted or unsubstituted alkylene; or substituted or unsubstituted heteroalkylene;

$X^1$ is

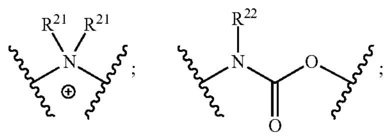

heterocyclylene; or heteroarylene;

$R^{21}$ is independently substituted or unsubstituted alkyl; or substituted or unsubstituted carbocyclyl; or two $R^{21}$ groups are joined to form an optionally substituted heterocyclyl ring;

$R^{22}$ is hydrogen; substituted or unsubstituted alkyl; substituted or unsubstituted carbocyclyl; or

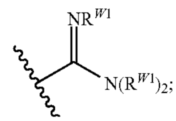

Ar is substituted or unsubstituted arylene;

each occurrence of Z is independently an amino acid;

each occurrence of Y is independently an amino acid;

E is a bond or an amino acid;

m is independently 1, 2, or 3;

$R^{40}$ is substituted or unsubstituted alkylene; or substituted or unsubstituted heteroalkylene;

A is a group of the formula:

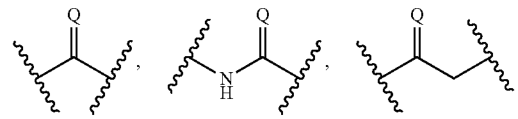

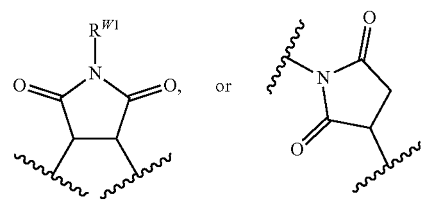

Q is —S— or —O—; and $R^{W1}$ is independently hydrogen, substituted or unsubstituted alkyl; or a nitrogen protecting group.

9. The compound of claim 1, or a pharmaceutically acceptable salt thereof, wherein -L- is a group of the formula:

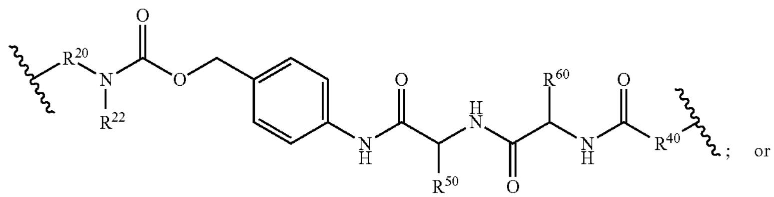

-continued

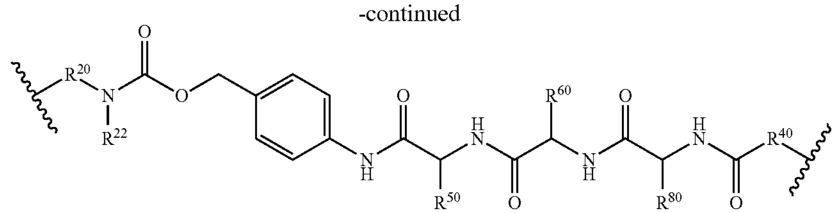;

wherein:

$R^{20}$ is substituted or unsubstituted $C_{1-6}$ alkylene;

$R^{22}$ is hydrogen, or substituted or unsubstituted $C_{1-6}$ alkyl;

$R^{40}$ is substituted or unsubstituted $C_{1-6}$ alkylene, or substituted or unsubstituted $C_{1-40}$ heteroalkylene;

$R^{50}$ is the sidechain of alanine, lysine, arginine, histidine, ornithine, or citrulline;

$R^{60}$ is the sidechain of alanine, valine, leucine, isoleucine, methionine, phenylalanine, or tryptophan; and $R^{80}$ is a substituted sidechain of a lysine, arginine, histidine, ornithine, or citrulline.

10. The compound of claim 1, or a pharmaceutically acceptable salt thereof, wherein -L- is a group of the formula:

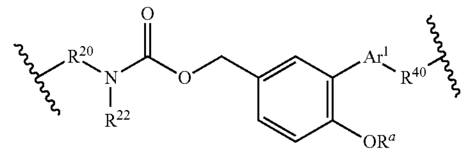;

wherein:

$R^{20}$ is substituted or unsubstituted $C_{1-6}$ alkylene;

$R^{22}$ is hydrogen, or substituted or unsubstituted $C_{1-6}$ alkyl;

$R^{40}$ is substituted or unsubstituted $C_{1-6}$ alkylene, or substituted or unsubstituted $C_{1-40}$ heteroalkylene;

$Ar^1$ is substituted or unsubstituted heteroarylene; and $R^a$ is a substituted heterocycle.

11. The compound of claim 1, or a pharmaceutically acceptable salt thereof, wherein -L-A- is a group of the formula:

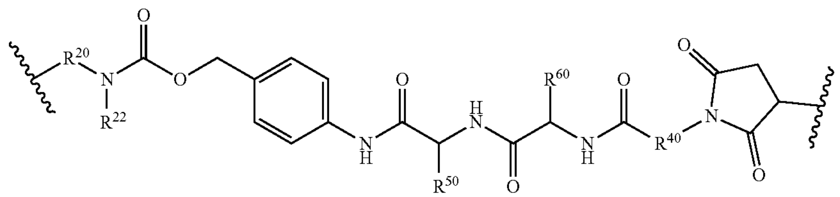;

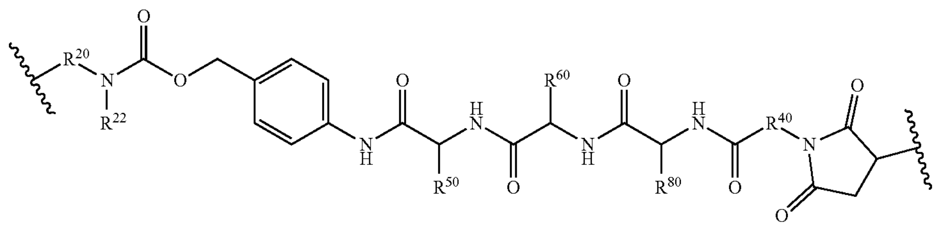;

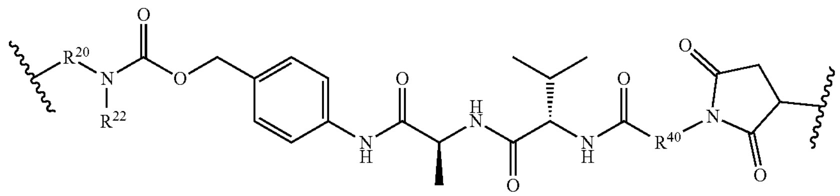;

-continued
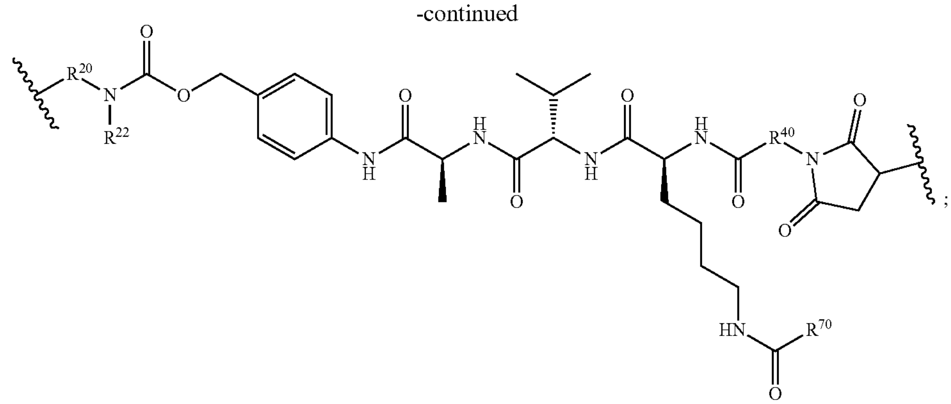
;
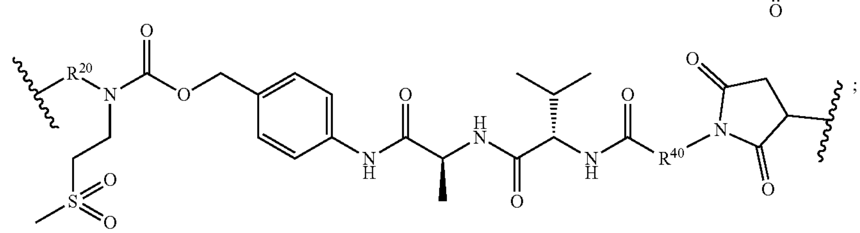
;
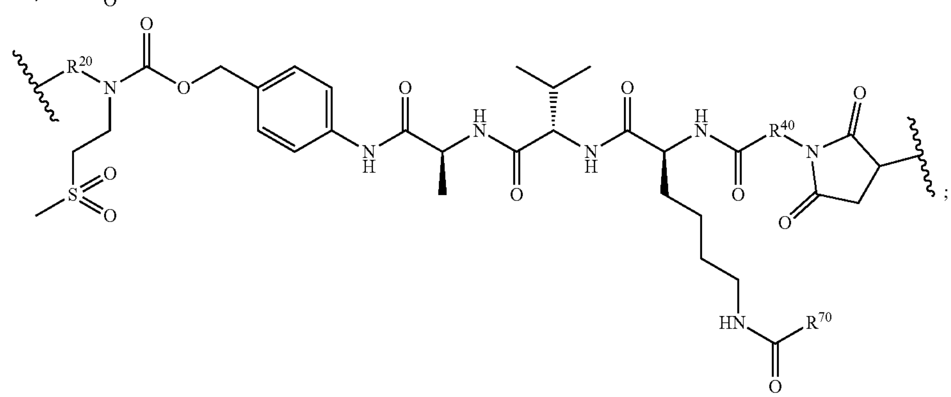
;
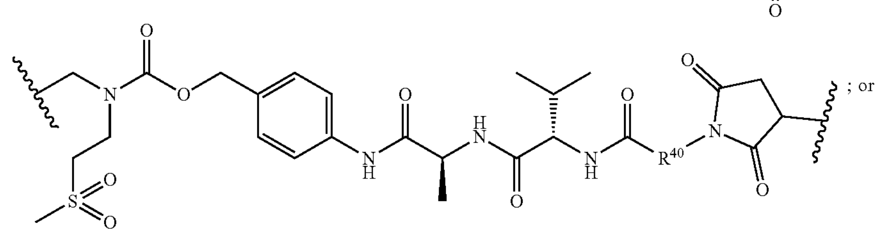
; or
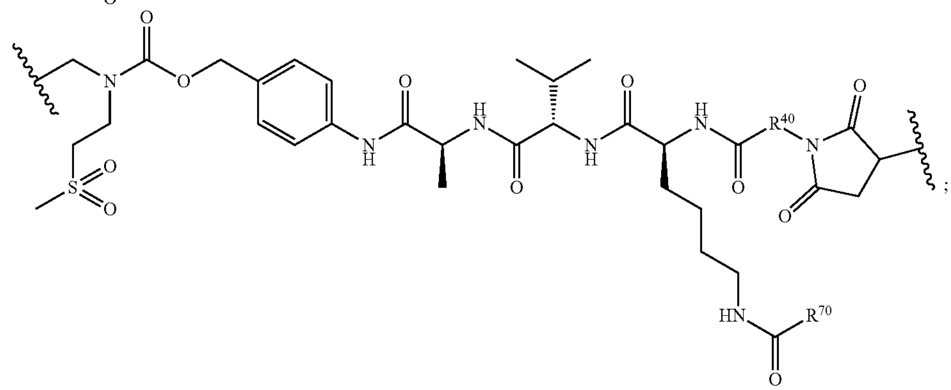
;
wherein:
$R^{20}$ is substituted or unsubstituted $C_{1-6}$ alkylene;
$R^{22}$ is hydrogen, or substituted or unsubstituted $C_{1-6}$ alkyl;
$R^{40}$ is substituted or unsubstituted $C_{1-6}$ alkylene, or substituted or unsubstituted $C_{1-40}$ heteroalkylene;
$R^{50}$ is the sidechain of alanine, lysine, arginine, histidine, ornithine, or citrulline;

$R^{60}$ is the sidechain of alanine, valine, leucine, isoleucine, methionine, phenylalanine, or tryptophan;

$R^{70}$ is substituted or unsubstituted heteroalkyl; and $R^{80}$ is a substituted sidechain of a lysine, arginine, histidine, ornithine, or citrulline.

12. The compound of claim 1, or a pharmaceutically acceptable salt thereof, wherein -L-A- is a group of the formula:

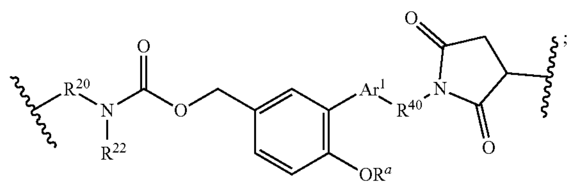

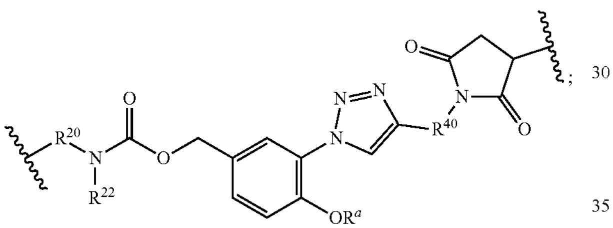

-continued

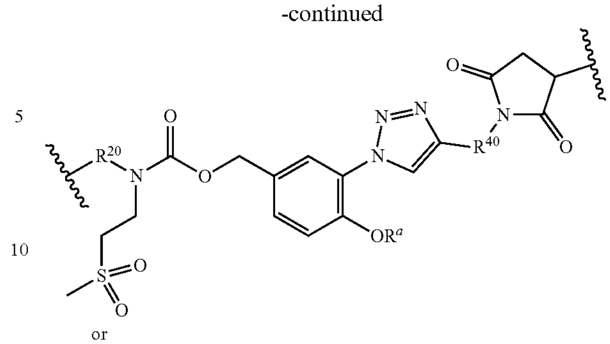

or

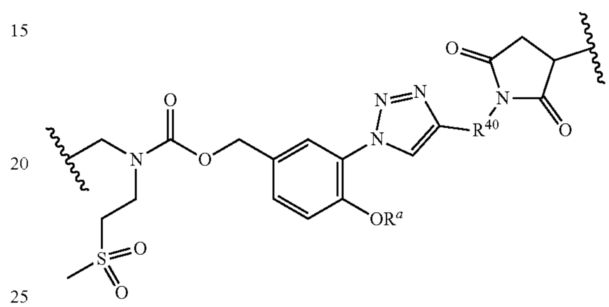

wherein:

$R^{20}$ is substituted or unsubstituted $C_{1-6}$ alkylene;

$R^{22}$ is hydrogen, or substituted or unsubstituted $C_{1-6}$ alkyl;

$R^{40}$ is substituted or unsubstituted $C_{1-6}$ alkylene, or substituted or unsubstituted $C_{1-40}$ heteroalkylene;

$Ar^1$ is substituted or unsubstituted heteroarylene; and $R^a$ is a substituted heterocycle.

13. The compound of claim 1, or a pharmaceutically acceptable salt thereof, wherein -L-A- is a group of the formula:

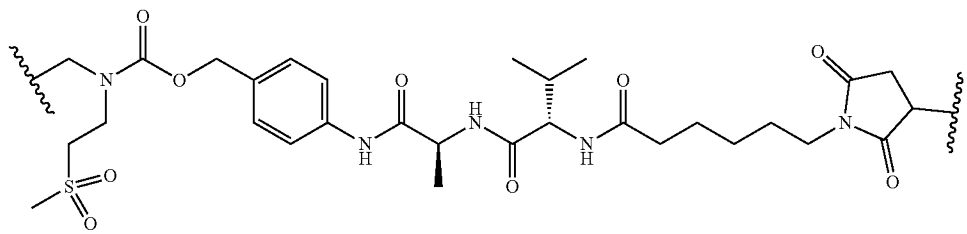

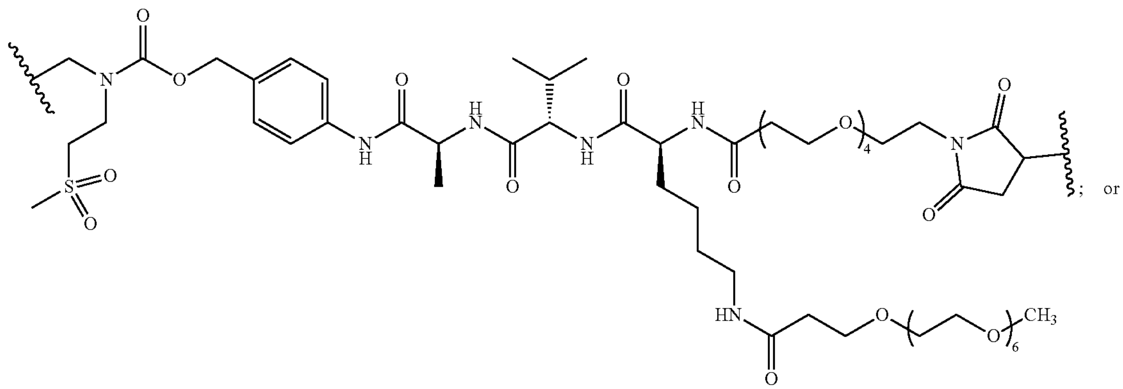

or

-continued

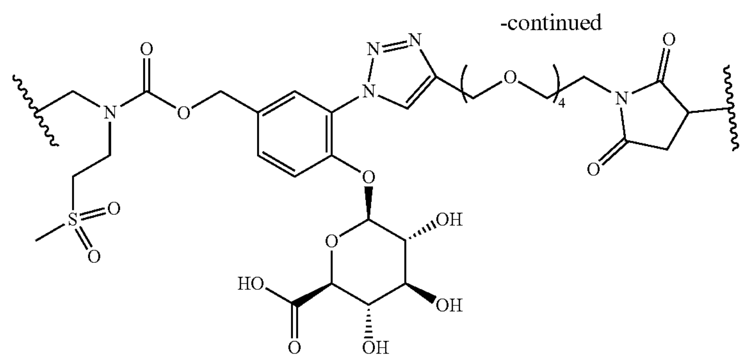

14. The compound of claim 1, or a pharmaceutically acceptable salt thereof, wherein B is an antibody selected from adecatumumab, afutuzumab, alemtuzumab, bavituximab, belimumab, bevacizumab, brentuximab, cantuzumab, cetuximab, citatuzumab, cixutumumab, conatumumab, dacetuzumab, elotuzumab, etaracizumab, farletuzumab, figitumumab, gemtuzumab, ibritumomab, inotuzumab, ipilimumab, iratumumab, labetuzumab, lexatumumab, lintuzumab, lucatumumab, mapatumumab, matuzumab, milatuzumab, necitumumab, nimotuzumab, ofatumumab, olaratumab, oportuzumab, panitumumab, pertuzumab, pritumumab, rituximab, robatumumab, sibrotuzumab, siltuximab, tacatuzumab, tigatuzumab, tositumomab, trastuzumab, tucotuzumab, veltuzumab, votumumab, zalutumumab, and antibody fragments thereof.

15. The compound of claim 1, wherein the compound is

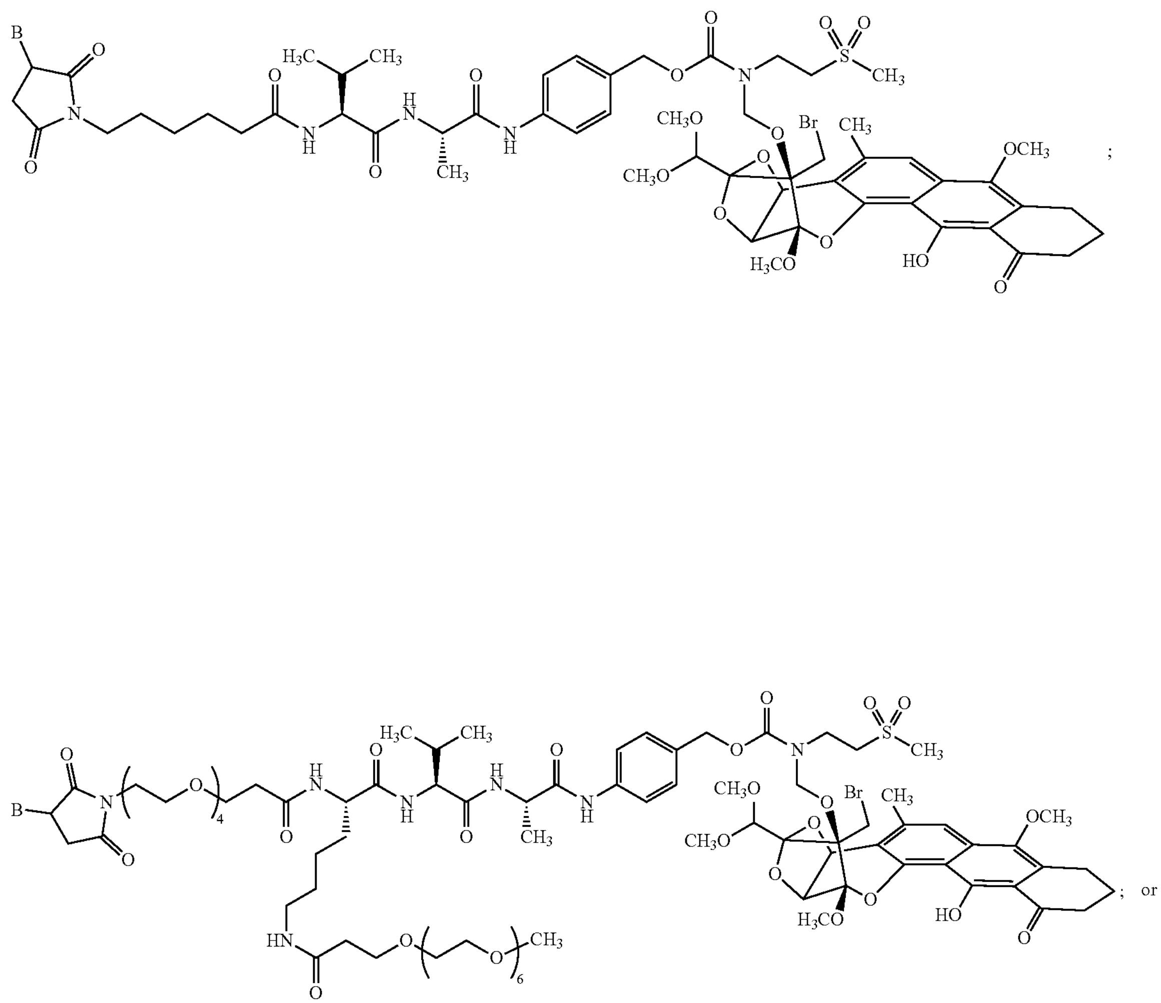

;

; or

-continued
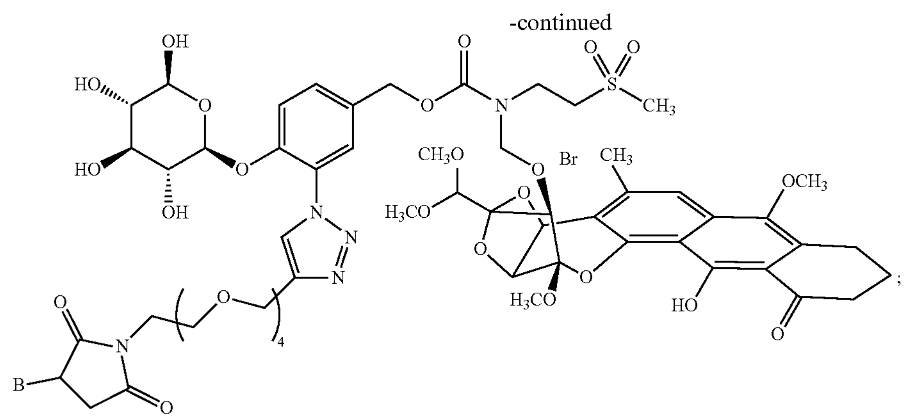
;
or a pharmaceutically acceptable salt thereof.
16. The compound of claim 2, wherein the compound is
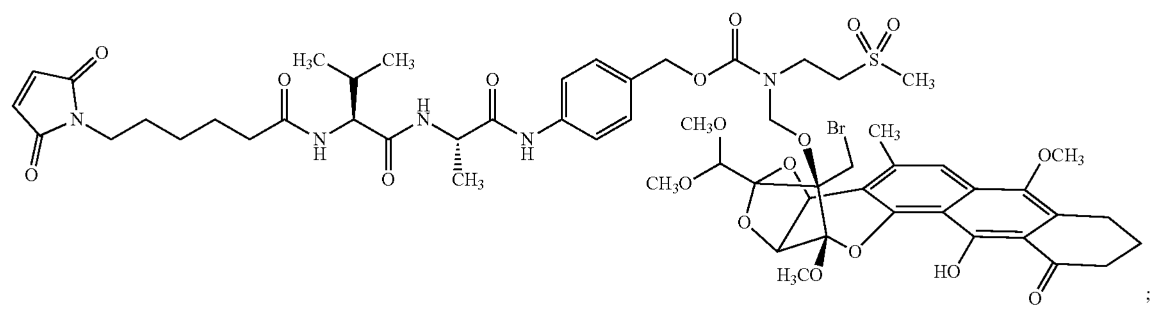
;
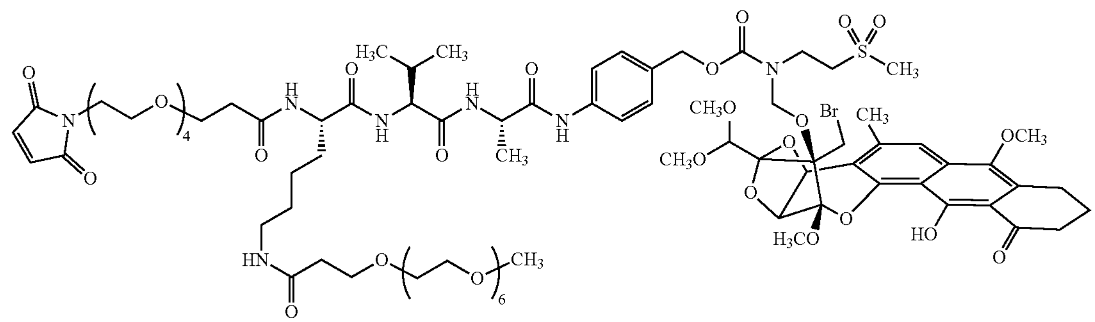
;
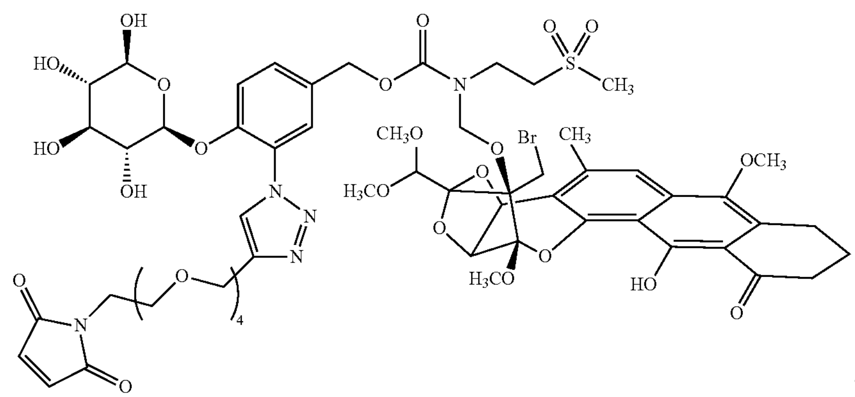
;

-continued

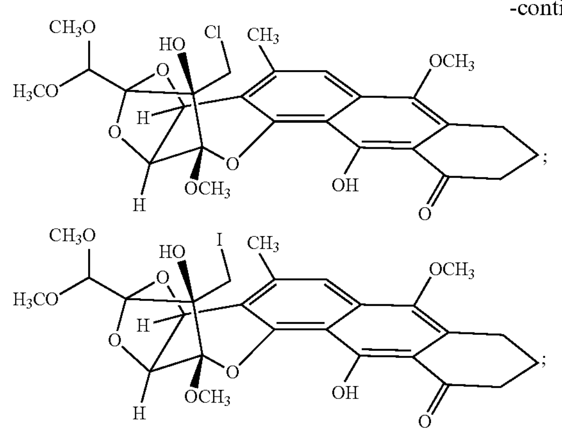

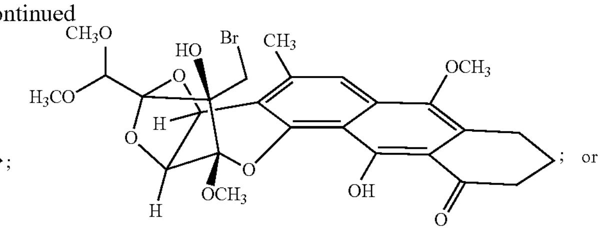

or or a pharmaceutically acceptable salt thereof.

17. A pharmaceutical composition comprising a compound of claim 1, or pharmaceutically acceptable salt thereof, and a pharmaceutically acceptable carrier.

18. A method of treating a cardiovascular disease, a proliferative disease, diabetic retinopathy, an inflammatory disease, an autoimmune disease, or an infectious disease in a subject in need thereof, the method comprising administering to the subject an effective amount of the compound of claim 1, or a pharmaceutically acceptable salt thereof.

19. A pharmaceutical composition comprising a compound of claim 2, or pharmaceutically acceptable salt thereof, and a pharmaceutically acceptable carrier.

20. A method of treating a cardiovascular disease, a proliferative disease, diabetic retinopathy, an inflammatory disease, an autoimmune disease, or an infectious disease in a subject in need thereof, the method comprising administering to the subject an effective amount of the compound of claim 2, or a pharmaceutically acceptable salt thereof.

* * * * *